US009297022B2

(12) United States Patent
Trick et al.

(10) Patent No.: US 9,297,022 B2
(45) Date of Patent: Mar. 29, 2016

(54) COMPOSITIONS AND METHODS FOR CONTROLLING PARASITIC NEMATODES

(75) Inventors: Harold N. Trick, Olsburg, KS (US); Jiarui Li, Manhattan, KS (US); Timothy C. Todd, Manhattan, KS (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 666 days.

(21) Appl. No.: 13/508,087

(22) PCT Filed: Nov. 11, 2010

(86) PCT No.: PCT/US2010/056358

§ 371 (c)(1),
(2), (4) Date: Jun. 7, 2012

(87) PCT Pub. No.: WO2011/060151

PCT Pub. Date: May 19, 2011

(65) Prior Publication Data

US 2012/0246765 A1 Sep. 27, 2012

Related U.S. Application Data

(60) Provisional application No. 61/260,248, filed on Nov. 11, 2009.

(51) Int. Cl.
*C12N 15/82* (2006.01)

(52) U.S. Cl.
CPC ........ *C12N 15/8285* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 7,456,335 | B2 | 11/2008 | Kogel et al. |
| 8,222,028 | B2 | 7/2012 | Zieler et al. |
| 2005/0091713 | A1 | 4/2005 | Atkinson |
| 2005/0158758 | A1 | 7/2005 | Baulcombe |
| 2007/0192903 | A1 | 8/2007 | Heck |
| 2009/0012029 | A1 | 1/2009 | Hussey et al. |
| 2009/0270254 | A1 | 10/2009 | Thielert et al. |

FOREIGN PATENT DOCUMENTS

| | | | |
|---|---|---|---|
| WO | WO 0137654 | A2 * | 5/2001 |
| WO | 2006/047495 | | 5/2006 |
| WO | 2007/104570 | | 9/2007 |
| WO | WO 2007104570 | A2 * | 9/2007 |

OTHER PUBLICATIONS

Lehner et al (2004) Breif. In Func. Genom. And Proteom. 3: 68-83.*
Alkharouf et al (2007) Exper. Parisitol. 115: 247-258.*

* cited by examiner

*Primary Examiner* — Brent T Page
(74) *Attorney, Agent, or Firm* — Casimir Jones S.C.

(57) ABSTRACT

The present invention relates to compositions and methods for controlling nematode infestation of plants or animals. In particular, the present invention provides vectors comprising sequences designed to control nematodes by RNA interference (RNAi) and transgenic plants transformed with such vectors.

3 Claims, 78 Drawing Sheets

FIG. 12

*Y25* of *Heterodera Glycines* (partial)(HM369132) (SEQ ID NO:1)

CTCCGCATTGGCCAACACTTTGGCCAAATTGGTGTTGCGCTACGCTGAGCTCAACAAGGGTGTCCCCTCAACT
GTTAATAAATTGGCGAGTGGTGCGCTGCTGCTCATCGCTTCAATCATTCATCTTGGCAAGTCGGGCTTGTGCA
AACAGCCGATCACTGAGGACGACTTGGACCGTTTGTCGACCACTGTTCGACTGATTGTTGACCAATGGCCGAA
AGCGGTGGATGTGTTTTTGAGAGAGTGCCGTGCTTCGTTGGAAAGCATGCTCAAGGCCAAGGGGGACGTGGA
CCGGCACGAACGCGACACAAAAGCGCCGAAGAAGAAAATTGT<u>GCAGCCCGACAAGACAATTATGTTCACGC</u>
<u>AGCTGTCCACACGCGTGTCAGAAAACGTGACGGACACAAATTTGTTTGATCTTTCGCTTTCCCAAGCGCTTGG</u>
<u>TACTGCACCCAAAACGACCAAATACACCTTTGCCAGCTCCAAACTGGGAAAAGTGATTCAGTTAGCCGGCTTT</u>
<u>TCGGATCCCGTCTATGCCGAGGCGTACGTCAACGTCAACCAATATGACATTGTATTGGACGTACTCGTGGTCA</u>
<u>ACCAGACTAGCGACACCTTGCAAAATTTGTCATTGGAACTCTC</u>GACCGTTGGCGACCTTAAATTGGTGGACAA
ACCCTCGCCGATTACTCTTGCACCTAACGACTTCACTAACATCAAAGCCACCGTAAAAGTGTCATCCACCGAA
AATGGAGTCATTTTCTCCACCATTGCTTATGATGTGCGAGGGTCGACCTCGGATCGAAATTGTGTGTACCTTG
AGGACATTCACATTGACATAATGGATTACATTGTGCCGGGCACTTGCACAGATACAGAATTTCGGAAAATGT
GGGCCGAATTTGAATGGGAGAACAAGGTCGGAGTTGTGACCCCAATTACGGACCTTCGACAATACTTGGACC
ATTTGTCCGCTCAAACAAATATGAAACTGCTGACAACAGACGCGGCATTGGAAGGCGATTGCGGTTTTCTGGC
GGCCAACTTCTGTGCCCATTCCATTTTTGGCGAGGATGCGTTGGCCAATGTTTCCGTTGAAAAGGCGGACCCA
CTGGATCCAATGAGTGCCATTATTGGCCATATTCGGATCAGGGCCAAGTCTCAGGGGATGGCACTTTCGCTGG
GGGACAAGATAAACCACGCGCAGAAGGAACGTAAGCCGGTGGAGAGGGGCGGCGGGGCGAGGGCAGTGGC
GAACGCTGCCGCGAAATGAATGAAGACGAGCAAAACGTTTAGCAATTTATTGCAAATAATATTTTAATCGCA
TCATTCACTGTTTTCCATGTTTTTCTTATTGTTTTTCTCGTCATTGTTAAATTTCTTTGTATTTTGTGATGTGATT
TAATATATTTCTTAATTTTGGGATTTGTTTACCTAAATTTCAAGCCGATCATTCATTATAAAAAATGTACTGAA
AAAAAAAAAAAAAAAAAAAAAA

Underlined sequences were chosen for RNAi construct.

FIG. 13

***Arx* of *Heterodera Glycines* (partial)(CD748919) (SEQ ID NO:2)**

AGTGATTCTCCTGTTCCTAATTGGCTGCTTAACATCGGACCAATTTCTTGCCATGCGTGGAACAAGGACAAAA
CTCAATTGGCTGTTTCGCCTTCCAACAACGAAATTCACATATTCGCTCGTTCGGAGACCGTTTGGAACCCGTTG
CACGTGCTAAGAGAACACGACTTGCTGATCACCGGATTGGATTGGGCTCCGAATACTAATCGGATTGTTTCAT
GTTCGCACGACAAAAATGCGTTTGTGTGGACATGGGAGGCTGAAAAGAACAGTTGGAAACCGGAGATGGTG
GTCGTTCGGATAAACAGAGCTGCCACCTGTGTCAAATGGTCGCCCAACGAAAACAAATTCGCCGTTGGGACG
GGTGCGCGTTTAGTCGCTATTTGTTATTACGAACGTGAAAATGACTGGTGGGTAGCGAAGCAAATCAAAAAG
CTGATTCGTTCCACGGTCACCTCATTGAATTGGCATCCCAACAACATTTTGTTGGCTGTTGGCGCCTGTGACTT
CAAAACGCGTGTTTTTTCTGCTTATGTGAAAGAGATTGACGAAAAACCAACGCCAAACCCTTGGGGGACCAA
AATGCCATTGGGAGAATTGCTCAAGGAGTACCAGT

Underlined sequences were chosen for RNAi construct.

FIG. 14

***Cpn-1* of *Heterodera Glycines* (partial)(GU074018) (SEQ ID NO:3)**

CACCAAGGCATCGATCAGGCTGTGGCAGCAGCCATTACGGAATTGAAGGCCATCTCGCGCCCCATTGCCACC
AGCAAGGAGATTGCGCAAGTGGGCTCCATTTCGGCCAACTCCGACAGCGCCATCGGCGACATCATCGCCCAG
GCCATGGAGAAGGTGGGCAAGGAGGGCGTGATAACCGTCGAGGATGGCAAGTCGCTGGAAAACGAACTGGA
TGTGGTGGAAGGCATGCAGTTCGACCGCGGCTACCTGAGCCCATACTTCATCAATGATCCGGACAAGCAACT
GGCGCGCCTGGATGACCCGCTGGTGCTGCTGTACGACAAAAAGATCAGCAATATCCGCGAGCTGCTGCCGGT
GCTGGAGCAGTCGGCCAAGGCCGGCAAGCCGCTGTTCATCGTGGCGGAGGATACAAAAAGCGA

This partial sequence was used for RNAi construct.

FIG. 15

*Prp-17* of *Heterodera Glycines* (AF113915) (full length)(SEQ ID NO:4)

ATTTGCTTAGATGGATTTGTTAAAATCTTACGACGGCTCTTCATCATCGGACAATGAACAAGAATTGGCAGAT
ATACCTTCTTCGTCCAATCACAACAAATTGCTCGCTTTGAAAATCCCATCCATCAACTTAACACCCAACGTGA
TTGAACAACGCGCCATTCAACAGGTTGCGGTTGTGGATCCAAAAACCAAAGAGTTGTATCACAATCCGCGCTT
CGACGAATTGTTTAGACCAGAGAGCGGCCCACAAAATCCGTTTAAAAGTGAACATCAACGAGCAGAAAAGA
ACACACTGACCGGCTATGTGGAGCCAGCGCATTTCAACGCCTTCCATTTTGAGCGTTCACTTCGCTCCTACGA
TACGCTTGGCTATGCGGATAATCCAACGGCAGACACAACCAGCGCAAAGTTCGTTGGTGACGTTGGACAAGC
GCAAGAAAAGGCCGGCGAGTCGCTTTTTGAATCAGTAAAAACTGGCGGACAGAAGCGAAAGAGAGTGATAA
ATTACGACGCATCAAACGTTGACGGATATACGGGACCGTGGGCAAGGTTTGAGGACGAGAAGACATTTGCTC
GACCGGACCCAGAATTGCAGAAGGAAATGGACGAAATTGTGCGGAAACGGAAACTGAAAAGTCGTGCTGGC
CGAAGAGCGGCCATCGCGGAATTGCATTTGGCAGAAGAGAGCACCAAATTGCACATAAAAGATGACACTGA
CTATTTGGGCCGTTCCTTTATGGAACCGCCGAAATACACGGGCACCAATCTGCGCGAGGACTTTGTGCCCGAC
CGCTGTTTCCCGCCCACAAAACAAGCACACACCTACAGCAGTCACACCAAACCGGTGACCGCCATCCGATGG
TTTCCTCGTAGTGCGCACATGTTTATCTCTTGTTCCATGGACGGAAAAGTCAAATTGTGGGAAGTGTACGGCA
ACCGTAAGTTGATCCGCACATACACTGGACACAAAGTGCCCGTGAAGGACATTTATTTTAACAACACCGGCA
CTGAATTTCTAAGTGCCGCTTATGACAATTACATCAAATTGTGGGACACTGAAACCGGTCAGGTGAAAAACC
GCTACACAATTGGAGGCCATCGGGCGTATGTGGTCAAATTCAACCCGGACGATGATAAACAAAACATTTTCA
TGGCCGGAATGTCCAACAAAAGATCATCCAATGGGACACGCGAACTGGCGAAATCGAACAAGAATACGAC
CGTCATTTGGGTCCAGTGAACTCGATCACCTTTTTCGACAAAAACCGTCGTTTCGTTTCTACTTCGGACGATAA
ATCTCTTCGCATTTGGGAATTTGGCATTCCCGTGGATACAAAACTGATTCAACATGCTGGACTACATTCCATTC
CTTCAATGACTAGGGCACCAAATGAAAAATGGATCGTTGGGCAGTCCATGGA<u>CAATCGAATTGTCCTTTTCCA</u>
<u>AATCGTCGATGACAAGTTGCGATTCGCTCGTAAAAAGGCCTTCCGTGGTCACAATACAGCAGGGTACGCCTG</u>
<u>CTCAACTGATTTTTCGCCAGAGATGAGTTTTCTCGCTTCCGGTGATGCGGACGGTAAAATCACAATGTGGGAC</u>
<u>TGGCGCACACACAAAATTGTCTCCACATGGAAGGCACATGATAATGTGTGCATTTCAACACTGTGGCATCCGC</u>
<u>ACGAGAAATCGCGGATGATTTCTTGCGGATGGGACAATGTAATCAAAATGTGGGTCTGACAATGAAGTAAAG</u>
CTGACGACGATTCAATGATTTAAAGTGAATTTATTTGTAATGTCTCAACCGATAAAAGGAAAAACGTCCAAA
AAAAAAAAAAAAAA

Underlined sequences were chosen for RNAi construct.

FIG. 16

***Rnr-1* of *Heterodera Glycines* (CD749124) (partial)(SEQ ID NO:5)**

GCTCACCGGTCAGCAAAGGCATTTTGCAATACGACATGTGGGATGTTGTACCAACGGATTTATGGGACTGGCC
GCTGCTCAAAGAACGCATTTCAAAGTTCGGTGTTCGGAACAGTTTGCTGGTCGCCCCTATGCCAACTGCTTCG
ACAGCACAAATCCTCGGCAACAATGAGTCCATTGAGCCGTACACTTCAAATGTGTACAGCCGTCGTGTCCTTT
CGGGAGACTTTCAAATTGTCAATCCGCATTTGATGAAGGATTTAATTGAACTCAATCTTTGGGATGATCAAAT
GAAGAACAGACTAATCGCGGAGAACGGATCGGTGCAGAACATCAAGCAGTTGCCGCAAGAAATCAAAGACC
TGTACAAGACCGTGTGGGAAATACCGCAGAAGGACATTTTGAAAATGGCCGCCGATCGCGCCGCTTTCATTG
ACCAAAGCCAATCCCTTAACATTCACATAGCGCAGCCGAACTATGCTAAACTGAGCTCCATGCACTTTTACGC
CTGGTCATTGGGACTTAAAACCGGGATGTATTACCTGCGCACTCGTCCGGCTGTCGATGCTGTTCAGTTCACT
GTGGACAAAATGGCCCTTCGGGGAACAATTGCCAAGGACGAATCTGTCGA

Underlined sequences were chosen for RNAi construct.

FIG. 17

***Fib-1* of *Heterodera Glycines* (CB279515) (partial)(SEQ ID NO:6)**

GCTGTGCACGCTGAACATGGTGCCGGGCGAGTCGGTGTACGGCGAGAAGCGCATCTCCTCCCAGCAGACCGA
AAATGCGCCGATTGCTGCAATAACG<u>CCGAAGACGGAAGAGACAACGAATGGCAGCAACGGTGTCTCAGCAC</u>
<u>CCACCGCCGCGGCTGCCGGCCCGGCACCGCCAGTCGAGTACCGGGTGTGGAACCCGTTCCGCTCCAAACTGG</u>
<u>CCGCCGCCGTCATGGCCGGCATTGAGGACACGCACATTTACCCGGGT</u>GCCCGTGTGCTTTATCTTGGCGCCGC
TTCCGGCACTTCCGTTTCCCATGTGTCCGACATCGTTGGACCCGAAGGCATGGTCTATGCAGTTGAGTTTTCAC
ATCGCAGTGGACGTGACCTGCTCGGCATGGCCAAGAAGCGGTCCAACGTGGTGCCAATTGTGGACGACGCAC
GGCACCCGCACAAATACTCCATGATGATTGGCATTGTGGACACAATTTTCTCGGACGTGGCACAGCCGGACC
AGGCACGGATTGTGGCACACAATGCGCACAAATTTCTGAAGA

Underlined sequences were chosen for RNAi construct.

FIG. 18

***Asb-1* of *Heterodera Glycines* (BI396626) (partial)(SEQ ID NO:7)**

AACCCCAGCATCTTCCAGAAAATCATTCTTCTCAACAAAGAGATTATTATCATGGAAGAGAATTTCTGTTGCT
TTGTGTTCGGATGGATTAACATTTACCTTTTCTTCCACACGGCTTTTCGTTATAAATTTGAAAAGTACGTATAC
AAAGTTACCCGTGAACGATTTGGCAAAATGAAGGCTTACATTGACAATGAATTGAAGGAAGCCATCGAGTTC
CGCAAGACTTCAAAGGAGCAGGCCGACTCGTTGAAAGCAGTGCATGAAAACTTTCCCACAATTTTCCAAGAG
AATTTGGCGCTGCAACTTGAAGCGACCTACCGAAAAAATGTGGACTACGCCTGGCAAGAGATGAAGCGTCGG
TTGGATTACCTGCAGGAAGTGCAAGCAATCAAAGACCGATTCAGCAAGGAAATGATGGTCAAACTGATCACT
GATGGCGTACGAAAACAAATTGAAATGAATGAGGGCGGAATTCGCGACAAATATTTGGACCAATGTATCGAA
CAACTTCGCGTTCTG

Underlined sequences were chosen for RNAi construct.

FIG. 19

***Rpt-1* of *Heterodera Glycines* (CB376265) (partial)(SEQ ID NO:8)**

CACGAAAATGTGGCGCCCACTGACATTGAGGAGGGAATGCGAGTGGGTGTGGACCGCAACAAATACCAGATT
CATTTGCCTTTGCCGGCAAAGATTGACGCGTCCGTTACGATGATGCAAGTGGAGGACAAGCCGGACGTTACCT
ACGCGGACATTGGCGGGTGCGAAGAACAGATCAAAAAGTTGCGTGAAGTGGTCGAGTTTCCGTTGCTTCAGC
CTGAGCGTTTCACGAGTTTGGGCATTGAGCCTCCGAAGGGCGTTTTGTTTTTTGGTCCGCCGGGCACCGGCAA
AACTTTGTGTGCCCGCGCGGTCGCCAATCGGACGGACGCGTGTTTCATCCGCGTCATCGGTTCCGAATTAGTC
AAAAAATACGTTGGCGAAGGCGCGCGCATGGTGCGCGAGCTGTTTTCGCTGGCTAAAACGAAAAAGGCGTGC
ATTCTCTTCTTCGACGAAGTCGACGCCATCGGCGGAGCGCGATTTGACGACGGAAAAGGGGGCGACAACGAA
GTGCAACGGACGATGCTCGAGTTGGTCAACCAACTGGACGGATTCGACTCACGCGGGGCCATCAAGGTTTTG
ATGGCCACCAACAGACCGGACACACTCGACCCGGCGCTCATTCGTCCCGGTCGCATT

Underlined sequences were chosen for RNAi construct.

FIG. 20

***F-55* of *Heterodera Glycines* (CA940536) (partial)(SEQ ID NO:9)**

GGGAAACCCGAATCTAAGGATTTGTACGTGCGACCGAACATCATCGCAAAACGCATCAGTGGCACGCTTGAG
GCACATGTCAACGGTTTCCGTTCACGTCGTTGCGCGGCGACAAAATTGAGGTGATGTACAACAACATCAAGC
ACGCCTTCTTCCAGCCGTGTGACAACGAAATGATCATTCTGTTGCACTTCCATTTGAAGAATCCAGTGCTGTG
GGGCAAAAAGAAATATTCGGATGTGCAATTCTTCACTGAAGTTGGCGAGATCACCACCGACTTGGGCAAGTA
CCATCACATGCAAGACAGGGACGACATTCAGAGCGAGCAGATGGAACGCGAAATGCGCAAGAAGCTGAACA
TGGCCTTCCAGAACTTCTGTGACAAAGTGTTTCGGATGACCAATGAGCAGGTGGACTTTGACACGCCGTTCAA
TGACTTGTCGTTCATCGGTGCCCCCCATCGGTCCACCGTTTCTCTGAAACCGACCTCGTCATGTTTGGTGCACC
TCACAGAATGGCCTCCATTTGTTGTCACACTTGACGAAGTGGAGTTGGTGCATTTTGAGCGTGTGTCCAGCAA
CACCAGCACATTCGACACGGTCATCGTCTTCAAAGATTACACCAAGAAGCCGCACATCATTGGCCAAATTCCA
TCTAACAACCTGGACAGTATCAAGGACTGGCTAAATTCTTGCGACATTCGCTACAGTGAAGGCCCAATGTCGC
TGAACTGGGCCAACATCATGA

Underlined sequences were chosen for RNAi construct.

FIG. 21

***Eat-3* of *Heterodera Glycines* (CB375718) (partial)(SEQ ID NO:10)**

GTTGATTTGGCGGAGAAAAACT<u>TGAGCAACCCGCATCGGATAAAGAAGATCCTCGACGGGAAACTATTTCCG</u>
<u>ATGAAAGCGCTCGGCTATTTCGGCGTTGTCACCGGCATGGACAAGCGGGACGCGAGCATTGCGGAGATCCGC</u>
<u>AAATACGAGGAGGACTTCTTCGAGAGTTCCAAACTCTTTAGGGATGGCGTTTTGAAGGCCACCCAAATGACG</u>
<u>ACGCGGAATATGTCATTGGCGGTTTCGGACTGTTTTTGGCGGATGGTTCGCGAATCCATCGAAGCGCAGGCGG</u>
<u>AAGCTTTCCGCGCCCATCGCTTCCATTTGGAGAACGGAA</u>GGAAAACAACTTTTGCGCACCACCCCGACTTGAC
CAGG

Underlined sequences were chosen for RNAi construct.

FIG. 22

*Vap-2* of *Heterodera Glycines* (AY033601) (partial)(SEQ ID NO:11)

ATGCACTTGATTAACTTAATCGCCCTCTTTTTCATGCTTTTCGGTAAGTCAATTGTTTAAATTCATTAGCGGGA
TAATTGGGTAATTATTTTGCTAATCGTTTCAAGGCCCATCCGTCCAGCAATACACAAAAACGCCAACGAATGA
GGACAAAGAAGCGGCTGTCAATTGTCACAACAAATTCCGATCGCAATTGGCCCTGGGCAATGCCGACAATAA
ATTGGGCGGCAACAAAATGCCAAAGGCGGGCAACATGCGTAAGTTTGAATGGGACGAAAACTTGGCCAAAC
TTGCGGATGAATGGGCCAACAAATGCACATTATCGCACTCGTGGAACGGCTGGGCAGGCGAAAATTTGGCAA
TGAATGGCGGAACATTTTCGAACAGTTCGATACAAATTGATAATTGTGGCTACTAATTGCCTGCT<u>TAAGAGGA
TGGCTTCGAGTACGCTTGCGGTCGCTGGTGGGACGAACTGAACCGTTACGGGTTCAACCCGGATCTGATTATG
ACCGGGGAAAACTTCAGTGGCATCGGCCATTGGACTCAGGTGACCTATTCATTATTTCGCCGTTTCTAGTCCC
ATTATTGCTAATTAGACACTAATTAGTTTTCTCTTCGTTTTGTTCAGATGGCGTGGGCCGACACCGACCGAATT
GGCTGTGCCATGGCACAAAACTGCCCAAATACCAATTGGAAAACATATGTGGTCTGCTGGTATTACACGGGG
TAATAATCAACCACTGATAAAACATAATTAGTTTACTAATACCCCTTTTAGTGGTAATTACTTTGGTGCGCCTG
TCTATTTGG</u>CCCGGGAGCCGTGCAGCAAATGCAAAGCAAATGACAAATGTGACAAAGCCACTGGACTTTGCT
CTCAATGA

Underlined sequences were chosen for RNAi construct.

FIG. 23

***Y25* of *Pratylenchus neglectus* (partial)(SEQ ID NO:12)**

GCAGCCCGACAAGACAATTATGTTCACGCGGCTGTCCACACGCGTGTCAGAAAACGTGACGGACACAAATTT
GTTTGATCTTTCGCTTTCCCAAGCGCTTGGTACTGCACCCAAAACGACCAAATACACCTTTGCCAGCTCCAAA
CTGGGAAAAGTGATTCAGTTAGCCGGCTCTTCGGATCCCGTCTATGCCGAGGCGTACGTCAACGTCAACCAAT
ATGACATTGTATTGGACGTACTCGTGGTCAACCAGACTGGCGACACCTTGCAAAATTTGTCATTGGAACTCTC
A

This partial sequence was used for RNAi construct.

FIG. 24

***Rnr-1* of *Pratylenchus neglectus* (partial)(SEQ ID NO:13)**

CAAGAAATCAAAGACCTGTACAAGACCGTGTGGGAAATACCGCAGAAGGACATTTTGAAAATGGCCGCCGAT
CGCGCCGCCTTCATTGACCAAAGCCAATCCCTTAACATTCACATAGCGCAGCCGAACTATGCTAAACTGAGCT
CCATGCACTTTTACGCCTGGTCATTGGGACTTAAAACCGGGATGTATTACCTGCGCACTCGTCCGGCTGTCGA
TGCTGTTCAGTTCACTGTGGACAAAATGGCCCT

This partial sequence was used for RNAi construct.

FIG. 25

***Y25* of *Radopholus similis* (partial)(SEQ ID NO:14)**

GCAGCCCGACAAGACAATTATGTTCACGCAGCTGTCCACACGCGTGTCAGAAAACGTGACGGACACAAATTT
GTTTGATCTTTCGCTTTCCCAAGCGCTTGGTACTGCACCCAAAACGACCAAATACACCTTTGCCAGCTCCAAA
CTGGGAAAAGTGATTCAGTTAGCCGGCTCTTCGGATCCCGTCTATGCCGAGGCGTACGTCAACGTCAACCAAT
ATGACATTGTATTGGACGTACTCGTGGTCAACCAGACTGGCGACACCTTGCAAATTGTCATTGGACTCTCA

This partial sequence was used for RNAi construct.

FIG. 26

***Rnr-1* of *Radopholus similis* (partial)(SEQ ID NO:15)**

AAGTACGTGTGCTGTGTGTGTATTCAGCCAGGACATTTTGAAAATGGCCGCCGATCGCGCCCTTTTCATTGAC
CAAAGCCAATCCCTTAACATTCACATAGCGCAGCCGAACTATGCTAAACTGAGCTCCATGCACTTTTACGCCT
GGTCATTGGGACTTAAAACCGGGATGTATTACCTGCGCACTCGTCCGGCTGTCGATGCTGTTCAGTTCACTGT
GGACAAAATGGCCCTA

This partial sequence was used for RNAi construct.

FIG. 27

***Rnr-1* of *Rotylenchulus reniformis* (partial)(SEQ ID NO:16)**

GCCGCCGATCGCGCCGCTTTCATTGACCAAAGCCAATCCCTTAACATTCACATAGCGCAGCCGAACTATGCTA
AACTGAGCTCCATGCACTTTTACGCCTGGTCATTGGGACTTAAAACCGGGATGTATTACCTGCGCACTCGTCC
GGCTGTCGATGCTGTTCAGTTCACTGTGGACAAAATGGCCCT

This partial sequence was used for RNAi construct.

Examples of Stacking constructs (pANDA35HK as backbone)

FIG. 29 cdk-1 (J12), H. glycines, (SEQ ID NO: 51)

> closed to cdk-5 in other nematodes, cdk-1 like in C. elegans
>gi|30220754|gb|CB935405.1|CB935405 rq39e06.y1 Heterodera glycines J3 Heterodera glycines cDNA 5' similar to TR:O18142 O18142 T27E9.3 PROTEIN. [1] ;, mRNA sequence

```
AGGAATTAAGTAATTTGCCATTGGTAATTGATAATCATGAAAATGAGCAACAACAACGACATGAGTGGTTAC
GAAAAATTGGGGAAAATTGGTGAAGGCACATATGGAACGTTCAAGGCAAGAAACAAGGACACCGAGCAAATT
GTTGCTCTTAAGATAGTACGACTGGATGATGAAGATGAAGGAGTTCCGTCTTCGGCACTGCGCGAAATTTGT
TTGTTGCGCGAACTACGACATGCAAATGTTGTGCGATTGCAGAATGTTGTGCATACAAACAAGACGCTGAAC
TTAGTCTTTGAATTTTGTGACCTTGATTTACGAAAATTTTTCGACACTTTGGATGGGCAAATCGACCAAAAA
GTTGTTCGTTCACTGATGCATCAGTTACTGTCCGGTTTATGCTATTGTCATGCGCACAATGTGCTTCATCGT
GATTTGAAGCCCCAGAATTTGTTGATCAATAATACAGTGAAAACTGCGCCACAATTAAAATTGGCTGATTTT
GGCCTTGCTAGACCGTTCGGAATCCCGGTCCGCTGTTATAGTGCAGAAGTTGTCACATTGTGGTATCGACCT
CCAGATGTTTTGTTGGGTGCCAAGCTATACAGCACGTCCATCGACATGTGGTCTGCAGGCTGCATTTTTGCT
GAAATTTCT
```

FIG. 30

Fzy-1 (J13) , H. glycines, (SEQ ID NO: 52)
>gi|29127137|gb|CB377841.1|CB377841 rq03e06.y1 Heterodera glycines J3 Heterodera glycines cDNA 5' similar to TR:Q9S7I8 Q9S7I8 WD-REPEAT PROTEIN-LIKE PROTEIN. [1] ;, mRNA sequence CATTGCCAAGAAGTTGGAAGCAAATGAGAACACCAACAATTTGAATACGTCCACTTCATGTCCGACGAGTCC
CGCTTCCAAATTGGAACAGCAGACGAAGAAACAAATGATGAGGGTCAAATCGGACAATGCAGTGAATTCGTT
GGCTGATTTTGACCAAGTTTGCGCATTTCGTAAGGGACTCGCTCCTCTAGCAAAATTCGGCCACAAACAGCA
GGTGAATGTGCTTTTTTCTTGTGTCCAGCCCACTTCCAGTTGTGTGAAACGGTCTCGTCGTTACGTTGCGAA
GGATCCCGAGAGAATGTTGGATGCGCCAGATTTATTAGACGATTTTTATTCGAATTTGATTGATTGGAGCAA
GACTAATTGTGTCGCCGTTGGCTTAGGATCAAAAATTTTTCAATGGAACGCGGGGACCGGTGCCGTGGATGA
GATAAAAGATTTCTCTGAAACGCATTCGCATCCAACTCTCGTCAAATGGTCTTGCGAAGGACAATATCTTGC
CGTTGGATTCAATGACGGACAATTAAAGTTGTTGGACAGCGCCACCAAAAAAGTGCTGAGAACAATTCACAC
GACGGCAAACATGCGATTGGCATGTGCCACATGGACACAC

FIG. 31

Tba-2 (J14) , H. glycines, (SEQ ID NO: 53)
>gi|27427737|gb|CA939257.1|CA939257 ru11e05.y1 Heterodera glycines J4 Heterodera glycines cDNA 5' similar to TR:P91910 P91910 ALPHA-TUBULIN MEC-12. [3] TR:O01907 TR:Q9TYG0 ;, mRNA sequence GACCTTACAAGTCGGCAAAGAAATCATCGACCCCGTCTTGGATCTGATTCGTCGCATCGCGGATAACTGCAC
CGGACTTCAAGGCTTTCTCATCTTCCATTCGTTCGGTGGTGGCACTGGCTCTGGGTTCACATCGCTGCTTAT
GGAACGTCTCTCTGTTGACTATGGGAAGAAGTCTAAGCTCGAGTTCTCCATCTACCCTGCTCCTCAAGTGTC
CACCGCTGTCGTTGAGCCGTACAATTCGGTGCTTACTACGCACACGACTCTCGAACACTCTGACTGTGCATT
TATGGTTGACAATGAGGCCATCTACGATATTTGTCGTCGAAATTTGGACGTGGAACGCCCTTCTTACACCAA
TTTGAACCGTTTGATTTCTCAAGTTGTCTCTTCGATAACCGCTTCACTTCGATTTGATGGTGCTTTGAATGT
CGATCTCACTGAATTCCAGACCAATCTTGTTCCTTATCCTCGAATTCACTTTCCTCTTGCGACTTATTCTCC
AGTTATCTCAGCTGAGAAGGCCTACCACGAATCATTGTCGGTTTCCGAAATCACCAACATGTGCTTTGAGCC
GTCCAACCAAATGGTCAAATGCGATCCACGTCACGGCAAATACATGGCCGTGTGCCTTCTCTACCGAGGTGA
CGTCGTCCCGAAGGATGTAAATGCGGCCATTGCTTCGATCAAAACGAACCGTTCAATTCAATTCGTGGACTG
GTGCCCGACCGGCTTCAAGGTTGGTATCAATTATCAACCTCCGACTGTTGTTCCCGGCGGTGACGTTGCCAA
AGTCCCACGT

FIG. 32

Arx-1 (J15) , H. glycines, (SEQ ID NO: 54)
>gi|28705655|gb|CB299515.1|CB299515 ru24a04.y1 Heterodera glycines J4 Heterodera glycines cDNA 5' similar to WP:CE25554 Y71F9AL.16 actin ;, mRNA sequence AGATTGATTGACTGATTGATGCATGCCAATTTGCCAGCTGCTGTAATTGATTGTGGCACCGGGTACACAAAG
CTTGGCTATGCAGGAAATTCGGAGCCACAGTTTATCATTCCGTCGGCTATCGCTGTCAAAGATGCGAATATT
TTGAAAAGTGTCGGCGGAAAAATCCCGGACTTGGACTTTTTCATCGGTGACGAGGCGTTGTCTCCTTCGGCT
GCGAATTATTTTGTTAAGTATCCAATTCGACATGGAATTGTCGACGATTGGGACCTAATGGAACGTTTTTGG
GAGCATTGCATTTTCAAATATTTGCGAGCCGAGCCCGAAGACCATTACTTTCTGTTGACAGAACCACCGCTG
AACACGCCGGAGAACCGCGAATTCACTGCCGAGATAATGTTCGAGTCGTTCAATGTGCCCGGCCTTTACATC
GCTGTCCAGGCTCTGCTCGCCTTGGCCGCTTCTTGGCAAACCCGCGAGTTCAACCACCGTTCTCTGACTGGC
CTTGTGGTGGACAGTGGAGACGGCGTCACCCATTGCATCCCGGTGTGTGATGGCTATGTCATCGGTTCTTGC
ATTAAGCACATTCCCATCGGCGGACGCGACATTACGTACTTTTTGCAG

FIG. 33

Tbb-2 (J17) , H. glycines, (SEQ ID NO: 55)

>gi|27428224|gb|CA939744.1|CA939744 ru07g03.y1 Heterodera glycines J4 Heterodera glycines cDNA 5' similar to TR:O61359 O61359 BETA-TUBULIN. ;, mRNA sequence TGNCCTTAGTGGCCTGGACAACTCAATGCCGACCTTCGCAAACTCCTTGATAGCATGGTCCCCTTCCCGCGT
CTGCACTTCTTCATGCCCGGCTTTGCGCCGCTTTCTGCGAAGGGAGCGGCTGCATATCAAGCGTGTTCCGTG
GCAGAACTGACCAAACAAATGTTCGACGCAAAGAACATGATGGCGGCGTGTGACCCGCGCCACGGCCGTTAT
TTGACAGTTGCGGCAATGTTCCGTGGTCGAATGTCGATGAGGGAAGTGGATGACCAAATGATGTCGGTGCAG
AACAAGAACTCCTCGTACTTCGTCGAATGGATTCCGAACAACGTGAAGACCGCTGTCTGTGACATTCCGCCC
CGTGGCCTCAAAATGTCGGCAACTTTCGTCGGAAACTCCACAGCCATTCAAGAACTTTTCAAACGCATTTCG
GAACAGTTCACTGCTATGTTCCGTCGCAAGGCTTTCCTCCATTGGTACACCGGTGAGGGCATGGACGAGATG
GAATTCACGGAAGCCGAGTCCAACATGAACGATTTGATCTCCGAGTATCAGCAGTACCAAGATGCCACCGTT
GACGATGAGGGCGAATACGAGGCTGAGGACACC

FIG. 34

Unc-26 (J20) , H. glycines, (SEQ ID NO: 56)
>gi|32320486|gb|CD748096.1|CD748096 rw32e10.y1 Heterodera glycines J4 Heterodera glycines cDNA 5' similar to SW:I5P2_HUMAN P32019 TYPE II INOSITOL-1,4,5-TRISPHOSPHATE 5-PHOSPHATASE PRECURSOR ;, mRNA sequence GCTCAAAGAACAGCAGCGGTTGCGCGTGGCGTTCAACGGCTTCATGGAGCAGCAGCCGAGCTTCGTCCCCAC
CTACAAATTCGACCCGGGCACACACAATTGGGACACGAGTGAAAAGAAGCGTGTGCCGGCGTGGTGCGACCG
CATTTTGTATTGGGTCAAGGACAAAAATGTCGGCATTGAACAAGTGACCTACGAATCGGCACACCAAGTTGT
GCTCAGTGACCACAAACCGGTGCTGAGCACATTCAGAGTCCAAGTGAAGAAGGTGGACAGGCCGAGAAGGAG
CGCAATTTATGAGCAGTTGTTGAGGGAAGTGGACAAACGTCAAAATGAACTTTTGCCCCAAATTACATTGTC
AAACACAGAATTCCATTTCGGCACCGTCCTCTTCGACCAGCCATCGTTGGCCGTGCTGACCATCACAAACAC
TGGACAAACGCCCACCCATTTCAGCTTCAAACCCGCGAGGCCCGAGGCTGACAGATTGGAGGAATGGCTGAC
CATAACGCCGCTCTCCTCTTTCATCGACGTTGGTGGTGCCGTGGAGGTCACTCTGCAAATCCTCGTCTTCGA
TGAGTCGGCCTGCAAAGTGCCAAAGGATGGCGCCGAATTGAGTTCCATTATCATTGTGCATCTTACGGGT

FIG. 35

Prp-4 (J21) , H. glycines, (SEQ ID NO: 57)
>gi|30220651|gb|CB935298.1|CB935298 rq38a11.y1 Heterodera glycines J3 Heterodera glycines cDNA 5' similar to TR:Q9Z2K5 Q9Z2K5 G BETA-LIKE PROTEIN GBL. ;, mRNA sequence CCTCGTGCCGAATTCGGCACGAGGGACATTTTTACCATGGGAATGACACGGCCAATGTTGGTTTCTGCCGCA
ATGGATGCCACCATTCGGATTTGGGACGTGGCATCGCAGAAACAGTTGGAGGCACTCCCCTACAAAGAATCC
CAGGTGAACAACATTTGCATTACGCCCGACGGTGCCCAACTGCTCGTCGGCGCATGGCAAAACATTCGTTTT
TACGATTTGCAATGTCCAACCGCGCAAGGACTACACACATTTTCTGTCCATGAGAAAAATGTGACTTCGGTC
GGCTTCCAAGTGGACGGTGCGTGGATGTACACGGGAGGGGAGGATTGCATGGCCAAAATTTGGGATATGCGC
AACAATCAGCTGAATTGCCAGAGGATATTCCAAGTGAACACGCCGGTGCACTCCGTTGTGCTGCATCCCAAC
CAAGTGGAGCTGATCGTTGCCGACTCCACCGGCGCCATTTATTTGTGGGATTTGCGCTCCGATCGGGACGAT
TCGCTGATCACCGAAGTGGACATGTCCGAATTTGTTGTTCACGTTGACATTGACCAAGTGGGGCGACAGTGT
GCGGCGGTGACAAACCGGGGCAATTTGTTTCTGTGGGACGTC

FIG. 36

Pfn-1 (J23) , H. glycines, (SEQ ID NO: 58)
>gi|29050167|gb|CB374607.1|CB374607 ru61h04.y1 Heterodera glycines J4 Heterodera glycines cDNA 5' similar to TR:Q9XW16 Q9XW16 Y18D10A.20 PROTEIN. [1] ;, mRNA sequence CTATTTTCTTTTTTTTCACCCTTTGACGACAAACAGAAGCAGCAATGAGTGGTTGGGATGCGTACATTCAGT
CATTGACTTCCAGTTGTGCGGAGATTACTCGCGTGGCCATAATTGGCAATTCGGACGCGAGTGTTTGGGCCA
GGACTGAAGGGGAGAACGAATTCAAGGCGAGTGAACCTGAGCTCAAGAAACTTGTCGGCCAATTCGATGATC
TTTCGCAAGTTCCGTCCGTCGGTGCCGACCTCGAGGGAATTCATTACATTGTGCCGCGAACGGATGAAAATC
TTATCTTTGGGAAGAGGGACAAAACGGGCTTTTTCGCTGTGAAGACCAAGTCCGCCATTCTGATCGCCATTT
ACAAGGACGAGGAAAGTGTCGTCGGCGCCGACGTGCGAGGGGCGGTGGAGAAAATGGCCAAATACCTTGAGG
ACGCCGGTTACTGAGCCGTTGCTCGGTTTCCTAAACGACTTTTGTGTTGCCAAACGAAAAGTGCTGAGAATG
GCTTTGACTTATTCTTCCAAATGCATTCCTTTTCCATCCCAAATGATCACTTATTATTTTATTATTACACAT
TCTGTGAAGTGCGCGTGCCGATTTCTTTTTTATTATTTGGCCTTTGGATGTGAATAATAAAAAGGTGTAACG
CTGAAA

FIG. 37

Vbh-1 (J7) , H. glycines, (SEQ ID NO: 59)
>gi|28567629|gb|CB279252.1|CB279252 rq42a12.y1 Heterodera glycines J3 Heterodera glycines cDNA 5' similar to WP:CE24451 Y54E10A.9 helicase ;, mRNA sequence ATGTGTTTTTGGCTGTTGGAAGAGTTGGGTCCACCTCTGAGAACATCGGTCAAAAAGTTGTTTGGGTTGAAG
AGCACAACAAACGCCATTTCCTGATGGATTTGCTCGATGCCAGTGAGCCCGAGGCACTAACACTGATTTTCG
TTGAAACCAAACGCGGCTGTGGAGATCTGAGTTACATGCTCCAGCAAGAAGGCTACCATTGCGTAGCAATCC
ATGGCGATTTGAAGCAAATGGAACGCGAGCGTCATTTGGAGAACTTCCGCAACGGAACGGCACCCATTTTGG
TGGCAACAGCAGTTGCCGCCCGTGGGTTGGACATTCCGAATGTCAAGCACGTGATCAATTATGACCTACCGA
ATGACATCGATGAATACGTGCACCGAATTGGCAGAACCGGCCGTGTGGGCAACATTGGAATGGCCACTAGCT
TTTTCAACGACAAAAACCGGAACATTTCTCATACTCACTAGTCTGATTGTGGAAGCAAACCAGGAATTGCCC
GATTGGCTCGAAGAAATGGCACGCGATTCAGGCCGACA

FIG. 38

RNAi construct sequence (containing underlined antisense fragment of *Y25*, shaded Gus linker and sense fragment of *Y25*)(SEQ ID NO:59):

GAGAGTTCCAATGACAAATTTTGCAAGGTGTCGCTAGTCTGGTTGACCACGAGTACGTCCAATACAATG
TCATATTGGTTGACGTTGACGTACGCCTCGGCATAGACGGGATCCGAAAAGCCGGCTAACTGAATCACT
TTTCCCAGTTTGGAGCTGGCAAAGGTGTATTTGGTCGTTTTGGGTGCAGTACCAAGCGCTTGGGAAAGCG
AAAGATCAAACAAATTTGTGTCCGTCACGTTTTCTGACACGCGTGTGGACAGCTGCGTGAACATAATTGT
CTTGTCGGGCTGCAATCGAATTCGGTACCGGATCCAGTCGACTGAATTGGTTCCCATGGTGGAGCCTGCT
TTTTTGTACAAACTTGTGATGACGGTATCGATAAGCTTGATATCTACCCGCTTCGCGTCGGCATCCGGTC
AGTGGCAGTGAAGGGCGAACAGTTCCTGATTAACCACAAACCGTTCTACTTTACTGGCTTTGGTCGTCAT
GAAGATGCGGACTTACGTGGCAAAGGATTCGATAACGTGCTGATGGTGCACGACCACGCATTAATGGAC
TGGATTGGGGCCAACTCCTACCGTACCTCGCATTACCCTTACGCTGAAGAGATGCTCGACTGGGCAGAT
GAACATGGCATCGTGGTGATTGATGAAACTGCTGCTGTCGGCTTTAACCTCTCTTTAGGCATTGGTTTCG
AAGCGGGCAACAAGCCGAAAGAACTGTACAGCGAAGAGGCAGTCAACGGGGAAACTCAGCAAGCGCA
CTTACAGGCGATTAAAGAGCTGATAGCGCGTGACAAAAACCACCCAAGCGTGGTGATGTGGAGTATTGC
CAACGAACCGGATACCCGTCCGCAAGTGCACGGGAATATTTCGCCACTGGCGGAAGCAACGCGTAAACT
CGACCCGACGCGTCCGATCACCTGCGTCAATGTAATGTTCTGCGACGCTCACACCGATACCATCAGCGA
TCTCTTTGATGTGCTGTGCCTGAACCGTTATTACGGATGGTATGTCCAAAGCGGCGATTTGGAAACGGCA
GAGAAGGTACTGGAAAAAGAACTTCTGGCCTGGCAGGAGAAACTGCATCAGCCGATTATCATCACCGA
ATACGGCGTGGATACGTTAGCCGGGCTGCACTCAATGTACACCGACATGTGGAGTGAAGAGTATCAGTG
TGCATGGCTGGATATGTATCACCGCGTCTTTGATCGCGTCAGCGCCGTCGTCGGTGAACAGGTATGGAAT
TTCGCCGATTTTGCGACCTCGCAAGGCATATTGCGCGTTGGCGGTAACAAGAAAGGGATCTTCACTCGA
TCGAATTCCTGCAGCCCGGGGGATCCACTAGATGCATGCTCGAGCGGCCGCCAGTGTGATGGATATCTG
CAGAATTCGCCCTTATCACAAGTTTGTACAAAAAAGCAGGCTCCACCATGGGAACCAATTCAGTCGACT
GGATCCGGTACCGAATTCGATTGCAGCCCGACAAGACAATTATGTTCACGCAGCTGTCCACACGCGTGT
CAGAAAACGTGACGGACACAAATTTGTTTGATCTTTCGCTTTCCCAAGCGCTTGGTACTGCACCCAAAAC
GACCAAATACACCTTTGCCAGCTCCAAACTGGGAAAAGTGATTCAGTTAGCCGGCTTTTCGGATCCCGTC
TATGCCGAGGCGTACGTCAACGTCAACCAATATGACATTGTATTGGACGTACTCGTGGTCAACCAGACT
AGCGACACCTTGCAAAATTTGTCATTGGAACTCTC

FIG. 39

RNAi construct sequence (containing underlined antisense fragment of *Arx-3*, shaded Gus linker and sense fragment of *Arx-3*) (SEQ ID NO:60):

GCAATTCTCCCAATGGCATTTTGGTCCCCCAAGGGTTTGGCGTTGGTTTTTCGTCAATCTCTTTCACATAA
GCAGAAAAAACACGCGTTTTGAAGTCACAGGCGCCAACAGCCAACAAAATGTTGTTGGGATGCCAATTC
AATGAGGTGACCGTGGAACGAATCAGCTTTTTGATTTGCTTCGCTACCCACCAGTCATTTTCACGTTCGT
AATAACAAATAGCGACTAAACGCGCACCCGTCCCAACGGCGAATTTGTTTTCGTTGGGCGACCATTTGA
CACAGGTGGCAGCTCTGTTTATCCGAACGACCACCATCTCCGGTTTCCAACTGTTCTTTTCAGCCTCCCAT
GTCCACACAAACGCATTTTTGTCGTGCGAACATGAAACAATCGAATTCGGTACCGGATCCAGTCGACTG
AATTGGTTCCCATGGTGGAGCCTGCTTTTTTGTACAAACTTGTGATGACGGTATCGATAAGCTTGATATC
TACCCGCTTCGCGTCGGCATCCGGTCAGTGGCAGTGAAGGGCGAACAGTTCCTGATTAACCACAAACCG
TTCTACTTTACTGGCTTTGGTCGTCATGAAGATGCGGACTTACGTGGCAAAGGATTCGATAACGTGCTGA
TGGTGCACGACCACGCATTAATGGACTGGATTGGGGCCAACTCCTACCGTACCTCGCATTACCCTTACGC
TGAAGAGATGCTCGACTGGGCAGATGAACATGGCATCGTGGTGATTGATGAAACTGCTGCTGTCGGCTT
TAACCTCTCTTTAGGCATTGGTTTCGAAGCGGGCAACAAGCCGAAAGAACTGTACAGCGAAGAGGCAGT
CAACGGGGAAACTCAGCAAGCGCACTTACAGGCGATTAAAGAGCTGATAGCGCGTGACAAAAACCACC
CAAGCGTGGTGATGTGGAGTATTGCCAACGAACCGGATACCCGTCCGCAAGTGCACGGGAATATTTCGC
CACTGGCGGAAGCAACGCGTAAACTCGACCCGACGCGTCCGATCACCTGCGTCAATGTAATGTTCTGCG
ACGCTCACACCGATACCATCAGCGATCTCTTTGATGTGCTGTGCCTGAACCGTTATTACGGATGGTATGT
CCAAAGCGGCGATTTGGAAACGGCAGAGAAGGTACTGGAAAAAGAACTTCTGGCCTGGCAGGAGAAAC
TGCATCAGCCGATTATCATCACCGAATACGGCGTGGATACGTTAGCCGGGCTGCACTCAATGTACACCG
ACATGTGGAGTGAAGAGTATCAGTGTGCATGGCTGGATATGTATCACCGCGTCTTTGATCGCGTCAGCG
CCGTCGTCGGTGAACAGGTATGGAATTTCGCCGATTTTGCGACCTCGCAAGGCATATTGCGCGTTGGCG
GTAACAAGAAAGGGATCTTCACTCGATCGAATTCCTGCAGCCCGGGGGATCCACTAGATGCATGCTCGA
GCGGCCGCCAGTGTGATGGATATCTGCAGAATTCGCCCTTATCACAAGTTTGTACAAAAAAGCAGGCTC
CACCATGGGAACCAATTCAGTCGACTGGATCCGGTACCGAATTCGATTGTTTCATGTTCGCACGACAAA
AATGCGTTTGTGTGGACATGGGAGGCTGAAAAGAACAGTTGGAAACCGGAGATGGTGGTCGTTCGGAT
AAACAGAGCTGCCACCTGTGTCAAATGGTCGCCCAACGAAAACAAATTCGCCGTTGGGACGGGTGCGCG
TTTAGTCGCTATTTGTTATTACGAACGTGAAAATGACTGGTGGGTAGCGAAGCAAATCAAAAAGCTGAT
TCGTTCCACGGTCACCTCATTGAATTGGCATCCCAACAACATTTTGTTGGCTGTTGGCGCCTGTGACTTC
AAAACGCGTGTTTTTTCTGCTTATGTGAAAGAGATTGACGAAAAACCAACGCCAAACCCTTGGGGGACC
AAAATGCCATTGGGAGAATTGC

FIG. 40

RNAi construct sequence (containing underlined antisense fragment of *Cpn-1*, shaded Gus linker and sense fragment of *Cpn-1*) (SEQ ID NO:61):

TCGCTTTTTGTATCCTCCGCCACGATGAACAGCGGCTTGCCGGCCTTGGCCGACTGCTCCAGCACCGGCAGCAGCTC
GCGGATATTGCTGATCTTTTTGTCGTACAGCAGCACCAGCGGGTCATCCAGGCGCGCCAGTTGCTTGTCCGGATCAT
TGATGAAGTATGGGCTCAGGTAGCCGCGGTCGAACTGCATGCCTTCCACCACATCCAGTTCGTTTTCCAGCGACTTG
CCATCCTCGACGGTTATCACGCCCTCCTTGCCCACCTTCTCCATGGCCTGGGCGATGATGTCGCCGATGGCGCTGTC
GGAGTTGGCCGAAATGGAGCCCACTTGCGCAATCTCCTTGCTGGTGGCAATGGGGCGCGAGATGGCCTTCAATTCC
GTAATGGCTGCTGCCACAGCCTGATCGATGCCTTGGTGAATCGAATTCGGTACCGGATCCAGTCGACTGAATTGGTT
CCCATGGTGGAGCCTGCTTTTTTGTACAAACTTGTGATGACGGTATCGATAAGCTTGATATCTACCCGCTTCGCGTC
GGCATCCGGTCAGTGGCAGTGAAGGGCGAACAGTTCCTGATTAACCACAAACCGTTCTACTTTACTGGCTTTGGTCG
TCATGAAGATGCGGACTTACGTGGCAAAGGATTCGATAACGTGCTGATGGTGCACGACCACGCATTAATGGACTGG
ATTGGGGCCAACTCCTACCGTACCTCGCATTACCCTTACGCTGAAGAGATGCTCGACTGGGCAGATGAACATGGCA
TCGTGGTGATTGATGAAACTGCTGCTGTCGGCTTTAACCTCTCTTTAGGCATTGGTTTCGAAGCGGGCAACAAGCCG
AAAGAACTGTACAGCGAAGAGGCAGTCAACGGGGAAACTCAGCAAGCGCACTTACAGGCGATTAAAGAGCTGATA
GCGCGTGACAAAAACCACCCAAGCGTGGTGATGTGGAGTATTGCCAACGAACCGGATACCCGTCCGCAAGTGCAC
GGGAATATTTCGCCACTGGCGGAAGCAACGCGTAAACTCGACCCGACGCGTCCGATCACCTGCGTCAATGTAATGT
TCTGCGACGCTCACACCGATACCATCAGCGATCTCTTTGATGTGCTGTGCCTGAACCGTTATTACGGATGGTATGTC
CAAAGCGGCGATTTGGAAACGGCAGAGAAGGTACTGGAAAAAGAACTTCTGGCCTGGCAGGAGAAACTGCATCAG
CCGATTATCATCACCGAATACGGCGTGGATACGTTAGCCGGGCTGCACTCAATGTACACCGACATGTGGAGTGAAG
AGTATCAGTGTGCATGGCTGGATATGTATCACCGCGTCTTTGATCGCGTCAGCGCCGTCGTCGGTGAACAGGTATGG
AATTTCGCCGATTTTGCGACCTCGCAAGGCATATTGCGCGTTGGCGGTAACAAGAAAGGGATCTTCACTCGATCGA
ATTCCTGCAGCCCGGGGGATCCACTAGATGCATGCTCGAGCGGCCGCCAGTGTGATGGATATCTGCAGAATTCGCC
CTTATCACAAGTTTGTACAAAAAAGCAGGCTCCACCATGGGAACCAATTCAGTCGACTGGATCCGGTACCGAATTC
GATTCACCAAGGCATCGATCAGGCTGTGGCAGCAGCCATTACGGAATTGAAGGCCATCTCGCGCCCCATTGCCACC
AGCAAGGAGATTGCGCAAGTGGGCTCCATTTCGGCCAACTCCGACAGCGCCATCGGCGACATCATCGCCCAGGCCA
TGGAGAAGGTGGGCAAGGAGGGCGTGATAACCGTCGAGGATGGCAAGTCGCTGGAAAACGAACTGGATGTGGTGG
AAGGCATGCAGTTCGACCGCGGCTACCTGAGCCCATACTTCATCAATGATCCGGACAAGCAACTGGCGCGCCTGGA
TGACCCGCTGGTGCTGCTGTACGACAAAAAGATCAGCAATATCCGCGAGCTGCTGCCGGTGCTGGAGCAGTCGGCC
AAGGCCGGCAAGCCGCTGTTCATCGTGGCGGAGGATACAAAAAGCGA

FIG. 41

RNAi construct sequence (containing underlined antisense fragment of *Prp-17*, shaded Gus linker and sense fragment of *Prp-17*) (SEQ ID NO:62):

CATTTTGATTACATTGTCCCATCCGCAAGAAATCATCCGCGATTTCTCGTGCGGATGCCACAGTGTTGAA
ATGCACACATTATCATGTGCCTTCCACGTGGAGACAATTTTGTGTGTGCGCCAGTCCCACATTGTGATTT
TACCGTCCGCATCACCGGAAGCGAGAAAACTAAGAAAAAAAAGAAAGGAATGCCTTTTGAATTATGTG
CTAGATAACCTCATCTCTGGCGAAAAATCAGTTGAGCAGGCGTACCCTGCTGTATTGTGACCACGGAAG
GCCTAATTTGTAAGGCACGATTAAAAAAATTCTTTTTCGTAAAACCACCTTTCTACGAGCGAATCGCAAC
TTGTCATCGACGATTTGGAAAAGGACAATTCGATTGAATCGAATTCGGTACCGGATCCAGTCGACTGAA
TTGGTTCCCATGGTGGAGCCTGCTTTTTTGTACAAACTTGTGATGACGGTATCGATAAGCTTGATATCTA
CCCGCTTCGCGTCGGCATCCGGTCAGTGGCAGTGAAGGGCGAACAGTTCCTGATTAACCACAAACCGTT
CTACTTTACTGGCTTTGGTCGTCATGAAGATGCGGACTTACGTGGCAAAGGATTCGATAACGTGCTGATG
GTGCACGACCACGCATTAATGGACTGGATTGGGGCCAACTCCTACCGTACCTCGCATTACCCTTACGCTG
AAGAGATGCTCGACTGGGCAGATGAACATGGCATCGTGGTGATTGATGAAACTGCTGCTGTCGGCTTTA
ACCTCTCTTTAGGCATTGGTTTCGAAGCGGGCAACAAGCCGAAAGAACTGTACAGCGAAGAGGCAGTCA
ACGGGGAAACTCAGCAAGCGCACTTACAGGCGATTAAAGAGCTGATAGCGCGTGACAAAAACCACCCA
AGCGTGGTGATGTGGAGTATTGCCAACGAACCGGATACCCGTCCGCAAGTGCACGGGAATATTTCGCCA
CTGGCGGAAGCAACGCGTAAACTCGACCCGACGCGTCCGATCACCTGCGTCAATGTAATGTTCTGCGAC
GCTCACACCGATACCATCAGCGATCTCTTTGATGTGCTGTGCCTGAACCGTTATTACGGATGGTATGTCC
AAAGCGGCGATTTGGAAACGGCAGAGAAGGTACTGGAAAAAGAACTTCTGGCCTGGCAGGAGAAACTG
CATCAGCCGATTATCATCACCGAATACGGCGTGGATACGTTAGCCGGGCTGCACTCAATGTACACCGAC
ATGTGGAGTGAAGAGTATCAGTGTGCATGGCTGGATATGTATCACCGCGTCTTTGATCGCGTCAGCGCC
GTCGTCGGTGAACAGGTATGGAATTTCGCCGATTTTGCGACCTCGCAAGGCATATTGCGCGTTGGCGGT
AACAAGAAAGGGATCTTCACTCGATCGAATTCCTGCAGCCCGGGGGATCCACTAGATGCATGCTCGAGC
GGCCGCCAGTGTGATGGATATCTGCAGAATTCGCCCTTATCACAAGTTTGTACAAAAAAGCAGGCTCCA
CCATGGGAACCAATTCAGTCGACTGGATCCGGTACCGAATTCGATTCAATCGAATTGTCCTTTTCCAAAT
CGTCGATGACAAGTTGCGATTCGCTCGTAGAAAGGTGGTTTTACGAAAAAGAATTTTTTTAATCGTGCCT
TACAAATTAGGCCTTCCGTGGTCACAATACAGCAGGGTACGCCTGCTCAACTGATTTTTCGCCAGAGATG
AGGTTATCTAGCACATAATTCAAAAGGCATTCCTTTCTTTTTTTTCTTAGTTTTCTCGCTTCCGGTGATGC
GGACGGTAAAATCACAATGTGGGACTGGCGCACACACAAAATTGTCTCCACGTGGAAGGCACATGATA
ATGTGTGCATTTCAACACTGTGGCATCCGCACGAGAAATCGCGGATGATTTCTTGCGGATGGGACAATG
TAATCAAAATG

FIG. 42

RNAi construct sequence (containing underlined antisense fragment of *Rnr-1*, shaded Gus linker and sense fragment of *Rnr-1*) (SEQ ID NO:63):

AGGGCCATTTTGTCCACAGTGAACTGAACAGCATCGACAGCCGGACGAGTGCGCAGGTAATACATCCCG
GTTTTAAGTCCCAATGACCAGGCGTAAAAGTGCATGGAGCTCAGTTTAGCATAGTTCGGCTGCGCTATGT
GAATGTTAAGGGATTGGCTTTGGTCAATGAAAGCGGCGCGATCGGCGGCCATTTTCAAAATGTCCTTCT
GCGGTATTTCCCACACGGTCTTGTACAGGTCTTTGATTTCTTGAATCGAATTCGGTACCGGATCCAGTCG
ACTGAATTGGTTCCCATGGTGGAGCCTGCTTTTTTGTACAAACTTGTGATGACGGTATCGATAAGCTTGA
TATCTACCCGCTTCGCGTCGGCATCCGGTCAGTGGCAGTGAAGGGCGAACAGTTCCTGATTAACCACAA
ACCGTTCTACTTTACTGGCTTTGGTCGTCATGAAGATGCGGACTTACGTGGCAAAGGATTCGATAACGTG
CTGATGGTGCACGACCACGCATTAATGGACTGGATTGGGGCCAACTCCTACCGTACCTCGCATTACCCTT
ACGCTGAAGAGATGCTCGACTGGGCAGATGAACATGGCATCGTGGTGATTGATGAAACTGCTGCTGTCG
GCTTTAACCTCTCTTTAGGCATTGGTTTCGAAGCGGGCAACAAGCCGAAAGAACTGTACAGCGAAGAGG
CAGTCAACGGGGAAACTCAGCAAGCGCACTTACAGGCGATTAAAGAGCTGATAGCGCGTGACAAAAAC
CACCCAAGCGTGGTGATGTGGAGTATTGCCAACGAACCGGATACCCGTCCGCAAGTGCACGGGAATATT
TCGCCACTGGCGGAAGCAACGCGTAAACTCGACCCGACGCGTCCGATCACCTGCGTCAATGTAATGTTC
TGCGACGCTCACACCGATACCATCAGCGATCTCTTTGATGTGCTGTGCCTGAACCGTTATTACGGATGGT
ATGTCCAAAGCGGCGATTTGGAAACGGCAGAGAAGGTACTGGAAAAAGAACTTCTGGCCTGGCAGGAG
AAACTGCATCAGCCGATTATCATCACCGAATACGGCGTGGATACGTTAGCCGGGCTGCACTCAATGTAC
ACCGACATGTGGAGTGAAGAGTATCAGTGTGCATGGCTGGATATGTATCACCGCGTCTTTGATCGCGTC
AGCGCCGTCGTCGGTGAACAGGTATGGAATTTCGCCGATTTTGCGACCTCGCAAGGCATATTGCGCGTT
GGCGGTAACAAGAAAGGGATCTTCACTCGATCGAATTCCTGCAGCCCGGGGGATCCACTAGATGCATGC
TCGAGCGGCCGCCAGTGTGATGGATATCTGCAGAATTCGCCCTTATCACAAGTTTGTACAAAAAAGCAG
GCTCCACCATGGGAACCAATTCAGTCGACTGGATCCGGTACCGAATTCGATTCAAGAAATCAAAGACCT
GTACAAGACCGTGTGGGAAATACCGCAGAAGGACATTTTGAAAATGGCCGCCGATCGCGCCGCTTTCAT
TGACCAAAGCCAATCCCTTAACATTCACATAGCGCAGCCGAACTATGCTAAACTGAGCTCCATGCACTTT
TACGCCTGGTCATTGGGACTTAAAACCGGGATGTATTACCTGCGCACTCGTCCGGCTGTCGATGCTGTTC
AGTTCACTGTGGACAAAATGGCCCT

FIG. 43

RNAi construct sequence (containing underlined antisense fragment of *Fib-1*, shaded Gus linker and sense fragment of *Fib-1*) (SEQ ID NO:64):

ACCCGGGTAAATGTGCGTGTCCTCAATGCCGGCCATGACGGCGGCGGCCAGTTTGGAGCGGAACGGGTT
CCACACCCGGTACTCGACTGGCGGTGCCGGGCCGGCAGCCGCGGCGGTGGGTGCTGAGACACCGTTGCT
GCCATTCGTTGTCTCTTCCGTCTTCGGAATCGAATTCGGTACCGGATCCAGTCGACTGAATTGGTTCCCA
TGGTGGAGCCTGCTTTTTTGTACAAACTTGTGATGACGGTATCGATAAGCTTGATATCTACCCGCTTCGC
GTCGGCATCCGGTCAGTGGCAGTGAAGGGCGAACAGTTCCTGATTAACCACAAACCGTTCTACTTTACT
GGCTTTGGTCGTCATGAAGATGCGGACTTACGTGGCAAAGGATTCGATAACGTGCTGATGGTGCACGAC
CACGCATTAATGGACTGGATTGGGGCCAACTCCTACCGTACCTCGCATTACCCTTACGCTGAAGAGATG
CTCGACTGGGCAGATGAACATGGCATCGTGGTGATTGATGAAACTGCTGCTGTCGGCTTTAACCTCTCTT
TAGGCATTGGTTTCGAAGCGGGCAACAAGCCGAAAGAACTGTACAGCGAAGAGGCAGTCAACGGGGAA
ACTCAGCAAGCGCACTTACAGGCGATTAAAGAGCTGATAGCGCGTGACAAAAACCACCCAAGCGTGGT
GATGTGGAGTATTGCCAACGAACCGGATACCCGTCCGCAAGTGCACGGGAATATTTCGCCACTGGCGGA
AGCAACGCGTAAACTCGACCCGACGCGTCCGATCACCTGCGTCAATGTAATGTTCTGCGACGCTCACAC
CGATACCATCAGCGATCTCTTTGATGTGCTGTGCCTGAACCGTTATTACGGATGGTATGTCCAAAGCGGC
GATTTGGAAACGGCAGAGAAGGTACTGGAAAAAGAACTTCTGGCCTGGCAGGAGAAACTGCATCAGCC
GATTATCATCACCGAATACGGCGTGGATACGTTAGCCGGGCTGCACTCAATGTACACCGACATGTGGAG
TGAAGAGTATCAGTGTGCATGGCTGGATATGTATCACCGCGTCTTTGATCGCGTCAGCGCCGTCGTCGGT
GAACAGGTATGGAATTTCGCCGATTTTGCGACCTCGCAAGGCATATTGCGCGTTGGCGGTAACAAGAAA
GGGATCTTCACTCGATCGAATTCCTGCAGCCCGGGGGATCCACTAGATGCATGCTCGAGCGGCCGCCAG
TGTGATGGATATCTGCAGAATTCGCCCTTATCACAAGTTTGTACAAAAAAGCAGGCTCCACCATGGGAA
CCAATTCAGTCGACTGGATCCGGTACCGAATTCGATTCCGAAGACGGAAGAGACAACGAATGGCAGCA
ACGGTGTCTCAGCACCCACCGCCGCGGCTGCCGGCCCGGCACCGCCAGTCGAGTACCGGGTGTGGAACC
CGTTCCGCTCCAAACTGGCCGCCGCCGTCATGGCCGGCATTGAGGACACGCACATTTACCCGGGT

FIG. 44

RNAi construct sequence (containing underlined antisense fragment of *Rpt-1*, shaded Gus linker and sense fragment of *Rpt-1*) (SEQ ID NO:65):

AATGCGACCGGGACGAATGAGCGCCGGGTCGAGTGTGTCCGGTCTGTTGGTGGCCATCAAAACCTTGATGGCCCCGCGTGAGT
CGAATCCGTCCAGTTGGTTGACCAACTCGAGCATCGTCCGTTGCACTTCGTTGTCGCCCCCTTTTCCGTCGTCAAATCGCGCTCCG
CCGATGGCGTCGACTTCGTCGAAGAAGAGAATGCACGCCTTTTTCGTTTTAGCCAGCGAAAACAGCTCGCGCACCATGCGCGCG
CCTTCGCCAACGTATTTTTTGACTAATTCGGAACCGATGACGCGGATGAAATCGAATTCGGTACCGGATCCAGTCGACTGAATTG
GTTCCCATGGTGGAGCCTGCTTTTTTGTACAAACTTGTGATGACGGTATCGATAAGCTTGATATCTACCCGCTTCGCGTCGGCATC
CGGTCAGTGGCAGTGAAGGGCGAACAGTTCCTGATTAACCACAAACCGTTCTACTTTACTGGCTTTGGTCGTCATGAAGATGCGG
ACTTACGTGGCAAAGGATTCGATAACGTGCTGATGGTGCACGACCACGCATTAATGGACTGGATTGGGGCCAACTCCTACCGTA
CCTCGCATTACCCTTACGCTGAAGAGATGCTCGACTGGGCAGATGAACATGGCATCGTGGTGATTGATGAAACTGCTGCTGTCG
GCTTTAACCTCTCTTTAGGCATTGGTTTCGAAGCGGGCAACAAGCCGAAAGAACTGTACAGCGAAGAGGCAGTCAACGGGGAA
ACTCAGCAAGCGCACTTACAGGCGATTAAAGAGCTGATAGCGCGTGACAAAAACCACCCAAGCGTGGTGATGTGGAGTATTGCC
AACGAACCGGATACCCGTCCGCAAGTGCACGGGAATATTTCGCCACTGGCGGAAGCAACGCGTAAACTCGACCCGACGCGTCCG
ATCACCTGCGTCAATGTAATGTTCTGCGACGCTCACACCGATACCATCAGCGATCTCTTTGATGTGCTGTGCCTGAACCGTTATTA
CGGATGGTATGTCCAAAGCGGCGATTTGGAAACGGCAGAGAAGGTACTGGAAAAAGAACTTCTGGCCTGGCAGGAGAAACTGC
ATCAGCCGATTATCATCACCGAATACGGCGTGGATACGTTAGCCGGGCTGCACTCAATGTACACCGACATGTGGAGTGAAGAGT
ATCAGTGTGCATGGCTGGATATGTATCACCGCGTCTTTGATCGCGTCAGCGCCGTCGTCGGTGAACAGGTATGGAATTTCGCCGA
TTTTGCGACCTCGCAAGGCATATTGCGCGTTGGCGGTAACAAGAAAGGGATCTTCACTCGATCGAATTCCTGCAGCCCGGGGGA
TCCACTAGATGCATGCTCGAGCGGCCGCCAGTGTGATGGATATCTGCAGAATTCGCCCTTATCACAAGTTTGTACAAAAAAGCAG
GCTCCACCATGGGAACCAATTCAGTCGACTGGATCCGGTACCGAATTCGATTTCATCCGCGTCATCGGTTCCGAATTAGTCAAAA
AATACGTTGGCGAAGGCGCGCGCATGGTGCGCGAGCTGTTTTCGCTGGCTAAAACGAAAAAGGCGTGCATTCTCTTCTTCGACG
AAGTCGACGCCATCGGCGGAGCGCGATTTGACGACGGAAAAGGGGGCGACAACGAAGTGCAACGGACGATGCTCGAGTTGGT
CAACCAACTGGACGGATTCGACTCACGCGGGGCCATCAAGGTTTTGATGGCCACCAACAGACCGGACACACTCGACCCGGCGCT
CATTCGTCCCGGTCGCATT

FIG. 45

RNAi construct sequence (containing underlined sense fragment of *F-55*, shaded Gus linker and antisense fragment of *F-55*) (SEQ ID NO:66):

TACAACAACATCAAGCACGCCTTCTTCCAGCCGTGTGACAACGAAATGATCATTCTGTTGCACTTCCATT
TGAAGAATCCAGTGCTGTGGGGCAAAAAGAAATATTCGGATGTGCAATTCTTCACTGAAGTTGGCGAGA
TCACCACCGACTTGGGCAAGTACCATCACATGCAAGACAGGGACGACATTCAGAGCGAGCAGATGGAA
CGCGAAATGCGAATCGAATTCGGTACCGGATCCAGTCGACTGAATTGGTTCCCATGGTGGAGCCTGCTT
TTTTGTACAAACTTGTGATGACGGTATCGATAAGCTTGATATCTACCCGCTTCGCGTCGGCATCCGGTCA
GTGGCAGTGAAGGGCGAACAGTTCCTGATTAACCACAAACCGTTCTACTTTACTGGCTTTGGTCGTCATG
AAGATGCGGACTTACGTGGCAAAGGATTCGATAACGTGCTGATGGTGCACGACCACGCATTAATGGACT
GGATTGGGGCCAACTCCTACCGTACCTCGCATTACCCTTACGCTGAAGAGATGCTCGACTGGGCAGATG
AACATGGCATCGTGGTGATTGATGAAACTGCTGCTGTCGGCTTTAACCTCTCTTTAGGCATTGGTTTCGA
AGCGGGCAACAAGCCGAAAGAACTGTACAGCGAAGAGGCAGTCAACGGGGAAACTCAGCAAGCGCAC
TTACAGGCGATTAAAGAGCTGATAGCGCGTGACAAAAACCACCCAAGCGTGGTGATGTGGAGTATTGCC
AACGAACCGGATACCCGTCCGCAAGTGCACGGGAATATTTCGCCACTGGCGGAAGCAACGCGTAAACTC
GACCCGACGCGTCCGATCACCTGCGTCAATGTAATGTTCTGCGACGCTCACACCGATACCATCAGCGAT
CTCTTTGATGTGCTGTGCCTGAACCGTTATTACGGATGGTATGTCCAAAGCGGCGATTTGGAAACGGCAG
AGAAGGTACTGGAAAAAGAACTTCTGGCCTGGCAGGAGAAACTGCATCAGCCGATTATCATCACCGAAT
ACGGCGTGGATACGTTAGCCGGGCTGCACTCAATGTACACCGACATGTGGAGTGAAGAGTATCAGTGTG
CATGGCTGGATATGTATCACCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAAAGGGATCTTCACTCGATC
GAATTCCTGCAGCCCGGGGGATCCACTAGATGCATGCTCGAGCGGCCGCCAGTGTGATGGATATCTGCA
GAATTCGCCCTTATCACAAGTTTGTACAAAAAAGCAGGCTCCACCATGGGAACCAATTCAGTCGACTGG
ATCCGGTACCGAATTCGATTCGCATTTCGCGTTCCATCTGCTCGCTCTGAATGTCGTCCCTGTCTTGCATG
TGATGGTACTTGCCCAAGTCGGTGGTGATCTCGCCAACTTCAGTGAAGAATTGCACATCCGAATATTTCT
TTTTGCCCCACAGCACTGGATTCTTCAAATGGAAGTGCAACAGAATGATCATTTCGTTGTCACACGGCTG
GAAGAAGGCGTGCTTGATGTTGTTGTA

FIG. 46

RNAi construct sequence (containing underlined sense fragment of *Eat-3*, shaded Gus linker and antisense fragment of *Eat-3*) (SEQ ID NO:67):

TTCCGTTCTCCAAATGGAAGCGATGGGCGCGGAAAGCTTCCGCCTGCGCTTCGATGGATTCGCGAACCA
TCCGCCAAAAACAGTCCGAAACCGCCAATGACATATTCCGCGTCGTCATTTGGGTGGCCTTCAAAACGC
CATCCCTAAAGAGTTTGGAACTCTCGAAGAAGTCCTCCTCGTATTTGCGGATCTCCGCAATGCTCGCGTC
CCGCTTGTCCATGCCGGTGACAACGCCGAAATAGCCGAGCGCTTTCATCGGAAATAGTTTCCCGTCGAG
GATCTTCTTTATCCGATGCGGGTTGCTCAAATCGAATTCGGTACCGGATCCAGTCGACTGAATTGGTTCC
CATGGTGGAGCCTGCTTTTTTGTACAAACTTGTGATGACGGTATCGATAAGCTTGATATCTACCCGCTTC
GCGTCGGCATCCGGTCAGTGGCAGTGAAGGGCGAACAGTTCCTGATTAACCACAAACCGTTCTACTTTA
CTGGCTTTGGTCGTCATGAAGATGCGGACTTACGTGGCAAAGGATTCGATAACGTGCTGATGGTGCACG
ACCACGCATTAATGGACTGGATTGGGGCCAACTCCTACCGTACCTCGCATTACCCTTACGCTGAAGAGA
TGCTCGACTGGGCAGATGAACATGGCATCGTGGTGATTGATGAAACTGCTGCTGTCGGCTTTAACCTCTC
TTTAGGCATTGGTTTCGAAGCGGGCAACAAGCCGAAAGAACTGTACAGCGAAGAGGCAGTCAACGGGG
AAACTCAGCAAGCGCACTTACAGGCGATTAAAGAGCTGATAGCGCGTGACAAAAACCACCCAAGCGTG
GTGATGTGGAGTATTGCCAACGAACCGGATACCCGTCCGCAAGTGCACGGGAATATTTCGCCACTGGCG
GAAGCAACGCGTAAACTCGACCCGACGCGTCCGATCACCTGCGTCAATGTAATGTTCTGCGACGCTCAC
ACCGATACCATCAGCGATCTCTTTGATGTGCTGTGCCTGAACCGTTATTACGGATGGTATGTCCAAAGCG
GCGATTTGGAAACGGCAGAGAAGGTACTGGAAAAAGAACTTCTGGCCTGGCAGGAGAAACTGCATCAG
CCGATTATCATCACCGAATACGGCGTGGATACGTTAGCCGGGCTGCACTCAATGTACACCGACATGTGG
AGTGAAGAGTATCAGTGTGCATGGCTGGATATGTATCACCGCGTCTTTGATCGCGTCAGCGCCGTCGTCG
GTGAACAGGTATGGAATTTCGCCGATTTTGCGACCTCGCAAGGCATATTGCGCGTTGGCGGTAACAAGA
AAGGGATCTTCACTCGATCGAATTCCTGCAGCCCGGGGGATCCACTAGATGCATGCTCGAGCGGCCGCC
AGTGTGATGGATATCTGCAGAATTCGCCCTTATCACAAGTTTGTACAAAAAAGCAGGCTCCACCATGGG
AACCAATTCAGTCGACTGGATCCGGTACCGAATTCGATTTGAGCAACCCGCATCGGATAAAGAAGATCC
TCGACGGGAAACTATTTCCGATGAAAGCGCTCGGCTATTTCGGCGTTGTCACCGGCATGGACAAGCGGG
ACGCGAGCATTGCGGAGATCCGCAAATACGAGGAGGACTTCTTCGAGAGTTCCAAACTCTTTAGGGATG
GCGTTTTGAAGGCCACCCAAATGACGACGCGGAATATGTCATTGGCGGTTTCGGACTGTTTTTGGCGGAT
GGTTCGCGAATCCATCGAAGCGCAGGCGGAAGCTTTCCGCGCCCATCGCTTCCATTTGGAGAACGGAA

FIG. 47

RNAi construct sequence (containing underlined sense fragment of *Vap-2*, shaded Gus linker and antisense fragment of *Vap-2*) (SEQ ID NO:68):

CCAAATAGACAGGCGCACCAAAGTAATTACCACTAAAAGGGGTATTAGTAAACTAATTATGTTTTATCA
GTGGTTGATTATTACCCCGTGTAATACCAGCAGACCACATATGTTTTCCAATTGGTATTTGGGCAGTTTT
GTGCCATGGCACAGCCAATTCGGTCGGTGTCGGCCCACGCCATCTGAACAAAACGAAGAGAAAACTAAT
TAGTGTCTAATTAGCAATAATGGGACTAGAAACGGCGAAATAATGAATAGGTCACCTGAGTCCAATGGC
CGATGCCACTGAAGTTTTCCCCGGTCATAATCAGATCCGGGTTGAACCCGTAACGGTTCAGTTCGTCCCA
CCAGCGACCGCAAGCGTACTCGAAGCCATCCTCTTAAATCGAATTCGGTACCGGATCCAGTCGACTGAA
TTGGTTCCCATGGTGGAGCCTGCTTTTTTGTACAAACTTGTGATGACGGTATCGATAAGCTTGATATCTA
CCCGCTTCGCGTCGGCATCCGGTCAGTGGCAGTGAAGGGCGAACAGTTCCTGATTAACCACAAACCGTT
CTACTTTACTGGCTTTGGTCGTCATGAAGATGCGGACTTACGTGGCAAAGGATTCGATAACGTGCTGATG
GTGCACGACCACGCATTAATGGACTGGATTGGGGCCAACTCCTACCGTACCTCGCATTACCCTTACGCTG
AAGAGATGCTCGACTGGGCAGATGAACATGGCATCGTGGTGATTGATGAAACTGCTGCTGTCGGCTTTA
ACCTCTCTTTAGGCATTGGTTTCGAAGCGGGCAACAAGCCGAAAGAACTGTACAGCGAAGAGGCAGTCA
ACGGGGAAACTCAGCAAGCGCACTTACAGGCGATTAAAGAGCTGATAGCGCGTGACAAAAACCACCCA
AGCGTGGTGATGTGGAGTATTGCCAACGAACCGGATACCCGTCCGCAAGTGCACGGGAATATTTCGCCA
CTGGCGGAAGCAACGCGTAAACTCGACCCGACGCGTCCGATCACCTGCGTCAATGTAATGTTCTGCGAC
GCTCACACCGATACCATCAGCGATCTCTTTGATGTGCTGTGCCTGAACCGTTATTACGGATGGTATGTCC
AAAGCGGCGATTTGGAAACGGCAGAGAAGGTACTGGAAAAAGAACTTCTGGCCTGGCAGGAGAAACTG
CATCAGCCGATTATCATCACCGAATACGGCGTGGATACGTTAGCCGGGCTGCACTCAATGTACACCGAC
ATGTGGAGTGAAGAGTATCAGTGTGCATGGCTGGATATGTATCACCGCGTCTTTGATCGCGTCAGCGCC
GTCGTCGGTGAACAGGTATGGAATTTCGCCGATTTTGCGACCTCGCAAGGCATATTGCGCGTTGGCGGT
AACAAGAAAGGGATCTTCACTCGATCGAATTCCTGCAGCCCGGGGGATCCACTAGATGCATGCTCGAGC
GGCCGCCAGTGTGATGGATATCTGCAGAATTCGCCCTTATCACAAGTTTGTACAAAAAAGCAGGCTCCA
CCATGGGAACCAATTCAGTCGACTGGATCCGGTACCGAATTCGATTTAAGAGGATGGCTTCGAGTACGC
TTGCGGTCGCTGGTGGGACGAACTGAACCGTTACGGGTTCAACCCGGATCTGATTATGACCGGGGAAAA
CTTCAGTGGCATCGGCCATTGGACTCAGGTGACCTATTCATTATTTCGCCGTTTCTAGTCCCATTATTGCT
AATTAGACACTAATTAGTTTTCTCTTCGTTTTGTTCAGATGGCGTGGGCCGACACCGACCGAATTGGCTG
TGCCATGGCACAAAACTGCCCAAATACCAATTGGAAAACATATGTGGTCTGCTGGTATTACACGGGGTA
ATAATCAACCACTGATAAAACATAATTAGTTTACTAATACCCCTTTTAGTGGTAATTACTTTGGTGCGCC
TGTCTATTTGG

FIG. 48

RNAi construct sequence (containing underlined sense fragment of *Asb-1*, shaded Gus linker and antisense fragment of *Asb-1*) (SEQ ID NO:69):

ATCGGTCTTTGATTGCTTGCACTTCCTGCAGGTAATCCAACCGACGCTTCATCTCTTGCCAGGCGTAGTC
CACATTTTTTCGGTAGGTCGCTTCAAGTTGCAGCGCCAAATTCTCTTGGAAAATTGTGGGAAAGTTTTCA
TGCACTGCTTTCAACGAGTCGGCCTGCTCCTTTGAAGTCTTGCGGAACTCGATGGCTTCCTTCAATTCATT
GTCAATGTAAGCCTTCATTTTGCCAAATCGTTCACGGGTAACTTTGTATACGTACTTTTCAAATTTATAAC
GAAAAGCCGTGTGGAAATCGAATTCGGTACCGGATCCAGTCGACTGAATTGGTTCCCATGGTGGAGCCT
GCTTTTTTGTACAAACTTGTGATGACGGTATCGATAAGCTTGATATCTACCCGCTTCGCGTCGGCATCCG
GTCAGTGGCAGTGAAGGGCGAACAGTTCCTGATTAACCACAAACCGTTCTACTTTACTGGCTTTGGTCGT
CATGAAGATGCGGACTTACGTGGCAAAGGATTCGATAACGTGCTGATGGTGCACGACCACGCATTAATG
GACTGGATTGGGGCCAACTCCTACCGTACCTCGCATTACCCTTACGCTGAAGAGATGCTCGACTGGGCA
GATGAACATGGCATCGTGGTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAACGGGGAAACTCAGCAAGC
GCACTTACAGGCGATTAAAGAGCTGATAGCGCGTGACAAAAACCACCCAAGCGTGGTGATGTGGAGTA
TTGCCAACGAACCGGATACCCGTCCGCAAGTGCACGGGAATATTTCGCCACTGGCGGAAGCAACGCGTA
AACTCGACCCGACGCGTCCGATCACCTGCGTCAATGTAATGTTCTGCGACGCTCACACCGATACCATCA
GCGATCTCTTTGATGTGCTGTGCCTGAACCGTTATTACGGATGGTATGTCCAAAGCGGCGATTTGGAAAC
GGCAGAGAAGGTACTGGAAAAAGAACTTCTGGCCTGGCAGGAGAAACTGCATCAGCCGATTATCATCA
CCGAATACGGCGTGGATACGTTAGCCGGGCTGCACTCAATGTACACCGACATGTGGAGTGAAGAGTATC
AGTGTGCATGGCTGGATATGTATCACCGCGTCTTTGATCGCGTCAGCGCCGTCGTCGGTGAACAGGTATG
GAATTTCGCCGATTTTGCGACCTCGCAAGGCATATTGCGCGTTGGCGGTAACAAGAAAGGGATCTTCAC
TCGATCGAATTCCTGCAGCCCGGGGGATCCACTAGATGCATGCTCGAGCGGCCGCCAGTGTGATGGATA
TCTGCAGAATTCGCCCTTATCACAAGTTTGTACAAAAAAGCAGGCTCCACCATGGGAACCAATTCAGTC
GACTGGATCCGGTACCGAATTCGATT<u>TCCACACGGCTTTTCGTTATAAATTTGAAAAGTACGTATACAAA
GTTACCCGTGAACGATTTGGCAAAATGAAGGCTTACATTGACAATGAATTGAAGGAAGCCATCGAGTTC
CGCAAGACTTCAAAGGAGCAGGCCGACTCGTTGAAAGCAGTGCATGAAAACTTTCCCACAATTTTCCAA
GAGAATTTGGCGCTGCAACTTGAAGCGACCTACCGAAAAAATGTGGACTACGCCTGGCAAGAGATGAA
GCGTCGGTTGGATTACCTGCAGGAAGTGCAAGCAATCAAAGACCGAT</u>

FIG. 49

RNAi construct sequence, ***Y25* of *Pratylenchus neglectus,*** (containing underlined sense fragment of *Y25*, shaded Gus linker and antisense fragment of *Y25*) (SEQ ID NO:70):

TGAGAGTTCCAATGACAAATTTTGCAAGGTGTCGCCAGTCTGGTTGACCACGAGTACGTCCAATACAAT
GTCATATTGGTTGACGTTGACGTACGCCTCGGCATAGACGGGATCCGAAGAGCCGGCTAACTGAATCAC
TTTTCCCAGTTTGGAGCTGGCAAAGGTGTATTTGGTCGTTTTGGGTGCAGTACCAAGCGCTTGGGAAAGC
GAAAGATCAAACAAATTTGTGTCCGTCACGTTTTCTGACACGCGTGTGGACAGCCGCGTGAACATAATT
GTCTTGTCGGGCTGCAATCGAATTCGGTACCGGATCCAGTCGACTGAATTGGTTCCCATGGTGGAGCCTG
CTTTTTTGTACAAACTTGTGATGACGGTATCGATAAGCTTGATATCTACCCGCTTCGCGTCGGCATCCGG
TCAGTGGCAGTGAAGGGCGAACAGTTCCTGATTAACCACAAACCGTTCTACTTTACTGGCTTTGGTCGTC
ATGAAGATGCGGACTTACGTGGCAAAGGATTCGATAACGTGCTGATGGTGCACGACCACGCATTAATGG
ACTGGATTGGGGCCAACTCCTACCGTACCTCGCATTACCCTTACGCTGAAGAGATGCTCGACTGGGCAG
ATGAACATGGCATCGTGGTGATTGATGAAACTGCTGCTGTCGGCTTTAACCTCTCTTTAGGCATTGGTTT
CGAAGCGGGCAACAAGCCGAAAGAACTGTACAGCGAAGAGGCAGTCAACGGGGAAACTCAGCAAGCG
CACTTACAGGCGATTAAAGAGCTGATAGCGCGTGACAAAAACCACCCAAGCGTGGTGATGTGGAGTATT
GCCAACGAACCGGATACCCGTCCGCAAGTGCACGGGAATATTTCGCCACTGGCGGAAGCAACGCGTAA
ACTCGACCCGACGCGTCCGATCACCTGCGTCAATGTAATGTTCTGCGACGCTCACACCGATACCATCAGC
GATCTCTTTGATGTGCTGTGCCTGAACCGTTATTACGGATGGTATGTCCAAAGCGGCGATTTGGAAACGG
CAGAGAAGGTACTGGAAAAAGAACTTCTGGCCTGGCAGGAGAAACTGCATCAGCCGATTATCATCACC
GAATACGGCGTGGATACGTTAGCCGGGCTGCACTCAATGTACACCGACATGTGGAGTGAAGAGTATCAG
TGTGCATGGCTGGATATGTATCACCGCGTCTTTGATCGCGTCAGCGCCGTCGTCGGTGAACAGGTATGGA
ATTTCGCCGATTTTGCGACCTCGCAAGGCATATTGCGCGTTGGCGGTAACAAGAAAGGGATCTTCACTC
GATCGAATTCCTGCAGCCCGGGGGATCCACTAGATGCATGCTCGAGCGGCCGCCAGTGTGATGGATATC
TGCAGAATTCGCCCTTATCACAAGTTTGTACAAAAAAGCAGGCTCCACCATGGGAACCAATTCAGTCGA
CTGGATCCGGTACCGAATTCGATTGCAGCCCGACAAGACAATTATGTTCACGCGGCTGTCCACACGCGT
GTCAGAAAACGTGACGGACACAAATTTGTTTGATCTTTCGCTTTCCCAAGCGCTTGGTACTGCACCCAAA
ACGACCAAATACACCTTTGCCAGCTCCAAACTGGGAAAAGTGATTCAGTTAGCCGGCTCTTCGGATCCC
GTCTATGCCGAGGCGTACGTCAACGTCAACCAATATGACATTGTATTGGACGTACTCGTGGTCAACCAG
ACTGGCGACACCTTGCAAAATTTGTCATTGGAACTCTCA

FIG. 50

RNAi construct sequence, ***Rnr-1* of *Pratylenchus neglectus,*** (containing underlined sense fragment of *Rnr-1*, shaded Gus linker and antisense fragment of *Rnr-1*) (SEQ ID NO:71):

AGGGCCATTTTGTCCACAGTGAACTGAACAGCATCGACAGCCGGACGAGTGCGCAGGTAATACATCCCG
GTTTTAAGTCCCAATGACCAGGCGTAAAAGTGCATGGAGCTCAGTTTAGCATAGTTCGGCTGCGCTATGT
GAATGTTAAGGGATTGGCTTTGGTCAATGAAGGCGGCGCGATCGGCGGCCATTTTCAAAATGTCCTTCT
GCGGTATTTCCCACACGGTCTTGTACAGGTCTTTGATTTCTTGAATCGAATTCGGTACCGGATCCAGTCG
ACTGAATTGGTTCCCATGGTGGAGCCTGCTTTTTTGTACAAACTTGTGATGACGGTATCGATAAGCTTGA
TATCTACCCGCTTCGCGTCGGCATCCGGTCAGTGGCAGTGAAGGGCGAACAGTTCCTGATTAACCACAA
ACCGTTCTACTTTACTGGCTTTGGTCGTCATGAAGATGCGGACTTACGTGGCAAAGGATTCGATAACGTG
CTGATGGTGCACGACCACGCATTAATGGACTGGATTGGGGCCAACTCCTACCGTACCTCGCATTACCCTT
ACGCTGAAGAGATGCTCGACTGGGCAGATGAACATGGCATCGTGGTGATTGATGAAACTGCTGCTGTCG
GCTTTAACCTCTCTTTAGGCATTGGTTTCGAAGCGGGCAACAAGCCGAAAGAACTGTACAGCGAAGAGG
CAGTCAACGGGGAAACTCAGCAAGCGCACTTACAGGCGATTAAAGAGCTGATAGCGCGTGACAAAAAC
CACCCAAGCGTGGTGATGTGGAGTATTGCCAACGAACCGGATACCCGTCCGCAAGTGCACGGGAATATT
TCGCCACTGGCGGAAGCAACGCGTAAACTCGACCCGACGCGTCCGATCACCTGCGTCAATGTAATGTTC
TGCGACGCTCACACCGATACCATCAGCGATCTCTTTGATGTGCTGTGCCTGAACCGTTATTACGGATGGT
ATGTCCAAAGCGGCGATTTGGAAACGGCAGAGAAGGTACTGGAAAAAGAACTTCTGGCCTGGCAGGAG
AAACTGCATCAGCCGATTATCATCACCGAATACGGCGTGGATACGTTAGCCGGGCTGCACTCAATGTAC
ACCGACATGTGGAGTGAAGAGTATCAGTGTGCATGGCTGGATATGTATCACCGCGTCTTTGATCGCGTC
AGCGCCGTCGTCGGTGAACAGGTATGGAATTTCGCCGATTTTGCGACCTCGCAAGGCATATTGCGCGTT
GGCGGTAACAAGAAAGGGATCTTCACTCGATCGAATTCCTGCAGCCCGGGGGATCCACTAGATGCATGC
TCGAGCGGCCGCCAGTGTGATGGATATCTGCAGAATTCGCCCTTATCACAAGTTTGTACAAAAAAGCAG
GCTCCACCATGGGAACCAATTCAGTCGACTGGATCCGGTACCGAATTCGATTCAAGAAATCAAAGACCT
GTACAAGACCGTGTGGGAAATACCGCAGAAGGACATTTTGAAAATGGCCGCCGATCGCGCCGCCTTCAT
TGACCAAAGCCAATCCCTTAACATTCACATAGCGCAGCCGAACTATGCTAAACTGAGCTCCATGCACTTT
TACGCCTGGTCATTGGGACTTAAAACCGGGATGTATTACCTGCGCACTCGTCCGGCTGTCGATGCTGTTC
AGTTCACTGTGGACAAAATGGCCCT

FIG. 51

RNAi construct sequence, ***Y25* of *Radopholus similis,*** (containing underlined sense fragment of *Y25*, shaded Gus linker and antisense fragment of *Y25*) (SEQ ID NO:72):

TGAGAGTCCAATGACAATTTGCAAGGTGTCGCCAGTCTGGTTGACCACGAGTACGTCCAATACAATGTC
ATATTGGTTGACGTTGACGTACGCCTCGGCATAGACGGGATCCGAAGAGCCGGCTAACTGAATCACTTT
TCCCAGTTTGGAGCTGGCAAAGGTGTATTTGGTCGTTTTGGGTGCAGTACCAAGCGCTTGGGAAAGCGA
AAGATCAAACAAATTTGTGTCCGTCACGTTTTCTGACACGCGTGTGGACAGCTGCGTGAACATAATTGTC
TTGTCGGGCTGCAATCGAATTCGGTACCGGATCCAGTCGACTGAATTGGTTCCCATGGTGGAGCCTGCTT
TTTTGTACAAACTTGTGATGACGGTATCGATAAGCTTGATATCTACCCGCTTCGCGTCGGCATCCGGTCA
GTGGCAGTGAAGGGCGAACAGTTCCTGATTAACCACAAACCGTTCTACTTTACTGGCTTTGGTCGTCATG
AAGATGCGGACTTACGTGGCAAAGGATTCGATAACGTGCTGATGGTGCACGACCACGCATTAATGGACT
GGATTGGGGCCAACTCCTACCGTACCTCGCATTACCCTTACGCTGAAGAGATGCTCGACTGGGCAGATG
AACATGGCATCGTGGTGATTGATGAAACTGCTGCTGTCGGCTTTAACCTCTCTTTAGGCATTGGTTTCGA
AGCGGGCAACAAGCCGAAAGAACTGTACAGCGAAGAGGCAGTCAACGGGGAAACTCAGCAAGCGCAC
TTACAGGCGATTAAAGAGCTGATAGCGCGTGACAAAAACCACCCAAGCGTGGTGATGTGGAGTATTGCC
AACGAACCGGATACCCGTCCGCAAGTGCACGGGAATATTTCGCCACTGGCGGAAGCAACGCGTAAACTC
GACCCGACGCGTCCGATCACCTGCGTCAATGTAATGTTCTGCGACGCTCACACCGATACCATCAGCGAT
CTCTTTGATGTGCTGTGCCTGAACCGTTATTACGGATGGTATGTCCAAAGCGGCGATTTGGAAACGGCAG
AGAAGGTACTGGAAAAAGAACTTCTGGCCTGGCAGGAGAAACTGCATCAGCCGATTATCATCACCGAAT
ACGGCGTGGATACGTTAGCCGGGCTGCACTCAATGTACACCGACATGTGGAGTGAAGAGTATCAGTGTG
CATGGCTGGATATGTATCACCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAAAGGGATCTTCACTCGATC
GAATTCCTGCAGCCCGGGGGATCCACTAGATGCATGCTCGAGCGGCCGCCAGTGTGATGGATATCTGCA
GAATTCGCCCTTATCACAAGTTTGTACAAAAAAGCAGGCTCCACCATGGGAACCAATTCAGTCGACTGG
ATCCGGTACCGAATTCGATTGCAGCCCGACAAGACAATTATGTTCACGCAGCTGTCCACACGCGTGTCA
GAAAACGTGACGGACACAAATTTGTTTGATCTTTCGCTTTCCCAAGCGCTTGGTACTGCACCCAAAACGA
CCAAATACACCTTTGCCAGCTCCAAACTGGGAAAAGTGATTCAGTTAGCCGGCTCTTCGGATCCCGTCTA
TGCCGAGGCGTACGTCAACGTCAACCAATATGACATTGTATTGGACGTACTCGTGGTCAACCAGACTGG
CGACACCTTGCAAATTGTCATTGGACTCTCA

FIG. 52

RNAi construct sequence, ***Rnr-1* of *Radopholus similis,*** (containing underlined sense fragment of *Rnr-1*, shaded Gus linker and antisense fragment of *Rnr-1*) (SEQ ID NO:73):

TAGGGCCATTTTGTCCACAGTGAACTGAACAGCATCGACAGCCGGACGAGTGCGCAGGTAATACATCCC
GGTTTTAAGTCCCAATGACCAGGCGTAAAAGTGCATGGAGCTCAGTTTAGCATAGTTCGGCTGCGCTAT
GTGAATGTTAAGGGATTGGCTTTGGTCAATGAAAAGGGCGCGATCGGCGGCCATTTTCAAAATGTCCTG
GCTGAATACACACACAGCACACGTACTTAATCGAATTCGGTACCGGATCCAGTCGACTGAATTGGTTCC
CATGGTGGAGCCTGCTTTTTTGTACAAACTTGTGATGACGGTATCGATAAGCTTGATATCTACCCGCTTC
GCGTCGGCATCCGGTCAGTGGCAGTGAAGGGCGAACAGTTCCTGATTAACCACAAACCGTTCTACTTTA
CTGGCTTTGGTCGTCATGAAGATGCGGACTTACGTGGCAAAGGATTCGATAACGTGCTGATGGTGCACG
ACCACGCATTAATGGACTGGATTGGGGCCAACTCCTACCGTACCTCGCATTACCCTTACGCTGAAGAGA
TGCTCGACTGGGCAGATGAACATGGCATCGTGGTGATTGATGAAACTGCTGCTGTCGGCTTTAACCTCTC
TTTAGGCATTGGTTTCGAAGCGGGCAACAAGCCGAAAGAACTGTACAGCGAAGAGGCAGTCAACGGGG
AAACTCAGCAAGCGCACTTACAGGCGATTAAAGAGCTGATAGCGCGTGACAAAAACCACCCAAGCGTG
GTGATGTGGAGTATTGCCAACGAACCGGATACCCGTCCGCAAGTGCACGGGAATATTTCGCCACTGGCG
GAAGCAACGCGTAAACTCGACCCGACGCGTCCGATCACCTGCGTCAATGTAATGTTCTGCGACGCTCAC
ACCGATACCATCAGCGATCTCTTTGATGTGCTGTGCCTGAACCGTTATTACGGATGGTATGTCCAAAGCG
GCGATTTGGAAACGGCAGAGAAGGTACTGGAAAAAGAACTTCTGGCCTGGCAGGAGAAACTGCATCAG
CCGATTATCATCACCGAATACGGCGTGGATACGTTAGCCGGGCTGCACTCAATGTACACCGACATGTGG
AGTGAAGAGTATCAGTGTGCATGGCTGGATATGTATCACCGCGTCTTTGATCGCGTCAGCGCCGTCGTCG
GTGAACAGGTATGGAATTTCGCCGATTTTGCGACCTCGCAAGGCATATTGCGCGTTGGCGGTAACAAGA
AAGGGATCTTCACTCGATCGAATTCCTGCAGCCCGGGGGATCCACTAGATGCATGCTCGAGCGGCCGCC
AGTGTGATGGATATCTGCAGAATTCGCCCTTATCACAAGTTTGTACAAAAAAGCAGGCTCCACCATGGG
AACCAATTCAGTCGACTGGATCCGGTACCGAATTCGATTAAGTACGTGTGCTGTGTGTGTATTCAGCCAG
GACATTTTGAAAATGGCCGCCGATCGCGCCCTTTTCATTGACCAAAGCCAATCCCTTAACATTCACATAG
CGCAGCCGAACTATGCTAAACTGAGCTCCATGCACTTTTACGCCTGGTCATTGGGACTTAAAACCGGGA
TGTATTACCTGCGCACTCGTCCGGCTGTCGATGCTGTTCAGTTCACTGTGGACAAAATGGCCCTA

FIG. 53

RNAi construct sequence, ***Rnr-1* of *Rotylenchulus reniformis*,** (containing underlined sense fragment of *Rnr-1*, shaded Gus linker and antisense fragment of *Rnr-1*) (SEQ ID NO:74):

AGGGCCATTTTGTCCACAGTGAACTGAACAGCATCGACAGCCGGACGAGTGCGCAGGTAATACATCCCG
GTTTTAAGTCCCAATGACCAGGCGTAAAAGTGCATGGAGCTCAGTTTAGCATAGTTCGGCTGCGCTATGT
GAATGTTAAGGGATTGGCTTTGGTCAATGAAAGCGGCGCGATCGGCGGCAATCGAATTCGGTACCGGAT
CCAGTCGACTGAATTGGTTCCCATGGTGGAGCCTGCTTTTTTGTACAAACTTGTGATGACGGTATCGATA
AGCTTGATATCTACCCGCTTCGCGTCGGCATCCGGTCAGTGGCAGTGAAGGGCGAACAGTTCCTGATTA
ACCACAAACCGTTCTACTTTACTGGCTTTGGTCGTCATGAAGATGCGGACTTACGTGGCAAAGGATTCGA
TAACGTGCTGATGGTGCACGACCACGCATTAATGGACTGGATTGGGGCCAACTCCTACCGTACCTCGCA
TTACCCTTACGCTGAAGAGATGCTCGACTGGGCAGATGAACATGGCATCGTGGTGATTGATGAAACTGC
TGCTGTCGGCTTTAACCTCTCTTTAGGCATTGGTTTCGAAGCGGGCAACAAGCCGAAAGAACTGTACAG
CGAAGAGGCAGTCAACGGGGAAACTCAGCAAGCGCACTTACAGGCGATTAAAGAGCTGATAGCGCGTG
ACAAAAACCACCCAAGCGTGGTGATGTGGAGTATTGCCAACGAACCGGATACCCGTCCGCAAGTGCAC
GGGAATATTTCGCCACTGGCGGAAGCAACGCGTAAACTCGACCCGACGCGTCCGATCACCTGCGTCAAT
GTAATGTTCTGCGACGCTCACACCGATACCATCAGCGATCTCTTTGATGTGCTGTGCCTGAACCGTTATT
ACGGATGGTATGTCCAAAGCGGCGATTTGGAAACGGCAGAGAAGGTACTGGAAAAAGAACTTCTGGCC
TGGCAGGAGAAACTGCATCAGCCGATTATCATCACCGAATACGGCGTGGATACGTTAGCCGGGCTGCAC
TCAATGTACACCGACATGTGGAGTGAAGAGTATCAGTGTGCATGGCTGGATATGTATCACCGCGTCTTT
GATCGCGTCAGCGCCGTCGTCGGTGAACAGGTATGGAATTTCGCCGATTTTGCGACCTCGCAAGGCATA
TTGCGCGTTGGCGGTAACAAGAAAGGGATCTTCACTCGATCGAATTCCTGCAGCCCGGGGGATCCACTA
GATGCATGCTCGAGCGGCCGCCAGTGTGATGGATATCTGCAGAATTCGCCCTTATCACAAGTTTGTACA
AAAAAGCAGGCTCCACCATGGGAACCAATTCAGTCGACTGGATCCGGTACCGAATTCGATTGCCGCCGA
TCGCGCCGCTTTCATTGACCAAAGCCAATCCCTTAACATTCACATAGCGCAGCCGAACTATGCTAAACTG
AGCTCCATGCACTTTTACGCCTGGTCATTGGGACTTAAAACCGGGATGTATTACCTGCGCACTCGTCCGG
CTGTCGATGCTGTTCAGTTCACTGTGGACAAAATGGCCCT

FIG. 54

RNAi construct sequence of Y25-Prp-17 (containing underlined sense fragment of Y25-Prp-17, shaded Gus linker and antisense fragment of Y25-Prp-17) (SEQ ID NO:75):

GCAGCCCGACAAGACAATTATGTTCACGCAGCTGTCCACACGCGTGTCAGAAAACGTGACGGACACAAATTTGTTT
GATCTTTCGCTTTCCCAAGCGCTTGGTACTGCACCCAAAACGACCAAATACACCTTTGCCAGCTCCAAACTGGGAAA
AGTGATTCAGTTAGCCGGCTTTTCGGATCCCGTCTATGCCGAGGCGTACGTCAACGTCAACCAATATGACATTGTAT
TGGACGTACTCGTGGTCAACCAGACTAGCGACACCTTGCAAAATTTGTCATTGGAACTCTCAAAGCTTCAATCGAAT
TGTCCTTTTCCAAATCGTCGATGACAAGTTGCGATTCGCTCGTAGAAAGGTGGTTTTACGAAAAAGAATTTTTTTAA
TCGTGCCTTACAAATTAGGCCTTCCGTGGTCACAATACAGCAGGGTACGCCTGCTCAACTGATTTTTCGCCAGAGAT
GAGGTTATCTAGCACATAATTCAAAAGGCATTCCTTTCTTTTTTTTCTTAGTTTTCTCGCTTCCGGTGATGCGGACGG
TAAAATCACAATGTGGGACTGGCGCACACACAAAATTGTCTCCACGTGGAAGGCACATGATAATGTGTGCATTTCA
ACACTGTGGCATCCGCACGAGAAATCGCGGATGATTTCTTGCGGATGGGACAATGTAATCAAAATGAATCGAATTC
GGTACCGGATCCAGTCGACTGAATTGGTTCCCATGGTGGAGCCTGCTTTTTTGTACAAACTTGTGATGACGGTATCG
ATAAGCTTGATATCTACCCGCTTCGCGTCGGCATCCGGTCAGTGGCAGTGAAGGGCGAACAGTTCCTGATTAACCA
CAAACCGTTCTACTTTACTGGCTTTGGTCGTCATGAAGATGCGGACTTACGTGGCAAAGGATTCGATAACGTGCTGA
TGGTGCACGACCACGCATTAATGGACTGGATTGGGGCCAACTCCTACCGTACCTCGCATTACCCTTACGCTGAAGA
GATGCTCGACTGGGCAGATGAACATGGCATCGTGGTGATTGATGAAACTGCTGCTGTCGGCTTTAACCTCTCTTTAG
GCATTGGTTTCGAAGCGGGCAACAAGCCGAAAGAACTGTACAGCGAAGAGGCAGTCAACGGGGAAACTCAGCAAG
CGCACTTACAGGCGATTAAAGAGCTGATAGCGCGTGACAAAAACCACCCAAGCGTGGTGATGTGGAGTATTGCCA
ACGAACCGGATACCCGTCCGCAAGTGCACGGGAATATTTCGCCACTGGCGGAAGCAACGCGTAAACTCGACCCGA
CGCGTCCGATCACCTGCGTCAATGTAATGTTCTGCGACGCTCACACCGATACCATCAGCGATCTCTTTGATGTGCTG
TGCCTGAACCGTTATTACGGATGGTATGTCCAAAGCGGCGATTTGGAAACGGCAGAGAAGGTACTGGAAAAAGAA
CTTCTGGCCTGGCAGGAGAAACTGCATCAGCCGATTATCATCACCGAATACGGCGTGGATACGTTAGCCGGGCTGC
ACTCAATGTACACCGACATGTGGAGTGAAGAGTATCAGTGTGCATGGCTGGATATGTATCACCGCGTCTTTGATCG
CGTCAGCGCCGTCGTCGGTGAACAGGTATGGAATTTCGCCGATTTTGCGACCTCGCAAGGCATATTGCGCGTTGGC
GGTAACAAGAAAGGGATCTTCACTCGATCGAATTCCTGCAGCCCGGGGGATCCACTAGATGCATGCTCGAGCGGCC
GCCAGTGTGATGGATATCTGCAGAATTCGCCCTTATCACAAGTTTGTACAAAAAAGCAGGCTCCACCATGGGAACC
AATTCAGTCGACTGGATCCGGTACCGAATTCGATTCATTTTGATTACATTGTCCCATCCGCAAGAAATCATCCGCGA
TTTCTCGTGCGGATGCCACAGTGTTGAAATGCACACATTATCATGTGCCTTCCACGTGGAGACAATTTTGTGTGTGC
GCCAGTCCCACATTGTGATTTTACCGTCCGCATCACCGGAAGCGAGAAAACTAAGAAAAAAAAGAAAGGAATGCC
TTTTGAATTATGTGCTAGATAACCTCATCTCTGGCGAAAAATCAGTTGAGCAGGCGTACCCTGCTGTATTGTGACCA
CGGAAGGCCTAATTTGTAAGGCACGATTAAAAAAATTCTTTTTCGTAAAACCACCTTTCTACGAGCGAATCGCAACT
TGTCATCGACGATTTGGAAAAGGACAATTCGATTGAAGCTTTGAGAGTTCCAATGACAAATTTTGCAAGGTGTCGC
TAGTCTGGTTGACCACGAGTACGTCCAATACAATGTCATATTGGTTGACGTTGACGTACGCCTCGGCATAGACGGG
ATCCGAAAAGCCGGCTAACTGAATCACTTTTCCCAGTTTGGAGCTGGCAAAGGTGTATTTGGTCGTTTTGGGTGCAG
TACCAAGCGCTTGGGAAAGCGAAAGATCAAACAAATTTGTGTCCGTCACGTTTTCTGACACGCGTGTGGACAGCTG
CGTGAACATAATTGTCTTGTCGGGCTGC

FIG. 55

RNAi construct sequence of Y25-Cpn-1 (containing underlined sense fragment of Y25-Cpn-1, shaded Gus linker and antisense fragment of Y25-Cpn-1) (SEQ ID NO:76):

GCAGCCCGACAAGACAATTATGTTCACGCAGCTGTCCACACGCGTGTCAGAAAACGTGACGGACACAAATTTGTTT
GATCTTTCGCTTTCCCAAGCGCTTGGTACTGCACCCAAAACGACCAAATACACCTTTGCCAGCTCCAAACTGGGAAA
AGTGATTCAGTTAGCCGGCTTTTCGGATCCCGTCTATGCCGAGGCGTACGTCAACGTCAACCAATATGACATTGTAT
TGGACGTACTCGTGGTCAACCAGACTAGCGACACCTTGCAAAATTTGTCATTGGAACTCTCAAGCTTAAGGCACCA
AGGCATCGATCAGGCTGTGGCAGCAGCCATTACGGAATTGAAGGCCATCTCGCGCCCCATTGCCACCAGCAAGGAG
ATTGCGCAAGTGGGCTCCATTTCGGCCAACTCCGACAGCGCCATCGGCGACATCATCGCCCAGGCCATGGAGAAGG
TGGGCAAGGAGGGCGTGATAACCGTCGAGGATGGCAAGTCGCTGGAAAACGAACTGGATGTGGTGGAAGGCATGC
AGTTCGACCGCGGCTACCTGAGCCCATACTTCATCAATGATCCGGACAAGCAACTGGCGCGCCTGGATGACCCGCT
GGTGCTGCTGTACGACAAAAAGATCAGCAATATCCGCGAGCTGCTGCCGGTGCTGGAGCAGTCGGCCAAGGCCGG
CAAGCCGCTGTTCATCGTGGCGGAGGATACAAAAAGCGAAATCGAATTCGGTACCGGATCCAGTCGACTGAATTGG
TTCCCATGGTGGAGCCTGCTTTTTTGTACAAACTTGTGATGACGGTATCGATAAGCTTGATATCTACCCGCTTCGCGT
CGGCATCCGGTCAGTGGCAGTGAAGGGCGAACAGTTCCTGATTAACCACAAACCGTTCTACTTTACTGGCTTTGGTC
GTCATGAAGATGCGGACTTACGTGGCAAAGGATTCGATAACGTGCTGATGGTGCACGACCACGCATTAATGGACTG
GATTGGGGCCAACTCCTACCGTACCTCGCATTACCCTTACGCTGAAGAGATGCTCGACTGGGCAGATGAACATGGC
ATCGTGGTGATTGATGAAACTGCTGCTGTCGGCTTTAACCTCTCTTTAGGCATTGGTTTCGAAGCGGGCAACAAGCC
GAAAGAACTGTACAGCGAAGAGGCAGTCAACGGGGAAACTCAGCAAGCGCACTTACAGGCGATTAAAGAGCTGAT
AGCGCGTGACAAAAACCACCCAAGCGTGGTGATGTGGAGTATTGCCAACGAACCGGATACCCGTCCGCAAGTGCA
CGGGAATATTTCGCCACTGGCGGAAGCAACGCGTAAACTCGACCCGACGCGTCCGATCACCTGCGTCAATGTAATG
TTCTGCGACGCTCACACCGATACCATCAGCGATCTCTTTGATGTGCTGTGCCTGAACCGTTATTACGGATGGTATGT
CCAAAGCGGCGATTTGGAAACGGCAGAGAAGGTACTGGAAAAAGAACTTCTGGCCTGGCAGGAGAAACTGCATCA
GCCGATTATCATCACCGAATACGGCGTGGATACGTTAGCCGGGCTGCACTCAATGTACACCGACATGTGGAGTGAA
GAGTATCAGTGTGCATGGCTGGATATGTATCACCGCGTCTTTGATCGCGTCAGCGCCGTCGTCGGTGAACAGGTATG
GAATTTCGCCGATTTTGCGACCTCGCAAGGCATATTGCGCGTTGGCGGTAACAAGAAAGGGATCTTCACTCGATCG
AATTCCTGCAGCCCGGGGGATCCACTAGATGCATGCTCGAGCGGCCGCCAGTGTGATGGATATCTGCAGAATTCGC
CCTTATCACAAGTTTGTACAAAAAAGCAGGCTCCACCATGGGAACCAATTCAGTCGACTGGATCCGGTACCGAATT
CGATTTCGCTTTTTGTATCCTCCGCCACGATGAACAGCGGCTTGCCGGCCTTGGCCGACTGCTCCAGCACCGGCAGC
AGCTCGCGGATATTGCTGATCTTTTTGTCGTACAGCAGCACCAGCGGGTCATCCAGGCGCGCCAGTTGCTTGTCCGG
ATCATTGATGAAGTATGGGCTCAGGTAGCCGCGGTCGAACTGCATGCCTTCCACCACATCCAGTTCGTTTTCCAGCG
ACTTGCCATCCTCGACGGTTATCACGCCCTCCTTGCCCACCTTCTCCATGGCCTGGGCGATGATGTCGCCGATGGCG
CTGTCGGAGTTGGCCGAAATGGAGCCCACTTGCGCAATCTCCTTGCTGGTGGCAATGGGGCGCGAGATGGCCTTCA
ATTCCGTAATGGCTGCTGCCACAGCCTGATCGATGCCTTGGTGCCTTAAGCTTGAGAGTTCCAATGACAAATTTTGC
AAGGTGTCGCTAGTCTGGTTGACCACGAGTACGTCCAATACAATGTCATATTGGTTGACGTTGACGTACGCCTCGGC
ATAGACGGGATCCGAAAAGCCGGCTAACTGAATCACTTTTCCCAGTTTGGAGCTGGCAAAGGTGTATTTGGTCGTTT
TGGGTGCAGTACCAAGCGCTTGGGAAAGCGAAAGATCAAACAAATTTGTGTCCGTCACGTTTTCTGACACGCGTGT
GGACAGCTGCGTGAACATAATTGTCTTGTCGGGCTGC

FIG. 56

RNAi construct sequence of Cpn-Rnr-1 (containing underlined antisense fragment of Cpn-Rnr-1, shaded Gus linker and sense fragment of Cpn-Rnr-1) (SEQ ID NO:77):

AGGGCCATTTTGTCCACAGTGAACTGAACAGCATCGACAGCCGGACGAGTGCGCAGGTAATACATCCCG
GTTTTAAGTCCCAATGACCAGGCGTAAAAGTGCATGGAGCTCAGTTTAGCATAGTTCGGCTGCGCTATGT
GAATGTTAAGGGATTGGCTTTGGTCAATGAAAGCGGCGCGATCGGCGGCCATTTTCAAAATGTCCTTCT
GCGGTATTTCCCACACGGTCTTGTACAGGTCTTTGATTTCTTGAAGCTTTCGCTTTTTGTATCCTCCGCCA
CGATGAACAGCGGCTTGCCGGCCTTGGCCGACTGCTCCAGCACCGGCAGCAGCTCGCGGATATTGCTGA
TCTTTTTGTCGTACAGCAGCACCAGCGGGTCATCCAGGCGCGCCAGTTGCTTGTCCGGATCATTGATGAA
GTATGGGCTCAGGTAGCCGCGGTCGAACTGCATGCCTTCCACCACATCCAGTTCGTTTTCCAGCGACTTG
CCATCCTCGACGGTTATCACGCCCTCCTTGCCCACCTTCTCCATGGCCTGGGCGATGATGTCGCCGATGG
CGCTGTCGGAGTTGGCCGAAATGGAGCCCACTTGCGCAATCTCCTTGCTGGTGGCAATGGGGCGCGAGA
TGGCCTTCAATTCCGTAATGGCTGCTGCCACAGCCTGATCGATGCCTTGGTGAATCGAATTCGGTACCGG
ATCCAGTCGACTGAATTGGTTCCCATGGTGGAGCCTGCTTTTTTGTACAAACTTGTGATGACGGTATCGA
TAAGCTTGATATCTACCCGCTTCGCGTCGGCATCCGGTCAGTGGCAGTGAAGGGCGAACAGTTCCTGATT
AACCACAAACCGTTCTACTTTACTGGCTTTGGTCGTCATGAAGATGCGGACTTACGTGGCAAAGGATTCG
ATAACGTGCTGATGGTGCACGACCACGCATTAATGGACTGGATTGGGGCCAACTCCTACCGTACCTCGC
ATTACCCTTACGCTGAAGAGATGCTCGACTGGGCAGATGAACATGGCATCGTGGTGATTGATGAAACTG
CTGCTGTCGGCTTTAACCTCTCTTTAGGCATTGGTTTCGAAGCGGGCAACAAGCCGAAAGAACTGTACA
GCGAAGAGGCAGTCAACGGGGAAACTCAGCAAGCGCACTTACAGGCGATTAAAGAGCTGATAGCGCGT
GACAAAAACCACCCAAGCGTGGTGATGTGGAGTATTGCCAACGAACCGGATACCCGTCCGCAAGTGCA
CGGGAATATTTCGCCACTGGCGGAAGCAACGCGTAAACTCGACCCGACGCGTCCGATCACCTGCGTCAA
TGTAATGTTCTGCGACGCTCACACCGATACCATCAGCGATCTCTTTGATGTGCTGTGCCTGAACCGTTAT
TACGGATGGTATGTCCAAAGCGGCGATTTGGAAACGGCAGAGAAGGTACTGGAAAAAGAACTTCTGGC
CTGGCAGGAGAAACTGCATCAGCCGATTATCATCACCGAATACGGCGTGGATACGTTAGCCGGGCTGCA
CTCAATGTACACCGACATGTGGAGTGAAGAGTATCAGTGTGCATGGCTGGATATGTATCACCGCGTCTTT
GATCGCGTCAGCGCCGTCGTCGGTGAACAGGTATGGAATTTCGCCGATTTTGCGACCTCGCAAGGCATA
TTGCGCGTTGGCGGTAACAAGAAAGGGATCTTCACTCGATCGAATTCCTGCAGCCCGGGGGATCCACTA
GATGCATGCTCGAGCGGCCGCCAGTGTGATGGATATCTGCAGAATTCGCCCTTATCACAAGTTTGTACA
AAAAAGCAGGCTCCACCATGGGAACCAATTCAGTCGACTGGATCCGGTACCGAATTCGATTCACCAAGG
CATCGATCAGGCTGTGGCAGCAGCCATTACGGAATTGAAGGCCATCTCGCGCCCCATTGCCACCAGCAA
GGAGATTGCGCAAGTGGGCTCCATTTCGGCCAACTCCGACAGCGCCATCGGCGACATCATCGCCCAGGC
CATGGAGAAGGTGGGCAAGGAGGGCGTGATAACCGTCGAGGATGGCAAGTCGCTGGAAAACGAACTGG
ATGTGGTGGAAGGCATGCAGTTCGACCGCGGCTACCTGAGCCCATACTTCATCAATGATCCGGACAAGC
AACTGGCGCGCCTGGATGACCCGCTGGTGCTGCTGTACGACAAAAAGATCAGCAATATCCGCGAGCTGC
TGCCGGTGCTGGAGCAGTCGGCCAAGGCCGGCAAGCCGCTGTTCATCGTGGCGGAGGATACAAAAAGC
GAAAGCTTCAAGAAATCAAAGACCTGTACAAGACCGTGTGGGAAATACCGCAGAAGGACATTTTGAAA
ATGGCCGCCGATCGCGCCGCTTTCATTGACCAAAGCCAATCCCTTAACATTCACATAGCGCAGCCGAAC
TATGCTAAACTGAGCTCCATGCACTTTTACGCCTGGTCATTGGGACTTAAAACCGGGATGTATTACCTGC
GCACTCGTCCGGCTGTCGATGCTGTTCAGTTCACTGTGGACAAAATGGCCCT

FIG. 57
Over-expression vector (pPTN289 as backbone)
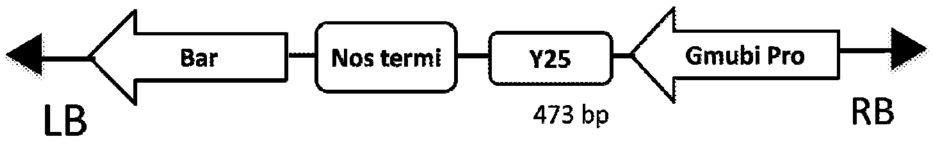
RNAi + over-expression vector (pRAP17 vector as backbone)
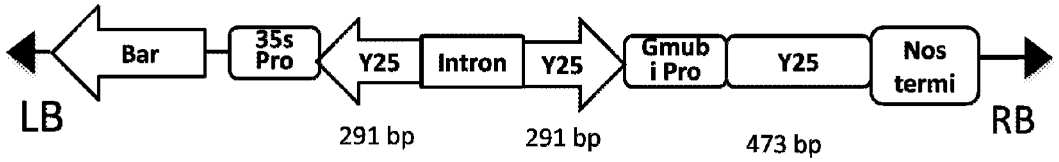

FIG. 58

Y25 gene fragment used for over-expressing in pPNT289 vector (SEQ ID NO:78)

cgatcactgaggacgacttggaccgtttgtcgaccactgttcgactgattgttgaccaatggccgaaagcggtggatgtgtttttgagagagtgccgtgcttcgttggaaa
gcatgctcaaggccaagggggacgtggaccggcacgaacgcgacacaaaagcgccgaagaagaaaattgtgcagcccgacaagacaattatgttcacgcagctgtcc
acacgcgtgtcagaaaacgtgacggacacaaatttgtttgatctttcgctttcccaagcgcttggtactgcacccaaaacgaccaaatacacctttgccagctccaaactg
ggaaaagtgattcagttagccggcttttcggatcccgtctatgccgaggcgtacgtcaacgtcaaccaatatgacattgtattggacgtactcgtggtcaaccagactagc
gacaccttgcaaaatttgtcattggaactctca

FIG. 59A.

| | | |
|---|---|---|
| HgY25 race 1 | GCAGCCCCGACAAGACAATTATGTTCACGCAGCTGTCCACA | 40 |
| HgY25 race 3 | GCAGCCCCGACAAGACAATTATGTTCACGCAGCTGTCCACA | 40 |
| HgY25 race 4 | GCAGCCCCGACAAGACAATTATGTTCACGCAGCTGTCCACA | 40 |
| LesionY25 | GCAGCCCCGACAAGACAATTATGTTCACGCGGCTGTCCACA | 40 |
| RsY25 | GCAGCCCCGACAAGACAATTATGTTCACGCAGCTGTCCACA | 40 |
| Consensus | gcagccccgacaagacaattatgttcacgc gctgtccaca | |
| HgY25 race 1 | CGCGTGTCAGAAAACGTGACGGACACAAATTTGTTTCATC | 80 |
| HgY25 race 3 | CGCGTGTCAGAAAACGTGACGGACACAAATTTGTTTCATC | 80 |
| HgY25 race 4 | CGCGTGTCAGAAAACGTGACGGACACAAATTTGTTTCATC | 80 |
| LesionY25 | CGCGTGTCAGAAAACGTGACGGACACAAATTTGTTTCATC | 80 |
| RsY25 | CGCGTGTCAGAAAACGTGACGGACACAAATTTGTTTCATC | 80 |
| Consensus | cgcgtgtcagaaaacgtgacggacacaaatttgtttcatc | |
| HgY25 race 1 | TTTCGCTTTCCCAAGCGCTTGGTACTGCACCCAAAACGAC | 120 |
| HgY25 race 3 | TTTCGCTTTCCCAAGCGCTTGGTACTGCACCCAAAACGAC | 120 |
| HgY25 race 4 | TTTCGCTTTCCCAAGCGCTTGGTACTGCACCCAAAACGAC | 120 |
| LesionY25 | TTTCGCTTTCCCAAGCGCTTGGTACTGCACCCAAAACGAC | 120 |
| RsY25 | TTTCGCTTTCCCAAGCGCTTGGTACTGCACCCAAAACGAC | 120 |
| Consensus | tttcgctttcccaagcgcttggtactgcacccaaaacgac | |
| HgY25 race 1 | CAAATACACCTTTGCCAGCTCCAAACTGGGAAAAGTCATT | 160 |
| HgY25 race 3 | CAAATACACCTTTGCCAGCTCCAAACTGGGAAAAGTCATT | 160 |
| HgY25 race 4 | CAAATACACCTTTGCCAGCTCCAAACTGGGAAAAGTCATT | 160 |
| LesionY25 | CAAATACACCTTTGCCAGCTCCAAACTGGGAAAAGTCATT | 160 |
| RsY25 | CAAATACACCTTTGCCAGCTCCAAACTGGGAAAAGTCATT | 160 |
| Consensus | caaatacacctttgccagctccaaactgggaaaagtcatt | |
| HgY25 race 1 | CAGTTAGCCGGCTTTTCGGATCCCGTCTATGCCCAGGCGT | 200 |
| HgY25 race 3 | CAGTTAGCCGGCTCTTCGGATCCCGTCTATGCCCAGGCGT | 200 |
| HgY25 race 4 | CAGTTAGCCGGCTTTTCGGATCCCGTCTATGCCCAGGCGT | 200 |
| LesionY25 | CAGTTAGCCGGCTCTTCGGATCCCGTCTATGCCCAGGCGT | 200 |
| RsY25 | CAGTTAGCCGGCTCTTCGGATCCCGTCTATGCCCAGGCGT | 200 |
| Consensus | cagttagccggct ttcggatcccgtctatgcccaggcgt | |
| HgY25 race 1 | ACGTCAACGTCAACCAATATGACATTGTATTGGACGTACT | 240 |
| HgY25 race 3 | ACGTCAACGTCAACCAATATGACATTGTATTGGACGTACT | 240 |
| HgY25 race 4 | ACGTCAACGTCAACCAATATGACATTGTATTGGACGTACT | 240 |
| LesionY25 | ACGTCAACGTCAACCAATATGACATTGTATTGGACGTACT | 240 |
| RsY25 | ACGTCAACGTCAACCAATATGACATTGTATTGGACGTACT | 240 |
| Consensus | acgtcaacgtcaaccaatatgacattgtattggacgtact | |
| HgY25 race 1 | CGTGGTCAACCAGACTAGCCACACCTTGCAAAATTTGTCA | 280 |
| HgY25 race 3 | CGTGGACAACCAGACTGGCCACACCTTGCAAAATTTGTCA | 280 |
| HgY25 race 4 | CGTGGTCAACCAGACTAGCCACACCTTGCAAAATTTGTCA | 280 |
| LesionY25 | CGTGGTCAACCAGACTGGCCACACCTTGCAAAATTTGTCA | 280 |
| RsY25 | CGTGGTCAACCAGACTGGCCACACCTTGCAAAATTTGTCA | 280 |
| Consensus | cgtgg caaccagact gccacaccttgcaaaatttgtca | |
| HgY25 race 1 | TTGGAACTCTC | 291 |
| HgY25 race 3 | TTGGAACTCTC | 291 |
| HgY25 race 4 | TTGGAACTCTC | 291 |
| LesionY25 | TTGGAACTCTC | 291 |
| RsY25 | TTGGAACTCTC | 291 |
| Consensus | ttggaactctc | |

FIG. 59B.

```
HgRnr-1 race CAAGAAATCAAAGACCTGTACAAGACCGTGTGGGAAATAC 40
HgRnr-1 race CAAGAAATCAAAGACCTGTACAAGACCGTGTGGGAAATAC 40
HgRnr-1 race CAAGAAATCAAAGACCTGTACAAGACCGTGTGGGAAATAC 40
Lesion Rnr-1 CAAGAAATCAAAGACCTGTACAAGACCGTGTGGGAAATAC 40
RS Rnr-1     CAAGAAATCAAAGACCTGTACAAGACCGTGTGGGAAATAC 40
Consensus    caagaaatcaaagacctgtacaagaccgtgtgggaaatac
HgRnr-1 race CGCAGAAGGACATTTTGAAAATGGCCGCCGATCGCGCCGC 80
HgRnr-1 race CGCAGAAGGACATTTTGAAAATGGCCGCCGATCGCGCCGC 80
HgRnr-1 race CGCAGAAGGACATTTTGAAAATGGCCGCCGATCGCGCCGC 80
Lesion Rnr-1 CGCAGAAGGACATTTTGAAAATGGCCGCCGATCGCGCCGC 80
RS Rnr-1     CGCAGAAGGACATTTTGAAAATGGCCGCCGATCGCGCCGC 80
Consensus    cgcagaaggacattttgaaaatggccgccgatcgcgccgc
HgRnr-1 race TTTCATTGACCAAAGCCAATCCCTTAACATTCACATAGCG 120
HgRnr-1 race TTTCATTGACCAAAGCCAATCCCTTAACATTCACATAGCG 120
HgRnr-1 race TTTCATTGACCAAAGCCAATCCCTTAACATTCACATAGCG 120
Lesion Rnr-1 CTTCATTGACCAAAGCCAATCCCTTAACATTCACATAGCG 120
RS Rnr-1     CTTCATTGACCAAAGCCAATCCCTTAACATTCACATAGCG 120
Consensus     ttcattgaccaaagccaatcccttaacattcacatagcg
HgRnr-1 race CAGCCGAACTATGCTAAACTGAGCTCCATGCACTTTTACG 160
HgRnr-1 race CAGCCGAACTATGCTAAACTGAGCTCCATGCACTTTTACG 160
HgRnr-1 race CAGCCGAACTATGCTAAACTGAGCTCCATGCACTTTTACG 160
Lesion Rnr-1 CAGCCGAACTATGCTAAACTGAGCTCCATGCACTTTTACG 160
RS Rnr-1     CAGCCGAACTATGCTAAACTGAGCTCCATGCACTTTTACG 160
Consensus    cagccgaactatgctaaactgagctccatgcacttttacg
HgRnr-1 race CCTGGTCATTGGGACTTAAAACCGGGATGTATTACCTGCG 200
HgRnr-1 race CCTGGTCATTGGGACTTAAAACCGGGATGTATTACCTGCG 200
HgRnr-1 race CCTGGTCATTGGGACTTAAAACCGGGATGTATTACCTGCG 200
Lesion Rnr-1 CCTGGTCATTGGGACTTAAAACCGGGATGTATTACCTGCG 200
RS Rnr-1     CCTGGTCATTGGGACTTAAAACCGGGATGTATTACCTGCG 200
Consensus    cctggtcattgggacttaaaaccgggatgtattacctgcg
HgRnr-1 race CACTCGTCCGGCTGTCGATGCTGTTCAGTTCACTGTGGAC 240
HgRnr-1 race CACTCGTCCGGCTGTCGATGCTGTTCAGTTCACTGTGGAC 240
HgRnr-1 race CACTCGTCCGGCTGTCGATGCTGTTCAGTTCACTGTGGAC 240
Lesion Rnr-1 CACTCGTCCGGCTGTCGATGCTGTTCAGTTCACTGTGGAC 240
RS Rnr-1     CACTCGTCCGGCTGTCGATGCTGTTCAGTTCACTGTGGAC 240
Consensus    cactcgtccggctgtcgatgctgttcagttcactgtggac
HgRnr-1 race AAAATGGCCCT 251
HgRnr-1 race AAAATGGCCCT 251
HgRnr-1 race AAAATGGCCCT 251
Lesion Rnr-1 AAAATGGCCCT 251
RS Rnr-1     AAAATGGCCCT 251
Consensus    aaaatggccct
```

FIG. 60

Actual sequence used for cdk-1 RNAi>J12 (exons)sequenced from cDNA (SEQ ID NO:89)

TCTAGCAAGGCCAAAATCAGCCAATTTTAATTGTGGCGCAGTTTTCACTGTATTATTGATCAACAAATTCTGGGGCTTCAAATCACGATGAAGCAC

ATTGTGCGCATGACAATAGCATAAACCGGACAGTAACTGATGCATCAGTGAACGAACAACTTTTTGGTCGATTTGCCCATCCAAAGTGTCGAAAAA

TTTTCGTAAATCAAGGTCACAAAATTCAAAGACTAAGTTCAGCGTCTTGTTTGTATGCACAACATTCTGCAATCGCACAACATTTGCATGTCGTAG

TTCGCGCAACAAACAAATTTCGCGCAGTGCCGAAGACGGAACTCCTTCATCTTCATCATCCAGTCGCACTATCTTAAGAGCAACAATTTGCTCGGT

GTCCTTGTTTCTTGCCTTGAAAACCGTTCCATATGTGCCTTCACCA

FIG. 61

Sequence of pANDA35HK/cdk-1 J12 RNAi construct sequence (containing underlined antisense and sense fragment of cdk-1 and shaded Gus linker)(SEQ ID NO:90)

TGGTGAAGGCACATATGGAACGGTTTTCAAGGCAAGAAACAAGGACACCGAGCAAATTGTTGCTCTTAAGATAGTGCGACTGGATGATGAAGATGA
AGGAGTTCCGTCTTCGGCACTGCGCGAAATTTGTTTGTTGCGCGAACTACGACATGCAAATGTTGTGCGATTGCAGAATGTTGTGCATACAAACAA
GACGCTGAACTTAGTCTTTGAATTTTGTGACCTTGATTTACGAAAATTTTTCGACACTTTGGATGGGCAAATCGACCAAAAAGTTGTTCGTTCACT
GATGCATCAGTTACTGTCCGGTTTATGCTATTGTCATGCGCACAATGTGCTTCATCGTGATTTGAAGCCCCAGAATTTGTTGATCAATAATACAGT
GAAAACTGCGCCACAATTAAAATTGGCTGATTTTGGCCTTGCTAGAAATCGAATTCGGTACCGGATCCAGTCGACTGAATTGGTTCCCATGGTGGA
GCCTGCTTTTTTGTACAAACTTGTGATGACGGTATCGATAAGCTTGATATCTACCCGCTTCGCGTCGGCATCCGGTCAGTGGCAGTGAAGGGCGAA
CAGTTCCTGATTAACCACAAACCGTTCTACTTTACTGGCTTTGGTCGTCATGAAGATGCGGACTTACGTGGCAAAGGATTCGATAACGTGCTGATG
GTGCACGACCACGCATTAATGGACTGGATTGGGGCCAACTCCTACCGTACCTCGCATTACCCTTACGCTGAAGAGATGCTCGACTGGGCAGATGAA
CATGGCATCGTGGTGATTGATGAAACTGCTGCTGTCGGCTTTAACCTCTCTTTAGGCATTGGTTTCGAAGCGGGCAACAAGCCGAAAGAACTGTAC
AGCGAAGAGGCAGTCAACGGGGAAACTCAGCAAGCGCACTTACAGGCGATTAAAGAGCTGATAGCGCGTGACAAAAACCACCCAAGCGTGGTGATG
TGGAGTATTGCCAACGAACCGGATACCCGTCCGCAAGTGCACGGGAATATTTCGCCACTGGCGGAAGCAACGCGTAAACTCGACCCGACGCGTCCG
ATCACCTGCGTCAATGTAATGTTCTGCGACGCTCACACCGATACCATCAGCGATCTCTTTGATGTGCTGTGCCTGAACCGTTATTACGGATGGTAT
GTCCAAAGCGGCGATTTGGAAACGGCAGAGAAGGTACTGGAAAAAGAACTTCTGGCCTGGCAGGAGAAACTGCATCAGCCGATTATCATCACCGAA
TACGGCGTGGATACGTTAGCCGGGCTGCACTCAATGTACACCGACATGTGGAGTGAAGAGTATCAGTGTGCATGGCTGGATATGTATCACCGCGTC
TTTGATCGCGTCAGCGCCGTCGTCGGTGAACAGGTATGGAATTTCGCCGATTTTGCGACCTCGCAAGGCATATTGCGCGTTGGCGGTAACAAGAAA
GGGATCTTCACTCGATCGAATTCCTGCAGCCCGGGGGATCCACTAGATGCATGCTCGAGCGGCCGCCAGTGTGATGGATATCTGCAGAATTCGCCC
TTATCACAAGTTTGTACAAAAAAGCAGGCTCCACCATGGGAACCAATTCAGTCGACTGGATCCGGTACCGAATTCGATTTCTAGCAAGGCCAAAAT
CAGCCAATTTTAATTGTGGCGCAGTTTTCACTGTATTATTGATCAACAAATTCTGGGGCTTCAAATCACGATGAAGCACATTGTGCGCATGACAAT
AGCATAAACCGGACAGTAACTGATGCATCAGTGAACGAACAACTTTTTGGTCGATTTGCCCATCCAAAGTGTCGAAAAATTTTCGTAAATCAAGGT
CACAAAATTCAAAGACTAAGTTCAGCGTCTTGTTTGTATGCACAACATTCTGCAATCGCACAACATTTGCATGTCGTAGTTCGCGCAACAAACAAA
TTTCGCGCAGTGCCGAAGACGGAACTCCTTCATCTTCATCATCCAGTCGCACTATCTTAAGAGCAACAATTTGCTCGGTGTCCTTGTTTCTTGCCT
TGAAAACCGTTCCATATGTGCCTTCACCA

FIG. 62

Actual sequence used for Fzy-1 RNAi>J13 (with intorns) sequenced from gDNA (SEQ ID NO:91)

CCACTTCATGTCCGACGAGTCCCGCTTCCAAATTGGAACAGCAGACGAAGAAACAAATGATGAGGGTCAAATCGGACAATGCAGTGAATTCGTTGG
CTGATTTTGACCAAGTTTGCGCATTTCGTAAGGGACTCGCTCCTCTAGCAAAATTCGGTAGATTAACTTTAATAAAGCCATGAATTTTACATCCAA
TTCATTCTCTGCAAGGCCACAAACAGCAGGTGAATGTGCTTTTTTCTTGTGTCCAGCCCACTTCCAGTTGTGTGAAACGGTCTCGTCGTTACGTTG
CGAAGGATCCCGAGAGAATGTTGGATGCGCCAGATTTATTAGACGATTTTTGTAAACATAATACAGAAAACATTTTTGCAACTACCTATTCAGATT
CGAATTTGATTGATTGGAGCAAGACTAATTGTGTCGCCGTTGGCTTAGGATCAAAAATTTTTCAATGGAACGCGGGGACCGGTGCCGTGGATGTCA
GTTCTTTTACAGTTTTTTCCACCAAATCTTGTGAATTTAAGGAGATAAAAGATTTCTCTGAAACGCATTCGCATCCAACTCTCGTCAAATGGTCTT
GCGAAGGACAATATCTTGCCG

FIG. 63

Sequence of pANDA35HK/fzy-1 J13 (containing underlined antisense and sense fragment of fzy-1 and shaded Gus linker)(SEQ ID NO:92)

CGGCAAGATATTGTCCTTCGCAAGACCATTTGACGAGAGTTGGATGCGAATGCGTTTCAGAGAAATCTTTTATCTCCTTAAATTCACAAGATTTGG
TGGAAAAAACTGTAAAAGAACTGACATCCACGGCACCGGTCCCCGCGTTCCATTGAAAAATTTTTGATCCTAAGCCAACGGCGACACAATTAGTCT
TGCTCCAATCAATCAAATTCGAATCTGAATAGGTAGTTGCAAAAATGTTTTCTGTATTATGTTTACAAAAATCGTCTAATAAATCTGGCGCATCCA
ACATTCTCTCGGGATCCTTCGCAACGTAACGACGAGACCGTTTCACACAACTGGAAGTGGGCTGGACACAAGAAAAAAGCACATTCACCTGCTGTT
TGTGGCCTTGCAGAGAATGAATTGGATGTAAAATTCATGGCTTTATTAAAGTTAATCTACCGAATTTTGCTAGAGGAGCGAGTCCCTTACGAAATG
CGCAAACTTGGTCAAAATCAGCCAACGAATTCACTGCATTGTCCGATTTGACCCTCATCATTTGTTTCTTCGTCTGCTGTTCCAATTTGGAAGCGG
GACTCGTCGGACATGAAGTGGAATCGAATTCGGTACCGGATCCAGTCGACTGAATTGGTTCCCATGGTGGAGCCTGCTTTTTTGTACAAACTTGTG
ATGACGGTATCGATAAGCTTGATATCTACCCGCTTCGCGTCGGCATCCGGTCAGTGGCAGTGAAGGGCGAACAGTTCCTGATTAACCACAAACCGT
TCTACTTTACTGGCTTTGGTCGTCATGAAGATGCGGACTTACGTGGCAAAGGATTCGATAACGTGCTGATGGTGCACGACCACGCATTAATGGACT
GGATTGGGGCCAACTCCTACCGTACCTCGCATTACCCTTACGCTGAAGAGATGCTCGACTGGGCAGATGAACATGGCATCGTGGTGATTGATGAAA
CTGCTGCTGTCGGCTTTAACCTCTCTTTAGGCATTGGTTTCGAAGCGGGCAACAAGCCGAAAGAACTGTACAGCGAAGAGGCAGTCAACGGGGAAA
CTCAGCAAGCGCACTTACAGGCGATTAAAGAGCTGATAGCGCGTGACAAAAACCACCCAAGCGTGGTGATGTGGAGTATTGCCAACGAACCGGATA
CCCGTCCGCAAGTGCACGGGAATATTTCGCCACTGGCGGAAGCAACGCGTAAACTCGACCCGACGCGTCCGATCACCTGCGTCAATGTAATGTTCT
GCGACGCTCACACCGATACCATCAGCGATCTCTTTGATGTGCTGTGCCTGAACCGTTATTACGGATGGTATGTCCAAAGCGGCGATTTGGAAACGG
CAGAGAAGGTACTGGAAAAAGAACTTCTGGCCTGGCAGGAGAAACTGCATCAGCCGATTATCATCACCGAATACGGCGTGGATACGTTAGCCGGGC
TGCACTCAATGTACACCGACATGTGGAGTGAAGAGTATCAGTGTGCATGGCTGGATATGTATCACCGCGTCTTTGATCGCGTCAGCGCCGTCGTCG
GTGAACAGGTATGGAATTTCGCCGATTTTGCGACCTCGCAAGGCATATTGCGCGTTGGCGGTAACAAGAAAGGGATCTTCACTCGATCGAATTCCT
GCAGCCCGGGGGATCCACTAGATGCATGCTCGAGCGGCCGCCAGTGTGATGGATATCTGCAGAATTCGCCCTTATCACAAGTTTGTACAAAAAAGC
AGGCTCCACCATGGGAACCAATTCAGTCGACTGGATCCGGTACCGAATTCGATTCCACTTCATGTCCGACGAGTCCCGCTTCCAAATTGGAACAGC
AGACGAAGAAACAAATGATGAGGGTCAAATCGGACAATGCAGTGAATTCGTTGGCTGATTTTGACCAAGTTTGCGCATTTCGTAAGGGACTCGCTC
CTCTAGCAAAATTCGGTAGATTAACTTTAATAAAGCCATGAATTTTACATCCAATTCATTCTCTGCAAGGCCACAAACAGCAGGTGAATGTGCTTT
TTTCTTGTGTCCAGCCCACTTCCAGTTGTGTGAAACGGTCTCGTCGTTACGTTGCGAAGGATCCCGAGAGAATGTTGGATGCGCCAGATTTATTAG
ACGATTTTTGTAAACATAATACAGAAAACATTTTTGCAACTACCTATTCAGATTCGAATTTGATTGATTGGAGCAAGACTAATTGTGTCGCCGTTG
GCTTAGGATCAAAAATTTTTCAATGGAACGCGGGGACCGGTGCCGTGGATGTCAGTTCTTTTACAGTTTTTTCCACCAAATCTTGTGAATTTAAGG
AGATAAAAGATTTCTCTGAAACGCATTCGCATCCAACTCTCGTCAAATGGTCTTGCGAAGGACAATATCTTGCCG

FIG. 64

Actual sequence used for tba-2 RNAi>J14 (with introns)sequenced from gDNA (SEQ ID NO:93)

TTTACATCCTTCGGGACGACGTCACCTCGGTAGAGAAGGCACACGGCCATGTATTTGCCGTGACGTGGATCGCATTTGACCATTTGGTTGGACGGC

TCAAAGCACATGTTGGTGATTTCGGAAACCGACAATGATTCGTGGTAGGCCTTCTCAGCTGAGATAACTGGAGAATAAGTCGCAAGAGGAAAGTGA

ATTCGAGGATAAGGAACAAGATTGGTCTAAAATGGAATAATTGATATCCAAGAAACAGCAGACTACAAAAGAACCTGGAATTCAGTGAGATCGACA

TTCAAAGCACCATCAAATCGAAGTGAAGCGGTTATCGAAGAGACAAC

FIG. 65

Sequence of pANDA35HK/tba-2 J14 (containing underlined antisense and sense fragment of tba-1 and shaded Gus linker)(SEQ ID NO:94)

GTTGTCTCTTCGATAACCGCTTCACTTCGATTTGATGGTGCTTTGAATGTCGATCTCACTGAATTCCAGGTTCTTTTGTAGTCTGCTGTTTCTTGG

ATATCAATTATTCCATTTTAGACCAATCTTGTTCCTTATCCTCGAATTCACTTTCCTCTTGCGACTTATTCTCCAGTTATCTCAGCTGAGAAGGCC

TACCACGAATCATTGTCGGTTTCCGAAATCACCAACATGTGCTTTGAGCCGTCCAACCAAATGGTCAAATGCGATCCACGTCACGGCAAATACATG

GCCGTGTGCCTTCTCTACCGAGGTGACGTCGTCCCGAAGGATGTAAAAATCGAATTCGGTACCGGATCCAGTCGACTGAATTGGTTCCCATGGTGG

AGCCTGCTTTTTTGTACAAACTTGTGATGACGGTATCGATAAGCTTGATATCTACCCGCTTCGCGTCGGCATCCGGTCAGTGGCAGTGAAGGGCGA

ACAGTTCCTGATTAACCACAAACCGTTCTACTTTACTGGCTTTGGTCGTCATGAAGATGCGGACTTACGTGGCAAAGGATTCGATAACGTGCTGAT

GGTGCACGACCACGCATTAATGGACTGGATTGGGGCCAACTCCTACCGTACCTCGCATTACCCTTACGCTGAAGAGATGCTCGACTGGGCAGATGA

ACATGGCATCGTGGTGATTGATGAAACTGCTGCTGTCGGCTTTAACCTCTCTTTAGGCATTGGTTTCGAAGCGGGCAACAAGCCGAAAGAACTGTA

CAGCGAAGAGGCAGTCAACGGGGAAACTCAGCAAGCGCACTTACAGGCGATTAAAGAGCTGATAGCGCGTGACAAAAACCACCCAAGCGTGGTGAT

GTGGAGTATTGCCAACGAACCGGATACCCGTCCGCAAGTGCACGGGAATATTTCGCCACTGGCGGAAGCAACGCGTAAACTCGACCCGACGCGTCC

GATCACCTGCGTCAATGTAATGTTCTGCGACGCTCACACCGATACCATCAGCGATCTCTTTGATGTGCTGTGCCTGAACCGTTATTACGGATGGTA

TGTCCAAAGCGGCGATTTGGAAACGGCAGAGAAGGTACTGGAAAAAGAACTTCTGGCCTGGCAGGAGAAACTGCATCAGCCGATTATCATCACCGA

ATACGGCGTGGATACGTTAGCCGGGCTGCACTCAATGTACACCGACATGTGGAGTGAAGAGTATCAGTGTGCATGGCTGGATATGTATCACCGCGT

CTTTGATCGCGTCAGCGCCGTCGTCGGTGAACAGGTATGGAATTTCGCCGATTTTGCGACCTCGCAAGGCATATTGCGCGTTGGCGGTAACAAGAA

AGGGATCTTCACTCGATCGAATTCCTGCAGCCCGGGGGATCCACTAGATGCATGCTCGAGCGGCCGCCAGTGTGATGGATATCTGCAGAATTCGCC

CTTATCACAAGTTTGTACAAAAAAGCAGGCTCCACCATGGGAACCAATTCAGTCGACTGGATCCGGTACCGAATTCGATTTTTACATCCTTCGGGA

CGACGTCACCTCGGTAGAGAAGGCACACGGCCATGTATTTGCCGTGACGTGGATCGCATTTGACCATTTGGTTGGACGGCTCAAAGCACATGTTGG

TGATTTCGGAAACCGACAATGATTCGTGGTAGGCCTTCTCAGCTGAGATAACTGGAGAATAAGTCGCAAGAGGAAAGTGAATTCGAGGATAAGGAA

CAAGATTGGTCTAAAATGGAATAATTGATATCCAAGAAACAGCAGACTACAAAAGAACCTGGAATTCAGTGAGATCGACATTCAAAGCACCATCAA

ATCGAAGTGAAGCGGTTATCGAAGAGACAAC

FIG. 66

Sequence used for arx-1 RNAi>J15 (with introns)sequenced from gDNA (SEQ ID NO:95)

TTTGCCAGCTGCTGTAATTGATTGTGGCACCGGGTAATTAAGAATTACTGCTTTTTGCGTTTTATTTTTCTTTTAAGGTACACAAAGCTTGGCTAT

GCAGGAAATTCGGAGCCACAGTTTATCATTCCGTCGGCTATCGCTGTCAAAGATGCGAATATTTTGAAAAGTGTCGGCGGAAAAATCCCGGACTTG

GACTTTTTCATCGGTGACGAGGCGTTGTCTCCTTCGGCTGCGAATTATTTTGTTAAGGTTCTGTTTTTCTCATTTTATTGTCTATTCCCAAAGTAT

ATTATGCTTTTCTCAGTATCCAATTCGACATGGAATTGTCGACGATTGGGACCTAATGGAACGTTTTTGGGAGCATTGCATTTTCAAATATTTGCG

AGCCGAGCCCGAAGACCATTACTTTCTGTTGGTTCGTCCGTATTCCCATCCATCCTTTCCGCTTTTAATTGCTAAAATTTCAGACAGAACCACCGC

TGAACACGCCGGAGAACCGCGAATTCACTGCCGAGATAATGTTCGAGTCGTTCAATGTGCCCGGCCTTTACATCGCTGTCCAGGCTCTGCTCGCCT

TGGCCGCTTCTTTGGCAAACCCGCGAGTTCAACCACCGTTCTCTGACTGG

FIG. 67

Sequence of pANDA35HK/arx-1 J15 (containing underlined antisense and sense fragment of arx-1 and shaded Gus linker)(SEQ ID NO:96)

CCAGTCAGAGAACGGTGGTTGAACTCGCGGGTTTGCCAAAGAAGCGGCCAAGGCGAGCAGAGCCTGGACAGCGATGTAAAGGCCGGGCACATTGAA
CGACTCGAACATTATCTCGGCAGTGAATTCGCGGTTCTCCGGCGTGTTCAGCGGTGGTTCTGTCTGAAATTTTAGCAATTAAAAGCGGAAAGGATG
GATGGGAATACGGACGAACCAACAGAAAGTAATGGTCTTCGGGCTCGGCTCGCAAATATTTGAAAATGCAATGCTCCCAAAAACGTTCCATTAGGT
CCCAATCGTCGACAATTCCATGTCGAATTGGATACTGAGAAAAGCATAATATACTTTGGGAATAGACAATAAAATGAGAAAAACAGAACCTTAACA
AAATAATTCGCAGCCGAAGGAGACAACGCCTCGTCACCGATGAAAAAGTCCAAGTCCGGGATTTTTCCGCCGACACTTTTCAAAATATTCGCATCT
TTGACAGCGATAGCCGACGGAATGATAAACTGTGGCTCCGAATTTCCTGCATAGCCAAGCTTTGTGTACCTTAAAAGAAAAATAAAACGCAAAAAG
CAGTAATTCTTAATTACCCGGTGCCACAATCAATTACAGCAGCTGGCAAAAATCGAATTCGGTACCGGATCCAGTCGACTGAATTGGTTCCCATGG
TGGAGCCTGCTTTTTTGTACAAACTTGTGATGACGGTATCGATAAGCTTGATATCTACCCGCTTCGCGTCGGCATCCGGTCAGTGGCAGTGAAGGG
CGAACAGTTCCTGATTAACCACAAACCGTTCTACTTTACTGGCTTTGGTCGTCATGAAGATGCGGACTTACGTGGCAAAGGATTCGATAACGTGCT
GATGGTGCACGACCACGCATTAATGGACTGGATTGGGGCCAACTCCTACCGTACCTCGCATTACCCTTACGCTGAAGAGATGCTCGACTGGGCAGA
TGAACATGGCATCGTGGTGATTGATGAAACTGCTGCTGTCGGCTTTAACCTCTCTTTAGGCATTGGTTTCGAAGCGGGCAACAAGCCGAAAGAACT
GTACAGCGAAGAGGCAGTCAACGGGGAAACTCAGCAAGCGCACTTACAGGCGATTAAAGAGCTGATAGCGCGTGACAAAAACCACCCAAGCGTGGT
GATGTGGAGTATTGCCAACGAACCGGATACCCGTCCGCAAGTGCACGGGAATATTTCGCCACTGGCGGAAGCAACGCGTAAACTCGACCCGACGCG
TCCGATCACCTGCGTCAATGTAATGTTCTGCGACGCTCACACCGATACCATCAGCGATCTCTTTGATGTGCTGTGCCTGAACCGTTATTACGGATG
GTATGTCCAAAGCGGCGATTTGGAAACGGCAGAGAAGGTACTGGAAAAAGAACTTCTGGCCTGGCAGGAGAAACTGCATCAGCCGATTATCATCAC
CGAATACGGCGTGGATACGTTAGCCGGGCTGCACTCAATGTACACCGACATGTGGAGTGAAGAGTATCAGTGTGCATGGCTGGATATGTATCACCG
CGTCTTTGATCGCGTCAGCGCCGTCGTCGGTGAACAGGTATGGAATTTCGCCGATTTTGCGACCTCGCAAGGCATATTGCGCGTTGGCGGTAACAA
GAAAGGGATCTTCACTCGATCGAATTCCTGCAGCCCGGGGGATCCACTAGATGCATGCTCGAGCGGCCGCCAGTGTGATGGATATCTGCAGAATTC
GCCCTTATCACAAGTTTGTACAAAAAAGCAGGCTCCACCATGGGAACCAATTCAGTCGACTGGATCCGGTACCGAATTCGATTTTTGCCAGCTGCT
GTAATTGATTGTGGCACCGGGTAATTAAGAATTACTGCTTTTTGCGTTTTATTTTTCTTTTAAGGTACACAAAGCTTGGCTATGCAGGAAATTCGG
AGCCACAGTTTATCATTCCGTCGGCTATCGCTGTCAAAGATGCGAATATTTTGAAAAGTGTCGGCGGAAAAATCCCGGACTTGGACTTTTTCATCG
GTGACGAGGCGTTGTCTCCTTCGGCTGCGAATTATTTTGTTAAGGTTCTGTTTTTCTCATTTTATTGTCTATTCCCAAAGTATATTATGCTTTTCT
CAGTATCCAATTCGACATGGAATTGTCGACGATTGGGACCTAATGGAACGTTTTTGGGAGCATTGCATTTTCAAATATTTGCGAGCCGAGCCCGAA
GACCATTACTTTCTGTTGGTTCGTCCGTATTCCCATCCATCCTTTCCGCTTTTAATTGCTAAAATTTCAGACAGAACCACCGCTGAACACGCCGGA
GAACCGCGAATTCACTGCCGAGATAATGTTCGAGTCGTTCAATGTGCCCGGCCTTTACATCGCTGTCCAGGCTCTGCTCGCCTTGGCCGCTTCTTT
GGCAAACCCGCGAGTTCAACCACCGTTCTCTGACTGG

FIG. 68

Actual sequence used for tbb-2 RNAi>J17 (exon)from cDNA (SEQ ID NO:97)

ACAACTCAATGCCGACCTTCGCAGACTTGCCGTTAACATGGTCCCCTTCCCGCGTCTGCACTTCTTCATGCCCGGCTTTGCGCCGCTTTCTGCGAA

GGGAGCGGCTGCATATCAAGCGTGTTCCGTGGCAGAACTGACCAAACAAATGTTCAACGCAAAGAACATGATGGCGGCGTGTGACCCGCGCCACGG

CCGTTATTTGACAGTTGCGGCAATGTTCCGTGGTCGAATGTCGATGAGGGAAGTGGATGACCAAATGATGTCGGTGCAGAACAAGAACTCCTCGTA

CTTCGTCGAATGGATTCCGAACAACGTGAAGACCGCTGTCTGTGACATTCCGCCCCGTGGCCTCAAAATGTCGGCAAACTTTCGTCGGAAA

FIG. 69

Sequence of pANDA35HK/tbb-2 J17 (containing underlined antisense and sense fragment of tbb-2 and shaded Gus linker)(SEQ ID NO:98)

TTTCCGACGAAAGTTTGCCGACATTTTGAGGCCACGGGGCGGAATGTCACAGACAGCGGTCTTCACGTTGTTCGGAATCCATTCGACGAAGTACGA
GGAGTTCTTGTTCTGCACCGACATCATTTGGTCATCCACTTCCCTCATCGACATTCGACCACGGAACATTGCCGCAACTGTCAAATAACGGCCGTG
GCGCGGGTCACACGCCGCCATCATGTTCTTTGCGTTGAACATTTGTTTGGTCAGTTCTGCCACGGAACACGCTTGATATGCAGCCGCTCCCTTCGC
AGAAAGCGGCGCAAAGCCGGGCATGAAGAAGTGCAGACGCGGGAAGGGGACCATGTTAACGGCAAGTCTGCGAAGGTCGGCATTGAGTTGTAATCG
AATTCGGTACCGGATCCAGTCGACTGAATTGGTTCCCATGGTGGAGCCTGCTTTTTTGTACAAACTTGTGATGACGGTATCGATAAGCTTGATATC
TACCCGCTTCGCGTCGGCATCCGGTCAGTGGCAGTGAAGGGCGAACAGTTCCTGATTAACCACAAACCGTTCTACTTTACTGGCTTTGGTCGTCAT
GAAGATGCGGACTTACGTGGCAAAGGATTCGATAACGTGCTGATGGTGCACGACCACGCATTAATGGACTGGATTGGGGCCAACTCCTACCGTACC
TCGCATTACCCTTACGCTGAAGAGATGCTCGACTGGGCAGATGAACATGGCATCGTGGTGATTGATGAAACTGCTGCTGTCGGCTTTAACCTCTCT
TTAGGCATTGGTTTCGAAGCGGGCAACAAGCCGAAAGAACTGTACAGCGAAGAGGCAGTCAACGGGGAAACTCAGCAAGCGCACTTACAGGCGATT
AAAGAGCTGATAGCGCGTGACAAAAACCACCCAAGCGTGGTGATGTGGAGTATTGCCAACGAACCGGATACCCGTCCGCAAGTGCACGGGAATATT
TCGCCACTGGCGGAAGCAACGCGTAAACTCGACCCGACGCGTCCGATCACCTGCGTCAATGTAATGTTCTGCGACGCTCACACCGATACCATCAGC
GATCTCTTTGATGTGCTGTGCCTGAACCGTTATTACGGATGGTATGTCCAAAGCGGCGATTTGGAAACGGCAGAGAAGGTACTGGAAAAAGAACTT
CTGGCCTGGCAGGAGAAACTGCATCAGCCGATTATCATCACCGAATACGGCGTGGATACGTTAGCCGGGCTGCACTCAATGTACACCGACATGTGG
AGTGAAGAGTATCAGTGTGCATGGCTGGATATGTATCACCGCGTCTTTGATCGCGTCAGCGCCGTCGTCGGTGAACAGGTATGGAATTTCGCCGAT
TTTGCGACCTCGCAAGGCATATTGCGCGTTGGCGGTAACAAGAAAGGGATCTTCACTCGATCGAATTCCTGCAGCCCGGGGGATCCACTAGATGCA
TGCTCGAGCGGCCGCCAGTGTGATGGATATCTGCAGAATTCGCCCTTATCACAAGTTTGTACAAAAAAGCAGGCTCCACCATGGGAACCAATTCAG
TCGACTGGATCCGGTACCGAATTCGATTACAACTCAATGCCGACCTTCGCAGACTTGCCGTTAACATGGTCCCCTTCCCGCGTCTGCACTTCTTCA
TGCCCGGCTTTGCGCCGCTTTCTGCGAAGGGAGCGGCTGCATATCAAGCGTGTTCCGTGGCAGAACTGACCAAACAAATGTTCAACGCAAAGAACA
TGATGGCGGCGTGTGACCCGCGCCACGGCCGTTATTTGACAGTTGCGGCAATGTTCCGTGGTCGAATGTCGATGAGGGAAGTGGATGACCAAATGA
TGTCGGTGCAGAACAAGAACTCCTCGTACTTCGTCGAATGGATTCCGAACAACGTGAAGACCGCTGTCTGTGACATTCCGCCCCGTGGCCTCAAAA
TGTCGGCAAACTTTCGTCGGAAA

FIG. 70

Sequence used for unc-26 RNAi>J20 (with introns) from gDNA (SEQ ID NO:99)

TCGTCCCCACCTACAAATTCGACCCGGGCACACACAATTGGGACACGAGGTGTTTTTAGGTGGCTAATAAAATACGTTTTACATACAATCACCCCC
TCCCCACCTTTCCCCTAATCGTTTGGTTTTTTAAACCATTTTTTGTTTTTGAGTGAAAAGAAGCGTGTGCCGGCGTGGTGCGACCGCATTTTGTAT
TGGGTCAAGGACAAAAATGTCGGCATTGAACAAGTGACCTACGAATCGGCACACCAAGGCAAGTGCGGATTTGGGAACAAAATGTTGGCGGAACAT
TCATAAATTCGGTGAAATTAAACCCATTTAGTTGTGCTCAGTGACCACAAACCGGTGCTGAGCACATTCAGAGTCCAAGTGAAGAAGGTGGACAGG
CCGAGAAGGAGCGCAATTTATGAGCAGGCAAAGAATTATTCAAATTGGCATTTGTTAATTAATGAATTACTTTTTTACAGTTGTTGAGGGAAGTGG
ACAAACGTCAAAATGAACTTTTGCCCCAAATTACATTGTCAAACACAGAAGTGAGTTGCATTTTTTTATTTCGGGTTTAATGTTGTGCAACATTAA
TTGTTGAACATTTTCACAACCGGTAAAACCATGGATTGGATATAGAGTTTTTCTCTGAGTATTTCCTGAGATATTCCGGAAAGACCCAATGATTTT
TTTCTTTTATTTCAAATTCAGGAAAACAATTTTTCTGGAAATATACAGAGAATTTAATTTCATTGTTACTAATACTTCGGGGTTGCAAAAAAGTGC
CTGATTTCTGTTTTTCCCCTTTGCAGTTCCATTTCGGCACCGTCCTCTTCGACCAGCCATCGTTGGCCGTGCTGACCATCACAAAACACTGGGACA
AAACGCCCACCCCATTTCAGCTTCAAACCCGCGGAGGCCCGAGGCTGACAGATTGAGATGGCTGACCATA

FIG. 71

Sequence in pANDA35HK/unc-26 J20 (containing underlined antisense and sense fragment of unc-26 and shaded Gus linker)(SEQ ID NO:100)

TATGGTCAGCCATCTCAATCTGTCAGCCTCGGGCCTCCGCGGGTTTGAAGCTGAAATGGGGTGGGCGTTTTGTCCCAGTGTTTTGTGATGGTCAGC

ACGGCCAACGATGGCTGGTCGAAGAGGACGGTGCCGAAATGGAACTGCAAAGGGGAAAAACAGAAATCAGGCACTTTTTTGCAACCCCGAAGTATT

AGTAACAATGAAATTAAATTCTCTGTATATTTCCAGAAAAATTGTTTTCCTGAATTTGAAATAAAAGAAAAAAATCATTGGGTCTTTCCGGAATAT

CTCAGGAAATACTCAGAGAAAAACTCTATATCCAATCCATGGTTTTACCGGTTGTGAAAATGTTCAACAATTAATGTTGCACAACATTAAACCCGA

AATAAAAAAATGCAACTCACTTCTGTGTTTGACAATGTAATTTGGGGCAAAAGTTCATTTTGACGTTTGTCCACTTCCCTCAACAACTGTAAAAAA

GTAATTCATTAATTAACAAATGCCAATTTGAATAATTCTTTGCCTGCTCATAAATTGCGCTCCTTCTCGGCCTGTCCACCTTCTTCACTTGGACTC

TGAATGTGCTCAGCACCGGTTTGTGGTCACTGAGCACAACTAAATGGGTTTAATTTCACCGAATTTATGAATGTTCCGCCAACATTTTGTTCCCAA

ATCCGCACTTGCCTTGGTGTGCCGATTCGTAGGTCACTTGTTCAATGCCGACATTTTTGTCCTTGACCCAATACAAAATGCGGTCGCACCACGCCG

GCACACGCTTCTTTTCACTCAAAAACAAAAAATGGTTTAAAAAACCAAACGATTAGGGGAAAGGTGGGGAGGGGGTGATTGTATGTAAAACGTATT

TTATTAGCCACCTAAAAACACCTCGTGTCCCAATTGTGTGTGCCCGGGTCGAATTTGTAGGTGGGGACGAAATCGAATTCGGTACCGGATCCAGTC

GACTGAATTGGTTCCCATGGTGGAGCCTGCTTTTTTGTACAAACTTGTGATGACGGTATCGATAAGCTTGATATCTACCCGCTTCGCGTCGGCATC

CGGTCAGTGGCAGTGAAGGGCGAACAGTTCCTGATTAACCACAAACCGTTCTACTTTACTGGCTTTGGTCGTCATGAAGATGCGGACTTACGTGGC

AAAGGATTCGATAACGTGCTGATGGTGCACGACCACGCATTAATGGACTGGATTGGGGCCAACTCCTACCGTACCTCGCATTACCCTTACGCTGAA

GAGATGCTCGACTGGGCAGATGAACATGGCATCGTGGTGATTGATGAAACTGCTGCTGTCGGCTTTAACCTCTCTTTAGGCATTGGTTTCGAAGCG

GGCAACAAGCCGAAAGAACTGTACAGCGAAGAGGCAGTCAACGGGGAAACTCAGCAAGCGCACTTACAGGCGATTAAAGAGCTGATAGCGCGTGAC

AAAAACCACCCAAGCGTGGTGATGTGGAGTATTGCCAACGAACCGGATACCCGTCCGCAAGTGCACGGGAATATTTCGCCACTGGCGGAAGCAACG

CGTAAACTCGACCCGACGCGTCCGATCACCTGCGTCAATGTAATGTTCTGCGACGCTCACACCGATACCATCAGCGATCTCTTTGATGTGCTGTGC

CTGAACCGTTATTACGGATGGTATGTCCAAAGCGGCGATTTGGAAACGGCAGAGAAGGTACTGGAAAAAGAACTTCTGGCCTGGCAGGAGAAACTG

CATCAGCCGATTATCATCACCGAATACGGCGTGGATACGTTAGCCGGGCTGCACTCAATGTACACCGACATGTGGAGTGAAGAGTATCAGTGTGCA

TGGCTGGATATGTATCACCGCGTCTTTGATCGCGTCAGCGCCGTCGTCGGTGAACAGGTATGGAATTTCGCCGATTTTGCGACCTCGCAAGGCATA

TTGCGCGTTGGCGGTAACAAGAAAGGGATCTTCACTCGATCGAATTCCTGCAGCCCGGGGGATCCACTAGATGCATGCTCGAGCGGCCGCCAGTGT

GATGGATATCTGCAGAATTCGCCCTTATCACAAGTTTGTACAAAAAAGCAGGCTCCACCATGGGAACCAATTCAGTCGACTGGATCCGGTACCGAA

TTCGATTTCGTCCCCACCTACAAATTCGACCCGGGCACACACAATTGGGACACGAGGTGTTTTTAGGTGGCTAATAAAATACGTTTTACATACAAT

CACCCCCTCCCCACCTTTCCCCTAATCGTTTGGTTTTTTAAACCATTTTTTGTTTTTGAGTGAAAAGAAGCGTGTGCCGGCGTGGTGCGACCGCAT

TTTGTATTGGGTCAAGGACAAAAATGTCGGCATTGAACAAGTGACCTACGAATCGGCACACCAAGGCAAGTGCGGATTTGGGAACAAAATGTTGGC

GGAACATTCATAAATTCGGTGAAATTAAACCCATTTAGTTGTGCTCAGTGACCACAAACCGGTGCTGAGCACATTCAGAGTCCAAGTGAAGAAGGT

GGACAGGCCGAGAAGGAGCGCAATTTATGAGCAGGCAAAGAATTATTCAAATTGGCATTTGTTAATTAATGAATTACTTTTTTACAGTTGTTGAGG

GAAGTGGACAAACGTCAAAATGAACTTTTGCCCCAAATTACATTGTCAAACACAGAAGTGAGTTGCATTTTTTTATTTCGGGTTTAATGTTGTGCA

ACATTAATTGTTGAACATTTTCACAACCGGTAAAACCATGGATTGGATATAGAGTTTTTCTCTGAGTATTTCCTGAGATATTCCGGAAAGACCCAA

TGATTTTTTTCTTTTATTTCAAATTCAGGAAAACAATTTTTCTGGAAATATACAGAGAATTTAATTTCATTGTTACTAATACTTCGGGGTTGCAAA

AAAGTGCCTGATTTCTGTTTTTCCCCTTTGCAGTTCCATTTCGGCACCGTCCTCTTCGACCAGCCATCGTTGGCCGTGCTGACCATCACAAAACAC

TGGGACAAAACGCCCACCCCATTTCAGCTTCAAACCCGCGGAGGCCCGAGGCTGACAGATTGAGATGGCTGACCATA

FIG. 72

Sequence used for prp-4 RNAi>J21 (exon)from cDNA (SEQ ID NO:101)

GAATCCCAGGTGAACAACATTTGCATTACGCCCGACGGTGCCCAACTGCTCGTCGGCGCATGGCAAAACATTCGTTTTTACGATTTGCAATGTCCA
ACCGCGCAAGGACTACACACATTTTCTGTCCATGAGAAAAATGTGACTTCGGTGGGCTTCCAAGTGGACGGTGCGTGGATGTACACGGGAGGGGAG
GATTGCATGGCCAAAATTTGGGATATGCGCAACAATCAGCTGAATTGCCAGAGGATATTCCAAGTGAACACGCCGGTGCACTCCGTTGTGCTGCAT
CCCAACCAAGTGGAGCTGATCGTTGCCGACTCCACCGGCGCCATTTATTTGTGGGATTTGCGCTCCGATCGGGACGATTCGCTGATCACCGAAGTG
GACATGCCCGAATTTGTTGTTCACGTTGACATTGACCAAGTGG

FIG. 73

Sequence in pANDA35HK/prp-4 J21 (containing underlined antisense and sense fragment of prp-4 and shaded Gus linker)(SEQ ID NO:102)

CCACTTGGTCAATGTCAACGTGAACAACAAATTCGGGCATGTCCACTTCGGTGATCAGCGAATCGTCCCGATCGGAGCGCAAATCCCACAAATAAA
TGGCGCCGGTGGAGTCGGCAACGATCAGCTCCACTTGGTTGGGATGCAGCACAACGGAGTGCACCGGCGTGTTCACTTGGAATATCCTCTGGCAAT
TCAGCTGATTGTTGCGCATATCCCAAATTTTGGCCATGCAATCCTCCCCTCCCGTGTACATCCACGCACCGTCCACTTGGAAGCCCACCGAAGTCA
CATTTTTCTCATGGACAGAAAATGTGTGTAGTCCTTGCGCGGTTGGACATTGCAAATCGTAAAAACGAATGTTTTGCCATGCGCCGACGAGCAGTT
GGGCACCGTCGGGCGTAATGCAAATGTTGTTCACCTGGGATTCAATCGAATTCGGTACCGGATCCAGTCGACTGAATTGGTTCCCATGGTGGAGCC
TGCTTTTTTGTACAAACTTGTGATGACGGTATCGATAAGCTTGATATCTACCCGCTTCGCGTCGGCATCCGGTCAGTGGCAGTGAAGGGCGAACAG
TTCCTGATTAACCACAAACCGTTCTACTTTACTGGCTTTGGTCGTCATGAAGATGCGGACTTACGTGGCAAAGGATTCGATAACGTGCTGATGGTG
CACGACCACGCATTAATGGACTGGATTGGGGCCAACTCCTACCGTACCTCGCATTACCCTTACGCTGAAGAGATGCTCGACTGGGCAGATGAACAT
GGCATCGTGGTGATTGATGAAACTGCTGCTGTCGGCTTTAACCTCTCTTTAGGCATTGGTTTCGAAGCGGGCAACAAGCCGAAAGAACTGTACAGC
GAAGAGGCAGTCAACGGGGAAACTCAGCAAGCGCACTTACAGGCGATTAAAGAGCTGATAGCGCGTGACAAAAACCACCCAAGCGTGGTGATGTGG
AGTATTGCCAACGAACCGGATACCCGTCCGCAAGTGCACGGGAATATTTCGCCACTGGCGGAAGCAACGCGTAAACTCGACCCGACGCGTCCGATC
ACCTGCGTCAATGTAATGTTCTGCGACGCTCACACCGATACCATCAGCGATCTCTTTGATGTGCTGTGCCTGAACCGTTATTACGGATGGTATGTC
CAAAGCGGCGATTTGGAAACGGCAGAGAAGGTACTGGAAAAAGAACTTCTGGCCTGGCAGGAGAAACTGCATCAGCCGATTATCATCACCGAATAC
GGCGTGGATACGTTAGCCGGGCTGCACTCAATGTACACCGACATGTGGAGTGAAGAGTATCAGTGTGCATGGCTGGATATGTATCACCGCGTCTTT
GATCGCGTCAGCGCCGTCGTCGGTGAACAGGTATGGAATTTCGCCGATTTTGCGACCTCGCAAGGCATATTGCGCGTTGGCGGTAACAAGAAAGGG
ATCTTCACTCGATCGAATTCCTGCAGCCCGGGGGATCCACTAGATGCATGCTCGAGCGGCCGCCAGTGTGATGGATATCTGCAGAATTCGCCCTTA
TCACAAGTTTGTACAAAAAAGCAGGCTCCACCATGGGAACCAATTCAGTCGACTGGATCCGGTACCGAATTCGATTGAATCCCAGGTGAACAACAT
TTGCATTACGCCCGACGGTGCCCAACTGCTCGTCGGCGCATGGCAAAACATTCGTTTTTACGATTTGCAATGTCCAACCGCGCAAGGACTACACAC
ATTTTCTGTCCATGAGAAAAATGTGACTTCGGTGGGCTTCCAAGTGGACGGTGCGTGGATGTACACGGGAGGGGAGGATTGCATGGCCAAAATTTG
GGATATGCGCAACAATCAGCTGAATTGCCAGAGGATATTCCAAGTGAACACGCCGGTGCACTCCGTTGTGCTGCATCCCAACCAAGTGGAGCTGAT
CGTTGCCGACTCCACCGGCGCCATTTATTTGTGGGATTTGCGCTCCGATCGGGACGATTCGCTGATCACCGAAGTGGACATGCCCGAATTTGTTGT
TCACGTTGACATTGACCAAGTGG

FIG. 74

Sequence used for pfn-1 RNAi>J23 (exon) from cDNA (SEQ ID NO:103)

CTTCCAGTTGTGCGGAGATTACTCGCGTGGCCATAATTGGCAATTCGGACGCGAGTGTTTGGGCCAGGACTGAAGGGGAGAACGAATTCAAGGCGA
GTGAGCCTGAGCTCAAGAAACTTGTCGGCCAATTCGATGATCTTTCGCAAGTTCCGTCCGTCGGTGCCGACCTCGAGGGAATTCATTACATTGTGC
CGCGAACGGATGAAAATCTTATCTTTGGGAAGAGGGACAAAACGGGCTTTTTCGCTGTGAAGACCAAGTCCGCCATTCTGATCGCCATTTACAAAG
ACGAGGAAAGTGTCGTCGGCGCCGACGTGCGAGGGGCGGTGGAGAAAATGGCCAAATACCTTGAGGACGCCGGTTACTGAGCCGTTGCTCGGTTTC
CTAAACGACTTTTGTGTTGCCAAACGAAAAAGTGCTGAGAATGGCTTTGACTTATTCTTCCAAATGCACTCCTTTTCC

FIG. 75

Sequence in pANDA35HK/pfn-1 J23 (containing underlined antisense and sense fragment of pfn-1 and shaded Gus linker)(SEQ ID NO:104)

GGAAAAGGAGTGCATTTGGAAGAATAAGTCAAAGCCATTCTCAGCACTTTTTCGTTTGGCAACACAAAAGTCGTTTAGGAAACCGAGCAACGGCTC
AGTAACCGGCGTCCTCAAGGTATTTGGCCATTTTCTCCACCGCCCCTCGCACGTCGGCGCCGACGACACTTTCCTCGTCTTTGTAAATGGCGATCA
GAATGGCGGACTTGGTCTTCACAGCGAAAAAGCCCGTTTTGTCCCTCTTCCCAAAGATAAGATTTTCATCCGTTCGCGGCACAATGTAATGAATTC
CCTCGAGGTCGGCACCGACGGACGGAACTTGCGAAAGATCATCGAATTGGCCGACAAGTTTCTTGAGCTCAGGCTCACTCGCCTTGAATTCGTTCT
CCCCTTCAGTCCTGGCCCAAACACTCGCGTCCGAATTGCCAATTATGGCCACGCGAGTAATCTCCGCACAACTGGAAGAATCGAATTCGGTACCGG
ATCCAGTCGACTGAATTGGTTCCCATGGTGGAGCCTGCTTTTTTGTACAAACTTGTGATGACGGTATCGATAAGCTTGATATCTACCCGCTTCGCG
TCGGCATCCGGTCAGTGGCAGTGAAGGGCGAACAGTTCCTGATTAACCACAAACCGTTCTACTTTACTGGCTTTGGTCGTCATGAAGATGCGGACT
TACGTGGCAAAGGATTCGATAACGTGCTGATGGTGCACGACCACGCATTAATGGACTGGATTGGGGCCAACTCCTACCGTACCTCGCATTACCCTT
ACGCTGAAGAGATGCTCGACTGGGCAGATGAACATGGCATCGTGGTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAACGGGGAAACTCAGCAAGCGCACTTACAGGCGATTAAAGAGCTGATAG
CGCGTGACAAAAACCACCCAAGCGTGGTGATGTGGAGTATTGCCAACGAACCGGATACCCGTCCGCAAGTGCACGGGAATATTTCGCCACTGGCGG
AAGCAACGCGTAAACTCGACCCGACGCGTCCGATCACCTGCGTCAATGTAATGTTCTGCGACGCTCACACCGATACCATCAGCGATCTCTTTGATG
TGCTGTGCCTGAACCGTTATTACGGATGGTATGTCCAAAGCGGCGATTTGGAAACGGCAGAGAAGGTACTGGAAAAAGAACTTCTGGCCTGGCAGG
AGAAACTGCATCAGCCGATTATCATCACCGAATACGGCGTGGATACGTTAGCCGGGCTGCACTCAATGTACACCGACATGTGGAGTGAAGAGTATC
AGTGTGCATGGCTGGATATGTATCACCGCGTCTTTGATCGCGTCAGCGCCGTCGTCGGTGAACAGGTATGGAATTTCGCCGATTTTGCGACCTCGC
AAGGCATATTGCGCGTTGGCGGTAACAAGAAAGGGATCTTCACTCGATCGAATTCCTGCAGCCCGGGGGATCCACTAGATGCATGCTCGAGCGGCC
GCCAGTGTGATGGATATCTGCAGAATTCGCCCTTATCACAAGTTTGTACAAAAAAGCAGGCTCCACCATGGGAACCAATTCAGTCGACTGGATCCG
GTACCGAATTCGATTCTTCCAGTTGTGCGGAGATTACTCGCGTGGCCATAATTGGCAATTCGGACGCGAGTGTTTGGGCCAGGACTGAAGGGGAGA
ACGAATTCAAGGCGAGTGAGCCTGAGCTCAAGAAACTTGTCGGCCAATTCGATGATCTTTCGCAAGTTCCGTCCGTCGGTGCCGACCTCGAGGGAA
TTCATTACATTGTGCCGCGAACGGATGAAAATCTTATCTTTGGGAAGAGGGACAAAACGGGCTTTTTCGCTGTGAAGACCAAGTCCGCCATTCTGA
TCGCCATTTACAAAGACGAGGAAAGTGTCGTCGGCGCCGACGTGCGAGGGGCGGTGGAGAAAATGGCCAAATACCTTGAGGACGCCGGTTACTGAG
CCGTTGCTCGGTTTCCTAAACGACTTTTGTGTTGCCAAACGAAAAAGTGCTGAGAATGGCTTTGACTTATTCTTCCAAATGCACTCCTTTTCC

FIG. 76

Sequence used for vbh-1 RNAi>J7 (with introns)from gDNA (SEQ ID NO:105)

TTGGGTCCACCTCTGAGAACATCGGTCAAAAAGTTGTTTGGGTTGAAGAGGTATAAACAGTTAAAACAAAGACCACAAATAGTGCATATTTCGAGT

TTTGCCTTCGTTTTAGCACAACAAACGCCATTTCCTGATGGATTTGCTCGATGCCAGTGAGCCCGAGGCACTAACACTGATTTTCGTTGAAACCAA

ACGCGGCTGTGGAGATGTAAAATGCATTCCATGAAATCTCACAATTTGGCCTTTTAAGCTGAGTTACATGCTCCAGCAAGAAGGCTACCATTGCGT

AGCAATCCATGGCGATTTGAAGCAGATGGAACGCGAGCGTCATTTGGAGAACTTCCGCAACGGAACGGCACCCATTTTGGTGGCAACAGCGGTTGC

CGCCCGTGGGTTGGACATTCCGAATGTCAAGCACGTGATCAATTATGACCTACCGGTGGGTGAATTTTAATCTGTTTTATGCCATTTTAAATAAAG

AATGACATCGATGAATACGTGCACCGAATTGGCAGAACCGGCCGTGTGGGCAACATTGGTCCGTTCCCATTTTAGTTAAGGTTTGTAAATGGTATA

TTTAGGAATGGCCACTAGCTTTTTCAACGACAAAAACCGGAACATTT

FIG. 77

Sequence in pANDA35HK/vbh-1 J7 (containing underlined antisense and sense fragment of vbh-1 and shaded Gus linker)(SEQ ID NO:106)

AAATGTTCCGGTTTTTGTCGTTGAAAAAGCTAGTGGCCATTCCTAAATATACCATTTACAAACCTTAACTAAAATGGGAACGGACCAATGTTGCCC

ACACGGCCGGTTCTGCCAATTCGGTGCACGTATTCATCGATGTCATTCTTTATTTAAAATGGCATAAAACAGATTAAAATTCACCCACCGGTAGGT

CATAATTGATCACGTGCTTGACATTCGGAATGTCCAACCCACGGGCGGCAACCGCTGTTGCCACCAAAATGGGTGCCGTTCCGTTGCGGAAGTTCT

CCAAATGACGCTCGCGTTCCATCTGCTTCAAATCGCCATGGATTGCTACGCAATGGTAGCCTTCTTGCTGGAGCATGTAACTCAGCTTAAAAGGCC

AAATTGTGAGATTTCATGGAATGCATTTTACATCTCCACAGCCGCGTTTGGTTTCAACGAAAATCAGTGTTAGTGCCTCGGGCTCACTGGCATCGA

GCAAATCCATCAGGAAATGGCGTTTGTTGTGCTAAAACGAAGGCAAAACTCGAAATATGCACTATTTGTGGTCTTTGTTTTAACTGTTTATACCTC

TTCAACCCAAACAACTTTTTGACCGATGTTCTCAGAGGTGGACCCAAAATCGAATTCGGTACCGGATCCAGTCGACTGAATTGGTTCCCATGGTGG

AGCCTGCTTTTTTGTACAAACTTGTGATGACGGTATCGATAAGCTTGATATCTACCCGCTTCGCGTCGGCATCCGGTCAGTGGCAGTGAAGGGCGA

ACAGTTCCTGATTAACCACAAACCGTTCTACTTTACTGGCTTTGGTCGTCATGAAGATGCGGACTTACGTGGCAAAGGATTCGATAACGTGCTGAT

GGTGCACGACCACGCATTAATGGACTGGATTGGGGCCAACTCCTACCGTACCTCGCATTACCCTTACGCTGAAGAGATGCTCGACTGGGCAGATGA

ACATGGCATCGTGGTGATTGATGAAACTGCTGCTGTCGGCTTTAACCTCTCTTTAGGCATTGGTTTCGAAGCGGGCAACAAGCCGAAAGAACTGTA

CAGCGAAGAGGCAGTCAACGGGGAAACTCAGCAAGCGCACTTACAGGCGATTAAAGAGCTGATAGCGCGTGACAAAAACCACCCAAGCGTGGTGAT

GTGGAGTATTGCCAACGAACCGGATACCCGTCCGCAAGTGCACGGGAATATTTCGCCACTGGCGGAAGCAACGCGTAAACTCGACCCGACGCGTCC

GATCACCTGCGTCAATGTAATGTTCTGCGACGCTCACACCGATACCATCAGCGATCTCTTTGATGTGCTGTGCCTGAACCGTTATTACGGATGGTA

TGTCCAAAGCGGCGATTTGGAAACGGCAGAGAAGGTACTGGAAAAAGAACTTCTGGCCTGGCAGGAGAAACTGCATCAGCCGATTATCATCACCGA

ATACGGCGTGGATACGTTAGCCGGGCTGCACTCAATGTACACCGACATGTGGAGTGAAGAGTATCAGTGTGCATGGCTGGATATGTATCACCGCGT

CTTTGATCGCGTCAGCGCCGTCGTCGGTGAACAGGTATGGAATTTCGCCGATTTTGCGACCTCGCAAGGCATATTGCGCGTTGGCGGTAACAAGAA

AGGGATCTTCACTCGATCGAATTCCTGCAGCCCGGGGGATCCACTAGATGCATGCTCGAGCGGCCGCCAGTGTGATGGATATCTGCAGAATTCGCC

CTTATCACAAGTTTGTACAAAAAAGCAGGCTCCACCATGGGAACCAATTCAGTCGACTGGATCCGGTACCGAATTCGATTTTGGGTCCACCTCTGA

GAACATCGGTCAAAAAGTTGTTTGGGTTGAAGAGGTATAAACAGTTAAAACAAAGACCACAAATAGTGCATATTTCGAGTTTTGCCTTCGTTTTAG

CACAACAAACGCCATTTCCTGATGGATTTGCTCGATGCCAGTGAGCCCGAGGCACTAACACTGATTTTCGTTGAAACCAAACGCGGCTGTGGAGAT

GTAAAATGCATTCCATGAAATCTCACAATTTGGCCTTTTAAGCTGAGTTACATGCTCCAGCAAGAAGGCTACCATTGCGTAGCAATCCATGGCGAT

TTGAAGCAGATGGAACGCGAGCGTCATTTGGAGAACTTCCGCAACGGAACGGCACCCATTTTGGTGGCAACAGCGGTTGCCGCCCGTGGGTTGGAC

ATTCCGAATGTCAAGCACGTGATCAATTATGACCTACCGGTGGGTGAATTTTAATCTGTTTTATGCCATTTTAAATAAAGAATGACATCGATGAAT

ACGTGCACCGAATTGGCAGAACCGGCCGTGTGGGCAACATTGGTCCGTTCCCATTTTAGTTAAGGTTTGTAAATGGTATATTTAGGAATGGCCACT

AGCTTTTTCAACGACAAAAACCGGAACATTT

COMPOSITIONS AND METHODS FOR CONTROLLING PARASITIC NEMATODES

CROSS-REFERENCE TO RELATED APPLICATIONS

This application is a U.S. §371 national phase entry of pending International Patent Application No. PCT/US2010/056358, international filing date Nov. 11, 2010, which claims the benefit of U.S. Provisional Application 61/260,248, filed Nov. 11, 2009, the entire contents of which are incorporated herein by reference.

STATEMENT REGARDING FEDERALLY SPONSORED RESEARCH OR DEVELOPMENT

This invention was made with U.S. Government support under grant number 2004-3560714970 awarded by the United States Department of Agriculture. The Government has certain rights to the invention.

FIELD OF THE INVENTION

The present invention relates to compositions and methods for controlling nematode infestation of plants or animals. In particular, the present invention provides vectors comprising sequences designed to control nematodes by RNA interference (RNAi) and transgenic plants transformed with such vectors.

BACKGROUND OF THE INVENTION

*Glycine max* (L.) Merr. (soybean) is the second largest crop in the United Sates, with an estimated annual value of 11 billion dollars. Plant parasites such as the *Heterodera glycines* Ichinohe and *Meloidogyne* spp. cause significant damage to soybean, with diseased plants exhibiting symptoms ranging from stunting, chlorosis and wilting to enhanced susceptibility to other diseases. Recent estimates of annual production losses by the *H. glycines*, the most damaging soybean pest, range from $460 million to 818 million for the US alone (Wrather and Koenning 2006). Nematicides, crop rotation and resistant varieties represent the current options for *H. glycines* management; however, each has serious limitations. Nematicides, including organophosphate and carbamate compounds, are extremely toxic and increase production costs. Crop rotation can require prolonged intervals without a host crop to be effective. Resistant cultivars have a narrow genetic base, while *H. glycines* populations display broad genetic diversity leading to frequent virulence selection (Dong et al. 1997). Many populations of *H. glycines*, for instance, are now able to reproduce on soybean cultivars derived from PI88788, the most widely used source of *H. glycines* resistance in the USA (Mitchum et al. 2007; Hershman et al. 2008). It is therefore imperative that new strategies for *H. glycines* control be explored to complement existing approaches.

Genetic engineering represents one promising approach to *H. glycines* management, but improving nematode resistance in plants through this method requires increased knowledge of potential target genes. The search for novel targets for genetically engineered resistance to *H. glycines* has led to intense study of the secretions of subventral and dorsal esophageal gland cells of the nematode, as they play important roles in the host-parasite interaction. As a result of these studies, genes encoding secreted proteins of *H. glycines* have been identified, including genes encoding polygalacturonase (Mahalingam et al. 1999) and chorismate mutase (Bekal et al. 2003). Numerous additional putative *H. glycines* parasitism genes have been identified using microarray analysis (Klink et al. 2007; Ithal et al. 2007; Klink et al. 2009a, b). Although the functions of many of these genes remain to be investigated, Alkharouf et al. (2007) and Klink et al. (2009c) have identified specific genes involved in female development by knocking out these genes' functions in vitro and in vivo, respectively.

RNA interference (RNAi) is a potentially powerful gene-silencing tool for analysis of gene function. The mechanism of RNAi was first identified in the free-living nematode *Caenorhabditis elegans*, in which the expression of unc22 gene was suppressed via the RNAi pathway (Fire et al. 1998). During this process, long double-stranded RNA is processed into 21-23 nucleotide siRNAs by Dicer, a member of the RNase family (Bernstein et al. 2001). The DCR-2/R2D2 complex binds to siRNAs and enhances sequence-specific messenger RNA degradation mediated by the RNA-initiated silencing complex (Liu et al. 2003). This pathway recently has shown promise as the basis of a novel control strategy for plant-parasitic nematodes, with numerous independent studies demonstrating suppression of target nematode populations following soaking nematodes in dsRNA solutions (Urwin et al. 2002; Bakhetia et al. 2005; Huang et al. 2006; Alkharouf et al. 2007) and, more importantly, using in planta transgenic systems expressing dsRNA fragments of nematode genes (Huang et al. 2006; Steeves et al. 2006; Yadav et al. 2006; Sindhu et al. 2009). Yadav et al. (2006) reported that RNAi was induced by using dsRNA fragments of two genes encoding an integrase and a splicing factor in the plant-parasitic nematode *M. incognita*, leading to protection against nematode infection in tobacco. The expression of root-knot nematode parasitism gene 16D10 dsRNA in transgenic *Arabidopsis* resulted in resistance against four major root knot nematode species (Huang et al. 2006), while Sindhu et al. (2009) obtained reductions in *H. schachtii* females ranging from 23 to 64% in transgenic *Arabidopsis* lines expressing RNAi constructs of four parasitism genes. RNA interference appears to be similarly effective against *H. glycines* in transformed soybean lines. Steeves et al. (2006) successfully produced transgenic soybean lines using this RNAi strategy targeting a major sperm protein of *H. glycines*. Bioassay data indicated transgenic plants had up to a 68% reduction in eggs $g^{-1}$ root tissue. The effects of plant-derived dsRNA molecules appeared to continue into the next generation.

Targets for host-delivered RNAi suppression of plant parasitic nematodes can be selected based on known RNAi effects on corresponding *C. elegans* genes. Alkharouf et al. (2007), for instance, used bioinformatics to yield 1,508 candidate *H. glycines* genes whose homologous genes of *C. elegans* have lethal phenotypes when silenced in *C. elegans*. They also reported in vitro silencing a conserved ribosomal gene from *H. glycines* (Hg-rps-23) resulted in dead and dying worms as shown by positive Sytox fluorescence. Klink et al. (2009c) used microarray analysis to demonstrate that 32 of 150 conserved *H. glycines* homologues of *C. elegans* genes with lethal phenotypes were induced during feeding site establishment, and subsequently inhibited female development by engineering transgenic soybean plants with tandem inverted repeats of selected homologs.

Novel approaches to SCN management are needed to complement current strategies, and prolong the effectiveness of available resistance genes.

SUMMARY OF THE INVENTION

The present invention relates to compositions and methods for controlling nematode infestation of plants. In particular, the present invention provides vectors comprising sequences designed to control nematodes by RNA interference (RNAi) and transgenic plants transformed with such vectors.

In some embodiments, the present invention provides transgenic plants comprising a first exogenous nucleic acid sequence having a sense sequence linked to its complementary antisense sequence and encoding a double stranded RNA that inhibits expression of a target pest gene (i.e., an RNAi construct) and a second exogenous sequence encoding at least a portion of said target pest gene. In some embodiments, the first exogenous nucleic acid sequence forms a hairpin structure when expressed. In some embodiments, the second exogenous sequence is expressed as an antisense RNA sequence. In some embodiments, the exogenous sequence is expressed as a sense RNA sequence. In some embodiments, the first exogenous sequence and said second exogenous sequence are present on the same vector. In some embodiments, the transgenic plant is a monocot or eudicot. In some embodiments, the transgenic plant is a crop, cereal, fruit, vegetable, or horticultural plant. In some embodiments, the sense and antisense sequences that form the RNAi construct correspond to a sequence derived from a gene selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the RNAi constructs comprise SEQ ID NOs:60-77, 90, 92, 94, 96, 98, 100, 102, 104, 106 and 108 and sequences at least 80%, 85%, 90%, 95%, or 99% identical thereto. In some embodiments, the target RNA molecule is selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the second exogenous sequence corresponds to a sequence derived from a gene selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the second exogenous sequence corresponds to a sequence derived from a gene selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto.

In some embodiments, the present invention provides systems for controlling a plant pest comprising at least one vector comprising a first exogenous nucleic acid sequence having a sense sequence linked to its complementary antisense sequence and encoding a double stranded RNA that inhibits expression of a target pest gene (i.e., an RNAi construct) and a second exogenous sequence encoding at least a portion of said target pest gene. In some embodiments, the sense and antisense sequences that form the RNAi construct correspond to a sequence derived from a gene selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the RNAi constructs comprise SEQ ID NOs:60-77, 90, 92, 94, 96, 98, 100, 102, 104, 106 and 108 and sequences at least 80%, 85%, 90%, 95%, or 99% identical thereto. In some embodiments, the target RNA molecule is selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the second exogenous sequence corresponds to a sequence derived from a gene selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the second exogenous sequence corresponds to a sequence derived from a gene selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the first exogenous sequence and said second exogenous sequence are present on the same vector. In some embodiments, the first exogenous sequence and the second exogenous sequence are on separate vectors. In some embodiments, the systems comprise vectors with RNAi constructs that target two or more pest target sequences and vectors that express sense or antisense sequences of the two or more pest target sequences. In some embodiments, the RNAi constructs are stacked constructs as described in more detail herein.

In some embodiments, the present invention provides methods of reducing damage due to pests comprising cultivating a transgenic plant comprising the system described above.

In some embodiments, the present invention provides a transgenic plant comprising a nucleic acid sequence having at least two sense sequences from at least two different target pest genes linked to at least two antisense sequences from said at least two different target pest genes so that said nucleic acid sequence encodes a double stranded RNA that inhibits expression of said at least two target pest genes. In some embodiments, the at least two target pest genes are selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the at least two target pest genes are selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto.

In some embodiments, the present invention provides a vector comprising a nucleic acid sequence having at least two sense sequences from at least two different target pest genes linked to at least two antisense sequences from said at least two different target pest genes so that said nucleic acid sequence encodes a double stranded RNA that inhibits expression of said at least two target pest genes. In some embodiments, the vectors comprise additional exogenous sequences encoding at least a portion of said at least two target pest genes. In some embodiments, the at least two target pest genes are selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the at least two target pest genes are selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto.

In some embodiments, the present invention provides methods of reducing damage due to pests comprising: cultivating a transgenic plant comprising the vectors described above.

In some embodiments, the present invention provides a transgenic plant comprising a first exogenous nucleic acid sequence having a sense sequence linked to its complementary antisense sequence and encoding a double stranded RNA that inhibits expression of a target gene, wherein said target gene is selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the target RNA molecule is at least 80%, 85%, 90%, 95% or 99% identical to a Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1 sequence. In some embodiments, the target RNA molecule is selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the sense and antisense strands in the double stranded RNA are linked by a linker sequence. In some embodiments, the linker sequence is a Gus linker.

In some embodiments, the present invention provides vectors comprising a first exogenous nucleic acid sequence having a sense sequence linked to its complementary antisense sequence and encoding a double stranded RNA that inhibits expression of a target gene, wherein said target gene is selected from the group consisting of Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the target RNA molecule is at least 80%, 85%, 90%, 95% or 99% identical to a Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1 sequence. In some embodiments, the target RNA molecule is selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the sense and antisense strands in the double stranded RNA are linked by a linker sequence. In some embodiments, the linker sequence is a Gus linker.

In some embodiments, the present invention provides methods of reducing damage due to pests comprising: cultivating a transgenic plant comprising a vector as described above.

In some embodiments, the present invention provides compositions comprising a part of a transgenic plant as described above. In some embodiments, the plant part is a seed, stem, leave, shoot, root or branch or combinations thereof. In some embodiments, the plant part is provided in an animal feed. In some embodiments, the seed are treated with a coating that reduces fungal infection or enhances germination.

DESCRIPTION OF THE FIGURES

FIG. 12. Partial nucleic acid sequence for Y25 of *Heterodera glycines* (HM369132) (SEQ ID NO:1).

FIG. 13. Partial nucleic acid sequence for Arx-3 of *Heterodera glycines* (CD748919) (SEQ ID NO:2).

FIG. 14. Partial nucleic acid sequence for Cpn-1 of *Heterodera glycines* (GU074018) (SEQ ID NO:3)

FIG. 15. Full length nucleic acid sequence for Prp-17 of *Heterodera glycines* (AF113915) (SEQ ID NO:4).

FIG. 16. Partial nucleic acid sequence for Rnr-1 of *Heterodera glycines* (CD749124) (SEQ ID NO:5).

FIG. 17. Partial nucleic acid sequence for Fib-1 of *Heterodera glycines* (CB279515) (SEQ ID NO:6).

FIG. 18. Partial nucleic acid sequence for Asb-1 of *Heterodera glycines* (BI396626) (SEQ ID NO:7).

FIG. 19. Partial nucleic acid sequence for Rpt-1 of *Heterodera glycines* (CB376265) (SEQ ID NO:8).

FIG. 20. Partial nucleic acid sequence for F-55 of *Heterodera glycines* (CA940536) (SEQ ID NO:9).

FIG. 21. Partial nucleic acid sequence for Eat-3 of *Heterodera glycines* (CB375718) (SEQ ID NO:10).

FIG. 22. Partial nucleic acid sequence for Vap-2 of *Heterodera glycines* (AY033601) (SEQ ID NO:11).

FIG. 23. Partial nucleic acid sequence for Y25 of *Pratylenchus neglectus* (SEQ ID NO:12).

FIG. 24. Partial nucleic acid sequence for Rnr-1 of *Pratylenchus neglectus* (SEQ ID NO:13).

FIG. 25. Partial nucleic acid sequence for Y25 of *Radopholus similis* (SEQ ID NO:14).

FIG. 26. Partial nucleic acid sequence for Rnr-1 of *Radopholus similis* (SEQ ID NO:15).

FIG. 27. Partial nucleic acid sequence for Rnr-1 of *Rotylenchulus reniformis* (SEQ ID NO:16).

FIG. 29. Partial nucleic acid sequence for Cdk-1 (J12), *H. glycines*, (SEQ ID NO: 51).

FIG. 30. Partial nucleic acid sequence for Fzy-1 (J13), *H. glycines*, (SEQ ID NO: 52).

FIG. 31. Partial nucleic acid sequence for Tba-2 (J14), *H. glycines*, (SEQ ID NO: 53).

FIG. 32. Partial nucleic acid sequence for Arx-1 (J15), *H. glycines*, (SEQ ID NO: 54).

FIG. 33. Partial nucleic acid sequence for Tbb-2 (J17), *H. glycines*, (SEQ ID NO: 55).

FIG. 34. Partial nucleic acid sequence for Unc-26 (J20), *H. glycines*, (SEQ ID NO: 56).

FIG. 35. Partial nucleic acid sequence for Prp-4 (J21), *H. glycines*, (SEQ ID NO: 57).

FIG. 36. Partial nucleic acid sequence for Pfn-1 (J23), *H. glycines*, (SEQ ID NO: 58).

FIG. 37. Partial nucleic acid sequence for Vbh-1 (J7), *H. glycines*, (SEQ ID NO: 59).

FIG. 38. RNAi construct sequence (containing underlined antisense fragment of Y25, shaded Gus linker and sense fragment of Y25) (SEQ ID NO:108).

FIG. 39. RNAi construct sequence (containing underlined antisense fragment of Arx-3, shaded Gus linker and sense fragment of Arx-3) (SEQ ID NO:60).

FIG. 40. RNAi construct sequence (containing underlined antisense fragment of Cpn-1, shaded Gus linker and sense fragment of Cpn-1) (SEQ ID NO:61).

FIG. 41. RNAi construct sequence (containing underlined antisense fragment of Prp-17, shaded Gus linker and sense fragment of Prp-17) (SEQ ID NO:62).

FIG. 42. RNAi construct sequence (containing underlined antisense fragment of Rnr-1, shaded Gus linker and sense fragment of Rnr-1) (SEQ ID NO:63).

FIG. 43. RNAi construct sequence (containing underlined antisense fragment of Fib-1, shaded Gus linker and sense fragment of Fib-1) (SEQ ID NO:64).

FIG. 44. RNAi construct sequence (containing underlined antisense fragment of Rpt-1, shaded Gus linker and sense fragment of Rpt-1) (SEQ ID NO:65).

FIG. 45. RNAi construct sequence (containing underlined sense fragment of F-55, shaded Gus linker and antisense fragment of F-55) (SEQ ID NO:66).

FIG. 46. RNAi construct sequence (containing underlined sense fragment of Eat-3, shaded Gus linker and antisense fragment of Eat-3) (SEQ ID NO:67).

FIG. 47. RNAi construct sequence (containing underlined sense fragment of Vap-2, shaded Gus linker and antisense fragment of Vap-2) (SEQ ID NO:68).

FIG. 48. RNAi construct sequence (containing underlined sense fragment of Asb-1, shaded Gus linker and antisense fragment of Asb-1) (SEQ ID NO:69).

FIG. 49. RNAi construct sequence, Y25 of *Pratylenchus neglectus*, (containing underlined sense fragment of Y25, shaded Gus linker and antisense fragment of Y25) (SEQ ID NO:70).

FIG. 50. RNAi construct sequence, Rnr-1 of *Pratylenchus neglectus*, (containing underlined sense fragment of Rnr-1, shaded Gus linker and antisense fragment of Rnr-1) (SEQ ID NO:71).

FIG. 51. RNAi construct sequence, Y25 of *Radopholus similis*, (containing underlined sense fragment of Y25, shaded Gus linker and antisense fragment of Y25) (SEQ ID NO:72).

FIG. 52. RNAi construct sequence, Rnr-1 of *Radopholus similis*, (containing underlined sense fragment of Rnr-1, shaded Gus linker and antisense fragment of Rnr-1) (SEQ ID NO:73).

FIG. 53. RNAi construct sequence, Rnr-1 of *Rotylenchulus reniformis*, (containing underlined sense fragment of Rnr-1, shaded Gus linker and antisense fragment of Rnr-1) (SEQ ID NO:74).

FIG. 54. RNAi construct sequence of Y25-Prp-17 (containing underlined sense fragment of Y25-Prp-17, shaded Gus linker and antisense fragment of Y25-Prp-17) (SEQ ID NO:75).

FIG. 55. RNAi construct sequence of Y25-Cpn-1 (containing underlined sense fragment of Y25-Cpn-1, shaded Gus linker and antisense fragment of Y25-Cpn-1) (SEQ ID NO:76).

FIG. 56. RNAi construct sequence of Cpn-Rnr-1 (containing underlined antisense fragment of Cpn-Rnr-1, shaded Gus linker and sense fragment of Cpn-Rnr-1) (SEQ ID NO:77).

FIG. 57. Schematic depiction of vectors for overexpression of target sequence with target siRNA.

FIG. 58. Y25 gene fragment used for over-expressing in pPTN289 vector (SEQ ID NO:78).

FIGS. 59A and 59B. Sequence comparison of Hg25 and HgRnr-1 genes among three different *Heterodera glycines* populations and *Radopholus similis*, root 1. The Y25 fragments (291 bp) and Rnr-1 (251 bp) from *H. glycines* (Hg) race 1, race 3, race 4 and *Radopholus similis* (RS) (SEQ ID NO:79, SEQ ID NO:80, SEQ ID NO:81, SEQ ID NO:82, SEQ ID NO:83, SEQ ID NO:84, SEQ ID NO:85, SEQ ID NO:86, respectively; consensus sequences SEQ ID NO:87 and SEQ ID NO:88, respectively, and Lesion Rnr-1 sequences SEQ ID NO:109 and 110, respectively), root lesion nematode *Pratylenchus neglectus* (lesion) were amplified using specific primers by PCR method. PCR products were cloned into pGEM-T easy vector, and sequenced by T7 primer. DNAman software was performed to compare the sequence difference.

FIG. 60. Actual sequence used for cdk-1 RNAi>J12 (exons) sequenced from cDNA (SEQ ID NO:89).

FIG. 61. Sequence of pANDA35HK/cdk-1 J12 RNAi construct sequence (containing underlined antisense and sense fragment of cdk-1 and shaded Gus linker) (SEQ ID NO:90).

FIG. 62. Actual sequence used for Fzy-1 RNAi>J13 (with introns) sequenced from gDNA (SEQ ID NO:91).

FIG. 63. Sequence of pANDA35HK/fzy-1 J13 (containing underlined antisense and sense fragment of fzy-1 and shaded Gus linker) (SEQ ID NO:92).

FIG. 64. Actual sequence used for tba-2 RNAi>J14 (with introns) sequenced from gDNA (SEQ ID NO:93).

FIG. 65. Sequence of pANDA35HK/tba-2 J14 (containing underlined antisense and sense fragment of tba-1 and shaded Gus linker) (SEQ ID NO:94).

FIG. 66. Sequence used for arx-1 RNAi>J15 (with introns) sequenced from gDNA (SEQ ID NO:95).

FIG. 67. Sequence of pANDA35HK/arx-1 J15 (containing underlined antisense and sense fragment of arx-1 and shaded Gus linker) (SEQ ID NO:96).

FIG. 68. Actual sequence used for tbb-2 RNAi>J17 (exon) from cDNA (SEQ ID NO:97).

FIG. 69. Sequence of pANDA35HK/tbb-2 J17 (containing underlined antisense and sense fragment of tbb-2 and shaded Gus linker) (SEQ ID NO:98).

FIG. 70. Sequence used for unc-26 RNAi>J20 (with introns) from gDNA (SEQ ID NO:99).

FIG. 71. Sequence in pANDA35HK/unc-26 J20 (containing underlined antisense and sense fragment of unc-26 and shaded Gus linker) (SEQ ID NO:100).

FIG. 72. Sequence used for prp-4 RNAi>J21 (exon) from cDNA (SEQ ID NO:101).

FIG. 73. Sequence in pANDA35HK/prp-4 J21 (containing underlined antisense and sense fragment of prp-4 and shaded Gus linker) (SEQ ID NO:102).

FIG. 74. Sequence used for pfn-1 RNAi>J23 (exon) from cDNA (SEQ ID NO:103).

FIG. 75. Sequence in pANDA35HK/pfn-1 J23 (containing underlined antisense and sense fragment of pfn-1 and shaded Gus linker) (SEQ ID NO:104).

FIG. 76. Sequence used for vbh-1 RNAi>J7 (with introns) from gDNA (SEQ ID NO:105).

FIG. 77. Sequence in pANDA35HK/vbh-1 J7 (containing underlined antisense and sense fragment of vbh-1 and shaded Gus linker) (SEQ ID NO:106).

DEFINITIONS

Figure 1:
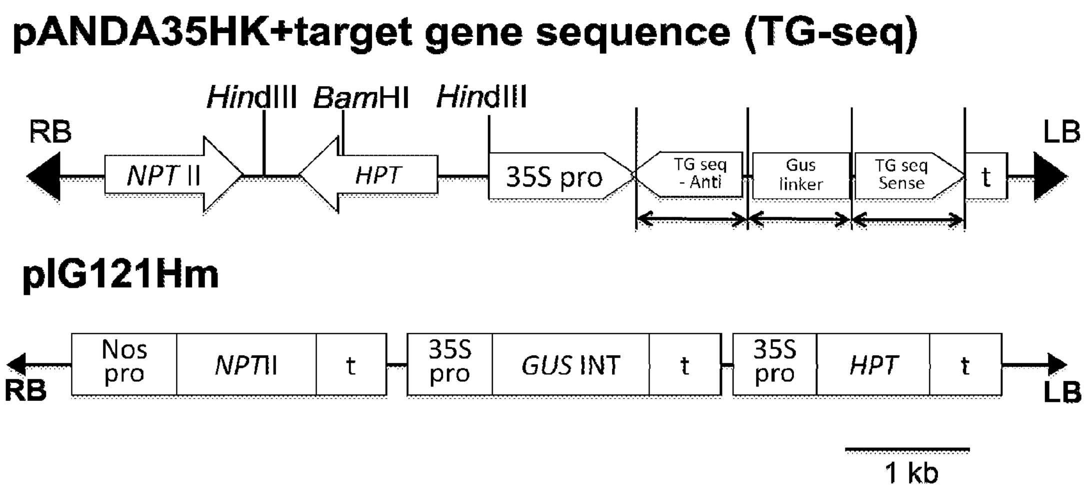
FIG. 1. T-DNA region of vectors pIG121Hm and pANDA35HK. a pIG121Hm. Right border (RB), left border (LB), Hygromycin resistance gene (HPT), Neomycin phosphotransferase gene (NPTII), intron-containing GUS gene (GUS INT), promoter nopaline synthase (PNos), promoter 35 s of CaMV (35S), terminator nopaline synthase (T) (Hiei et al. 1994). b pANDA35HK. Left border (LB), right border (RB), Kanamycin resistance gene, driven by NOS promoter (NPTII), Hygromycin resistance gene, driven by 35S promoter (HPT), Nos terminator (T). Fib-1 or Y25 fragments were achieved by PCR. Sense and antisense gene fragments were inserted into pANDA35 HK by Gateway cloning strategy.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae. It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term plant cell "compartments or organelles" is used in its broadest sense. The term includes but is not limited to, the endoplasmic reticulum, Golgi apparatus, trans Golgi network, plastids including chloroplasts, proplastids, and leucoplasts, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The term "heterologous," when used in reference to DNA sequences or genes, means a DNA sequence encoding a protein, polypeptide, RNA, or a portion of any thereof, whose exact amino acid sequence is not normally found in the host cell, but is introduced by standard gene transfer techniques.

The term "nematode" as used herein refers to worms that are members of the phylum Nemata.

The term "RNA interference" or "RNAi" refers to the silencing or decreasing of gene expression by iRNA or siRNAs. It is the process of sequence-specific, posttranscriptional gene silencing in animals and plants, initiated by iRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "interfering RNA (iRNA)" refers to a double stranded RNA molecule that mediates RNA interference (RNAi). At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the RNAi antisense strand. RNAi may also contain additional sequences; non-limiting examples of such sequences include linking sequences, or loops, as well as stem and other folded structures.

siRNAs generally comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

As used herein, the term "loop sequence" refers to a nucleic acid sequence that is placed between two nucleic sequences that are complementary to each other and which forms a loops when the complementary nucleic acid sequences hybridize to one another.

The term "nematode target RNA" as used herein refers to an RNA that is expressed in a nematode.

The term "double stranded nematode RNA sequence" refers to an iRNA that is specific for a nematode target RNA.

The term "inhibits the proliferation of nematodes" refers to a reduction in nematode parasitism of a host organism. A variety of assays may be used to measure proliferation, including, but not limited to measuring the number of roots cysts that develop in plants exposed to nematodes.

As used herein, the term "orally active to prevent the proliferation of nematodes" refers to a double stranded nematode RNA sequence that inhibits the proliferation of nematodes when orally ingested by the nematodes.

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target. In a preferred embodiment, a homolog has a greater than 60% sequence identity, and more preferable greater than 75% sequence identity, and still more preferably greater than 90% sequence identity, with a reference sequence.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seed tissue) in the relative absence of expression of the same nucleotide sequence of interest in a different type of tissue (e.g., leave tissue). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap (1994) Plant Mol. Biol. 24:119-127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "transfection", "transformation", "transfected" and "transformed" are used interchangeably and refer to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" *Agrobacteria; Agrobacterium* strains which cause production of octopine (e.g., strain LBA4404, AchS, B6) are referred to as "octopine-type" *Agrobacteria*; and *Agrobacterium* strains which cause production of agropine (e.g., strain EHA105, EHA101, A281) are referred to as "agropine-type" *Agrobacteria.*

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (i.e., a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature.

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to compositions and methods for controlling nematode infestation of plants or animals. In particular, the present invention provides vectors comprising sequences designed to control nematodes by RNA interference (RNAi) and transgenic plants transformed with such vectors. The compositions and methods of the present invention can be used to inhibit the growth and reproduction of a number of nematodes species, including, but not limited to plant parasitic nematodes and nematodes in the following genera: *Acontylus, Criconemella, Pseudhalenchus, Afenestrata, Cucullitylenchus, Lelenchus, Psilenchus, Aglenchus, Cryphodera, Pterotylenchus, Allotylenchus, Cynipanguina, Macrotrophurus, Punctodera, Amplimerlinius, Malenchus, Anguina, Discocriconemella, Meloidodera, Radopholus, Antarctenchus, Ditylenchus, Meloidoderita, Rhizonema, Antarctylus, Dolichodera, Meloidogyne, Rotylenchulus, Aorolaimus, Dolichodorus, Meloinema, Rotylenchus, Aphasmatylenchus, Duotylenchus, Merlinius, Apratylenchoides, Miculenchus, Sarisodera, Atalodera, Ecphyadophora, Mitranema, Sauertylenchus, Atetylenchus, Ecphyadophoroides, Morulaimus, Scutellonema, Atylenchus, Epicharinema, Mukazia, Senegalonema, Eutylenchus, Sphaeronema, Bakernema, Nacobbodera, Subanguina, Basiria, Filenchus, Nacobbus, Sychnotylenchus, Basirienchus, Nagelus, Basiroides, Bellodera, Geocenamus, Neodolichodorus, Thada, Belonolaimus, Globodera, Neopsilenchus, Thecavermiculatus, Blandicephalanema, Gracilacus, Neothada, Trichotylenchus, Boleodorus, Gracilancea, Nothocriconemoides, Triversus, Brachydorus, Trophonema, Bursadera, Halenchus, Ogma, Trophotylenchulus, Helicotylenchus, Paraphelenchus, Trophurus, Cacopaurus, Hemicriconemoides, Pararotylenchus, Tylenchocriconema, Cactodera, Hemicycliophora, Paratrophurus, Tylenchorhynchus, Caloosia, Heterodera, Paratylenchus, Tylenchulus, Cambellenchus, Hirschmanniella, Pateracephalanema, Tylenchus, Carphodorus, Hoplolaimus, Pleurotylenchus, Tylodorus, Cephalenchus, Hoplotylus, Polenchus, Clavilenchus, Coslenchus, Hylonema, Pratylenchoides, Verutus, Criconema, Pratylenchus, Zygotylenchus*; and animal parasitic nematodes of the following genera: *Trichuris, Acylostoma, Necator, Strongyloides, Toxocara, Baylisacaris, Trichinella, Draccunculus, Filarioidea, Onchocerca, Loa, Dirofilaria*, and *Anisakis.*

I. RNAi Systems, Constructs and Vectors

RNAi refers to the introduction of homologous double stranded RNA (dsRNA) to target a specific gene product, resulting in post transcriptional silencing of that gene. This phenomena was first reported in *Caenorhabditis elegans* by Guo and Kemphues (Par-1, A gene required for establishing polarity in *C. elegans* embryos, encodes a putative Ser/Thr kinase that is asymmetrically distributed, 1995, Cell, 81 (4) 611-620) and subsequently Fire et al. (Potent and specific genetic interference by double-stranded RNA in *Caenorhabditis elegans,* 1998, Nature 391: 806-811) discovered that it is the presence of dsRNA, formed from the annealing of sense and antisense strands present in the in vitro RNA preps, that is responsible for producing the interfering activity.

The present invention contemplates the use of RNA interference (RNAi) to downregulate the expression of genes needed for pest viability and reproduction, thus reducing pest infestation of plants. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs.

Carthew has reported (Curr. Opin. Cell Biol. 13(2):244-248 (2001) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

In preferred embodiments, the dsRNA used to initiate RNAi, may be isolated from native source or produced by known means, e.g., transcribed from DNA. The promoters and vectors described in more detail below are suitable for producing dsRNA. RNA is synthesized either in vivo or in vitro. In some embodiments, endogenous RNA polymerase of the cell may mediate transcription in vivo, or cloned RNA polymerase can be used for transcription in vivo or in vitro. In other embodiments, the RNA is provided transcription from a transgene in vivo or an expression construct. In some embodiments, the RNA strands are polyadenylated; in other embodiments, the RNA strands are capable of being translated into a polypeptide by a cell's translational apparatus. In still other embodiments, the RNA is chemically or enzymatically synthesized by manual or automated reactions. In further embodiments, the RNA is synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. In some embodiments, the RNA is dried for storage or dissolved in an aqueous solution. In other embodiments, the solution contains buffers or salts to promote annealing, and/or stabilization of the duplex strands.

In some embodiments, the dsRNA is transcribed from the vectors as two separate stands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp up to about 100, 200, 300, 0r 400 bp in length. In preferred embodiments, the isolated RNAs of the present invention mediate degradation of the target RNA.

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group. In some embodiments, the amount of target RNA (mRNA) is reduced in the cells of the target organism (e.g., *H. glycines*) exposed to target specific double stranded RNA as compared to target organisms that have not been exposed to target specific double stranded RNA.

In some embodiments, the present invention provides systems that enhance the effectiveness of RNAi constructs. In some embodiments, the systems comprise vectors that express an RNAi construct for a target RNA molecule, such as a target pest RNA molecule, and a sense or antisense sequence corresponding to at least a portion of the target RNA molecule. Exemplary vectors for use in this system are depicted in FIG. 57. In some embodiments, the sense or antisense sequence corresponds to the sequence used in the RNAi construct. The sense or antisense sequence can either correspond to the full length target sequence or to a portion of the target sequence. In some embodiments, the sense or antisense sequence is at least as long as the target sequence chosen for the RNAi construct. In some embodiments, these two sequences are encoded on the same vector, while in other embodiments, the RNAi construct and sense or antisense sequences are encoded on separate vectors. In some embodiments, the sense or antisense sequence is operably linked to a promoter that allows overexpression of the sense or antisense sequence. In some embodiments, the promoter is a constitutive plant promoter. Suitable vectors for expression of the RNAi construct and sense or antisense sequence are described in more detail below and in the Examples.

The present invention is not limited to any mechanism of action. Indeed, an understanding of the mechanism of action is not necessary to practice the present invention. Nevertheless, it is contemplated that the RNAi effect is enhanced by overexpression of either part or the full target RNA sequence (in either sense or antisense orientation) at least including the fragment used for the RNAi construct hairpin together with the RNAi hairpin in the same or separate vectors. This results in up regulation of the amount of siRNA both in terms of concentration and number of individual molecule species in the transgenic plant. This in turn increases the amount and number of siRNA species the parasitic nematode, insect or pathogenic fungus will ingest/absorb so that it will give rise to an increased level of plant protection for plants.

In some embodiments the target RNA molecule used in this system is an RNA molecule of an organism that is a plant pest. Examples of such plant pests include, but are not limited to, parasites such nematodes and insects as well as pathogenic fungi. In some preferred embodiments, the pest is a nematode.

In some embodiments, the present invention provides RNAi constructs for a target RNA molecule, vectors that express the RNAi constructs and transgenic plants comprising the RNAi construct/vectors. In some embodiments, the target RNA molecule is selected from the group consisting of Cpn-1, Prp-17, Y25, Rnr-1, Arx-3, Fib-1, and Asb-1. The target RNA molecule may be derived from nematodes of various species, including, but not limited to *Heterodera glycines, Meloidogyne incognita, M. javanic, M hapla, Globedera* spp., *Pratylenchus neglectus* and *P. thornei, Radopholus similis*, and *Rotylenchulus reniformis*. In some embodiments, the target RNA molecule is at least 80%, 85%, 90%, 95%, or 99% identical to Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1 gene sequences. As described above, the RNAi construct corresponding to the target RNA molecule may be varying lengths. In preferred embodiments, the RNAi construct comprising a first exogenous nucleic acid sequence having a sense sequence linked to its complementary antisense sequence and encoding a double stranded RNA that inhibits expression of a target RNA molecule, wherein said target gene is selected from the group consisting of genes at least 80%, 85%, 90%, 95%, or 99% identical to Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-1. In some embodiments, the target RNA molecule is selected from the group consisting of SEQ ID NOs:1-7, 12-22, and 51-59 and sequences at least 80%, 85%, 90%, 95%, or 99% identical thereto. As shown in Example 3, use of RNAi constructs corresponding to the genes results in at least 33% reduction of nematode eggs (e.g., *H. glycines* eggs) per gram of roots in a hairy root assay. RNAi constructs to other target RNA molecule may be used in conjunction with the currently described systems and RNAi constructs. Exemplary additional target RNA molecules are described, for example, in U.S. Pat. No. 7,803,984, incorporated herein by reference in its entirety.

TABLE 1

Exemplary RNAi Target Sequences

| Gene | SEQ ID NO: | Sequence |
|---|---|---|
| Y25 | 17 | GCAGCCCGACAAGACAATTATGTTCACGCAGC<br>TGTCCACACGCGTGTCAGAAAACGTGACGGAC<br>ACAAATTTGTTTGATCTTTCGCTTTCCCAAGC<br>GCTTGGTACTGCACCCAAAACGACCAAATACA<br>CCTTTGCCAGCTCCAAACTGGGAAAAGTGATT<br>CAGTTAGCCGGCTTTTCGGATCCCGTCTATGC<br>CGAGGCGTACGTCAACGTCAACCAATATGACA<br>TTGTATTGGACGTACTCGTGGTCAACCAGACT<br>AGCGACACCTTGCAAAATTTGTCATTGGAACT<br>CTC |
| Arx-3 | 18 | GTTTCATGTTCGCACGACAAAAATGCGTTTGT<br>GTGGACATGGGAGGCTGAAAAGAACAGTTGGA<br>AACCGGAGATGGTGGTCGTTCGGATAAACAGA<br>GCTGCCACCTGTGTCAAATGGTCGCCCAACGA<br>AAACAAATTCGCCGTTGGGACGGGTGCGCGTT<br>TAGTCGCTATTTGTTATTACGAACGTGAAAAT<br>GACTGGTGGGTAGCGAAGCAAATCAAAAAGCT<br>GATTCGTTCCACGGTCACCTCATTGAATTGGC<br>ATCCCAACAACATTTTGTTGGCTGTTGGCGCC<br>TGTGACTTCAAAACGCGTGTTTTTTCTGCTTA<br>TGTGAAAGAGATTGACGAAAAACCAACGCCAA<br>ACCCTTGGGGGACCAAAATGCCATTGGGAGAA<br>TTGC |
| Prp-17 | 19 | CAATCGAATTGTCCTTTTCCAAATCGTCGATG<br>ACAAGTTGCGATTCGCTCGTAAAAAGGCCTTC<br>CGTGGTCACAATACAGCAGGGTACGCCTGCTC<br>AACTGATTTTTCGCCAGAGATGAGTTTTCTCG<br>CTTCCGGTGATGCGGACGGTAAAATCACAATG<br>TGGGACTGGCGCACACACAAAATTGTCTCCAC<br>ATGGAAGGCACATGATAATGTGTGCATTTCAA<br>CACTGTGGCATCCGCACGAGAAATCGCGGATG<br>ATTTCTTGCGGATGGGACAATGTAATCAAAAT<br>G |
| Rnr-1 | 20 | CAAGAAATCAAAGACCTGTACAAGACCGTGTG<br>GGAAATACCGCAGAAGGACATTTTGAAAATGG<br>CCGCCGATCGCGCCGCTTTCATTGACCAAAGC<br>CAATCCCTTAACATTCACATAGCGCAGCCGAA<br>CTATGCTAAACTGAGCTCCATGCACTTTTACG<br>CCTGGTCATTGGGACTTAAAACCGGGATGTAT<br>TACCTGCGCACTCGTCCGGCTGTCGATGCTGT<br>TCAGTTCACTGTGGACAAAATGGCCCT |
| Fib-1 | 21 | CCGAAGACGGAAGAGACAACGAATGGCAGCAA<br>CGGTGTCTCAGCACCCACCGCCGCGGCTGCCG<br>GCCCGGCACCGCCAGTCGAGTACCGGGTGTGG<br>AACCCGTTCCGCTCCAAACTGGCCGCCGCCGT<br>CATGGCCGGCATTGAGGACACGCACATTTACC<br>CGGG |
| Asb-1 | 22 | TCCACACGGCTTTTCGTTATAAATTTGAAAAG<br>TACGTATACAAAGTTACCCGTGAACGATTTGG<br>CAAAATGAAGGCTTACATTGACAATGAATTGA<br>AGGAAGCCATCGAGTTCCGCAAGACTTCAAAG<br>GAGCAGGCCGACTCGTTGAAAGCAGTGCATGA<br>AAACTTTCCCACAATTTTCCAAGAGAATTTGG<br>CGCTGCAACTTGAAGCGACCTACCGAAAAAAT<br>GTGGACTACGCCTGGCAAGAGATGAAGCGTCG<br>GTTGGATTACCTGCAGGAAGTGCAAGCAATCA<br>AAGACCGAT |

In some embodiments, the RNAi construct of the present invention comprise a first exogenous nucleic acid sequence having a sense sequence linked to its complementary antisense sequence and encoding a double stranded RNA that inhibits expression of a target RNA molecule. In some embodiments, the RNAi constructs comprise SEQ ID NOs: 60-77, 90, 92, 94, 96, 98, 100, 102, 104, 106 and 108 and sequences at least 80%, 85%, 90%, 95%, or 99% identical thereto. These RNAi constructs comprise sense and antisense sequence corresponding to a portion of the target pest sequence joined by a linker so that a double stranded siRNA is formed upon expression of the construct. In some embodiments, the target RNA molecule is at least 80%, 85%, 90%, 95% or 99% identical to a Cpn-1, Prp-17, Y25, Rnr-1, Arx-3, Fib-1, Asb-1, Cdk-1, Fzy-1, Tba-2, Arx-1, Tbb-2, Unc-26, Prp-4, Pfn-1, and Vbh-sequence. In some embodiments, the target RNA molecule is selected from the group consisting of SEQ ID NOs:1-7, 12-22, 51-59, 89, 91, 93, 95, 97, 99, 101, 103, and 105 and sequences at least 80%, 85%, 90%, 95%, or 99% identical thereto. In some embodiments, the sense and antisense strands in the double stranded RNA are linked by a linker sequence. In some embodiments, the linker sequence is a Gus linker. In some embodiments, where a sense or antisense sequence corresponding to the target sequence is co-expressed with the RNAi construct, the sense or antisense sequence may be selected from sequences corresponding to SEQ ID NOs:1-7, 12-22, 51-59, 89, 91, 93, 95, 97, 99, 101, 103, and 105 and sequences at least 80%, 85%, 90%, 95%, or 99% identical thereto, or portions thereof, so long as the co-expressed sequence corresponds to the sequence contained within the RNAi construct.

The sequences described above and RNAi constructs comprising the sequences are described in Table 1 and FIGS. 12-26, 29-58, and 60-67.

Figure 28:
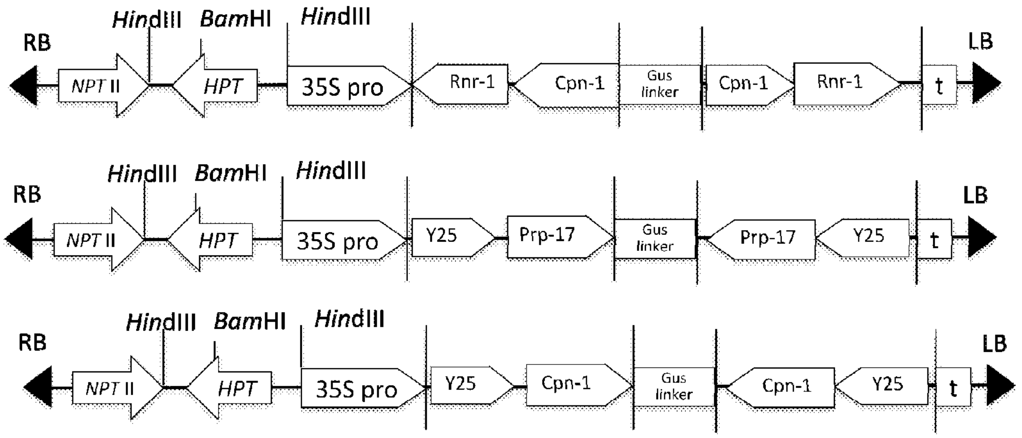
FIG. 28. Schematic depiction of stacked RNAi constructs.

In some embodiments, RNAi constructs of the present invention are "stacked constructs." In some embodiments, stacked RNAi constructs comprise a nucleic acid sequence having at least two sense sequences from at least two different target pest genes linked to at least two complementary antisense sequences from said at least two different target pest genes so that said nucleic acid sequence encodes a double stranded RNA that inhibits expression of said at least two target pest genes. In some embodiments, the sense and antisense strands in the double stranded RNA are linked by a linker sequence. In some embodiments, the linker sequence is a Gus linker. In some embodiments, the stacked RNAi constructs comprise sense and antisense sequences from 2, 3, 4, 5, 6, 7, 8, 9, or 10 target RNA molecules. The sense and antisense sequences are preferably operably linked so that upon expression, a double stranded RNAi constructs is formed. Exemplary stacked constructs are depicted in FIG. 28. Sequences for stacked RNAi constructs are exemplified by SEQ ID NOs:75-77. The stacked RNAi constructs may comprise sense and antisense sequence to a variety of target RNA molecules. Exemplary target RNA molecules include, but are not limited to, those RNA molecules described in detail above. Suitable vectors are described in detail below.

II. Transgenic Plants

In some embodiments, the present invention provides transgenic plants that express the RNAi constructs and systems described above. It is contemplated that pests (e.g., nematodes) feeding on the transgenic plants ingest the dsRNA molecules, which in turn decrease the abundance of target RNA within the pest species. This results in decreased pest infestation and decreased plant damage.

A heterologous gene encoding an RNAi gene of the present invention, which includes variants of the RNAi gene, includes any suitable sequence that encodes a double stranded molecule specific for a pest target RNA molecule. Preferably, the heterologous gene is provided within an expression vector such that transformation with the vector results in expression of the double stranded RNA molecule; suitable vectors are described below. As described above, in some embodiments, the vectors further comprise a sequence encoding a sense or antisense RNA that is expressed in addition to the RNAi construct.

In yet other embodiments of the present invention, a transgenic plant comprises a heterologous gene encoding a RNAi gene of the present invention operably linked to an inducible promoter, and is grown either in the presence of the an inducing agent, or is grown and then exposed to an inducing agent. In still other embodiments of the present invention, a transgenic plant comprises a heterologous gene encoding an RNAi gene of the present invention and/or a sense or antisense sequence operably linked to a promoter which is either tissue specific or developmentally specific, and is grown to the point at which the tissue is developed or the developmental stage at which the developmentally-specific promoter is activated. Such promoters include seed and root specific promoters. In still other embodiments of the present invention, the transgenic plant comprises an RNAi gene of the present invention and/or a sense or antisense sequence operably linked to constitutive promoter. In further embodiments, the transgenic plants of the present invention express at least one double stranded RNA molecule at a level sufficient to reduce the proliferation of nematodes as compared to the proliferation of nematodes observed in a nontransgenic plant. In some embodiments, the transgenic plants of the invention coexpress at least one sense or antisense RNA molecule at a level sufficient to enhance the reduction the proliferation of a pest as compared to the proliferation of pests observed in a nontransgenic plant 1. Plants The methods of the present invention are not limited to any particular plant. Indeed, a variety of plants are contemplated, including but not limited to soybean, wheat, oats, milo, sorghum, cotton, tomato, potato, tobacco, pepper, rice, corn, barley, *Brassica*, pine, and commercial cultivars can be transformed with heterologous genes. In cases where that is not possible, non-commercial cultivars of plants can be transformed, and the trait for expression of the RNAi gene of the present invention moved to commercial cultivars by breeding techniques well-known in the art.

2. Vectors

The methods of the present invention contemplate the use of at least one heterologous gene encoding an RNAi gene and/or an antisense or sense sequence. Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.).

In general, these vectors comprise a nucleic acid sequence of the invention encoding an RNAi gene and/or an antisense or sense sequence (as described above) operably linked to a promoter and other regulatory sequences (e.g., enhancers, polyadenylation signals, etc.) required for expression in a plant. In some embodiments, the RNAi gene and/or an antisense or sense sequence are arranged in a bicistronic expression unit. In other embodiments, the RNAi gene and/or an antisense or sense sequence are operably linked to separate promoters.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (e.g., phaseolin, napin, oleosin, and a promoter for soybean beta conglycin (Beachy et al. (1985) EMBO J. 4: 3047-3053)). In some preferred embodiments, the promoter is a phaseolin promoter. All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding the RNAi gene and/or an antisense or sense sequence.

In preparing a construct comprising a nucleic acid sequence encoding a RNAi gene of the present invention, various DNA fragments can be manipulated, so as to provide for the DNA sequences in the desired orientation (e.g., sense or antisense) orientation. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In some embodiments of the present invention the nucleic acid sequence of interest is introduced directly into a plant.

One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

3. Transformation Techniques

Once a nucleic acid sequence encoding an RNAi gene and/or an antisense or sense sequence of the present invention is operatively linked to an appropriate promoter(s) and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, the vector is introduced through ballistic particle acceleration using devices (e.g., available from Agracetus, Inc., Madison, Wis. and Dupont, Inc., Wilmington, Del.). (See e.g., U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In other embodiments, direct transformation in the plastid genome is used to introduce the vector into the plant cell (See e.g., U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857). In still further embodiments, the vector may also be introduced into the plant cells by electroporation (Fromm, et al. (1985) Proc. Natl Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In addition to direct transformation, in some embodiments, the vectors comprising a nucleic acid sequence encoding a RNAi gene of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species which are susceptible infection by *Agrobacterium* may be transformed in vitro. Alternatively, plants may be transformed in vivo, such as by transformation of a whole plant by *Agrobacteria* infiltration of adult plants, as in a "floral dip" method (Bechtold N, Ellis J, Pelletier G (1993) Cr. Acad. Sci. III-Vie 316: 1194-1199).

4. Regeneration

After selecting for transformed plant material that can express the heterologous gene encoding a RNAi gene of the present invention, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins Shoots and roots normally develop simultaneously. Efficient regeneration will depend on the medium, on the genotype, and on the history of the culture. The reproducibility of regeneration depends on the control of these variables.

5. Generation of Transgenic Lines

Transgenic lines are established from transgenic plants by tissue culture propagation. The presence of nucleic acid sequences encoding a RNAi gene of the present invention (including mutants or variants thereof) may be transferred to related varieties by traditional plant breeding techniques.

These transgenic lines are then utilized for evaluation of oil production and other agronomic traits.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade).

Example 1

Rapid in Planta Evaluation of Root Expressed Transgenes in Chimeric Soybean Plants Production of stable transgenic plants is one factor that limits rapid evaluation of tissue specific transgene expression. To hasten the assessment of transgenes in planta, we evaluated the use of chimeric soybean seedlings expressing transgenic products in roots. Tap roots from four-day old seedlings (cultivars 'Jack' and KS4704) were excised and hairy roots were induced from hypocotyls via *Agrobacterium rhizogenes*-mediated transformation. Inoculated hypocotyls were screened on a MS-based medium containing either 200 mg/L kanamycin or 20 mg/L hygromycin. Beta-glucuronidase (GUS) activity assay indicated that highest GUS expression was observed in hypocotyls exposed to a 4-d pre-inoculation time, a neutral pH (7.0) for the co-cultivation medium. A 170-bp of the Fib-1 gene and 292-bp of the Y25C1A.5 gene fragments, both related to nematode reproduction and fitness, were cloned independently into pANDA35HK vector using a Gateway cloning strategy. The resulting RNAi constructs of the genes fragments were transformed into soybean using the chimeric hairy root system and evaluated for its effect on soybean cyst nematode (*Heterodera glycines*) fecundity. Confirmation of transformation was attained by polymerase chain reaction and Southern-blot analysis, and some potential for suppression of *H. glycines* reproduction was detected for the two constructs. This method takes on average four weeks to produce chimeric plants ready for transgene analysis.

Materials and Methods

Bacterial Strains and Vectors.

*Agrobacterium rhizogenes* strains R1000 and K599 were used in the transformation experiments. The binary vectors include pIG121Hm (Hiei et al. 1994), pBINmGFP5-ER (obtained from MRC laboratory of Molecular Biology, UK) and pANDA35HK (a kind gift from Ko Shimamoto, Japan). All the three vectors contain the nptII gene that confers resistance to kanamycin, and additionally pIG121Hm and pANDA35HK include hygromycin resistance gene driven by cauliflower mosaic virus (CaMV) 35S promoter. In addition, pIG121Hm contains gus gene with an intron driven by CaMV35S promoter; pBINmGFP5-ER harbors a modified version of GFP with enhanced fluorescence, also driven by CaMV35S promoter; pANDA35HK has a RNA interference cassette under the control of CaMV35S promoter (FIG. 1).

Cloning of Fib-1 and Y25C1A.5 (Y25) Genes from Soybean Cyst Nematode and RNA Interference Constructs.

The sequences of Fib-1 gene and Y25 gene from *C. elegans* were obtained from http://www.wormbase.org, and the corresponding clones were T01C3.7.1 and 2D377. The homologous Fib-1 (CB279515) and Y25 (CB824330) sequences from *H. glycines* were identified from datasets in http://www.nematode.net. Specific primers Fib-F (5'-CCGAAGACGGAAGAGACAAC-3') (SEQ ID NO:23) and Fib-R (5'-ACCCGGGTAAATGTGCGTGTC-3') (SEQ ID NO:24) for amplifying Fib-1 gene and Y25-F (5'-GCAGCCCGACAAGACAAT-3') (SEQ ID NO:25) and Y25-R (5'-TGAGAGTTCCAATGACAAAT-3') (SEQ ID NO:26) for amplifying Y25 gene were designed based on the gene's sequence. Using *H. glycines* genomic DNA as template, 170-bp and 292-bp fragments of Fib-1 and Y25 genes, respectively were obtained via polymerase chain reaction (PCR). PCR products were independently ligated into pGEM-T easy vector (Promega) and subsequently subcloned into pENTR4 vectors by EcoRI restriction sites. The pENTR4 vector carrying Fib-1 gene or the Y25 fragment was recombined with pANDA35HK vector using the LR clonase enzyme mix (Cat No. 11791-019, Invitrogen) to create the RNA interference expression vectors (FIG. 1). The Fib-1 or Y25 gene was in complementary orientation, separated by 930-bp GUS linker fragment, and driven by CaMV35S promoter. The RNAi construct was introduced into *Agrobacterium rhizogenes* strains R1000 and K599 bp the freezing-thaw method (Chen et al. 1994).

Hairy Roots Induction and Production of Chimeric Plants.

Seeds of soybean varieties Jack and KS4704 were obtained from the soybean breeding program at Kansas State University. Seeds were put into plates and surface sterilized using chlorine gas (3.3 mL concentrated 12 M HCl added into 100 mL 5.25% chlorine bleach) overnight. After that, the plates were wrapped with plastic bag for later use. Sterilized soybean seeds were cultured in the 12 MS liquid medium [½ MS (Murashige and Skoog 1962) basal nutrient salts subtracting 5 mM $NH4^-$ and 20 mM $NO3^-$, B5 (Gamborg et al. 1968) vitamins, 1.90 g/L MES and 0.5% sucrose (pH 5.7)] at 25° C. for germination. To optimize the physiological conditions of explants, 3, 4, 5 and 6 days of pre-inoculation were compared on the ½ MS liquid medium. R1000 and K599 carrying different vectors were cultured on dishes with 50 mg/L kanamycin and/or 50 mg/L hygromycin B for 24 hr at 25° C. R1000 and K599 were scraped off the dishes and resolved in 0.5 mL 12 PS buffer (Vieweg et al. 2004) with 0.3-0.6 $OD_{600nm}$. Soybean seedlings were inoculated by an injection for three times parallel to the vascular bundle of hypocotyl, similar to *Vicia hirsuta* by Quandt et al. (1993). After inoculation, soybean seedlings were co-cultivated in ½ MS liquid medium that was adjusted with different pH values (5.0, 5.7, 7.0).

Figure 2:
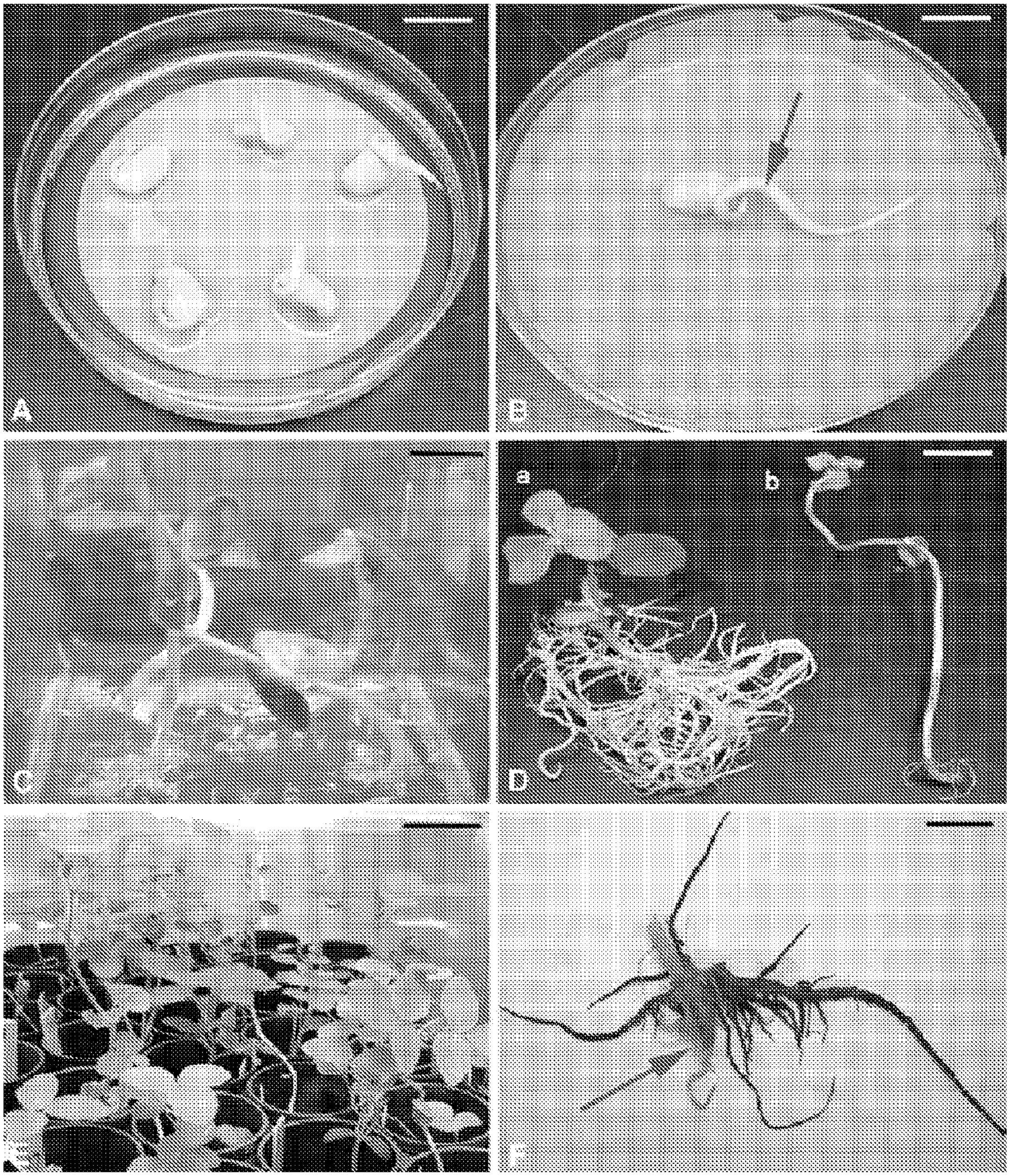
FIG. 2. Generation of transformed roots by *A. rhizogenes* (R1000). a Four days after 'Jack' seeds were placed on ½ MS medium for germination. Bar 1 cm. b Growth of Jack seeds 4 days after injection with R1000 containing pIG121Hm vector (GUS gene included) in the hypocotyls. The tap roots were excised before injection. Arrow shows the injection site of Jack cotyledon. Bar 1 cm. c Selection in MS medium with Kanamycin (200 mg/L). Bar 1 cm. d Morphological aspect of branched transgenic roots (a) and roots transformed with R1000 lacking vectors (b) 3 weeks after injection. Bar 2 cm. e Chimeric plants transferred to soil. Bar 5 cm. f An example of b-glucuronidase (GUS) histochemical assay of transgenic roots transformed with pIG121Hm. Although most roots are transgenic, there are a few that are not (i.e. escapes). Arrow one non-transgenic root. Bar 2 cm.

After three days co-cultivation, the roots together with cotyledons were transferred onto selection medium (MS medium added with kanamycin or hygromycin). In the selection medium, different concentrations of kanamycin (50, 100, 200, 300 mg/L) and hygromycin (5, 10, 15, 20, 25 mg/L) were in contrast, respectively. About three or four weeks later, as transgenic roots were produced, the chimeric seedlings were transplanted into soil and grown at 22° C. (16 h light/8 h dark) (FIG. 2). It takes on average four weeks to finish the complete process. Roots were harvested for preparing DNA isolation. To examine different parameters on the transformation efficiency, GUS assay was done for the chimeric seedlings transformed with pIG121Hm. Experiments were performed with three replicates on 50 seedlings each per treatment. Means of percentage of roots covered with blue sectors were calculated.

PCR of Transgenic Roots.

Hairy root tissues (about 100 mg) were harvested and genomic DNA was extracted according to the methods of Delloporta et al. (1983). PCR analysis was done with Hybaid limited PCR express thermal cycler (Thermo Hybaid, Fraklin, Mass., USA). Specific primers oriR (5'-GCTTCCTCGCTCACTGACTC-3') (SEQ ID NO:107) and oriF (5'-GGAGAAAGGCGGACAGGAAT-3') (SEQ ID NO:27) were used to amplify the origene (expected 346 bp). Gus-F1 (5'-CACGTAAGTCCGCATCTTCA-3') (SEQ ID NO:28) situated within Gus linker sequence was paired with Fib-R (5'-ACCCGGGTAAATGTGCGTGTC-3') (SEQ ID NO:29) or Y25-R (5'-TGAGAGTTCCAATGACAAAT-3') (SEQ ID NO:30) to identify the presence of Fib-1 or Y25 gene, respectively. The PCR amplification was carried out for 30 cycles. The initial denaturation reaction was done at 94° C. for 8 min. Each cycle was performed with denaturation (94° C., 1 min), annealing (56° C., 45 s) and extension (72° C., 50 s). PCR mixture consisted of 50-100 ng of plant DNA, 5 µl of 10 9 Taq buffer, 2.0 µl of 2.5 mM dNTP, 0.25 µl of Taq DNA polymerase (5 U µl-1, New England Biolabs Inc), 1 µl of 10 pmol each pair of primers in a final volume of 50 µl. The PCR products were separated by electrophoresis on 1.0% agarose gels in 1× TAE buffer and were observed by fluorescence with UV light after staining with ethidium bromide.

Visual Observation of GFP and Histochemical GUS Assay.

Imaging of GFP was performed using Leica MZIII fluorescence stereomicroscope (Leica Microsystems GmbH, Wetzlar, Germany). The microscope was equipped with a fluorescence module containing a Leica 106Z lamp housing 50 or 100 W high-pressure mercury vapor burners and two GFP filter sets (470/40 nm). The GUS activity of hairy roots transformed with pIG121 Hm was visualized with a staining solution containing 1 mM 5-bromo-4-chloro-3-indolyl-b-D-glucuronide (X-gluc) as reported by Jefferson (1987). All the materials were incubated overnight at 37° C. in plastic plates.

Southern Blot Analysis.

Genomic DNAs of hairy roots transformed with R1000 containing pANDA35HK: Fib-1 were isolated using the method referred to Murray and Thompson (1980). DNA was digested with SacI, an enzyme which linearizes pANDA35HK: Fib-1 between attR and Nos terminator. Fifteen microgram DNA from roots of each sample was digested over-night, and gel electrophoresed together with positive control vector pANDA35HK: Fib-1 (50 pg) and genomic DNA from a nontransformed plant. The template for probe was obtained by digestion of pHygr in pUC119 using BamHI, and the probe was synthesized with a-32P [dCTP] labeled using DNA polymerase I large (Klenow) fragment (Fisher scientific, USA). Gel electrophoresis, DNA blotting and hybridization were following Sambrook et al. (1989).

Bioassay.

To explore suppression of nematode reproduction in transformed roots, chimeric plants expressing Fib-1 or Y25 RNAi were transplanted from tissue culture into D40 Deepots (Stuewe and Sons Inc., Corvallis, Oreg.) with 450 mL soil infested with 4,500 eggs 100 cm-3 of soil of a HG Type 2.7 population of *H. glycines*. Soybean plants inoculated with only R1000 containing no vectors were used as negative controls. Eleven negative controls were put in the same medium without kanamycin added for tissue culture as plants transformed with Fib-1. Transplanted soybeans were acclimated to lower humidity conditions and grown in the SCN-infested soil at 26° C. day/24° C. night with a 16-h photoperiod and a light intensity of 360 lmol photons m-2 s-1. After 5 weeks, roots from each plant were washed with a high-pressure water spray to dislodge cysts. Dislodged cysts were collected onto a 100-lm-pore sieve and enumerated under a dissecting microscope. Cysts from each sample were ruptured by mechanical grinding to release eggs and second-stage juveniles (J2) (Niblack et al. 1993). Eggs and J2 were collected onto a 25-lm-pore sieve and enumerated under a compound microscope at 409 magnification. The root mass from which cysts were collected was dried for 5 days at 60° C. and the dry weight was recorded.

Statistical Analysis.

All data were subjected to analysis of variance using the GLM procedure in SAS (SAS Institute, Cary, N.C.). Numbers of cysts and eggs g-1 root were log 10-transformed prior to analysis to reduce heterogeneity of variances. Means were separated using the PDIFF option in SAS.

Results.

Establishment of Soybean Hairy Roots Transgenic System.

In this study, we developed in planta chimeric system in soybean to evaluate root-expressed transgenes. Chimeric soybean plants were obtained by the induction of transgenic hairy roots on non-transformed shoots after inoculation with *Agrobacterium rhizogenes*. The majority of the root organogenesis was localized at the bacterial inoculation sites. There are 1-3 roots produced from one inoculation site on average. These roots exhibited the hairy root phenotype whereas roots induced at other locations on the hypocotyls did not possess the hairy root phenotype. Under antibiotic selection the lateral roots became brown and necrotic (FIG. 2) similar to hypocotyls transformed with *A. rhizogenes* R1000 lacking a binary plasmid (FIG. 2D, b).

Although the majority of roots were transgenic, not all the roots formed on the hypocotyls were transgenic as demonstrated by the GUS assay or GFP observation (FIGS. **2*f*, 3**). A few adventitious roots forming from the injection sites were observed in most experiments using GFP and GUS as reporter genes and NPTII as the selectable marker. However, these escapes were not significant as 90±2.5% SE of the roots regenerated were transgenic. For the hairy roots transformed with *A. rhizogenes* R1000 containing pANDA35HK: Fib-1, different antibiotics concentrations were tried on the selection medium. Experiments indicated that 200 mg/L kanamycin, or 20 mg/L hygromycin could be used for the selection of soybean culture. Higher concentrations of kanamycin (more than 200 mg/L) or hygromycin (more than 20 mg/L) resulted in a significant inhibition of hairy root formation.

Analysis of Transformation Parameters.

Two *A. rhizogenes* strains R1000 and K599 were tested for the regeneration of transformed roots. Both strains were effective at inducing the formation of regenerated hairy roots however *A. rhizogenes* R1000 was more efficient than K599 in producing transgenic roots as indicated by the number of seedlings producing branched roots exhibiting GUS activity (Table 2). GUS expression was also used to compare transformation competency of two soybean cultivars ("Jack" and KS4704). Transformation efficiency was observed to be higher in "Jack" than KS4704. Preinoculation time in ½ MS medium was important for the expression of GUS in soybean seedlings (Table 3). Preinoculation time of 4 days gave the highest expression (23.3%), compared to 3 days (17.7%), 5 days (18.5%) and 6 days (16.7%). A neutral pH of 7.0 for the co-culture medium showed highest GUS expression as compared to a pH 5.0 or pH 5.7 (Table 4).

TABLE 2

Effect of *A. rhizogenes* strains and cultivars on expression of GUS gene in soybean seedlings

| *A. rhizogenes* | No. of seedlings expressing Gus/Total No. seedlings inoculated (%) | |
|---|---|---|
| Strain | Jack | KS4704 |
| R1000 | 25.4 ± 0.14 a | 18.5 ± 0.14 b |
| K599 | 18.2 ± 0.14 b | 14.8 ± 0.14 c |

Transformation efficiency as reflected by Gus expression was assessed 3 weeks after inoculation with *A. rhizogenes* for both cultivars. Values are given as transformation frequency (%) and are the means±S.E. of three replications on 50 seedlings each. Different letters show significant differences among treatments according to procedure GLM-PDIFF option in SAS

TABLE 3

Effect of pre-inoculation time on the transformation efficiency of soybean seedlings

| Pre-culture time (days) | Frequency of GUS positive seedlings/Total seedlings (%) |
|---|---|
| 3 | 17.7 ± 0.18 b |
| 4 | 23.3 ± 0.22 a |
| 5 | 18.5 ± 0.21 b |
| 6 | 16.7 ± 0.20 b |

Soybean cultivar Jack seeds were put in the ½ MS medium for preinoculation. The co-culture medium is ½ MS medium with pH 7.0. *A. rhizogenes* strains R1000 containing pIG121Hm was used for inoculation. Means±SE followed with the same letters were not significantly different (P=0.05) according to SAS PDIFF option.

TABLE 4

Effect of pH values in the co-culture medium on the transformation efficiency of soybean seedlings

| pH value | Frequency of GUS positive seedlings/Total seedlings (%) |
|---|---|
| 5.0 | 15.2 ± 0.15 b |
| 5.7 | 16.6 ± 0.12 b |
| 7.0 | 22.2 ± 0.32 a |

Soybean cultivar Jack seeds were put in the pre-inoculation medium (½ MS) for 4 days. *A. rhizogenes* strains R1000 containing pIG121Hm was used for inoculation. Means±SE followed with the same letters were not significantly different (P=0.05) under the same treatment according to SAS PDIFF option.

Figure 3:
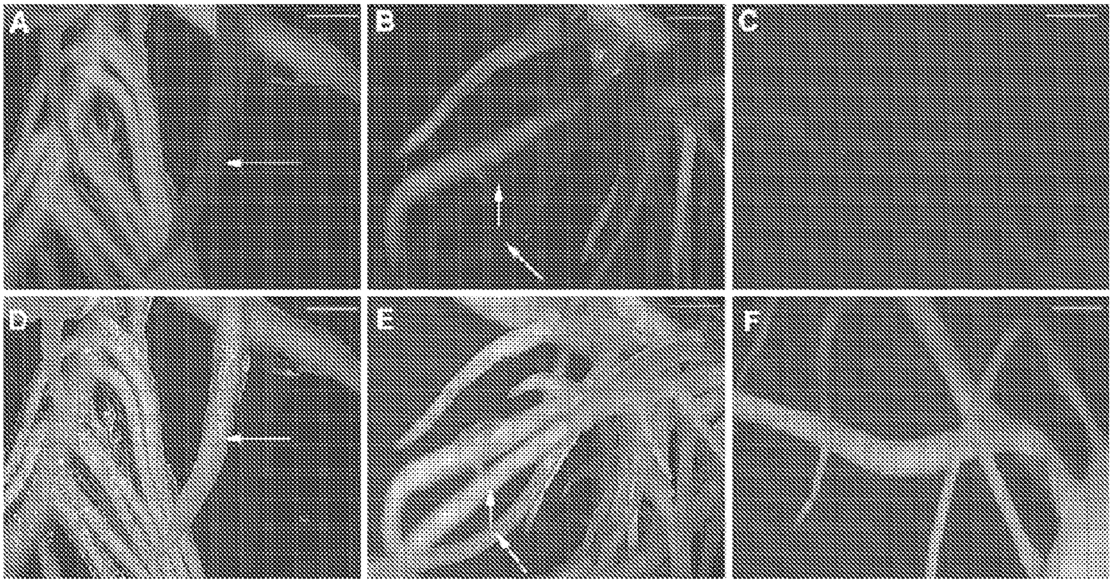
FIG. 3. GFP expression in transgenic roots. a-c roots viewed under fluorescence stereomicroscope Leica MZ FLIII with the GFP filter. d-f same roots as a, b and c (respectively) viewed under normal light. a, b, d and e are from seedlings transformed with R1000 containing pBINmGFP5-ER vector. c and f are from a seedling transformed with only R1000 (no binary vector present). Note that as in the case of GUS staining in FIG. 2, most, but not all roots appear to be transgenic in a and b (arrows the non transgenic roots). Bar 5 mm.

The activity of GFP was detected in most of transgenic hairy roots transformed with R1000 harboring binary vector pBINmGFP5-ER (FIG. 3), indicating GFP gene was inserted into hairy roots and had expressed. No GFP activity was observed in the roots transformed with R1000 containing no vectors or non-transgenic control roots. The efficiency of GFP expression in different parameters was similar to that of GUS (data not shown). We observed on average one to three non-transformed roots per seedling.

Molecular Analysis of Putative Roots.

Figure 4:
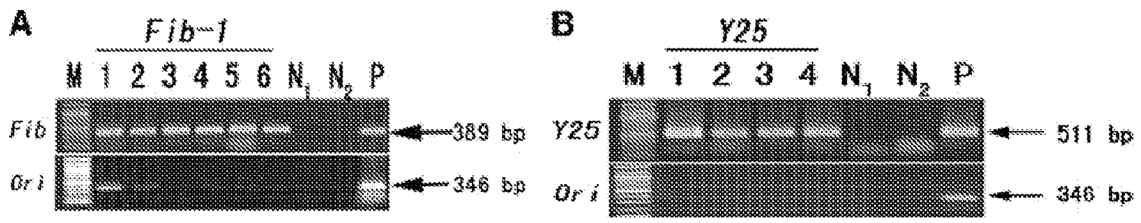
FIG. 4. PCR Results of Fib-1 and Y25 genes and ColE on gene amplification in transformed roots. a The amplification results of Fib-1 gene. GUS-F1 (within Gus linker, located close to site b) and Fib-R were used for amplifying Fib-1 gene. 100 bp ladder (M), PCR results from genomic DNAs of six independent transgenic hairy roots transformed with pANDA35HK: Fib-1 (1-6) vector pANDA35HK: Fib-1(P). b The amplification results of Y25 gene. GUS-F1 and Y25-R were used for amplifying Y25 gene. PCR results from genomic DNAs of four independent transgenic hairy roots transformed with pANDA35HK: Y25 (1-4), vector pANDA35HK:Y25 (P), negative control 1, PCR results from genomic DNAs of soybean plants transformed with only R1000 (N1), negative control 2 (N2), PCR results from genomic DNAs of non-transgenic soybean roots.
Figure 5:
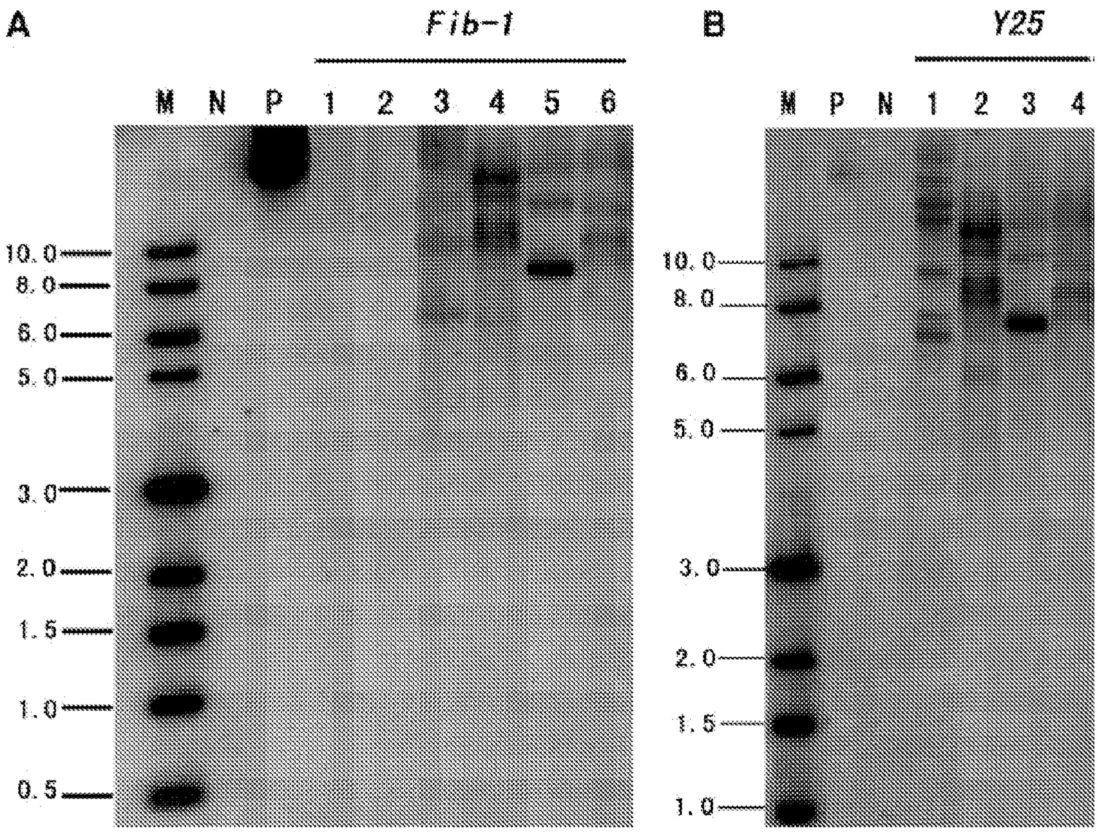
FIG. 5 Southern blot analysis of composite hairy roots. All the genomic DNAs were digested by SacI. a six independent hairy roots transformed with pANDA35HK: Fib-1 (1-6). b four independent transgenic hairy roots transformed with pANDA35HK:Y25 (1-4). pANDA35HK vector (50 pg) (P), negative control, soybean plants transformed with only R1000 (N). HPT gene digested from pUC119 using BamHI was used as template for synthesizing probe.
Figure 6:
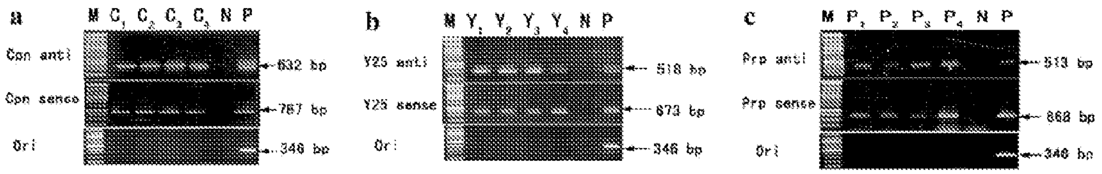
FIG. 6. PCR analysis of Cpn-1, Y25 and Prp-17 genes and ColE on replication site. a The amplification results of Cpn-1 gene. GUS-F1 (located close to 5' end of Gus linker) and Cpn reverse were used for amplifying Cpn-1 gene antisense fragment; GUS-R1 (located close to 3' end of Gus linker) and Cpn reverse were used for amplifying Cpn-1 gene sense fragment. M 1 kb ladder for Cpn-1 gene and 100 bp ladder for on gene, C1-C4 PCR results from genomic DNAs of roots of four independent transgenic composite plants transformed with pANDA35HK: Cpn-1, P vector pANDA35HK:Cpn-1. b The amplification results of Y25 gene. GUS-F1 and Y25 reverse, GUS-R1 and Y25 reverse were used for amplifying Y25 gene antisense and sense fragments, separately. Y1-Y4 PCR results from genomic DNAs of roots of four independent composite plants transformed with pANDA35HK: Y25, P vector pANDA35HK: Y25. c The amplification results of Prp-17 gene. GUS-F1 and Prp-17 reverse, GUS-R1 and Prp-17 reverse were used for amplifying Prp-17 gene antisense and sense fragments, separately. P1-P4 PCR results from genomic DNAs of roots of four independent transgenic composite plants transformed with pANDA35HK: Prp-17, P vector pANDA35HK: Prp-17. N negative control, PCR results from genomic DNAs of roots of soybean plants transformed with only K599 containing no binary vectors.

PCR analysis was performed on genomic DNAs of hairy roots to demonstrate the T-DNA transfer. All the putative transgenic roots contained the bands of expected size (389 bp) for the Fib-1 gene, whereas the negative controls (non-transformed roots and roots transformed with only R1000) did not amplify the gene fragment (FIG. 4*a*). To detect the presence of *A. rhizogenes* contamination, the origene which situated outside the left and right borders in the pANDA35HK vector was selected for amplification from all the roots above. A 346 bp band corresponding to the ColE expected size was detected in root samples 1 and 2, suggesting that the two samples had *A. rhizogenes* contamination. All the roots tested were all positive for the amplification of Y25 gene and no *Agrobacterium* contamination was detected (FIG. 4*b*). Southern blot analysis was performed to further confirm the integration of T-DNA in soybean hairy roots. Results from the Southern blot correlated well with the results obtained through the PCR analysis (FIG. 5). Hybridization results indicated that three to seven bands were detected in the Fib-1 hairy roots samples from number 3 to 6 and Y25 samples from number 1 to 4. As expected, no signals were found in Fib-1 root samples number 1, 2 and plants transformed with only R1000. The Southern blot results were matched with PCR results, confirming that the PCR results of identifying transgenic roots are reliable.

Bioassay.

To examine the effect of transgenic soybean roots on *H. glycines* reproduction, a bioassay was performed by exposing hairy roots transformed with pANDA35HK: Fib-1 and pANDA35HK: Y25 to nematode-infested soil. The integration of Fib-1 and Y25 had been confirmed by PCR with genomic DNA of each independent transgenic plant (data not shown). Back-transformed means of log 10-transformed data of cysts $g^{-1}$ root tissue and eggs $g^{-1}$ root tissue were summarized in Table 5. Although the Fib-1 RNAi plants displayed a 25% reduction in cyst $g^{-1}$ root tissue and a 37% reduction in eggs $g^{-1}$ root tissue compared to negative plants, the effect was variable and not statistically significant. However, in contrast with control, the Y25 RNAi plants demonstrated a 71% reduction in the number of SCN cysts per gram root and a 85% reduction was found in the number of eggs per gram root in Y25 RNAi roots which was significant.

TABLE 5

Comparison of *Heterodera glycines* reproduction from the bioassay with negative control and Fib-1, Y25 transgenic soybean roots

| Treatment | No. of Plants | Cysts $g^{-1}$ root | Eggs $g^{-1}$ root |
|---|---|---|---|
| Control roots[a] | 16 | 401 a | 17,660 a |
| Fib-1 roots[b] | 10 | 301 a | 11,000 a |
| Y25C1A.5[c] | 12 | 115 b | 2,587 b |

Values followed by a different letter were significantly different at P ≤ 0.05 according to procedure GLM-PDIFF option in SAS. Values represent back-transformed means of log10-transformed data
[a]Soybean plants inoculated with only R1000 as negative control
[b]Soybean plants inoculated with pANDA35HK: Fib-1
[c]Soybean plants inoculated with pANDA35HK: Y25

Discussion

Chimeric transgenic systems have been successfully used to study nodulation and other biological functions in roots of *Medicago truncatula, Arachis hypogaea* and *Coffea Arabica* (Akasaka et al. 1998; Alpizar et al. 2006; Boisson-Dernier et al. 2001). We developed an in planta chimeric soybean system using hairy roots expressing transgenes that can be used to study a variety of high throughput root related topics including resistance to root-parasitic nematodes. In our system, chimeric plants were obtained within four weeks by inducing hairy roots on non-transformed hypocotyls after inoculation with *Agrobacterium rhizogenes*. Many of the previous studies on nematode parasitism have used in vitro cultures of hairy roots which can have significant limitations for testing transgenes (Remeeus et al. 1998; Kifle et al. 1999; Cho et al. 2000; Hwang et al. 2000; Cai et al. 2003). For example, Cho et al. (2000) demonstrated a highly efficient in vitro hairy root system using kanamycin sulfate as a selection agent. Although Cho et al. (2000) used his system to culture soybean cyst nematodes, the roots could only be tested in vitro. Therefore, this method had the disadvantages that no plants could be regenerated and nematodes were required to be aseptic prior to inoculation onto the hairy roots.

A few reports have used similar composite hairy root systems to study root gene expression. Quandt et al. (1993) and Vieweg et al. (2004) introduced the hairy root transgenic system for *Vicia hirsuta* and other species; however, there was no selection for transgenic roots and therefore a number of non-transgenic roots were observed. Similarly, Collier et al. (2005) developed ex vitro composite plants free of selection. In GFP studies of composite soybean plants, Collier observed roughly 50% of the roots were not transgenic. The method described in Collier combined a modified transformation protocol of Quandt et al. (1993) with a screening process of transgenic roots in selection medium. Based on GUS assay, more than 90% of the total root population per chimeric plant was transgenic with the current protocol. The percentage of transgenic roots we obtained in the current methodology were significantly higher than the composite plants obtained by Collier et al. (2005), as our chimeric plants were screened in selection medium.

A GUS assay was used for monitoring the effect of different parameters on the transformation efficiency of our system. Although K599 is often used for hairy root transformation in legumes (Cho et al. 2000; Cho et al. 2004; Kereszt et al. 2007; Savka et al. 1990), more hairy roots and higher transgenic efficiency were achieved by using R1000 than K599 in our experiments. A pre-inoculation time of 4 days gave the highest expression compared to 3, 5 and 6 days, perhaps owing to the fact that the mitotic state of target tissue can affect transformation. This is in accordance with previous reports that plant cell conditions can be an important factor for transformation efficiency (Tepfer 1984; Kifle et al. 1999). A pH of 7.0 for the co-culture medium had the best effect on expression, suggesting a more favorable microenvironment for vir induction on the surface of hypocotyls of soybean, although Stachel et al. (1986) reported that vir induction dropped down at pH 6.0 and above. Santare'm et al. (1998) also utilized pH 7.0 in their soybean cotyledon culture medium and obtained good GUS expression.

The transgenic roots produced from individual chimeric plants were pooled for Southern analysis. One to three roots were observed to regenerate from a single inoculation site and PCR analysis of individual roots demonstrated that about 10% of these where non-transgenic roots. Based on these observations the multiple bands detected were most likely the result of multiple independent transformation events rather than one high-copy event. The multiple independent integrations may also give rise to variable expression levels of transgene, increasing variability in bioassays. Moreover, approximately 10% of the regenerated roots were not transgenic according to the GUS assay results. Considering this potential risk, we have put GFP expression cassette into the vector pANDA35HK allowing us to eliminate non-transformed roots more efficiently.

Nonetheless our primary goal with the hairy root assays is to rapidly identify candidate genes that have the greatest impact to suppress nematode growth and thus the greatest potential of being field-deployed. Even with the inherent variability of this technique, it is possible to identify those genes with the highest potential to accomplish our goal. The most promising genes identified from the composite plants will be used to stably transform soybean and then will be further validated for SCN suppression.

The production of chimeric plants with transgenic hairy roots can be used to test transgenes of nematode resistance. The *H. glycines* Fib-1 gene was chosen for the study because in five separate RNAi experiments of *C. elegans* Fib-1, either larva lethal or maternal sterile phenotypes were observed (Hanazawa et al. 2001; Kamath et al. 2003; Piano et al. 2002; Simmer et al. 2003; Sonnichsen et al. 2005). Although the *H. glycines* Fib-1 gene RNAi did not exhibit either of these phenotypes, the bioassay did demonstrate the potential for the suppression of *H. glycines* cyst development. Fib-1 encodes a fibrillin, a member of a small family of extracellular glycoproteins. Little is known for this family and it is possible that another family member complemented Fib-1's loss of function, resulting in the limited effect observed for this study. In addition, Y25 gene from *C. elegans* encodes a beta subunit of the coatomer (COPI) complex (Kirchhausen T, 2000; Nickel et al. 2002). Mass RNAi assays of *C. elegans* Y25 indicated that Y25 is required for fertility, adult viability, osmoregulation, and general health (Kamath et al. 2003; Nickel et al. 2002). RNAi of *H. glycines* Y25 gene in soybean significantly reduced the cysts and eggs of *H. glycines* confirming that the gene plays important roles for nematode health and fertility. These results suggest the potential for suppression of *H. glycines* reproduction exists for RNA interference of the Fib-1 gene, and Y25 RNAi is more promising for nematode control.

Expression data from transgenic roots transformed with RNAi constructions demonstrated siRNA species homologous with the target nematode genes were present in the root samples. We also tried to detect siRNA molecules in the aerial portions of the composite plants, but we were unable to confirm siRNA movement throughout the plant. This is in contrast to Limpens et al. (2004), who reported RNA silencing can spread to the non-transgenic shoots of chimeric plants. Discrepancies between these two studies could simply reflect a lower amount of siRNA produced in the current study that was insufficient to be detected in the aerial portions. Regardless, the use of chimeric plants was shown to be a fast and reliable in planta method for testing transgene efficacy against root pathogens.

In summary, we have established an *Agrobacterium rhizogenes*-mediated soybean chimeric transgenic system that can be used to rapidly evaluate root-expressed transgenes. Compared to the genetic transformation and recovery of stable transgenic soybean plants, the production of chimeric hairy root plants takes much less time (around one month), is efficient and less labor intensive. This genetic transformation method can be used as a tool for functional genomics in determining factors associated with root biology including root development, tolerances to abiotic stress, and resistance to biotic stresses.

Example 2

Host-Derived Suppression of Nematode Reproductive and Fitness Genes Decreases Fecundity of *Heterodera Glycines* Ichinohe To control *Heterodera glycines* Ichinohe (soybean cyst nematode) in *Glycine max* (L.) Merr. (soybean), we evaluated the use of producing transgenic soybean seedlings expressing small interfering RNAs (siRNAs) against specific *H. glycines* genes. Gene fragments of three genes related to nematode reproduction or fitness (Cpn-1, Y25 and Prp-17) were PCR-amplified using specific primers and independently cloned into the pANDA35HK RNAi vector using a Gateway cloning strategy. Soybean roots were transformed with these constructions using a composite plant system. Confirmation of transformation was attained by PCR and Southern blot analysis. Transgene expression was detected using reverse transcription PCR (RT-PCR) and expression of siRNAs was confirmed in transgenic plants using northern blot analysis. Bioassays performed on transgenic composite plants expressing double-stranded RNA fragments of Cpn-1, Y25 and Prp-17 genes resulted in a 95, 81 and 79% reduction for eggs eroot, respectively. Furthermore, we demonstrated a significant reduction in transcript levels of the Y25 and Prp-17 genes of the nematodes feeding on the transgenic roots via real-time RT-PCR whereas the expression of nontarget genes were not affected. The results of this study demonstrate that over-expression of RNA interference constructs of nematode reproduction or fitness-related genes can effectively control *H. glycines* infection with levels of suppression comparable to conventional resistance.

Materials and Methods

Bacterial Strains, Vectors, and Soybean Seed.

*Agrobacterium rhizogenes* strain K599 was used in the transformation experiments. The binary vector pANDA35HK was a kind gift from Ko Shimamoto, Japan (Miki and Shimamoto 2004). pANDA35HK has a RNA interference cassette under the control of constitutive 35S cauliflower mosaic virus (CaMV35S) promoter. This vector contains the nptII gene that confers resistance to kanamycin, and a hygromycin phosphotransferase gene (HPT) driven by CaMV35S promoter. Soybean (*Glycine max* L.) seeds variety-KS4607 were obtained by a kind gift from Dr. William T. Schapaugh, Kansas State University. KS4607 is susceptible to *H. glycines* HG Type 7 population. Seeds were surface-sterilized using chlorine gas (3.3 mL concentrated HCl added into 100 mL chlorine bleach) in a closed container overnight. Seeds were then placed in the laminar flow hood for 30 min to remove residue chlorine gas and stored in sealed petri plates.

Cloning of Candidate Genes from *H. glycines* and RNA Interference Constructs.

The selection of target genes from *H. glycines* was based on following criteria: their sequences should be specific so that RNAi of these genes would not affect function of soybean genes. The homologous Cpn-1 (GU074018), Y25 (CB824330) and Prp-17 (AF113915) from *H. glycines* were discovered from datasets in nematode.net. Specific primers for amplifying these genes are listed in Table 6. Using nematode cDNAs as template, 408-, 294- and 289-bp fragments of Cpn-1, Y25 and Prp-17 genes were obtained through PCR method, separately. Cloning of the PCR products into pANDA35HK was performed as described in Li et al. (2010). Briefly, the PCR products were first ligated into pGEM-T Easy vector (Promega, Wis., USA) and then subcloned into pENTR4 vectors by EcoRI restriction sites. Subsequently, the pENTR4 vectors carrying three genes were independently recombined with pANDA35HK vectors using LR clonase (Invitrogen, Calif., USA). The resulting RNAi expression vectors (pANDA35HK:Cpn-1, pANDA35HK:Prp-17 and pANDA35HK: Y25) each contained the gene of interest (GOI) fragments in complementary orientation, separated by 930-bp GUS linker fragment, and driven by CaMV35S promoter. The RNAi constructs were introduced into *A. rhizogenes* strain K599 bp the freeze-thaw method (Chen et al. 1994).

TABLE 6

Primer sequences used for amplifying target genes

| Primer name | Sequences |
|---|---|
| Cpn-1 forward | 5'-CACCAAGGCATCGATCAGGCTGTG-3' (SEQ ID NO: 31) |
| Cpn-1 reverse | 5'-CGCCTTCGATATCCTCCGCCA-3' (SEQ ID NO: 32) |
| Y25 forward | 5'-GCAGCCCGACAAGACAAT-3' (SEQ ID NO: 33) |
| Y25 reverse | 5'-TGAGAGTTCCAATGACAAAT-3' (SEQ ID NO: 34) |
| Prp-17 forward | 5'-CAATCGAATTGTCCTTTTCCA-3' (SEQ ID NO: 35) |
| Prp-17 reverse | 5'-CATTTTGATTACATTGTCCCATC-3' (SEQ ID NO: 36) |

*Agrobacterium rhizogenes*-Mediated Production of Hairy Roots and composite plants.

K599s carrying pANDA35HK:Cpn-1, pANDA35HK: Prp-17 and pANDA35HK: Y25 were cultured on LB medium with 50 mg/L kanamycin and 50 mg/L hygromycin B for 24 h at room temperature. K599s carrying different constructs were resolved in 0.5 mL ½ PS buffer with 0.3-0.6 $OD_{600nm}$. Four-day-old soybean seedlings were inoculated by an injection three times parallel to the vascular bundle of hypocotyl, as described by Li et al. (2010). The formation and selection of composite plants were also accomplished as described by Li et al. (2010).

Polymerase Chain Reaction (PCR) of Transgenic Roots.

Hairy roots tissues from composite plants (about 20 mg) were harvested and genomic DNAs were extracted according to the method of Delloporta et al. (1983). PCR analysis was done with Hybaid limited PCR express thermal cycler (Perkin-Elmer Corporation, CA, USA). Specific primers oriR (5'-GCTTCCTCGCTCACTGACTC-3') (SEQ ID NO:37) and oriF (5'-GGAGAAAGGCGGACAGGAAT-3') (SEQ ID NO:38) were used to amplify the origin (ori) replication site (expected 346 bp). Gus-F1 (5'-CACGTAAGTCCGCATCTTCA-3') (SEQ ID NO:39) and Gus-R1 (5'-GTATCAGTGTGCATGGCTGG-3') (SEQ ID NO:40) situating within Gus linker was paired with Cpn-1 reverse or Y25 reverse or Prp-17 reverse to identify the presence of sense and antisense fragments of Cpn-1, Y25 and Prp-17 genes, respectively. The PCR amplification was carried out for 32 cycles. The initial denaturation reaction was done at 94° C. for 8 min. Each cycle was performed with denaturation (94° C., 1 min), annealing (56° C., 45 s) and extension (72° C., 50 s). PCR mixture consisted of 50-100 ng of plant DNA, 5 μl of 10× Taq buffer, 2.0 μl of 5 mM dNTP, 0.25 μl of Taq DNA polymerase (5 U μl-1, New England Biolabs Inc, MA, USA), 1 μl of 10 pmol each pair of primers in a final volume of 50 μl. The PCR products were separated by electrophoresis on 1.0% agarose gels in 19 TAE buffer and were observed by fluorescence with UV light after staining with ethidium bromide.

Southern Blot Analysis.

Genomic DNAs of hairy roots from composite plants transformed with K599 containing pANDA35HK:Cpn-1 or pANDA35HK: Y25 or pANDA35HK:Prp-17 or not were isolated using the method referred to Murray and Thompson (1980). DNAs were digested with SacI which only cuts once in the multiple cloning sites located between GOI and Nos terminator in the binary vector pANDA35HK. Fifteen microgram DNA from roots of each sample was digested overnight, and together with positive control pANDA35HK (50 pg) and 1 kb DNA ladder were loaded in each lane. The template for probe synthesis was obtained by digestion of HPT gene in PUC119 using BamHI, and the probe was synthesized with a-32P [dCTP] labeled using DNA polymerase I large (Klenow) fragment (Fisher scientific, PA, USA). Gel electrophoresis, DNA blotting and hybridization were done following Sambrook et al. (1989).

RT-PCR.

Total RNAs from different transgenic roots of composite plants together with roots transformed with only *A. rhizogenes* strain K599 were isolated using Trizol reagent (Invitrogen, Calif., USA). For RT-PCR, 1 μg of total RNA was reverse transcribed using AMV Reverse Transcriptase (Promega, Wis., USA) following manufacturer's instructions. RT-PCR was performed using gene-specific primers for ribosomal S21 gene (RibF, 5'-CTAAGATGCAGAACGAGGAAGG-3' (SEQ ID NO:41), and RibR, 5'-GAGAGCAAAAGTGGAGAAATGG-3' (SEQ ID NO:42)) and GUS linker (GusF, 5'-CATGAAGATGCGGACTTACG-3'(SEQ ID NO:43) and GusR, 5'-ATCCACGCCGTATTCGG-3' (SEQ ID NO:44)). The primers listed in Table 5 were used for the amplification of three different target genes, separately. PCR cycling comprised an initial step at 94° C. for 8 min, followed by 31 cycles at 94° C. for 1 min, 58° C. for 45 s, and 72° C. for 50 s.

Northern Blot Analysis.

Total RNAs from roots of different transgenic plants were isolated using Trizol reagent (Invitrogen, Calif., USA). Low molecular weight (LMW) RNAs were then separated from high molecular weight (HMW) RNAs using Qiagen RNA/DNA kit (Valencia, Calif., USA) according to protocols described by Steeves et al. (2006). The HMW RNAs were transferred onto Hybond™ N+ nylon membranes (Amersham Pharmacia Biotech, NJ, USA) using capillary transferring method. The LMW RNAs (12 μg) were separated by electrophoresis on a polyacrylamide gel [including a 6% (w/v) stacking gel and a 15% (w/v) separating gel] containing 7 M urea and 0.59 TBE. RNAs from the gel were transferred onto Hybond™ N+ nylon membranes using electric transferring device and the membranes were cross linked using UV cross linking Both HMW and LMW RNA membranes were hybridized overnight at 42° C. in Ultrasensitive Hybridization Buffer (Ambion, Tex., USA). The 408-, 294- and 289-bp fragments of Cpn-1, Y25 and Prp-17 gene fragments were selected as templates for synthesizing probes and probes were labeled radioactively by a random priming technique. After hybridization, membranes were washed in 29 SSC, 0.1% SDS and 0.29 SSC, 0.1% SDS and exposed in a phosphorimage cassette and visualized with the Storm 840 gel imaging system (GE Healthcare, NJ, USA).

Bioassay.

To explore the suppression of nematode reproduction in transformed roots, composite plants expressing the RNAi vectors of Cpn-1, Y25 and Prp-17 were transplanted from tissue culture into D40 Deepots (Stuewe and Sons, Inc., Corvallis, Oreg.) with 4,500 eggs 100 cm-3 of soil of a HG Type 7 (race 3) *H. glycines* population. The nematode population originated from a naturally infested commercial soybean field in Cherokee Co., KS, and was maintained on a susceptible soybean variety under greenhouse conditions. The universally susceptible soybean cultivar KS4607 was transformed as described above for use in bioassays. Soybean plants inoculated with K599 containing an empty pANDA35HK vector were used as negative controls. Negative controls were put in the same medium for tissue culture as plants transformed with Cpn-1, Y25 and Prp-17. The conditions for growth of composite plants and controls, and bioassay process were described by Steeves et al. (2006).

Data collected from each bioassay were subjected to analysis of variance using the GLM procedure in SAS (SAS Institute, NC, USA). Numbers of cysts $g^{-1}$ root, eggs $g^{-1}$ root and eggs $cyst^{-1}$ were log 10-transformed before analysis to reduce heterogeneity of variances. Least squares means (LSMEANS) were employed to compare the reproductive potential of *H. glycines* on transgenic and control plants.

Real-Time RT-PCR of Candidate Genes from Nematodes Feeding on Transgenic Roots.

Composite plants expressing Y25 and Prp-17 RNAi constructs independently were applied with HG Type 7 populations of *H. glycines* cysts. 5 weeks post-infection, *H. glycines* cysts were collected from composite plants. Total RNA was isolated from collected nematodes using the protocol described by http://cmgm.stanford.edu/-kimlab/germline/experimental_procedures.htm. Nematodes feeding on composite plants inoculated with K599 containing no binary vectors were used as negative controls.

Real-time RT-PCR was performed to analyze the transcript abundance of nematode genes. Gene-specific primers external to the RNAi target regions were designed as shown in Table 7. RNA was reverse transcribed into cDNA by using AMV kit (Promega, Wis., USA) according to the manufacturer's protocol. Endogenous mRNA levels were measured by qRT-PCR based on the SYBR Green detection system using the ABI Prism 7000 Sequence Detection system and the SYBR Green PCR Kit (Applied Biosystems, CA, USA), according to the manufacturer's instructions. The PCRs were performed in an iCycler (Bio-Rad, Hercules, Calif., USA) using the following program: 95° C. for 5 min, and 40 cycles of 95° C. for 30, 56° C. for 15 s and 72° C. for 30 s.

Following PCR amplification, dissociation curves application (Applied Biosystems CA, USA) to ensure that only a single PCR product was amplified. The dissociation program was 95° C. for 1 min, 55° C. for 1 min followed by a slow ramp from 55° C. to 95° C. The experiment included three biological replications for each gene, and each biological replication was assayed by using three technical replications. *H. glycines* beta-actin (Genbank accession No. AF318603), a constitutively expressed gene, was used as internal control to normalize gene expression levels. The expression levels of target gene compared to beta-actin control was determined by using 2-DDCT method as described by Livak and Schmittgen (2001). Using the fold change values for the three biological replications within each experiment, t tests were performed for each RNAi construct at each time point.

from plant premRNA splicing factor was used for our RNAi constructs. The *H. glycines* Cpn-1 gene (GU074018) was inadvertently amplified, as we attempted to amplify the *H. glycines* Eft-1 gene (AW871659) with expected silencing embryonic lethal phenotype. However, the sequence we amplified had ~60% identity with a putative 60 KD chaperonin gene from *Heterodera schachtii* (CD750139) and 83% identity with a *Bordetella holmesii* strain ATCC 51541 Cpn60 gene (AY123715). There is no information currently available on the silencing effects of this gene.

Composite Plants Induction.

*Agrobacterium rhizogenes* K599s carrying either pANDA35HK: Cpn-1, pANDA35HK: Y25 or pANDA35HK: Prp-17 binary vector induced composite plants to produce numerous roots growing from the wound sites on the induction medium supplemented with 200 mg/L kanamycin sulfate. The majority of the roots resembled the hairy root phenotype typical of *A. rhizogenes* induction. Plants inoculated with K599 containing the empty vector pANDA35HK (i.e., no target gene) produced hairy root phenotype as above. Control plants inoculated with K599 containing no binary vectors typically had very poor root development on the selection medium.

PCR Analysis and Southern Blot Hybridization.

Figure 7:
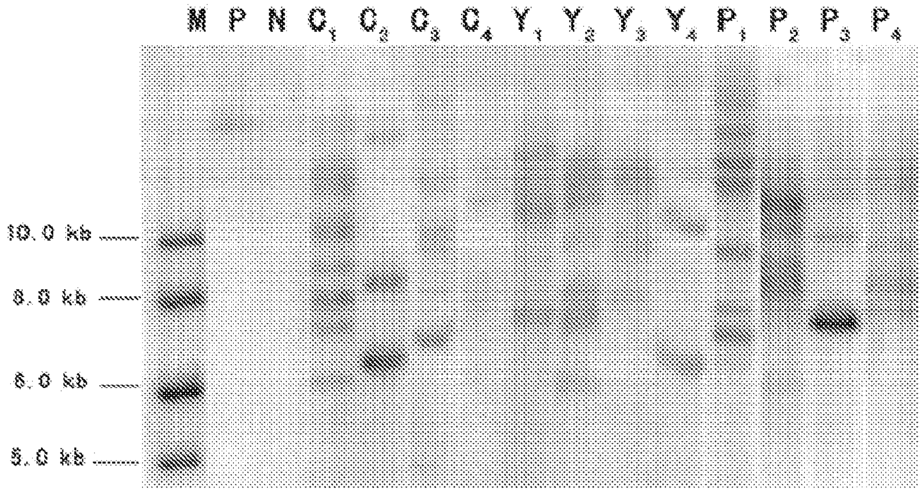
FIG. 7. Southern blot analysis of Cpn-1, Y25 and Prp-17 transformed roots. Genomic DNAs from roots of independent composite plants digested with SacI and probed with BamHI-digested HPT gene fragment. M 1 kb marker, P undigested pANDA35HK vector (50 pg). N negative control soybean plants transformed with only K599 (no binary vector), C1-C4, Y1-Y4, and P1-P4 DNAs from roots of composite plants transformed with pANDA35HK:Cpn-1, pANDA35HK: Y25, and pANDA35HK:Prp-17, respectively.
Figure 8:
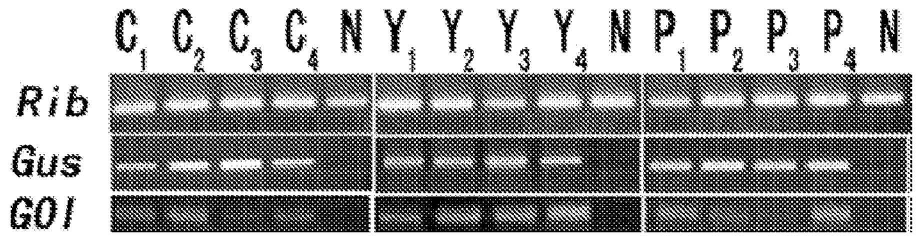
FIG. 8. RT-PCR analysis of Cpn-1, Y25 and Prp-17 transformed roots. RibF and RibR were used for amplification of Rib gene (Ribosomal-521, CF921751); GusF and GusR were used for amplification of Gus linker fragment. Cpn-1 forward and Cpn-1 reverse, Y25 forward and Y25 reverse, Prp-17 forward and Prp-17 reverse were used for amplifying Cpn-1, Y25 and Prp-17 genes, separately. C1-C4 roots of four independent composite plants transformed with pANDA35HK: Cpn-1, Y1-Y4 roots of four independent composite plants transformed with pANDA35HK: Y25, P1-P4 roots of four independent transgenic composite plants transformed with pANDA35HK: Prp-17. N negative control, soybean roots transformed with only K599. GOI gene of interest.

PCR was performed on genomic DNAs of roots from separate composite plants to initially screen for plant transformation. Sampled plants were tested for presence of both sense and antisense fragments of the *H. glycines* genes and for the absence of the on replication site located outside of the T-DNA region of pANDA35HK. As shown in FIG. 7, both the sense and antisense fragments of the *H. glycines* genes were amplified from all putative transgenic roots that grew rapidly under selection. No amplification of the on replication site was observed from all the tested root samples, suggesting that all the samples were free from *A. rhizogenes* contamination. For the plants transformed with RNAi constructs of Cpn-1, Y25 and Prp-17 genes, C1-C4, Y1-Y4 and P1-P4 were positive for the amplification of Cpn-1, Y25, and Prp-17 genes, respectively. Southern blot analysis confirmed the integration of T-DNA in soybean composite plants. Consistent with above PCR results, hybridization results indicated that integration was detected in the root samples C1-C4, Y1-Y4 and P1-P4, but not in root samples transformed with only K599 (no binary vector) (FIG. 8).

TABLE 7

List of primers used in real-time RT-PCR analysis

| Name | Sequence | Gene name | Product size |
|---|---|---|---|
| ACT-F | CGGCATGGGACAGA AGGA (SEQ ID NO: 45) | H. glycines-actin | 63 |
| ACT-R | CGTCAGAATACCACG CTTGGA(SEQ ID NO: 46) | | |
| Prp-F real | CCTACGATACGCTTGG CTATG (SEQ ID NO: 47) | Prp-17 gene | 152 |
| Prp-R real | ATTTATCACTCTCTTTCG CTTCTG (SEQ ID NO: 48) | | |
| Y25-F real | CGATCACTGAGGACG ACTTGG (SEQ ID NO: 49) | Y25 gene | 106 |
| Y25-R real | AACGAAGCACGGCAC TCTC (SEQ ID NO: 50) | | |

Results

Targeted *H. glycines* Genes.

Three *H. glycines* genes, Cpn-1, Y25 and Prp-17, were selected for this study. The genes Y25 and Prp-17 were chosen based on reports of lethal or sterile phenotypes resulting from silencing the homologous *C. elegans* genes. The *H. glycines* Y25 gene (CB824330) has 69% similarity with the homologous *C. elegans* Y25 gene (NM 062040) and codes for a beta subunit of the coatomer (COPI) complex (Kirchhausen 2000; Nickel et al. 2002). The *H. glycines* Prp-17 gene (AF113915) encodes a pre-mRNA splicing factor, which shares 72% similarity with the *C. elegans* Prp-17 gene (NM 060450) for the whole ORF (open reading frame). The unique 30 partial *H. glycines* Prp-17 gene fragment which is different Northern Blot Analysis of Gene of Interests and RT-PCR Analysis.

To monitor whether RNAi fragments of different GOIs were transcribed, HMW RNAs from roots of 20 independent Y25 RNAi composite plants were isolated and northern blot analysis was performed using probes labeled with 294-bp Y25 gene fragment used for pANDA35HK: Y25 construct. The integral Y25 fragment was not detected for the hybridization, suggesting that the transcripts of Y25 RNAi were potentially processed (data not shown).

Figure 9:
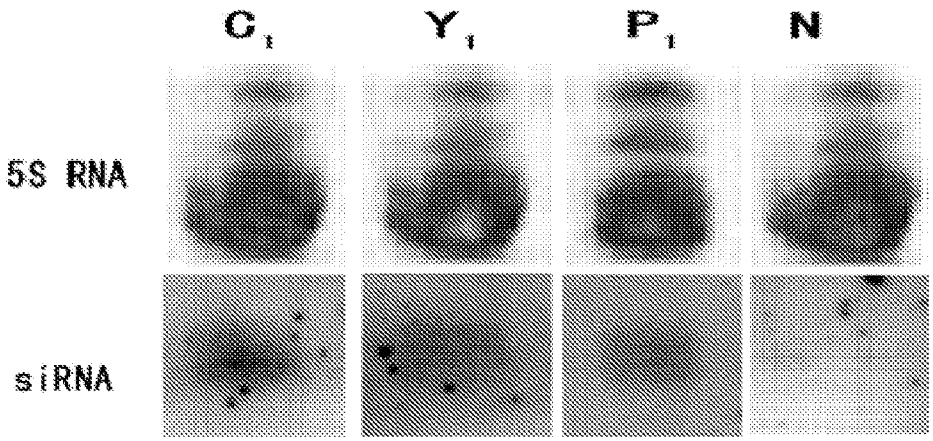
FIG. 9. siRNAs detection in Cpn-1, Y25 and Prp-17 transformed roots. C1 roots from one composite plant transformed with *A. rhizogenes* K599 containing pANDA35HK:Cpn-1, Y1 roots from one composite plant transformed with *A. rhizogenes* K599 containing pANDA35HK:Y25, P1 roots from one composite plant transformed with *A. rhizogenes* K599 containing pANDA35HK:Prp-17, N roots of soybean plants transformed with only K599. 408 bp Cpn-1, 294 bp Y25 and 289 bp Prp-17 were used for the synthesis of probes separately, and hybridized with C1, Y1 and P1 in turn. As negative control (N) had no signals with either of three different probes, hybridization result was only shown with 294-bp Y25 fragment synthesized probe.

RT-PCR was done with primers GusF and GusR towards Gus linker sequence to confirm transcription of the RNAi cassette of Cpn-1, Y25 and Prp-17 genes. Roots of four independent composite plants from each of three constructs along with control roots from plants infected with K599 only (no binary vector) were analyzed. Strong bands were detected in each of putative samples corresponding to the Gus linker transcripts. The appropriate GOIs used for the RNAi constructs were detected in each sample although the intensity of this band was considerably less than that detected for the Gus linker transcripts (FIG. 9).

siRNAs Detection in Transformed Roots.

Figure 10:
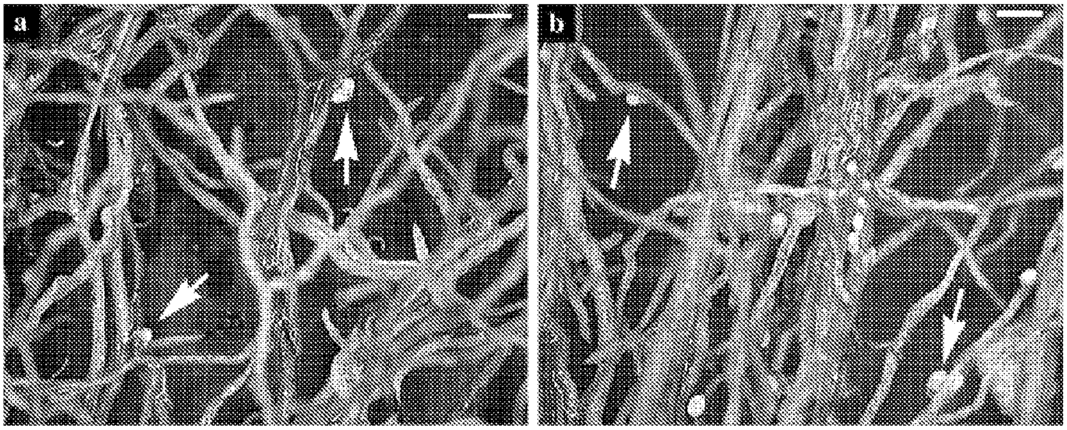
FIG. 10. Comparison of *H. glycines* resistance in Cpn-1 RNAi transgenic composite plants and controls 5 weeks after inoculation. a Transgenic Cpn-1 RNAi plant with significantly less cysts development on roots. b Composite plants transformed with empty vector pANDA35HK showing numerous cysts on roots. Arrows indicate cysts on the roots. Bar 1 mm.

LMW RNAs were differentially isolated from roots of independent Cpn-1, Y25 and Prp-17 transgenic plants showing positive for RT-PCR analysis of Gus linker, and a northern blot analysis was performed to explore whether RNAi fragments of GOIs were processed into siRNAs. Radioactive-labeled probes were synthesized using 408 bp Cpn-1, 294 bp Y25 and 289 bp Prp-17 sense fragments, respectively. Consistent with the results of RT-PCR on Gus linker, FIG. 10 demonstrates the transcripts were processed into siRNAs (~21-23 nt in length) in transgenic roots transformed with pANDA35HK vectors harboring each GOI.

Bioassays.

Figure 11:
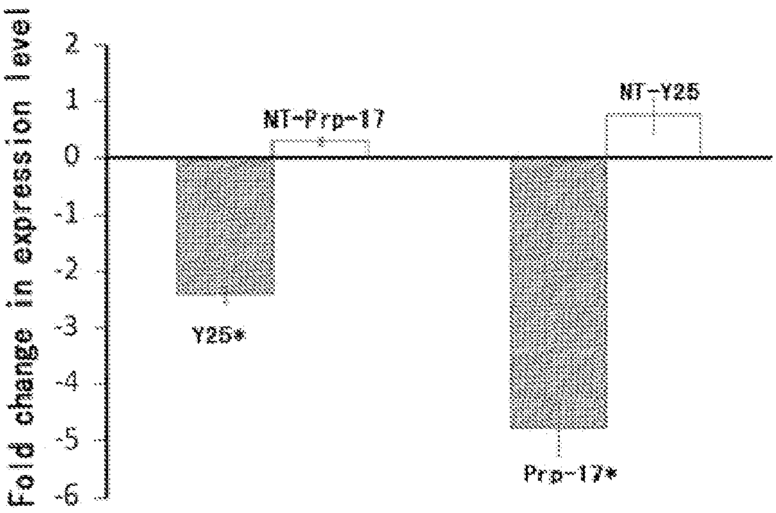
FIG. 11. Real-time RT-PCR results showing the down-regulation of target *H. glycines* genes Y25 and Prp-17 mRNA transcript levels by host-induced RNAi. Y25 and Prp-17 are two different *H. glycines* samples obtained from Y25 and Prp-17 RNAi composite plants of 5 weeks after *H. glycines* inoculation. Nematodes feeding on composite plants inoculated with K599 containing no binary vector were used as negative controls. The *H. glycines* beta-actin (AF318603) gene was used as an endogenous reference for normalization between samples. Data were provided as fold reduction in expression levels (2-DDCT)±standard deviation of the mean based on duplicate qRT-PCR assays of three independent experiments. The relative expression of non-target (NT) gene remain unchanged in each experiment. *P<0.05.

Bioassays were performed by inoculating *H. glycines* on composite plants independently transformed with pANDA35HK:Cpn-1, pANDA35HK: Y25 and pANDA35HK: Prp-17 to detect suppression of *H. glycines* reproduction on transgenic soybean plants. Transformations of the composite plants were verified by PCR analysis (data not shown). Visual inspections of the roots at the completion of the bioassay indicated a marked difference in cyst numbers observed between negative control and the transgenic roots (FIG. 11). For composite plants transformed with Cpn-1, Y25 and Prp-17 RNAi constructs, mean values of cysts $g^{-1}$ root tissue were 552, 1,286 and 1,574, mean values of eggs $g^{-1}$ root tissue were 16,398, 56,104 and 61,432, and mean values of eggs cyst-1 were 55, 48, and 41, respectively (Table 8). In contrast, the control plants transformed with the empty pANDA35HK vector had mean values of 3,364 cysts $g^{-1}$ root tissue, 298,813 eggs $g^{-1}$ root tissue and 92 eggs $cyst^{-1}$. This translates to an 84, 62 and 53% reduction for cysts $g^{-1}$ root, a 95, 81 and 79% reduction for eggs g root, and a 40, 48 and 55% suppression for eggs $cyst^{-1}$ for composite plants transformed with Cpn-1, Y25 and Prp-17 RNAi constructs, respectively. Transgenic plants with all three target genes were significantly different (P B 0.05) from negative controls in numbers of cysts $g^{-1}$ root tissue, while Cpn-1 and Y25 RNAi transgenic plants were significantly different from negative controls for numbers of eggs $g^{-1}$ root tissue. Y25 and Prp-17 RNAi transgenic plants displayed statistically significant reductions in eggs $cyst^{-1}$.

TABLE 8

Comparison of *H. glycines* reproduction on composite plants

| Treatment | No of Plants | Cysts g−1 root | Eggs $g^{-1}$ root | Eggs $cyst^{-1}$ |
|---|---|---|---|---|
| Cpn-1 roots[a] | 32 | 552* | 16,398* | 55 |
| Y25 roots[b] | 31 | 1,286* | 56,104* | 48* |
| Prp-17 Roots[c] | 26 | 1,574* | 61,432 | 41* |
| Control roots[d] | 35 | 3,364 | 298,813 | 92 |

Values represent back-transformed means of log10-transformed data
*Significant reduction ($P \leq 0.05$)
[a]Soybean plants inoculated with K599 containing pANDA35HK: Cpn-1
[b]Soybean plants inoculated with K599 containing pANDA35HK: Y25
[c]Soybean plants inoculated with K599 containing pANDA35HK: Prp-17
[d]Soybean plants inoculated with K599 containing pANDA35HK as negative controls Down-Regulation of Candidate Genes in Nematodes Feeding on Composite Plants Transformed with Different RNAi Constructs.

Total RNAs extracted from nematodes feeding on roots of soybean composite plants at 5 weeks post-inoculation were used in real-time RT-PCR analysis to analyze the transcript abundance of target genes in each RNA sample. Real-time RT-PCR was not performed for nematodes feeding on plants transformed with Cpn-1 RNAi construct as the quality and quantity of isolated RNA was insufficient to perform the analysis.

A 2.41-fold down-regulation of the Y25 transcripts was observed in nematodes feeding on Y25 RNAi transgenic soybean plants, which is equivalent to a 59% reduction in Y25 gene expression compared to the nematodes feeding on composite plants transformed with K599 containing no binary vectors. The expression of Prp-17 as a non-target gene was measured in nematodes feeding on Y25 RNAi transgenic soybean plants and soybean plants transformed with K599 containing no binary vectors. The transcript levels of Prp-17 did not change in these nematodes (FIG. 11).

For nematodes feeding on Prp-17 RNAi transgenic soybean plants, a 4.76-fold down-regulation of the Prp-17 transcripts was observed when compared to the nematodes feeding on composite plants transformed with K599 containing no binary vectors. This value is equivalent to a 79% reduction in Prp-17 gene expression. The Y25 transcript levels were also measured in these two nematode samples as a non-target control and were not altered significantly (FIG. 11). These results confirmed that all of the targeted *H. glycines* genes displayed specific down-regulation for their mRNA transcripts in the nematodes collected from composite plants transformed with the corresponding RNAi constructs at 5 weeks post-inoculation.

Discussion

The transformation of soybean roots with transcripts of three different *H. glycines* genes (Cpn-1, Y25 and Prp-17) designed to induce an RNA interference effect in the nematodes significantly suppressed *H. glycines* reproduction and development. Additionally, the nematodes feeding on Y25 and Prp-17 RNAi transgenic soybean roots displayed significant suppression of Y25 and Prp-17 mRNA transcripts, respectively, as quantified by real-time RTPCR analysis. Target genes were selected using the strategy of Alkharouf et al. (2007), who compared an EST database of *H. glycines* with the *C. elegans* genome and found that 1,500 of the more than 8,000 conserved genes had lethal phenotypes in *C. elegans*. Our results confirmed the validity of this approach for finding gene targets for transgenic resistance to *H. glycines* in soybean. Klink et al. (2009c) recently refined this strategy by employing an Affymetrix soybean Genechip and microarray analyses to find a subset of those *H. glycines* genes with similarity to *C. elegans* genes having mutant lethal phenotypes that were induced during parasitism by the nematodes.

The Y25 gene from *C. elegans* encodes a beta subunit of the coatomer (COPI) complex (Kirchhausen 2000; Nickel et al. 2002). RNAi assays of *C. elegans* Y25 indicated that expression of this gene is required for fertility, adult viability, osmoregulation, and general health (Nickel et al. 2002; Kamath et al. 2003). In an earlier study (Li et al. 2010), we demonstrated that chimeric plants of a partially resistant soybean cultivar 'Jack' expressing RNAi construct of the Y25 gene had significantly fewer numbers of cysts g root (71% reduction) and eggs g-1 root (85% reduction) compared to non-transgenic plants after transplantation into soil infested with *H. glycines* HG Type 2.7. In the current study, composite plants of the susceptible soybean cultivar 'KS4607' expressing Y25 RNAi displayed similar effects (62 and 81% reductions in numbers of cysts and eggs $g^{-1}$ root, respectively), when transplanted into soil infested with *H. glycines* HG type 7. These results corroborate each other, indicating that Y25 RNAi-transformed roots provide consistent levels of resistance against *H. glycines*.

The Prp-17 gene product is required for the second step of pre-mRNA splicing, and *C. elegans* transformed with RNAi of the *C. elegans* Prp-17 gene displayed a phenotype of embryonic lethal (Fraser et al. 2000; Maeda et al. 2001; Simmer et al. 2003; Sonnichsen et al. 2005). In our study, RNAi of the *H. glycines* Prp-17 gene resulted in significant reductions in cysts $g^{-1}$ root tissue (53% reduction) and eggs $cyst^{-1}$ (79% reduction) in the transgenic soybean plants inoculated with *H. glycines*, indicating that this gene also plays an important role in *H. glycines* fitness or reproduction, which supported the important role of Prp-17 gene in *C. elegans*. As reported in Alkharouf et al. (2007), greater than 95% lethality of pi-J2 was observed for *H. glycines* soaked in dsRNA solution of a ribosomal gene Hg-rps-23. In addition, inverted repeat constructs of three genes Hg-rps-3a, Hg-rps-4 and Hg-spk-1 involved in different aspects of mRNA metabolism were associated with 81-88% reductions in numbers of *H. glycines* cysts on transgenic soybean roots (Klink et al. 2009c). Yadav et al. (2006) reported that double-stranded RNA fragments of two genes encoding an integrase and a splicing factor induced RNAi in the plant-parasitic nematode *M. incognita* and protected tobacco against infection. All of these genes are involved in mRNA metabolism, suggesting that genes involved in mRNA metabolism may be particularly sensitive to RNAi and should, therefore, make good target genes for *H. glycines* control.

The cloning of *H. glycines* Cpn-1 fragment was serendipitous. We attempted to amplify *H. glycines* Eft-1 gene using two specific primers, although the BLAST result of the PCR products we obtained showed the sequence we amplified had no identity with Eft-1 gene, but had a 60% identity with a putative 60 kD chaperonin gene from *Heterodera schachtii* (CD750139) and an 83% identity with *Bordetella holmesii* strain ATCC 51541 Cpn60 gene (AY123715). Although no published information on a silencing phenotype was available for this gene, the transgenic composite plants transformed with *H. glycines* Cpn-1 RNAi construct in our experiments displayed robust resistance against *H. glycines*. The 84-95% reductions in numbers of cysts and eggs g-1 root on Cpn-1 RNAi-transformed plants are comparable to the level of resistance in commercialized soybean cultivars, which are categorized as moderately resistant or resistant based on reductions ≥70 and 90%, respectively, in numbers of females that develop on the tested cultivars compared to a standard susceptible cultivar (Schmitt and Shannon 1992).

We have screened RNAi constructs of more than ten different *H. glycines* genes, including the three genes featured in this report, through composite plant bioassay. Plants transformed with the remaining RNAi constructs showed no significant reductions for *H. glycines* development or reproduction. The target genes were chosen based on the embryonic lethal or adult lethal phenotype of silencing of corresponding *C. elegans* genes. The nucleic acid sequence similarity between *H. glycines* and *C. elegans* of these genes was around 50-80%. It is possible that these genes were not orthologs of the *C. elegans* genes and therefore do not hold the same functions in *H. glycines*. Alternatively, there may be functional redundancies within *H. glycines* genome making these target genes non-essential.

Sindhu et al. (2009) reported that RNAi of four parasitism genes cloned from *H. glycines* led to reduction of developing females of *H. schachtii* ranging from 23 to 64%. As stated in the article of Sindhu et al. (2009), at least 90% nucleotide identity was found between those two species *H. glycines* and *H. schachtii*, though only a couple of mis-matching nucleotides may reduce the RNAi effects. RNAi is a highly specific method of gene silencing. For example, Tuschl and colleagues demonstrated that even a single base mismatch between a siRNA and its mRNA target prevented gene silencing (Elbashir et al. 2001). The target genes selected for our study (Cpn-1, Y25 and Prp-17) were more effective in controlling *H. glycines* than the parasitism genes reported in Sindhu et al. (2009), likely because we made specific RNAi constructs using *H. glycines* genes.

Improving soybean resistance against *H. glycines* by genetic engineering requires effective genes and soybean transformation. The traditional stable soybean transformation process is very time consuming and labor intensive. Therefore, there is an urgent need for the development of more rapid methods to identify the function and suitability of target genes. Several options available for this purpose have serious limitations. Feeding *C. elegans* with bacteria expressing *H. glycines* Cpn-1, Y25 or Prp-17 derived dsRNA fragments would not be likely to produce useful results as *H. glycines* Y25 or Prp-17 genes only share 69 and 72% similarity with corresponding *C. elegans* genes, respectively, and *H. glycines* Cpn-1 gene has even lower homology with *C. elegans* genes. As demonstrated by Bakhetia et al. (2005), no phenotype was observed when *C. elegans* was fed with bacteria expressing *M. incognita* dual oxidase gene, which had 65% nucleotide identity with the corresponding *C. elegans* gene. Although transformation of plant-parasitic nematodes represents another approach, attempts to do so have been hindered by the obligate nature of parasitism and low recovery rates.

Composite plant transgenic systems consist of a wildtype shoot with transgenic roots induced by *Agrobacterium rhizogenes* (Hansen et al. 1989). The composite plant systems can produce transgenic material much faster than methods resulting in stable transgenic plants (Collier et al. 2005; Klink et al. 2009c). Recently, Li et al. (2010) demonstrated the value of composite plant transformation for evaluating root-expressed transgenes. In this study, composite soybean plants expressing RNAi constructs were proven to be effective for the rapid identification of target genes, although some variation in results may occur due to the fact that a limited number of roots induced from inoculation sites may escape transformation or because roots derived from one soybean seedling may represent multiple transgenic events. Our goal is to identify the most effective *H. glycines* genes for targeting *H. glycines* reproduction or parasite fitness using this transgenic system. After confirming the effectiveness of RNAi constructs of target genes, such as Cpn-1, Y25 and Prp-17, we are producing stable transgenic plants using particle bombardment mediated method. To date, we have obtained several T1 transgenic lines, and homozygous lines of each will be subjected to *H. glycines* bioassay testing to confirm the results of our composite plant bioassays.

In conclusion, our results provided robust support for the hypothesis that host-delivered dsRNA molecules can be an effective strategy for *H. glycines* gene suppression and *H. glycines* control, and the application of RNAi constructs associated with a composite plant transgenic system provides rapid identification of genes involved in nematode resistance. This strategy also could lead to a better understanding of host-parasite interactions and to the control of other pathogens and insect pests.

Example 3

Results of Hairy Root Bioassay for Different Target Sequences

RNAi sequences from the genes listed in Tables 9a and 9b were cloned into the destination vector pANDA35HK by Gateway cloning method as described in detail above. *Agrobacterium rhizogenes* K599 containing all these RNAi constructs were used for hairy roots transformation, and the composite plants with hairy roots were used for bioassay. RNAi constructs were used for stable transformation mediated by gene gun.

TABLE 9A

Bioassay results of RNAi constructs containing different SCN target genes

| Name | Targeted nematode life stage | Genbank Accession No. | RNAi constructs | Hairy roots | Bioassay Eggs reduction | # of Stable transgenic events |
|---|---|---|---|---|---|---|
| Cpn-1 | — | GU074018 | Completed | Completed | 85% | 3 |
| Prp-17 | — | AF113915 | Completed | Completed | 79% | 3 |
| Y25 | J3 | CB824330 | Completed | Completed | 65% | 1 |
| Rnr-1 | J4 | CD749124 | Completed | Completed | 54% | 2 |
| Arx-3 | J4 | CD748919 | Completed | Completed | 46% | — |
| Fib-1 | J3 | CB279515 | Completed | Completed | 37% | 3 |
| Asb-1 | J2 | BI396626 | Completed | Completed | 33% | 1 |
| Vap-2 | — | AY033601 | Completed | Completed | 31% | — |
| F-55 | Egg | CA940536 | Completed | Completed | 0% | — |
| Rpt-1 | Virgin female | CB376265 | Completed | Completed | 0% | — |
| Eat-3 | Virgin female | CB375718 | Completed | Completed | 0% | — |

TABLE 9b

Bioassay results of RNAi constructs containing different SCN target genes

| Name | Target stage | Genbank Accession No. | Bioassay Eggs reduction | Bioassay Cyst reduction |
|---|---|---|---|---|
| cdk-1 (J12) | Juvenile | CB935405 | 71% | 65% |
| fzy-1 (J13) | Juvenile | CB377841 | 78% | 70% |
| tba-2 (J14) | Juvenile | CB935405 | 63% | 49% |
| arx-1 (J15) | Juvenile | CB299515 | 84% | 68% |
| tbb-2 (J17) | Juvenile | CA939744 | 61% | 50% |
| unc-26 (J20) | Juvenile | CD748096 | 56% | 47% |
| prp-4 (J21) | Juvenile | CB935298 | 60% | 54% |
| pfn-1 (J23) | Juvenile | CB374607 | 74% | 61% |
| vbh-1 (J7) | Juvenile | CB279252 | * | * |

* bioassay not performed

Example 4

Testing of Stacked Constructs

Three RNAi stacking constructs have been made: Cpn-Rnr-1, Cpn-Y25, and Y25-Prp-17. Hairy roots bioassay has been performed for some of the constructs. Bioassay results showed that composite plants derived from stacking constructs Y25-Prp17 RNAi showed more reductions for cysts/g root and eggs/g root than plants derived from Y25 RNAi construct, compared with non-transgenic roots. The reductions for cyst/g root are 61% and 34% for Y25-Prp 17 and Y25 separately, and eggs/g root reductions are 75% and 43% for them, separately.

Example 5

Enhancement of siRNA Amount by Over-Expressing Nematode Genes in Stable Transgenic Soybean Plants Transformed with RNAi Constructs of SCN Genes Stable transgenic plants transformed with RNAi constructs of Y25 (a.k.a. Y25C1A.5). have been obtained and advanced to the $T_2$ generation. Small RNA sequencing using an Illumina Genetic Analyzer showed that soybean dicer-like (DCL) ribonuclease cleaved expressing Y25 dsRNAs formed by nematode inverted repeats into 20~25 nt siRNAs. To enhance the levels of siRNA species of the Y25 target gene we cloned a fragment of the Y25 gene (FIG. 58), which is longer than the fragment used for RNAi construct and expressed the gene fragment with a *G. max* ubiquitin promoter, into a pPTN289 (See FIG. 57) vector containing bar gene which confers bialaphos resistance. We germinated seeds from homozygous $T_2$ soybean lines transformed with Y25 RNAi construct and transformed this line with the above vector. By enhancing the target signal within the soybean plant we should expect to see an enhanced level of siRNA species within the plant and greater delivery of these molecules to the feeding nematodes.

Example 6

Sequences Conservation of Target Genes within and Among Plant Parasitic Species

Currently, resistance to SCN in soybean are limited to certain populations, that is not all genetic sources of resistance are equally effective to all SCN populations. Additionally current genetic resistances are species specific. For example, the genetic resistance for SCN does not give resistance to root knot nematodes. By using RNAi technology targeting gene sequences, which are conserved among different SCN populations and other nematode parasites, we should be able to provide broader resistance against nematodes. We amplified two target genes Y25 (294 bp) and Rnr-1 (251 bp) from SCN race 1, 3, 4 and *Radophlus similis*, root lesion nematode *Pratylenchus neglectus*, and the sequencing results showed 99% similarity for the two genes among all these nematode populations (FIGS. 59A and 59B). We expect the sequences from *Meloidogyne* spp. to be equally similar. We also would expect that these sequences will provide broad resistance to all nematodes that share sequence homology and if these traits are transferred to other plants such as wheat, tomato pineapple and various other plants that are affected by parasitic nematodes, resistance could be achieved as demonstrated with transgenic soybeans.

REFERENCES

Akasaka Y, Mii M, Daimon H (1998) Morphological alterations and root nodule formation in *Agrobacterium rhizogenes*-mediated transgenic hairy roots of peanut (*Arachis hypogaea* L.). Ann Bot 81:355-362

Alpizar E, Dechamp E, Espeout S, Royer M, Lecouls A C, Nicole M, Bertrand B, Lashermes P, Etienne H (2006) Efficient production of *Agrobacterium rhizogenes*-transformed roots and chimeric plants for studying gene expression in coffee roots. Plant Cell Report 25:959-967

Anderson T R, Tenuta A (1998) First report of *Fusarium solani f.* sp. glycines causing sudden death syndrome of soybean in Canada. Plant Dis 82:448

Aoki T, O'Donnell K, Scandiani M M (2005) Sudden death syndrome of soybean in South America is caused by four species of *Fusarium: Fusarium brasiliense* sp. nov., *F. cuneirostrum* sp. nov., *F. tucumaniae*, and *F. virguliforme. Mycoscience* 46:162-183

Bakhetia M, Charlton W, Atkinson H J, McPherson M J (2005) RNA interference of dual oxidase in the plant nematode *Meloidogyne incognita*. MPMI 18:1099-1106

Boisson-Dernier A, Chabaud M, Garcia F, Be'card G, Rosenberg C, Barker D G (2001) *Agrobacterium rhizogenes*-transformed roots of *Medicago truncatula* for the study of nitrogen-fixing and endomycorrhizal symbiotic associations. Mol Plant Microbe Interact 14:695-700

Cai D, Thurau T, Tian Y, Lange T, Yeh K W, Jung C (2003) Sporamin-mediated resistance to beet cyst nematodes (*Heterodera schachtii Schm.*) is dependent on trypsin inhibitory activity in sugar beet (*Beta vulgaris* L.) hairy roots. Plant Mol Biol 51:839-849

Chen H, Nelson R S, Sherwood J L (1994) Enhanced recovery of transformants of *Agrobacterium tumefaciens* after freeze-thaw transformation and drug selection. Biotechniques 16:664-670 Cho H J, Farrand S K, Noel G R, Widholm J M (2000) High-efficiency induction of soybean hairy roots and propagation of the soybean cyst nematode. Planta 210:195-204

Cho H J, Brotherton J E, Widholm J M (2004) Use of the tobacco feedback-insensitive anthranilate synthase gene (ASA2) as a selectable marker for legume hairy root transformation. Plant Cell Rep 23:104-113

Christey M C (2001) Use of Ri-mediated transformation for production of transgenic plants. In Vitro Cell Dev Biol Plant 37:687-700

Collier R, Fuchs B, Walter N, Lutke W K, Taylor C G (2005) Ex vitro chimeric plants: an inexpensive, rapid method for root biology. Plant J 43:449-457

Delloporta S L, Wood J, Hicks J B (1983) A plant DNA minipreparation:version II. Plant Mol Biol Rep 4:19

Dong K, Barker K R, Opperman C H (1997) Genetics of soybean *Heterodera glycines* interactions. J Nematol 29:509-522

Gally M, Ramos A M, Dokmetzian D, Lopez S E (2007) Genetic variability of Phytophthora sojae isolates from Argentina. Mycologia 99:877-883

Gamborg O L, Miller R A, Ojima K (1968) Nutrient requirements of suspension cultures of soybean root cells. Exp Cell Res 50:151-158

Hanazawa M, Mochii M, Ueno N, Kohara Y, Iino Y (2001) Use of cDNA subtraction and RNA interference screens in combination reveals genes required for germ-line development in *Caenorhabditis elegans*. Proc Natl Acad Sci USA 98:8686-8691

Hayashi S, Gresshoff P M, Kinkema M (2008) Molecular analysis of lipoxygenases associated with nodule development in soybean. Mol. Plant Microbe Interact 21:843-853

Hiei Y, Ohta S, Komari T, Kumashiro T (1994) Efficient transformation of rice (*Oryza sativa* L.) mediated by *Agrobacterium* and sequence analysis of the boundaries of the T-DNA. Plant J 6:271-282

Huang G, Allen R, Davis E L, Baum T J, Hussey R S (2006) Engineering broad root-knot resistance in transgenic plants by RNAi silencing of a conserved and essential root-knot nematode parasitism gene. Proc Natl Acad Sci USA 103:14302-14306

Hwang C F, Bhakta A V, Truesdell G M, Pudlo W M, Williamson V M (2000) Evidence for a role of the N terminus and leucine-rich repeat region of the Mi gene product in regulation of localized cell death. Plant cell 12:1319-1329

Jefferson R A, Kavanagh T A, Bevan M W (1987) GUS fusions: betaglucuronidase as a sensitive and versatile gene fusion marker in higher plants. EMBO J 6:3901-3907

Kamath R S, Fraser A G, Dong Y, Poulin G, Durbin R, Gotta M, Kanapin A, Le Bot N, Moreno S, Sohrmann M, Welchman D, Zipperlen P, Ahringer J (2003) Systematic functional analysis of the *Caenorhabditis elegans* genome using RNAi. Nature 421:231-237

Kereszt A, Dong-Xue Li, Indrasumunar A, Nyugen C, Nontachaiyapoom S, Gresshoff P M (2007) Testing gene function in transgenic soybean roots. Nat Protoc 2:948-952

Kifle S, Shao M, Jung C, Cai D (1999) An improved transformation protocol for studying gene expression in hairy roots of sugar beet (*Beta vulgaris* L.). Plant Cell Rep 18:514-519

Kirchhausen T (2000) Three ways to make a vesicle. Nat Rev Mol Cell Biol 1:187-198

Limpens E, Ramos J, Franken C, Raz V, Compaan B, Franssen H, Bisseling T, Geurts R (2004) RNA interference in *Agrobacterium rhizogenes*-transformed roots of *Arabidopsis* and *Medicago truncatula*. J Exp Bot 55:983-992

Murashige T, Skoog F (1962) A revised medium for rapid growth and bioassay with tobacco tissue cultures. Physiol Plant 15:473-497

Murray M G, Thompson W F (1980) Rapid isolation of high molecular weight plant DNA. Nucleic Acids Res 8:4321-4325

Nakajima T, Mitsueda T, Charchar M J D (1996) First occurrence of sudden death syndrome of soybean in Brazil. Jpn Agric Res Q 30:31-34

Niblack T L, Heinz R D, Smith G S, Donald P A (1993) Distribution, density, and diversity of *Heterodera glycines* in Missouri. J Nematol 25:880-886

Nickel W, Brugger B, Wieland F T (2002) Vesicular transport: the core machinery of COPI recruitment and budding. J Cell Sci 115:3235-3240

Olhoft P M, Flagel L E, Donovan C L, Somers D A (2003) Efficient soybean transformation using hygromycin B selection in the cotyledonary-node method. Planta 216: 723-735

Ornatowski W, Jayaraj J, Todd T C, Schapaugh W T, Muthukrishnan S, Trick H N (2004) Introduction and constitutive expression of a tobacco hornworm (Manduca sexta) chitinase gene in soybean. In Vitro Cell Dev Biol Plant 40:260-265

Piano F, Schetter A J, Morton D G, Gunsalus K C, Reinke V, Kim S K, Kemphues K J (2002) Gene clustering based on RNAi phenotypes of ovary-enriched genes in *C. elegans*. Curr Biol 12:1959-1964 Ploper D (1993) Si'ndrome de la muerte su'bita: nueva enfermedad de lasoja en el noroeste argentino. Avance Agroindustrial Ano 13:5-9

Quandt H J, Puhler A, Broer I (1993) Transgenic root nodules of *Vicia* hirsute: a fast and efficient system for the study of gene expression in indeterminate-type nodules. Mol Plant Microbe Interact 6:699-706

Remeeus P M, van Bezooijen J, Wijbrandi J, van Bezooijen J (1998) In vitro testing is a reliable way to screen the temperature sensitivity of resistant tomatoes against *Meloidogyne incognita*. In: Proceedings of 5th international symposium on crop protection, Universiteit Gent, Belgium 63(2b):635-640

Rupe J C, Correll J C, Guerber J C, Becton C M, Gbur E E, Cummings M S, Yount P A (2001) Differentiation of the sudden death syndrome pathogen of soybean, *Fusarium solani* f. sp. glycines, from other isolates of *F. solani* based on cultural morphology, pathogenicity, and mitochondrial DNA restriction fragment length polymorphisms. Can J Bot 79:829-835

Sambrook J, Fritsch E F, Maniatis T (1989) Molecular cloning: a laboratory manual, 2nd edn. Cold Spring Harbor Laboratory Press, New York Santare'm E R, Trick H N, Essig J S, Finer J J (1998) Sonication-assisted *Agrobacterium*-mediated transformation of soybean immature cotyledons: optimization of transient expression. Plant Cell Rep 17:752-759

Savka M A, Ravillion B, Noel G R, Farrand S K (1990) Induction of hairy roots on cultivated soybean genotypes and their use to propagate the soybean cyst nematode. Phytopathology 80:503-508

Simmer F, Moorman C, van der Linden A M, Kuijk E, van den Berghe P V E, Kamath F S, Fraser A G, Ahringer J, Plasterk R H A (2003) Genome-wide RNAi of *C. elegans* using the hypersensitive rrf-3 strain reveals novel gene functions. PLoS Biol 1:77-84

Sonnichsen B, Koski L B, Walsh A, Marschall P, Neumann B, Brehm M, Alleaume A M, Artelt J, Bettencourt P, Cassin E, Hewitson M, Holz C, Khan M, Lazik S, Martin C, Nitzsche B, Ruer M, Stamford J, Winzi M, Heinkel R, Roder M, Finell J, Hantsch H, Jones S J, Jones M, Piano F, Gunsalus K C, Oegema K, Gonczy P, Coulson A, Hyman A A, Echeverri C J (2005) Full-genome RNAi profiling of early embryogenesis in *Caenorhabditis elegans*. Nature 434: 462-469

Stachel S E, Messens E, Van Montagu M, Zambryski P (1985) Identification of signal molecules produced by wounded plant cells which activate the T-DNA transfer process in *Agrobacterium tumefaciens*. Nature 318:624-629

Stachel S E, Nester E W, Zambryski P (1986) A plant cell factor induces *Agrobacterium tumefaciens* vir gene expression. Proc Natl Acad Sci USA 83:379-383

Steeves R M, Todd T C, Essig J S, Trick H N (2006) Transgenic soybeans expressing siRNAs specific to a major sperm protein gene suppress *Heterodera glycines* reproduction. Funct Plant Biol 33:991-999

Tepfer D (1984) Transformation of several species of higher plants by *Agrobacterium rhizogenes*: sexual transmission of the transformed genotype and phenotype. Cell 47:959-967

Tepfer D, Metzger L, Prost R (1989) Use of roots transformed by *Agrobacterium rhizogenes* in rhizosphere research: applications in studies of cadmium assimilation from sewage sludges. Plant Mol Biol 13:295-302

Vieweg M F, Fruhling M, Quandt H J, Heim U, Baumlein H, Puhler A, Kuster H, Andreas M P (2004) The promoter of the *Vicia faba* L. leghemoglobin gene VfLb29 is specifically activated in the infected cells of root nodules and in the arbuscule-containing cells of mycorrhizal roots from different legume and nonlegume plants. Mol Plant Microbe Interact 17:62-69

Wrather J A, Koenning S R (2006) Estimates of disease effects on soybean yields in the United States 2003-2005. J Nematol 38:173-180

Yadav B C, Veluthambi K, Subramaniam K (2006) Host-generated double stranded RNA induces RNAi in plant-parasitic nematodes and protects the host from infection. Mol Biochem Parasitol 148:219-222

Zhu Y J, Agbayani R, Moore P H (2007) Ectopic expression of Dahlia merckii defensin DmAMP1 improves papaya resistance to Phytophthora palmivora by reducing pathogen vigor. Planta 226:87-97

Alkharouf N W, Klink V P, Matthews B F (2007) Identification of *Heterodera glycines* (soybean cyst nematode [SCN]) cDNA sequences with high identity to those of *Caenorhabditis elegans* having lethal mutant or RNAi phenotypes. Exp Parasitol 115:247-258

Bekal S, Niblack T L, Lambert K N (2003) A chorismate mutase from the soybean cyst nematode *Heterodera glycines* shows polymorphisms that correlate with virulence. Mol Plant Microbe Interact 16:439-446

Bernstein E, Caudy A A, Hammond S M, Hannon G J (2001) Role for a bidentate ribonuclease in the initiation step of RNA interference. Nature 409:363-366

Chen H, Nelson R S, Sherwood J L (1994) Enhanced recovery of transformants of *Agrobacterium tumefaciens* after freeze-thaw transformation and drug selection. Biotechniques 16:664-670

Elbashir S M, Martinez J, Patkaniowska A, Lendeckel W, Tuschl T (2001) Functional anatomy of siRNAs for mediating efficient RNAi in *Drosophila melanogaster* embryo lysate. EMBO J 20:6877-6888

Fire A, Xu S, Montgomery M K, Kostas S A, Driver S E, Mello C C (1998) Potent and specific genetic interference by doublestranded RNA in *Caenorhabditis elegans*. Nature 391:806-811

Fraser A G, Kamath R S, Zipperlen P, Martinez-Campos M, Sohrmann M, Ahringer J A (2000) Functional genomic analysis of *C elegans* chromosome I by systematic RNA interference. Nature 408:325-330

Hansen J, Jorgensen J E, Stougaard J, Marcher K A (1989) Hairy roots—a short cut to transgenic root nodules. Plant Cell Rep 8:12-15

Hershman D E, Heinz R D, Kennedy B S (2008) Soybean cyst nematode, *Heterodera glycines*, populations adapting to resistant soybean cultivars in Kentucky. Plant Dis 92:1475

Ithal N, Recknor J, Nettleton D, Hearne L, Maier T, Baum T J, Mitchum M G (2007) Parallel genome-wide expression profiling of host and pathogen during soybean cyst nematode infection of soybean. Mol Plant Microbe Interact 20(3):293-305

Klink V P, Overall C C, Alkharouf N W, MacDonald M H, Matthews B F (2007) Laser capture microdissection (LCM) and comparative microarray expression analysis of syncytial cells isolated from incompatible and compatible soybean (*Glycine max*) roots infected by the soybean cyst nematode (*Heterodera glycines*). Planta 226:1389-1409

Klink V P, Hosseini P, MacDonald M H, Alkharouf N W, Matthews B F (2009a) Population-specific gene expression in the plant pathogenic nematode *Heterodera glycines* exists prior to infection and during the onset of a resistant or susceptible reaction in the roots of the *Glycine max* genotype Peking BMC Genomics 10:111. doi:10.1186/1471-2164-10-111

Klink V P, Hosseini P, Matsye P, Alkharouf N W, Matthews B F (2009b) A gene expression analysis of syncytia laser microdissected from the roots of the *Glycine max* (soybean) genotype PI 548402 (Peking) undergoing a resistant reaction after infection by *Heterodera glycines* (soybean cyst nematode). Plant Mol Biol 71:525-567

Klink V P, Kim K H, Martins V, Macdonald M H, Beard H S, Alkharouf N W, Lee S K, Park S C, Matthews B F (2009c) A correlation between host-mediated expression of parasite genes as tandem inverted repeats and abrogation of development of female *Heterodera glycines* cyst formation during infection of *Glycine max*. Planta 230:53-71

Li J R, Todd T C, Trick H N (2010) Rapid in planta evaluation of root expressed transgenes in chimeric soybean plants. Plant Cell Rep 29:113-123

Liu Q H, Rand T A, Kalidas S, Du F, Kim H E, Smith D P, Wang X D (2003) R2D2, a bridge between the initiation and effector steps of the *Drosophila* RNAi pathway. Science 26:1921-1925

Livak K J, Schmittgen T D (2001) Analysis of relative gene expression data using real-time quantitative PCR and the 2(−Delta Delta C(T)) method. Methods 25:402-408

Maeda I, Kohara Y, Yamamoto M, Sugimoto A (2001) Large-scale analysis of gene function in *Caenorhabditis elegans* by highthroughput RNAi. Curr Biol 11:171-176

Mahalingam R, Wang G, Knap H T (1999) Polygalacturonase and polygalacturonase inhibitor protein: gene isolation and transcription in *Glycine max-Heterodera glycines* interactions. Mol Plant Microbe Interact 12:490-498

Miki D, Shimamoto K (2004) Simple RNAi vectors for stable and transient suppression of gene function in rice. Plant Cell Physiol 45:490-495

Mitchum M G, Wrather J A, Heinz R D, Shannon J G, Danekas G (2007) Variability in distribution and virulence phenotypes of *Heterodera glycines* in Missouri during 2005. Plant Dis 91:1473-1476

Schmitt D P, Shannon G (1992) Differentiating soybean responses to *Heterodera glycines* races. Crop Sci 32:275-277

Simmer F, Moorman C, van der Linden A M, Kuijk E, van den Berghe P V E, Kamath F S, Fraser A G, Ahringer J, Plasterk R H A (2003)

Genome-wide RNAi of *C. elegans* using the hypersensitive rrf-3 strain reveals novel gene functions. PLoS Biol 1:77-84

Sindhu A S, Maier T R, Mitchum M G, Hussey R S, Davis E L, Baum T J (2009) Effective and specific in planta RNAi in cyst nematodes: expression interference of four parasitism genes reduces parasitic success. J Exp Bot 60:315-324

Urwin P E, Lilley C J, Atkinson H J (2002) Ingestion of double stranded RNA by pre-parasitic juvenile cyst nematodes leads to RNA interference. Mol Plant Microbe Interact 15:747-752

Wrather J A, Koenning S R (2006) Estimates of disease effects on soybean yields in the United States 2003-2005. J Nematol 38:173-180

Yadav B C, Veluthambi K, Subramaniam K (2006) Host-generated double stranded RNA induces RNAi in plant-parasitic nematodes and protects the host from infection. Mol Biochem Parasitol 148:219-222

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, plant biology, biochemistry, or related fields are intended to be within the scope of the following claims.

We claim:

1. A transgenic soybean plant comprising an exogenous nucleic acid sequence forming a hairpin structure when expressed, said exogenous nucleic acid sequence comprising a sense sequence of from about 18 to 25 nucleotides in length from a *Heterodera glycines* gene selected from the group consisting of Cpn-1, Prp-17, Y25, Rnr-1 linked to its complementary antisense sequence and encoding a double stranded RNA that inhibits expression of said *Heterodera glycines* gene when expressed.

2. A system for controlling a plant pest comprising:

at least one vector comprising an exogenous nucleic acid sequence forming a hairpin structure when expressed, said exogenous nucleic acid sequence comprising a sense sequence of from about 18 to 25 nucleotides in length from a *Heterodera glycines* gene selected from the group consisting of Cpn-1, Prp-17, Y25, Rnr-1 linked to its complementary antisense sequence and encoding a double stranded RNA that inhibits expression of said *Heterodera glycines* gene.

3. A method of reducing damage due to pests comprising:

cultivating a transgenic plant comprising the system of claim 2.

* * * * *

SEQUENCE LISTING

```
<160> NUMBER OF SEQ ID NOS: 110

<210> SEQ ID NO 1
<211> LENGTH: 1477
<212> TYPE: DNA
<213> ORGANISM: Heterodera Glycines

<400> SEQUENCE: 1

ctccgcattg gccaacactt tggccaaatt ggtgttgcgc tacgctgagc tcaacaaggg      60

tgtcccctca actgttaata aattggcgag tggtgcgctg ctgctcatcg cttcaatcat     120

tcatcttggc aagtcgggct tgtgcaaaca gccgatcact gaggacgact tggaccgttt     180

gtcgaccact gttcgactga ttgttgacca atggccgaaa gcggtggatg tgtttttgag     240

agagtgccgt gcttcgttgg aaagcatgct caaggccaag gggacgtgg accggcacga      300

acgcgacaca aaagcgccga agaagaaaat tgtgcagccc gacaagacaa ttatgttcac     360
```

gcagctgtcc acacgcgtgt cagaaaacgt gacggacaca aatttgtttg atctttcgct 420
ttcccaagcg cttggtactg cacccaaaac gaccaaatac acctttgcca gctccaaact 480
gggaaaagtg attcagttag ccggcttttc ggatcccgtc tatgccgagg cgtacgtcaa 540
cgtcaaccaa tatgacattg tattggacgt actcgtggtc aaccagacta gcgacacctt 600
gcaaaatttg tcattggaac tctcgaccgt tggcgacctt aaattggtgg acaaaccctc 660
gccgattact cttgcaccta acgacttcac taacatcaaa gccaccgtaa aagtgtcatc 720
caccgaaaat ggagtcattt tctccaccat tgcttatgat gtgcgagggt cgacctcgga 780
tcgaaattgt gtgtaccttg aggacattca cattgacata atggattaca ttgtgccggg 840
cacttgcaca gatacagaat ttcggaaaat gtgggccgaa tttgaatggg agaacaaggt 900
cggagttgtg accccaatta cggaccttcg acaatacttg gaccatttgt ccgctcaaac 960
aaatatgaaa ctgctgacaa cagacgcggc attggaaggc gattgcggtt ttctggcggc 1020
caacttctgt gcccattcca tttttggcga ggatgcgttg gccaatgttt ccgttgaaaa 1080
ggcggaccca ctggatccaa tgagtgccat tattggccat attcggatca gggccaagtc 1140
tcaggggatg gcactttcgc tgggggacaa gataaaccac gcgcagaagg aacgtaagcc 1200
ggtggagagg ggcggcgggg cgagggcagt ggcgaacgct gccgcgaaat gaatgaagac 1260
gagcaaaacg tttagcaatt tattgcaaat aatattttaa tcgcatcatt cactgttttc 1320 catgttttc ttattgtttt tctcgtcatt gttaaatttc tttgtatttt gtgatgtgat 1380
ttaatatatt tcttaatttt gggatttgtt tacctaaatt tcaagccgat cattcattat 1440
aaaaaatgta ctgaaaaaaa aaaaaaaaaa aaaaaaa 1477

<210> SEQ ID NO 2
<211> LENGTH: 616
<212> TYPE: DNA
<213> ORGANISM: Heterodera Glycines

<400> SEQUENCE: 2
agtgattctc ctgttcctaa ttggctgctt aacatcggac caatttcttg ccatgcgtgg 60
aacaaggaca aaactcaatt ggctgtttcg ccttccaaca acgaaattca catattcgct 120
cgttcggaga ccgtttggaa cccgttgcac gtgctaagag aacacgactt gctgatcacc 180
ggattggatt gggctccgaa tactaatcgg attgtttcat gttcgcacga caaaaatgcg 240
tttgtgtgga catgggaggc tgaaaagaac agttggaaac cggagatggt ggtcgttcgg 300
ataaacagag ctgccacctg tgtcaaatgg tcgcccaacg aaaacaaatt cgccgttggg 360
acgggtgcgc gtttagtcgc tatttgttat tacgaacgtg aaaatgactg gtgggtagcg 420
aagcaaatca aaaagctgat tcgttccacg gtcacctcat tgaattggca tcccaacaac 480
attttgttgg ctgttggcgc ctgtgacttc aaaacgcgtg ttttttctgc ttatgtgaaa 540
gagattgacg aaaaaccaac gccaaaccct tgggggacca aaatgccatt gggagaattg 600
ctcaaggagt accagt 616

<210> SEQ ID NO 3
<211> LENGTH: 422
<212> TYPE: DNA
<213> ORGANISM: Heterodera Glycines

<400> SEQUENCE: 3
caccaaggca tcgatcaggc tgtggcagca gccattacgg aattgaaggc catctcgcgc 60

-continued

```
cccattgcca ccagcaagga gattgcgcaa gtgggctcca tttcggccaa ctccgacagc    120

gccatcggcg acatcatcgc ccaggccatg gagaaggtgg gcaaggaggg cgtgataacc    180

gtcgaggatg gcaagtcgct ggaaaacgaa ctggatgtgg tggaaggcat gcagttcgac    240

cgcggctacc tgagcccata cttcatcaat gatccggaca agcaactggc gcgcctggat    300

gacccgctgg tgctgctgta cgacaaaaag atcagcaata tccgcgagct gctgccggtg    360

ctggagcagt cggccaaggc cggcaagccg ctgttcatcg tggcggagga tacaaaaagc    420

ga                                                                   422


<210> SEQ ID NO 4
<211> LENGTH: 1822
<212> TYPE: DNA
<213> ORGANISM: Heterodera Glycines

<400> SEQUENCE: 4

atttgcttag atggatttgt taaaatctta cgacggctct tcatcatcgg acaatgaaca     60

agaattggca gatatacctt cttcgtccaa tcacaacaaa ttgctcgctt tgaaaatccc    120

atccatcaac ttaacaccca acgtgattga acaacgcgcc attcaacagg ttgcggttgt    180

ggatccaaaa accaaagagt tgtatcacaa tccgcgcttc gacgaattgt ttagaccaga    240

gagcggccca caaaatccgt ttaaaagtga acatcaacga gcagaaaaga acacactgac    300

cggctatgtg gagccagcgc atttcaacgc cttccatttt gagcgttcac ttcgctccta    360

cgatacgctt ggctatgcgg ataatccaac ggcagacaca accagcgcaa agttcgttgg    420

tgacgttgga caagcgcaag aaaaggccgg cgagtcgctt tttgaatcag taaaaactgg    480

cggacagaag cgaaagagag tgataaatta cgacgcatca aacgttgacg gatatacggg    540

accgtgggca aggtttgagg acgagaagac atttgctcga ccggacccag aattgcagaa    600

ggaaatggac gaaattgtgc ggaaacggaa actgaaaagt cgtgctggcc gaagagcggc    660

catcgcggaa ttgcatttgg cagaagagag caccaaattg cacataaaag atgacactga    720

ctatttgggc cgttccttta tggaaccgcc gaaatacacg ggcaccaatc tgcgcgagga    780

ctttgtgccc gaccgctgtt tcccgcccac aaaacaagca cacacctaca gcagtcacac    840

caaaccggtg accgccatcc gatggtttcc tcgtagtgcg cacatgttta tctcttgttc    900

catggacgga aaagtcaaat tgtgggaagt gtacggcaac cgtaagttga tccgcacata    960

cactggacac aaagtgcccg tgaaggacat ttattttaac aacaccggca ctgaatttct   1020

aagtgccgct tatgacaatt acatcaaatt gtgggacact gaaaccggtc aggtgaaaaa   1080

ccgctacaca attggaggcc atcgggcgta tgtggtcaaa ttcaacccgg acgatgataa   1140

acaaaacatt ttcatggccg gaatgtccaa caaaaagatc atccaatggg acacgcgaac   1200

tggcgaaatc gaacaagaat acgaccgtca tttgggtcca gtgaactcga tcaccttttt   1260

cgacaaaaac cgtcgtttcg tttctacttc ggacgataaa tctcttcgca tttgggaatt   1320

tggcattccc gtggatacaa aactgattca acatgctgga ctacattcca ttccttcaat   1380

gactagggca ccaaatgaaa aatggatcgt tgggcagtcc atggacaatc gaattgtcct   1440

tttccaaatc gtcgatgaca agttgcgatt cgctcgtaaa aaggccttcc gtggtcacaa   1500

tacagcaggg tacgcctgct caactgattt ttcgccagag atgagttttc tcgcttccgg   1560

tgatgcggac ggtaaaatca caatgtggga ctggcgcaca cacaaaattg tctccacatg   1620

gaaggcacat gataatgtgt gcatttcaac actgtggcat ccgcacgaga aatcgcggat   1680

gatttcttgc ggatgggaca atgtaatcaa aatgtgggtc tgacaatgaa gtaaagctga   1740
```

cgacgattca atgatttaaa gtgaatttat ttgtaatgtc tcaaccgata aaaggaaaaa 1800
cgtccaaaaa aaaaaaaaaa aa 1822

<210> SEQ ID NO 5
<211> LENGTH: 631
<212> TYPE: DNA
<213> ORGANISM: Heterodera Glycines

<400> SEQUENCE: 5
gctcaccggt cagcaaaggc attttgcaat acgacatgtg ggatgttgta ccaacggatt 60
tatgggactg gccgctgctc aaagaacgca tttcaaagtt cggtgttcgg aacagtttgc 120
tggtcgcccc tatgccaact gcttcgacag cacaaatcct cggcaacaat gagtccattg 180
agccgtacac ttcaaatgtg tacagccgtc gtgtcctttc gggagacttt caaattgtca 240
atccgcattt gatgaaggat ttaattgaac tcaatctttg ggatgatcaa atgaagaaca 300
gactaatcgc ggagaacgga tcggtgcaga acatcaagca gttgccgcaa gaaatcaaag 360
acctgtacaa gaccgtgtgg gaaataccgc agaaggacat tttgaaaatg gccgccgatc 420
gcgccgcttt cattgaccaa agccaatccc ttaacattca catagcgcag ccgaactatg 480
ctaaactgag ctccatgcac ttttacgcct ggtcattggg acttaaaacc gggatgtatt 540
acctgcgcac tcgtccggct gtcgatgctg ttcagttcac tgtggacaaa atggcccttc 600
ggggaacaat tgccaaggac gaatctgtcg a 631

<210> SEQ ID NO 6
<211> LENGTH: 548
<212> TYPE: DNA
<213> ORGANISM: Heterodera Glycines

<400> SEQUENCE: 6
gctgtgcacg ctgaacatgg tgccgggcga gtcggtgtac ggcgagaagc gcatctcctc 60
ccagcagacc gaaaatgcgc cgattgctgc aataacgccg aagacggaag agacaacgaa 120
tggcagcaac ggtgtctcag cacccaccgc cgcggctgcc ggcccggcac cgccagtcga 180
gtaccgggtg tggaacccgt tccgctccaa actggccgcc gccgtcatgg ccggcattga 240
ggacacgcac atttacccgg gtgcccgtgt gctttatctt ggcgccgctt ccggcacttc 300
cgtttcccat gtgtccgaca tcgttggacc cgaaggcatg gtctatgcag ttgagttttc 360
acatcgcagt ggacgtgacc tgctcggcat ggccaagaag cggtccaacg tggtgccaat 420
tgtggacgac gcacggcacc cgcacaaata ctccatgatg attggcattg tggacacaat 480
tttctcggac gtggcacagc cggaccaggc acggattgtg gcacacaatg cgcacaaatt 540
tctgaaga 548

<210> SEQ ID NO 7
<211> LENGTH: 522
<212> TYPE: DNA
<213> ORGANISM: Heterodera Glycines

<400> SEQUENCE: 7
aaccccagca tcttccagaa aatcattctt ctcaacaaag agattattat catggaagag 60
aatttctgtt gctttgtgtt cggatggatt aacatttacc ttttcttcca cacggctttt 120
cgttataaat ttgaaaagta cgtatacaaa gttacccgtg aacgatttgg caaaatgaag 180
gcttacattg acaatgaatt gaaggaagcc atcgagttcc gcaagacttc aaaggagcag 240
gccgactcgt tgaaagcagt gcatgaaaac tttcccacaa ttttccaaga gaatttggcg 300
ctgcaacttg aagcgaccta ccgaaaaaat gtggactacg cctggcaaga gatgaagcgt 360
cggttggatt acctgcagga agtgcaagca atcaaagacc gattcagcaa ggaaatgatg 420
gtcaaactga tcactgatgg cgtacgaaaa caaattgaaa tgaatgaggg cggaattcgc 480
gacaaatatt tggaccaatg tatcgaacaa cttcgcgttc tg 522

<210> SEQ ID NO 8
<211> LENGTH: 636
<212> TYPE: DNA
<213> ORGANISM: Heterodera Glycines

<400> SEQUENCE: 8
cacgaaaatg tggcgcccac tgacattgag gagggaatgc gagtgggtgt ggaccgcaac 60
aaataccaga ttcatttgcc tttgccggca aagattgacg cgtccgttac gatgatgcaa 120
gtggaggaca agccggacgt tacctacgcg gacattggcg ggtgcgaaga acagatcaaa 180
aagttgcgtg aagtggtcga gtttccgttg cttcagcctg agcgtttcac gagtttgggc 240
attgagcctc cgaagggcgt tttgtttttt ggtccgccgg gcaccggcaa aactttgtgt 300
gcccgcgcgg tcgccaatcg gacggacgcg tgtttcatcc gcgtcatcgg ttccgaatta 360
gtcaaaaaat acgttggcga aggcgcgcgc atggtgcgcg agctgttttc gctggctaaa 420
acgaaaaagg cgtgcattct cttcttcgac gaagtcgacg ccatcggcgg agcgcgattt 480
gacgacggaa aagggggcga caacgaagtg caacggacga tgctcgagtt ggtcaaccaa 540
ctggacggat tcgactcacg cggggccatc aaggttttga tggccaccaa cagaccggac 600
acactcgacc cggcgctcat tcgtcccggt cgcatt 636

<210> SEQ ID NO 9
<211> LENGTH: 747
<212> TYPE: DNA
<213> ORGANISM: Heterodera Glycines

<400> SEQUENCE: 9
gggaaacccg aatctaagga tttgtacgtg cgaccgaaca tcatcgcaaa acgcatcagt 60
ggcacgcttg aggcacatgt caacggtttc cgttcacgtc gttgcgcggc gacaaaattg 120
aggtgatgta caacaacatc aagcacgcct tcttccagcc gtgtgacaac gaaatgatca 180
ttctgttgca cttccatttg aagaatccag tgctgtgggg caaaaagaaa tattcggatg 240
tgcaattctt cactgaagtt ggcgagatca ccaccgactt gggcaagtac catcacatgc 300
aagacaggga cgacattcag agcgagcaga tggaacgcga aatgcgcaag aagctgaaca 360
tggccttcca gaacttctgt gacaaagtgt ttcggatgac caatgagcag gtggactttg 420
acacgccgtt caatgacttg tcgttcatcg gtgcccccca tcggtccacc gtttctctga 480
aaccgacctc gtcatgtttg gtgcacctca cagaatggcc tccatttgtt gtcacacttg 540
acgaagtgga gttggtgcat tttgagcgtg tgtccagcaa caccagcaca ttcgacacgg 600
tcatcgtctt caaagattac accaagaagc cgcacatcat tggccaaatt ccatctaaca 660
acctggacag tatcaaggac tggctaaatt cttgcgacat tcgctacagt gaaggcccaa 720
tgtcgctgaa ctgggccaac atcatga 747

<210> SEQ ID NO 10
<211> LENGTH: 366
<212> TYPE: DNA
<213> ORGANISM: Heterodera Glycines -continued

<400> SEQUENCE: 10
gttgatttgg cggagaaaaa cttgagcaac ccgcatcgga taaagaagat cctcgacggg 60
aaactatttc cgatgaaagc gctcggctat ttcggcgttg tcaccggcat ggacaagcgg 120
gacgcgagca ttgcggagat ccgcaaatac gaggaggact tcttcgagag ttccaaactc 180
tttagggatg gcgttttgaa ggccacccaa atgacgacgc ggaatatgtc attggcggtt 240
tcggactgtt tttggcggat ggttcgcgaa tccatcgaag cgcaggcgga agctttccgc 300
gcccatcgct tccatttgga gaacggaagg aaaacaactt ttgcgcacca ccccgacttg 360
accagg 366

<210> SEQ ID NO 11
<211> LENGTH: 881
<212> TYPE: DNA
<213> ORGANISM: Heterodera Glycines

<400> SEQUENCE: 11
atgcacttga ttaacttaat cgccctcttt ttcatgcttt tcggtaagtc aattgtttaa 60
attcattagc gggataattg ggtaattatt ttgctaatcg tttcaaggcc catccgtcca 120
gcaatacaca aaaacgccaa cgaatgagga caaagaagcg gctgtcaatt gtcacaacaa 180
attccgatcg caattggccc tgggcaatgc cgacaataaa ttgggcggca acaaaatgcc 240
aaaggcgggc aacatgcgta agtttgaatg ggacgaaaac ttggccaaac ttgcggatga 300
atgggccaac aaatgcacat tatcgcactc gtggaacggc tgggcaggcg aaaatttggc 360
aatgaatggc ggaacatttt cgaacagttc gatacaaatt gataattgtg gctactaatt 420
gcctgcttaa gaggatggct tcgagtacgc ttgcggtcgc tggtgggacg aactgaaccg 480
ttacgggttc aacccggatc tgattatgac cggggaaaac ttcagtggca tcggccattg 540
gactcaggtg acctattcat tatttcgccg tttctagtcc cattattgct aattagacac 600
taattagttt tctcttcgtt ttgttcagat ggcgtgggcc gacaccgacc gaattggctg 660
tgccatggca caaaactgcc caaataccaa ttggaaaaca tatgtggtct gctggtatta 720
cacggggtaa taatcaacca ctgataaaac ataattagtt tactaatacc ccttttagtg 780
gtaattactt tggtgcgcct gtctatttgg cccgggagcc gtgcagcaaa tgcaaagcaa 840
atgacaaatg tgacaaagcc actggacttt gctctcaatg a 881

<210> SEQ ID NO 12
<211> LENGTH: 292
<212> TYPE: DNA
<213> ORGANISM: Pratylenchus neglectus

<400> SEQUENCE: 12
gcagcccgac aagacaatta tgttcacgcg gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gctcttcgga 180
tcccgtctat gccgaggcgt acgtcaacgt caaccaatat gacattgtat tggacgtact 240
cgtggtcaac cagactggcg acaccttgca aaatttgtca ttggaactct ca 292

<210> SEQ ID NO 13
<211> LENGTH: 251
<212> TYPE: DNA
<213> ORGANISM: Pratylenchus neglectus

<400> SEQUENCE: 13
caagaaatca aagacctgta caagaccgtg tgggaaatac cgcagaagga cattttgaaa 60
atggccgccg atcgcgccgc cttcattgac caaagccaat cccttaacat tcacatagcg 120
cagccgaact atgctaaact gagctccatg cacttttacg cctggtcatt gggacttaaa 180
accgggatgt attacctgcg cactcgtccg gctgtcgatg ctgttcagtt cactgtggac 240
aaaatggccc t 251

<210> SEQ ID NO 14
<211> LENGTH: 289
<212> TYPE: DNA
<213> ORGANISM: Radopholus similis

<400> SEQUENCE: 14
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gctcttcgga 180
tcccgtctat gccgaggcgt acgtcaacgt caaccaatat gacattgtat tggacgtact 240
cgtggtcaac cagactggcg acaccttgca aattgtcatt ggactctca 289

<210> SEQ ID NO 15
<211> LENGTH: 235
<212> TYPE: DNA
<213> ORGANISM: Radopholus similis

<400> SEQUENCE: 15
aagtacgtgt gctgtgtgtg tattcagcca ggacattttg aaaatggccg ccgatcgcgc 60
ccttttcatt gaccaaagcc aatcccttaa cattcacata gcgcagccga actatgctaa 120
actgagctcc atgcactttt acgcctggtc attgggactt aaaaccggga tgtattacct 180
gcgcactcgt ccggctgtcg atgctgttca gttcactgtg gacaaaatgg cccta 235

<210> SEQ ID NO 16
<211> LENGTH: 188
<212> TYPE: DNA
<213> ORGANISM: Rotylenchulus reniformis

<400> SEQUENCE: 16
gccgccgatc gcgccgcttt cattgaccaa agccaatccc ttaacattca catagcgcag 60
ccgaactatg ctaaactgag ctccatgcac ttttacgcct ggtcattggg acttaaaacc 120
gggatgtatt acctgcgcac tcgtccggct gtcgatgctg ttcagttcac tgtggacaaa 180
atggccct 188

<210> SEQ ID NO 17
<211> LENGTH: 291
<212> TYPE: DNA
<213> ORGANISM: Artificial Sequence
<220> FEATURE:
<223> OTHER INFORMATION: Synthetic

<400> SEQUENCE: 17
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gcttttcgga 180
tcccgtctat gccgaggcgt acgtcaacgt caaccaatat gacattgtat tggacgtact 240

-continued

```
cgtggtcaac cagactagcg acaccttgca aaatttgtca ttggaactct c              291


<210> SEQ ID NO 18
<211> LENGTH: 388
<212> TYPE: DNA
<213> ORGANISM: Artificial Sequence
<220> FEATURE:
<223> OTHER INFORMATION: Synthetic

<400> SEQUENCE: 18

gtttcatgtt cgcacgacaa aaatgcgttt gtgtggacat gggaggctga aaagaacagt     60

tggaaaccgg agatggtggt cgttcggata aacagagctg ccacctgtgt caaatggtcg    120

cccaacgaaa acaaattcgc cgttgggacg ggtgcgcgtt tagtcgctat ttgttattac    180

gaacgtgaaa atgactggtg ggtagcgaag caaatcaaaa agctgattcg ttccacggtc    240

acctcattga attggcatcc caacaacatt ttgttggctg ttggcgcctg tgacttcaaa    300

acgcgtgttt tttctgctta tgtgaaagag attgacgaaa aaccaacgcc aaacccttgg    360

gggaccaaaa tgccattggg agaattgc                                       388


<210> SEQ ID NO 19
<211> LENGTH: 289
<212> TYPE: DNA
<213> ORGANISM: Artificial Sequence
<220> FEATURE:
<223> OTHER INFORMATION: Synthetic

<400> SEQUENCE: 19

caatcgaatt gtccttttcc aaatcgtcga tgacaagttg cgattcgctc gtaaaaaggc     60

cttccgtggt cacaatacag cagggtacgc ctgctcaact gatttttcgc cagagatgag    120

ttttctcgct tccggtgatg cggacggtaa aatcacaatg tgggactggc gcacacacaa    180

aattgtctcc acatggaagg cacatgataa tgtgtgcatt tcaacactgt ggcatccgca    240

cgagaaatcg cggatgattt cttgcggatg ggacaatgta atcaaaatg                289


<210> SEQ ID NO 20
<211> LENGTH: 251
<212> TYPE: DNA
<213> ORGANISM: Artificial Sequence
<220> FEATURE:
<223> OTHER INFORMATION: Synthetic

<400> SEQUENCE: 20

caagaaatca aagacctgta caagaccgtg tgggaaatac cgcagaagga cattttgaaa     60

atggccgccg atcgcgccgc tttcattgac caaagccaat cccttaacat tcacatagcg    120

cagccgaact atgctaaact gagctccatg cacttttacg cctggtcatt gggacttaaa    180

accgggatgt attacctgcg cactcgtccg gctgtcgatg ctgttcagtt cactgtggac    240

aaaatggccc t                                                         251


<210> SEQ ID NO 21
<211> LENGTH: 164
<212> TYPE: DNA
<213> ORGANISM: Artificial Sequence
<220> FEATURE:
<223> OTHER INFORMATION: Synthetic

<400> SEQUENCE: 21

ccgaagacgg aagagacaac gaatggcagc aacggtgtct cagcacccac cgccgcggct     60
```

-continued gccggcccgg caccgccagt cgagtaccgg gtgtggaacc cgttccgctc caaactggcc 120
gccgccgtca tggccggcat tgaggacacg cacatttacc cggg 164

<210> SEQ ID NO 22
<211> LENGTH: 297
<212> TYPE: DNA
<213> ORGANISM: Artificial Sequence
<220> FEATURE:
<223> OTHER INFORMATION: Synthetic

<400> SEQUENCE: 22
tccacacggc ttttcgttat aaatttgaaa agtacgtata caaagttacc cgtgaacgat 60
ttggcaaaat gaaggcttac attgacaatg aattgaagga agccatcgag ttccgcaaga 120
cttcaaagga gcaggccgac tcgttgaaag cagtgcatga aaactttccc acaattttcc 180
aagagaattt ggcgctgcaa cttgaagcga cctaccgaaa aaatgtggac tacgcctggc 240
aagagatgaa gcgtcggttg gattacctgc aggaagtgca agcaatcaaa gaccgat 297

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ccgaagacgg aagagacaac 20

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
acccgggtaa atgtgcgtgt c 21

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
gcagcccgac aagacaat 18

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
tgagagttcc aatgacaaat 20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ggagaaaggc ggacaggaat 20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
cacgtaagtc cgcatcttca 20

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
acccgggtaa atgtgcgtgt c 21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tgagagttcc aatgacaaat 20

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
caccaaggca tcgatcaggc tgtg 24

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
cgccttcgat atcctccgcc a 21

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
gcagcccgac aagacaat 18

<210> SEQ ID NO 34

<211> LENGTH: 20
<212> TYPE: DNA
<213> ORGANISM: Artificial Sequence
<220> FEATURE:
<223> OTHER INFORMATION: Synthetic

<400> SEQUENCE: 34
tgagagttcc aatgacaaat 20

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
caatcgaatt gtccttttcc a 21

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
cattttgatt acattgtccc atc 23

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gcttcctcgc tcactgactc 20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ggagaaaggc ggacaggaat 20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
cacgtaagtc cgcatcttca 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gtatcagtgt gcatggctgg 20

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
ctaagatgca gaacgaggaa gg 22

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42
gagagcaaaa gtggagaaat gg 22

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
catgaagatg cggacttacg 20

<210> SEQ ID NO 44
<211> LENGTH: 17
<212> TYPE: DNA
<213> ORGANISM: Artificial Sequence
<220> FEATURE:
<223> OTHER INFORMATION: Synthetic

<400> SEQUENCE: 44
atccacgccg tattcgg 17

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
cggcatggga cagaagga 18

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
cgtcagaata ccacgcttgg a 21

<210> SEQ ID NO 47
<211> LENGTH: 21
<212> TYPE: DNA

<213> ORGANISM: Artificial Sequence
<220> FEATURE:
<223> OTHER INFORMATION: Synthetic

<400> SEQUENCE: 47
cctacgatac gcttggctat g 21

<210> SEQ ID NO 48
<211> LENGTH: 24
<212> TYPE: DNA
<213> ORGANISM: Artificial Sequence
<220> FEATURE:
<223> OTHER INFORMATION: Synthetic

<400> SEQUENCE: 48
atttatcact ctctttcgct tctg 24

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
cgatcactga ggacgacttg g 21

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
aacgaagcac ggcactctc 19

<210> SEQ ID NO 51
<211> LENGTH: 657
<212> TYPE: DNA
<213> ORGANISM: Heterodera Glycines

<400> SEQUENCE: 51
aggaattaag taatttgcca ttggtaattg ataatcatga aaatgagcaa caacaacgac 60
atgagtggtt acgaaaaatt ggggaaaatt ggtgaaggca catatggaac gttcaaggca 120
agaaacaagg acaccgagca aattgttgct cttaagatag tacgactgga tgatgaagat 180
gaaggagttc cgtcttcggc actgcgcgaa atttgtttgt tgcgcgaact acgacatgca 240
aatgttgtgc gattgcagaa tgttgtgcat acaaacaaga cgctgaactt agtctttgaa 300
ttttgtgacc ttgatttacg aaaatttttc gacactttgg atgggcaaat cgaccaaaaa 360
gttgttcgtt cactgatgca tcagttactg tccggtttat gctattgtca tgcgcacaat 420
gtgcttcatc gtgatttgaa gccccagaat ttgttgatca ataatacagt gaaaactgcg 480
ccacaattaa aattggctga ttttggcctt gctagaccgt tcggaatccc ggtccgctgt 540
tatagtgcag aagttgtcac attgtggtat cgacctccag atgttttgtt gggtgccaag 600
ctatacagca cgtccatcga catgtggtct gcaggctgca tttttgctga aatttct 657

<210> SEQ ID NO 52
<211> LENGTH: 616
<212> TYPE: DNA
<213> ORGANISM: Heterodera Glycines

<400> SEQUENCE: 52
cattgccaag aagttggaag caaatgagaa caccaacaat ttgaatacgt ccacttcatg 60
tccgacgagt cccgcttcca aattggaaca gcagacgaag aaacaaatga tgagggtcaa 120
atcggacaat gcagtgaatt cgttggctga ttttgaccaa gtttgcgcat ttcgtaaggg 180
actcgctcct ctagcaaaat tcggccacaa acagcaggtg aatgtgcttt tttcttgtgt 240
ccagcccact tccagttgtg tgaaacggtc tcgtcgttac gttgcgaagg atcccgagag 300
aatgttggat gcgccagatt tattagacga tttttattcg aatttgattg attggagcaa 360
gactaattgt gtcgccgttg gcttaggatc aaaaattttt caatggaacg cggggaccgg 420
tgccgtggat gagataaaag atttctctga aacgcattcg catccaactc tcgtcaaatg 480
gtcttgcgaa ggacaatatc ttgccgttgg attcaatgac ggacaattaa agttgttgga 540
cagcgccacc aaaaaagtgc tgagaacaat tcacacgacg gcaaacatgc gattggcatg 600
tgccacatgg acacac 616

<210> SEQ ID NO 53
<211> LENGTH: 802
<212> TYPE: DNA
<213> ORGANISM: Heterodera Glycines

<400> SEQUENCE: 53
gaccttacaa gtcggcaaag aaatcatcga ccccgtcttg gatctgattc gtcgcatcgc 60
ggataactgc accggacttc aaggctttct catcttccat tcgttcggtg gtggcactgg 120
ctctgggttc acatcgctgc ttatggaacg tctctctgtt gactatggga agaagtctaa 180
gctcgagttc tccatctacc ctgctcctca agtgtccacc gctgtcgttg agccgtacaa 240
ttcggtgctt actacgcaca cgactctcga acactctgac tgtgcattta tggttgacaa 300
tgaggccatc tacgatattt gtcgtcgaaa tttggacgtg gaacgccctt cttacaccaa 360
tttgaaccgt ttgatttctc aagttgtctc ttcgataacc gcttcacttc gatttgatgg 420
tgctttgaat gtcgatctca ctgaattcca gaccaatctt gttccttatc ctcgaattca 480
ctttcctctt gcgacttatt ctccagttat ctcagctgag aaggcctacc acgaatcatt 540
gtcggtttcc gaaatcacca acatgtgctt tgagccgtcc aaccaaatgg tcaaatgcga 600
tccacgtcac ggcaaataca tggccgtgtg ccttctctac cgaggtgacg tcgtcccgaa 660
ggatgtaaat gcggccattg cttcgatcaa aacgaaccgt tcaattcaat tcgtggactg 720
gtgcccgacc ggcttcaagg ttggtatcaa ttatcaacct ccgactgttg ttcccggcgg 780
tgacgttgcc aaagtcccac gt 802

<210> SEQ ID NO 54
<211> LENGTH: 624
<212> TYPE: DNA
<213> ORGANISM: Heterodera Glycines

<400> SEQUENCE: 54
agattgattg actgattgat gcatgccaat ttgccagctg ctgtaattga ttgtggcacc 60
gggtacacaa agcttggcta tgcaggaaat tcggagccac agtttatcat tccgtcggct 120
atcgctgtca aagatgcgaa tattttgaaa agtgtcggcg gaaaaatccc ggacttggac 180
tttttcatcg gtgacgaggc gttgtctcct tcggctgcga attattttgt taagtatcca 240
attcgacatg gaattgtcga cgattgggac ctaatggaac gtttttggga gcattgcatt 300
ttcaaatatt tgcgagccga gcccgaagac cattactttc tgttgacaga accaccgctg 360
aacacgccgg agaaccgcga attcactgcc gagataatgt tcgagtcgtt caatgtgccc 420
ggcctttaca tcgctgtcca ggctctgctc gccttggccg cttcttggca aacccgcgag 480
ttcaaccacc gttctctgac tggccttgtg gtggacagtg gagacggcgt cacccattgc 540
atcccggtgt gtgatggcta tgtcatcggt tcttgcatta agcacattcc catcggcgga 600
cgcgacatta cgtacttttt gcag 624

<210> SEQ ID NO 55
<211> LENGTH: 609
<212> TYPE: DNA
<213> ORGANISM: Heterodera Glycines
<220> FEATURE:
<221> NAME/KEY: misc_feature
<222> LOCATION: (3)..(3)
<223> OTHER INFORMATION: n is a, c, g, or t

<400> SEQUENCE: 55
tgnccttagt ggcctggaca actcaatgcc gaccttcgca aactccttga tagcatggtc 60
cccttcccgc gtctgcactt cttcatgccc ggctttgcgc cgctttctgc gaagggagcg 120
gctgcatatc aagcgtgttc cgtggcagaa ctgaccaaac aaatgttcga cgcaaagaac 180
atgatggcgg cgtgtgaccc gcgccacggc cgttatttga cagttgcggc aatgttccgt 240
ggtcgaatgt cgatgaggga agtggatgac caaatgatgt cggtgcagaa caagaactcc 300
tcgtacttcg tcgaatggat tccgaacaac gtgaagaccg ctgtctgtga cattccgccc 360
cgtggcctca aaatgtcggc aactttcgtc ggaaactcca cagccattca agaacttttc 420
aaacgcattt cggaacagtt cactgctatg ttccgtcgca aggctttcct ccattggtac 480
accggtgagg gcatggacga gatggaattc acggaagccg agtccaacat gaacgatttg 540
atctccgagt atcagcagta ccaagatgcc accgttgacg atgagggcga atacgaggct 600
gaggacacc 609

<210> SEQ ID NO 56
<211> LENGTH: 646
<212> TYPE: DNA
<213> ORGANISM: Heterodera Glycines

<400> SEQUENCE: 56
gctcaaagaa cagcagcggt tgcgcgtggc gttcaacggc ttcatggagc agcagccgag 60
cttcgtcccc acctacaaat tcgacccggg cacacacaat tgggacacga gtgaaaagaa 120
gcgtgtgccg gcgtggtgcg accgcatttt gtattgggtc aaggacaaaa atgtcggcat 180
tgaacaagtg acctacgaat cggcacacca agttgtgctc agtgaccaca aaccggtgct 240
gagcacattc agagtccaag tgaagaaggt ggacaggccg agaaggagcg caatttatga 300
gcagttgttg agggaagtgg acaaacgtca aaatgaactt ttgccccaaa ttacattgtc 360
aaacacagaa ttccatttcg gcaccgtcct cttcgaccag ccatcgttgg ccgtgctgac 420
catcacaaac actggacaaa cgcccaccca tttcagcttc aaacccgcga ggcccgaggc 480
tgacagattg gaggaatggc tgaccataac gccgctctcc tctttcatcg acgttggtgg 540
tgccgtggag gtcactctgc aaatcctcgt cttcgatgag tcggcctgca aagtgccaaa 600
ggatggcgcc gaattgagtt ccattatcat tgtgcatctt acgggt 646

<210> SEQ ID NO 57
<211> LENGTH: 618

<212> TYPE: DNA
<213> ORGANISM: Heterodera Glycines

<400> SEQUENCE: 57

```
cctcgtgccg aattcggcac gagggacatt tttaccatgg gaatgacacg gccaatgttg     60
gtttctgccg caatggatgc caccattcgg atttgggacg tggcatcgca gaaacagttg    120
gaggcactcc cctacaaaga atcccaggtg aacaacattt gcattacgcc cgacggtgcc    180
caactgctcg tcggcgcatg gcaaaacatt cgtttttacg atttgcaatg tccaaccgcg    240
caaggactac acacattttc tgtccatgag aaaaatgtga cttcggtcgg cttccaagtg    300
gacggtgcgt ggatgtacac gggaggggag gattgcatgg ccaaaatttg ggatatgcgc    360
aacaatcagc tgaattgcca gaggatattc caagtgaaca cgccggtgca ctccgttgtg    420
ctgcatccca accaagtgga gctgatcgtt gccgactcca ccggcgccat ttatttgtgg    480
gatttgcgct ccgatcggga cgattcgctg atcaccgaag tggacatgtc cgaatttgtt    540
gttcacgttg acattgacca agtggggcga cagtgtgcgg cggtgacaaa ccggggcaat    600
ttgtttctgt gggacgtc                                                  618
```

<210> SEQ ID NO 58
<211> LENGTH: 654
<212> TYPE: DNA
<213> ORGANISM: Heterodera Glycines

<400> SEQUENCE: 58

```
ctattttctt ttttttcacc ctttgacgac aaacagaagc agcaatgagt ggttgggatg     60
cgtacattca gtcattgact tccagttgtg cggagattac tcgcgtggcc ataattggca    120
attcggacgc gagtgtttgg gccaggactg aaggggagaa cgaattcaag gcgagtgaac    180
ctgagctcaa gaaacttgtc ggccaattcg atgatctttc gcaagttccg tccgtcggtg    240
ccgacctcga gggaattcat tacattgtgc cgcgaacgga tgaaaatctt atctttggga    300
agagggacaa aacgggcttt ttcgctgtga agaccaagtc cgccattctg atcgccattt    360
acaaggacga ggaaagtgtc gtcggcgccg acgtgcgagg ggcggtggag aaaatggcca    420
aataccttga ggacgccggt tactgagccg ttgctcggtt tcctaaacga cttttgtgtt    480
gccaaacgaa aagtgctgag aatggctttg acttattctt ccaaatgcat tccttttcca    540
tcccaaatga tcacttatta ttttattatt acacattctg tgaagtgcgc gtgccgattt    600
ctttttttatt atttggcctt tggatgtgaa taataaaaag gtgtaacgct gaaa         654
```

<210> SEQ ID NO 59
<211> LENGTH: 542
<212> TYPE: DNA
<213> ORGANISM: Heterodera Glycines

<400> SEQUENCE: 59

```
atgtgttttt ggctgttgga agagttgggt ccacctctga gaacatcggt caaaaagttg     60
tttgggttga agagcacaac aaacgccatt tcctgatgga tttgctcgat gccagtgagc    120
ccgaggcact aacactgatt ttcgttgaaa ccaaacgcgg ctgtggagat ctgagttaca    180
tgctccagca agaaggctac cattgcgtag caatccatgg cgatttgaag caaatggaac    240
gcgagcgtca tttggagaac ttccgcaacg gaacggcacc cattttggtg gcaacagcag    300
ttgccgcccg tgggttggac attccgaatg tcaagcacgt gatcaattat gacctaccga    360
atgacatcga tgaatacgtg caccgaattg gcagaaccgg ccgtgtgggc aacattggaa    420
```

```
tggccactag ctttttcaac gacaaaaacc ggaacatttc tcatactcac tagtctgatt    480

gtggaagcaa accaggaatt gcccgattgg ctcgaagaaa tggcacgcga ttcaggccga    540

ca                                                                    542
```

```
<210> SEQ ID NO 60
<211> LENGTH: 1961
<212> TYPE: DNA
<213> ORGANISM: Artificial Sequence
<220> FEATURE:
<223> OTHER INFORMATION: Synthetic

<400> SEQUENCE: 60

gcaattctcc caatggcatt ttggtccccc aagggtttgg cgttggtttt tcgtcaatct     60

ctttcacata agcagaaaaa acacgcgttt tgaagtcaca ggcgccaaca gccaacaaaa    120

tgttgttggg atgccaattc aatgaggtga ccgtggaacg aatcagcttt ttgatttgct    180

tcgctaccca ccagtcattt tcacgttcgt aataacaaat agcgactaaa cgcgcacccg    240

tcccaacggc gaatttgttt tcgttgggcg accatttgac acaggtggca gctctgttta    300

tccgaacgac caccatctcc ggtttccaac tgttcttttc agcctcccat gtccacacaa    360

acgcattttt gtcgtgcgaa catgaaacaa tcgaattcgg taccggatcc agtcgactga    420

attggttccc atggtggagc ctgctttttt gtacaaactt gtgatgacgg tatcgataag    480

cttgatatct acccgcttcg cgtcggcatc cggtcagtgg cagtgaaggg cgaacagttc    540

ctgattaacc acaaaccgtt ctactttact ggctttggtc gtcatgaaga tgcggactta    600

cgtggcaaag gattcgataa cgtgctgatg gtgcacgacc acgcattaat ggactggatt    660

ggggccaact cctaccgtac ctcgcattac ccttacgctg aagagatgct cgactgggca    720

gatgaacatg gcatcgtggt gattgatgaa actgctgctg tcggctttaa cctctcttta    780

ggcattggtt tcgaagcggg caacaagccg aaagaactgt acagcgaaga ggcagtcaac    840

ggggaaactc agcaagcgca cttacaggcg attaaagagc tgatagcgcg tgacaaaaac    900

cacccaagcg tggtgatgtg gagtattgcc aacgaaccgg atacccgtcc gcaagtgcac    960

gggaatattt cgccactggc ggaagcaacg cgtaaactcg acccgacgcg tccgatcacc   1020

tgcgtcaatg taatgttctg cgacgctcac accgatacca tcagcgatct ctttgatgtg   1080

ctgtgcctga accgttatta cggatggtat gtccaaagcg gcgatttgga aacggcagag   1140

aaggtactgg aaaaagaact tctggcctgg caggagaaac tgcatcagcc gattatcatc   1200

accgaatacg gcgtggatac gttagccggg ctgcactcaa tgtacaccga catgtggagt   1260

gaagagtatc agtgtgcatg gctggatatg tatcaccgcg tctttgatcg cgtcagcgcc   1320

gtcgtcggtg aacaggtatg gaatttcgcc gattttgcga cctcgcaagg catattgcgc   1380

gttggcggta acaagaaagg gatcttcact cgatcgaatt cctgcagccc gggggatcca   1440

ctagatgcat gctcgagcgg ccgccagtgt gatggatatc tgcagaattc gcccttatca   1500

caagtttgta caaaaaagca ggctccacca tgggaaccaa ttcagtcgac tggatccggt   1560

accgaattcg attgtttcat gttcgcacga caaaaatgcg tttgtgtgga catgggaggc   1620

tgaaaagaac agttggaaac cggagatggt ggtcgttcgg ataaacagag ctgccacctg   1680

tgtcaaatgg tcgcccaacg aaaacaaatt cgccgttggg acgggtgcgc gtttagtcgc   1740

tatttgttat tacgaacgtg aaaatgactg gtgggtagcg aagcaaatca aaaagctgat   1800

tcgttccacg gtcacctcat tgaattggca tcccaacaac attttgttgg ctgttggcgc   1860

ctgtgacttc aaaacgcgtg ttttttctgc ttatgtgaaa gagattgacg aaaaaccaac   1920
```

gccaaaccct tgggggacca aaatgccatt gggagaattg c 1961

<210> SEQ ID NO 61
<211> LENGTH: 2029
<212> TYPE: DNA
<213> ORGANISM: Artificial Sequence
<220> FEATURE:
<223> OTHER INFORMATION: Synthetic

<400> SEQUENCE: 61
tcgctttttg tatcctccgc cacgatgaac agcggcttgc cggccttggc cgactgctcc 60
agcaccggca gcagctcgcg gatattgctg atctttttgt cgtacagcag caccagcggg 120
tcatccaggc gcgccagttg cttgtccgga tcattgatga agtatgggct caggtagccg 180
cggtcgaact gcatgccttc caccacatcc agttcgtttt ccagcgactt gccatcctcg 240
acggttatca cgccctcctt gcccaccttc tccatggcct gggcgatgat gtcgccgatg 300
gcgctgtcgg agttggccga aatggagccc acttgcgcaa tctccttgct ggtggcaatg 360
gggcgcgaga tggccttcaa ttccgtaatg gctgctgcca cagcctgatc gatgccttgg 420
tgaatcgaat tcggtaccgg atccagtcga ctgaattggt tcccatggtg gagcctgctt 480
ttttgtacaa acttgtgatg acggtatcga taagcttgat atctacccgc ttcgcgtcgg 540
catccggtca gtggcagtga agggcgaaca gttcctgatt aaccacaaac cgttctactt 600
tactggcttt ggtcgtcatg aagatgcgga cttacgtggc aaaggattcg ataacgtgct 660
gatggtgcac gaccacgcat taatggactg gattggggcc aactcctacc gtacctcgca 720
ttacccttac gctgaagaga tgctcgactg ggcagatgaa catggcatcg tggtgattga 780
tgaaactgct gctgtcggct ttaacctctc tttaggcatt ggtttcgaag cgggcaacaa 840
gccgaaagaa ctgtacagcg aagaggcagt caacggggaa actcagcaag cgcacttaca 900
ggcgattaaa gagctgatag cgcgtgacaa aaaccaccca agcgtggtga tgtggagtat 960
tgccaacgaa ccggataccc gtccgcaagt gcacgggaat atttcgccac tggcggaagc 1020
aacgcgtaaa ctcgacccga cgcgtccgat cacctgcgtc aatgtaatgt tctgcgacgc 1080
tcacaccgat accatcagcg atctctttga tgtgctgtgc ctgaaccgtt attacggatg 1140
gtatgtccaa agcggcgatt tggaaacggc agagaaggta ctggaaaaag aacttctggc 1200
ctggcaggag aaactgcatc agccgattat catcaccgaa tacggcgtgg atacgttagc 1260
cgggctgcac tcaatgtaca ccgacatgtg gagtgaagag tatcagtgtg catggctgga 1320
tatgtatcac cgcgtctttg atcgcgtcag cgccgtcgtc ggtgaacagg tatggaattt 1380
cgccgatttt gcgacctcgc aaggcatatt gcgcgttggc ggtaacaaga aagggatctt 1440
cactcgatcg aattcctgca gcccggggga tccactagat gcatgctcga gcggccgcca 1500
gtgtgatgga tatctgcaga attcgccctt atcacaagtt tgtacaaaaa agcaggctcc 1560
accatgggaa ccaattcagt cgactggatc cggtaccgaa ttcgattcac caaggcatcg 1620
atcaggctgt ggcagcagcc attacggaat tgaaggccat ctcgcgcccc attgccacca 1680
gcaaggagat tgcgcaagtg ggctccattt cggccaactc cgacagcgcc atcggcgaca 1740
tcatcgccca ggccatggag aaggtgggca aggagggcgt gataaccgtc gaggatggca 1800
agtcgctgga aaacgaactg gatgtggtgg aaggcatgca gttcgaccgc ggctacctga 1860
gcccatactt catcaatgat ccggacaagc aactggcgcg cctggatgac ccgctggtgc 1920
tgctgtacga caaaaagatc agcaatatcc gcgagctgct gccggtgctg gagcagtcgg 1980
ccaaggccgg caagccgctg ttcatcgtgg cggaggatac aaaaagcga 2029

<210> SEQ ID NO 62
<211> LENGTH: 1951
<212> TYPE: DNA
<213> ORGANISM: Artificial Sequence
<220> FEATURE:
<223> OTHER INFORMATION: Synthetic

<400> SEQUENCE: 62
cattttgatt acattgtccc atccgcaaga aatcatccgc gatttctcgt gcggatgcca 60
cagtgttgaa atgcacacat tatcatgtgc cttccacgtg gagacaattt tgtgtgtgcg 120
ccagtcccac attgtgattt taccgtccgc atcaccggaa gcgagaaaac taagaaaaaa 180
aagaaaggaa tgccttttga attatgtgct agataacctc atctctggcg aaaaatcagt 240
tgagcaggcg taccctgctg tattgtgacc acggaaggcc taatttgtaa ggcacgatta 300
aaaaaattct ttttcgtaaa accacctttc tacgagcgaa tcgcaacttg tcatcgacga 360
tttggaaaag gacaattcga ttgaatcgaa ttcggtaccg gatccagtcg actgaattgg 420
ttcccatggt ggagcctgct tttttgtaca aacttgtgat gacggtatcg ataagcttga 480
tatctacccg cttcgcgtcg gcatccggtc agtggcagtg aagggcgaac agttcctgat 540
taaccacaaa ccgttctact ttactggctt tggtcgtcat gaagatgcgg acttacgtgg 600
caaaggattc gataacgtgc tgatggtgca cgaccacgca ttaatggact ggattggggc 660
caactcctac cgtacctcgc attaccctta cgctgaagag atgctcgact gggcagatga 720
acatggcatc gtggtgattg atgaaactgc tgctgtcggc tttaacctct ctttaggcat 780
tggtttcgaa gcgggcaaca agccgaaaga actgtacagc gaagaggcag tcaacgggga 840
aactcagcaa gcgcacttac aggcgattaa agagctgata gcgcgtgaca aaaaccaccc 900
aagcgtggtg atgtggagta ttgccaacga accggatacc cgtccgcaag tgcacgggaa 960
tatttcgcca ctggcggaag caacgcgtaa actcgacccg acgcgtccga tcacctgcgt 1020
caatgtaatg ttctgcgacg ctcacaccga taccatcagc gatctctttg atgtgctgtg 1080
cctgaaccgt tattacggat ggtatgtcca aagcggcgat ttggaaacgg cagagaaggt 1140
actggaaaaa gaacttctgg cctggcagga gaaactgcat cagccgatta tcatcaccga 1200
atacggcgtg gatacgttag ccgggctgca ctcaatgtac accgacatgt ggagtgaaga 1260
gtatcagtgt gcatggctgg atatgtatca ccgcgtcttt gatcgcgtca gcgccgtcgt 1320
cggtgaacag gtatggaatt tcgccgattt tgcgacctcg caaggcatat tgcgcgttgg 1380
cggtaacaag aaagggatct tcactcgatc gaattcctgc agcccggggg atccactaga 1440
tgcatgctcg agcggccgcc agtgtgatgg atatctgcag aattcgccct tatcacaagt 1500
ttgtacaaaa aagcaggctc caccatggga accaattcag tcgactggat ccggtaccga 1560
attcgattca atcgaattgt ccttttccaa atcgtcgatg acaagttgcg attcgctcgt 1620
agaaaggtgg ttttacgaaa aagaattttt ttaatcgtgc cttacaaatt aggccttccg 1680
tggtcacaat acagcagggt acgcctgctc aactgatttt tcgccagaga tgaggttatc 1740
tagcacataa ttcaaaaggc attcctttct tttttttctt agttttctcg cttccggtga 1800
tgcggacggt aaaatcacaa tgtgggactg gcgcacacac aaaattgtct ccacgtggaa 1860
ggcacatgat aatgtgtgca tttcaacact gtggcatccg cacgagaaat cgcggatgat 1920
ttcttgcgga tgggacaatg taatcaaaat g 1951

<210> SEQ ID NO 63
<211> LENGTH: 1687
<212> TYPE: DNA
<213> ORGANISM: Artificial Sequence
<220> FEATURE:
<223> OTHER INFORMATION: Synthetic

<400> SEQUENCE: 63
agggccattt tgtccacagt gaactgaaca gcatcgacag ccggacgagt gcgcaggtaa 60
tacatcccgg ttttaagtcc caatgaccag gcgtaaaagt gcatggagct cagtttagca 120
tagttcggct gcgctatgtg aatgttaagg gattggcttt ggtcaatgaa agcggcgcga 180
tcggcggcca ttttcaaaat gtccttctgc ggtatttccc acacggtctt gtacaggtct 240
ttgatttctt gaatcgaatt cggtaccgga tccagtcgac tgaattggtt cccatggtgg 300
agcctgcttt tttgtacaaa cttgtgatga cggtatcgat aagcttgata tctacccgct 360
tcgcgtcggc atccggtcag tggcagtgaa gggcgaacag ttcctgatta accacaaacc 420
gttctacttt actggctttg gtcgtcatga agatgcggac ttacgtggca aaggattcga 480
taacgtgctg atggtgcacg accacgcatt aatggactgg attggggcca actcctaccg 540
tacctcgcat tacccttacg ctgaagagat gctcgactgg gcagatgaac atggcatcgt 600
ggtgattgat gaaactgctg ctgtcggctt taacctctct ttaggcattg gtttcgaagc 660
gggcaacaag ccgaaagaac tgtacagcga agaggcagtc aacggggaaa ctcagcaagc 720
gcacttacag gcgattaaag agctgatagc gcgtgacaaa aaccacccaa gcgtggtgat 780
gtggagtatt gccaacgaac cggatacccg tccgcaagtg cacgggaata tttcgccact 840
ggcggaagca acgcgtaaac tcgacccgac gcgtccgatc acctgcgtca atgtaatgtt 900
ctgcgacgct cacaccgata ccatcagcga tctctttgat gtgctgtgcc tgaaccgtta 960
ttacggatgg tatgtccaaa gcggcgattt ggaaacggca gagaaggtac tggaaaaaga 1020
acttctggcc tggcaggaga aactgcatca gccgattatc atcaccgaat acggcgtgga 1080
tacgttagcc gggctgcact caatgtacac cgacatgtgg agtgaagagt atcagtgtgc 1140
atggctggat atgtatcacc gcgtctttga tcgcgtcagc gccgtcgtcg gtgaacaggt 1200
atggaatttc gccgattttg cgacctcgca aggcatattg cgcgttggcg gtaacaagaa 1260
agggatcttc actcgatcga attcctgcag cccgggggat ccactagatg catgctcgag 1320
cggccgccag tgtgatggat atctgcagaa ttcgccctta tcacaagttt gtacaaaaaa 1380
gcaggctcca ccatgggaac caattcagtc gactggatcc ggtaccgaat tcgattcaag 1440
aaatcaaaga cctgtacaag accgtgtggg aaataccgca gaaggacatt ttgaaaatgg 1500
ccgccgatcg cgccgctttc attgaccaaa gccaatccct taacattcac atagcgcagc 1560
cgaactatgc taaactgagc tccatgcact tttacgcctg gtcattggga cttaaaaccg 1620
ggatgtatta cctgcgcact cgtccggctg tcgatgctgt tcagttcact gtggacaaaa 1680
tggccct 1687

<210> SEQ ID NO 64
<211> LENGTH: 1515
<212> TYPE: DNA
<213> ORGANISM: Artificial Sequence
<220> FEATURE:
<223> OTHER INFORMATION: Synthetic

<400> SEQUENCE: 64
acccgggtaa atgtgcgtgt cctcaatgcc ggccatgacg gcggcggcca gtttggagcg 60

-continued

```
gaacgggttc cacacccggt actcgactgg cggtgccggg ccggcagccg cggcggtggg    120
tgctgagaca ccgttgctgc cattcgttgt ctcttccgtc ttcggaatcg aattcggtac    180
cggatccagt cgactgaatt ggttcccatg gtggagcctg ctttttgta caaacttgtg     240
atgacggtat cgataagctt gatatctacc cgcttcgcgt cggcatccgg tcagtggcag    300
tgaagggcga acagttcctg attaaccaca aaccgttcta ctttactggc tttggtcgtc    360
atgaagatgc ggacttacgt ggcaaaggat tcgataacgt gctgatggtg cacgaccacg    420
cattaatgga ctggattggg gccaactcct accgtacctc gcattaccct tacgctgaag    480
agatgctcga ctgggcagat gaacatggca tcgtggtgat tgatgaaact gctgctgtcg    540
gctttaacct ctctttaggc attggtttcg aagcgggcaa caagccgaaa gaactgtaca    600
gcgaagaggc agtcaacggg gaaactcagc aagcgcactt acaggcgatt aaagagctga    660
tagcgcgtga caaaaaccac ccaagcgtgg tgatgtggag tattgccaac gaaccggata    720
cccgtccgca agtgcacggg aatatttcgc cactggcgga agcaacgcgt aaactcgacc    780
cgacgcgtcc gatcacctgc gtcaatgtaa tgttctgcga cgctcacacc gataccatca    840
gcgatctctt tgatgtgctg tgcctgaacc gttattacgg atggtatgtc caaagcggcg    900
atttggaaac ggcagagaag gtactggaaa aagaacttct ggcctggcag gagaaactgc    960
atcagccgat tatcatcacc gaatacggcg tggatacgtt agccgggctg cactcaatgt   1020
acaccgacat gtggagtgaa gagtatcagt gtgcatggct ggatatgtat caccgcgtct   1080
ttgatcgcgt cagcgccgtc gtcggtgaac aggtatggaa tttcgccgat tttgcgacct   1140
cgcaaggcat attgcgcgtt ggcggtaaca agaaagggat cttcactcga tcgaattcct   1200
gcagcccggg ggatccacta gatgcatgct cgagcggccg ccagtgtgat ggatatctgc   1260
agaattcgcc cttatcacaa gtttgtacaa aaaagcaggc tccaccatgg gaaccaattc   1320
agtcgactgg atccggtacc gaattcgatt ccgaagacgg aagagacaac gaatggcagc   1380
aacggtgtct cagcacccac cgccgcggct gccggcccgg caccgccagt cgagtaccgg   1440
gtgtggaacc cgttccgctc caaactggcc gccgccgtca tggccggcat tgaggacacg   1500
cacatttacc cgggt                                                    1515
```

<210> SEQ ID NO 65
<211> LENGTH: 1789
<212> TYPE: DNA
<213> ORGANISM: Artificial Sequence
<220> FEATURE:
<223> OTHER INFORMATION: Synthetic

<400> SEQUENCE: 65

```
aatgcgaccg ggacgaatga gcgccgggtc gagtgtgtcc ggtctgttgg tggccatcaa     60
aaccttgatg gccccgcgtg agtcgaatcc gtccagttgg ttgaccaact cgagcatcgt    120
ccgttgcact tcgttgtcgc cccctttcc gtcgtcaaat cgcgctccgc cgatggcgtc     180
gacttcgtcg aagaagagaa tgcacgcctt tttcgtttta gccagcgaaa acagctcgcg    240
caccatgcgc gcgccttcgc caacgtattt tttgactaat tcggaaccga tgacgcggat    300
gaaatcgaat tcggtaccgg atccagtcga ctgaattggt tcccatggtg gagcctgctt    360
ttttgtacaa acttgtgatg acggtatcga taagcttgat atctacccgc ttcgcgtcgg    420
catccggtca gtggcagtga agggcgaaca gttcctgatt aaccacaaac cgttctactt    480
tactggcttt ggtcgtcatg aagatgcgga cttacgtggc aaaggattcg ataacgtgct    540
gatggtgcac gaccacgcat taatggactg gattggggcc aactcctacc gtacctcgca    600
```

ttacccttac gctgaagaga tgctcgactg ggcagatgaa catggcatcg tggtgattga 660
tgaaactgct gctgtcggct ttaacctctc tttaggcatt ggtttcgaag cgggcaacaa 720
gccgaaagaa ctgtacagcg aagaggcagt caacggggaa actcagcaag cgcacttaca 780
ggcgattaaa gagctgatag cgcgtgacaa aaaccaccca agcgtggtga tgtggagtat 840
tgccaacgaa ccggataccc gtccgcaagt gcacgggaat atttcgccac tggcggaagc 900
aacgcgtaaa ctcgacccga cgcgtccgat cacctgcgtc aatgtaatgt tctgcgacgc 960
tcacaccgat accatcagcg atctctttga tgtgctgtgc ctgaaccgtt attacggatg 1020
gtatgtccaa agcggcgatt tggaaacggc agagaaggta ctggaaaaag aacttctggc 1080
ctggcaggag aaactgcatc agccgattat catcaccgaa tacggcgtgg atacgttagc 1140
cgggctgcac tcaatgtaca ccgacatgtg gagtgaagag tatcagtgtg catggctgga 1200
tatgtatcac cgcgtctttg atcgcgtcag cgccgtcgtc ggtgaacagg tatggaattt 1260
cgccgatttt gcgacctcgc aaggcatatt gcgcgttggc ggtaacaaga aagggatctt 1320
cactcgatcg aattcctgca gcccggggga tccactagat gcatgctcga gcggccgcca 1380
gtgtgatgga tatctgcaga attcgccctt atcacaagtt tgtacaaaaa agcaggctcc 1440
accatgggaa ccaattcagt cgactggatc cggtaccgaa ttcgatttca tccgcgtcat 1500
cggttccgaa ttagtcaaaa aatacgttgg cgaaggcgcg cgcatggtgc gcgagctgtt 1560
ttcgctggct aaaacgaaaa aggcgtgcat tctcttcttc gacgaagtcg acgccatcgg 1620
cggagcgcga tttgacgacg gaaaaggggg cgacaacgaa gtgcaacgga cgatgctcga 1680
gttggtcaac caactggacg gattcgactc acgcggggcc atcaaggttt tgatggccac 1740
caacagaccg gacacactcg acccggcgct cattcgtccc ggtcgcatt 1789

<210> SEQ ID NO 66
<211> LENGTH: 1621
<212> TYPE: DNA
<213> ORGANISM: Artificial Sequence
<220> FEATURE:
<223> OTHER INFORMATION: Synthetic

<400> SEQUENCE: 66
tacaacaaca tcaagcacgc cttcttccag ccgtgtgaca acgaaatgat cattctgttg 60
cacttccatt tgaagaatcc agtgctgtgg ggcaaaaaga aatattcgga tgtgcaattc 120
ttcactgaag ttggcgagat caccaccgac ttgggcaagt accatcacat gcaagacagg 180
gacgacattc agagcgagca gatggaacgc gaaatgcgaa tcgaattcgg taccggatcc 240
agtcgactga attggttccc atggtggagc ctgctttttt gtacaaactt gtgatgacgg 300
tatcgataag cttgatatct acccgcttcg cgtcggcatc cggtcagtgg cagtgaaggg 360
cgaacagttc ctgattaacc acaaaccgtt ctactttact ggctttggtc gtcatgaaga 420
tgcggactta cgtggcaaag gattcgataa cgtgctgatg gtgcacgacc acgcattaat 480
ggactggatt ggggccaact cctaccgtac ctcgcattac ccttacgctg aagagatgct 540
cgactgggca gatgaacatg gcatcgtggt gattgatgaa actgctgctg tcggctttaa 600
cctctcttta ggcattggtt tcgaagcggg caacaagccg aaagaactgt acagcgaaga 660
ggcagtcaac ggggaaactc agcaagcgca cttacaggcg attaaagagc tgatagcgcg 720
tgacaaaaac cacccaagcg tggtgatgtg gagtattgcc aacgaaccgg atacccgtcc 780
gcaagtgcac gggaatattt cgccactggc ggaagcaacg cgtaaactcg acccgacgcg 840

-continued tccgatcacc tgcgtcaatg taatgttctg cgacgctcac accgatacca tcagcgatct 900
ctttgatgtg ctgtgcctga accgttatta cggatggtat gtccaaagcg gcgatttgga 960
aacggcagag aaggtactgg aaaaagaact tctggcctgg caggagaaac tgcatcagcc 1020
gattatcatc accgaatacg gcgtggatac gttagccggg ctgcactcaa tgtacaccga 1080
catgtggagt gaagagtatc agtgtgcatg gctggatatg tatcaccgcg tctttgatcg 1140
cgtcagcgcc gtcgtcggtg aacaggtatg gaatttcgcc gattttgcga cctcgcaagg 1200
catattgcgc gttggcggta acaagaaagg gatcttcact cgatcgaatt cctgcagccc 1260
gggggatcca ctagatgcat gctcgagcgg ccgccagtgt gatggatatc tgcagaattc 1320
gcccttatca caagtttgta caaaaaagca ggctccacca tgggaaccaa ttcagtcgac 1380
tggatccggt accgaattcg attcgcattt cgcgttccat ctgctcgctc tgaatgtcgt 1440
ccctgtcttg catgtgatgg tacttgccca agtcggtggt gatctcgcca acttcagtga 1500
agaattgcac atccgaatat ttctttttgc cccacagcac tggattcttc aaatggaagt 1560
gcaacagaat gatcatttcg ttgtcacacg gctggaagaa ggcgtgcttg atgttgttgt 1620
a 1621

<210> SEQ ID NO 67
<211> LENGTH: 1797
<212> TYPE: DNA
<213> ORGANISM: Artificial Sequence
<220> FEATURE:
<223> OTHER INFORMATION: Synthetic

<400> SEQUENCE: 67
ttccgttctc caaatggaag cgatgggcgc ggaaagcttc cgcctgcgct tcgatggatt 60
cgcgaaccat ccgccaaaaa cagtccgaaa ccgccaatga catattccgc gtcgtcattt 120
gggtggcctt caaaacgcca tccctaaaga gtttggaact ctcgaagaag tcctcctcgt 180
atttgcggat ctccgcaatg ctcgcgtccc gcttgtccat gccggtgaca acgccgaaat 240
agccgagcgc tttcatcgga aatagtttcc cgtcgaggat cttctttatc cgatgcgggt 300
tgctcaaatc gaattcggta ccggatccag tcgactgaat tggttcccat ggtggagcct 360 gctttttgt acaaacttgt gatgacggta tcgataagct tgatatctac ccgcttcgcg 420
tcggcatccg gtcagtggca gtgaagggcg aacagttcct gattaaccac aaaccgttct 480
actttactgg ctttggtcgt catgaagatg cggacttacg tggcaaagga ttcgataacg 540
tgctgatggt gcacgaccac gcattaatgg actggattgg ggccaactcc taccgtacct 600
cgcattaccc ttacgctgaa gagatgctcg actgggcaga tgaacatggc atcgtggtga 660
ttgatgaaac tgctgctgtc ggctttaacc tctctttagg cattggtttc gaagcgggca 720
acaagccgaa agaactgtac agcgaagagg cagtcaacgg ggaaactcag caagcgcact 780
tacaggcgat taaagagctg atagcgcgtg acaaaaacca cccaagcgtg gtgatgtgga 840
gtattgccaa cgaaccggat acccgtccgc aagtgcacgg gaatatttcg ccactggcgg 900
aagcaacgcg taaactcgac ccgacgcgtc cgatcacctg cgtcaatgta atgttctgcg 960
acgctcacac cgataccatc agcgatctct ttgatgtgct gtgcctgaac cgttattacg 1020
gatggtatgt ccaaagcggc gatttggaaa cggcagagaa ggtactggaa aaagaacttc 1080
tggcctggca ggagaaactg catcagccga ttatcatcac cgaatacggc gtggatacgt 1140
tagccgggct gcactcaatg tacaccgaca tgtggagtga agagtatcag tgtgcatggc 1200
tggatatgta tcaccgcgtc tttgatcgcg tcagcgccgt cgtcggtgaa caggtatgga 1260

```
atttcgccga ttttgcgacc tcgcaaggca tattgcgcgt tggcggtaac aagaaaggga   1320

tcttcactcg atcgaattcc tgcagcccgg gggatccact agatgcatgc tcgagcggcc   1380

gccagtgtga tggatatctg cagaattcgc ccttatcaca agtttgtaca aaaaagcagg   1440

ctccaccatg ggaaccaatt cagtcgactg gatccggtac cgaattcgat ttgagcaacc   1500

cgcatcggat aaagaagatc ctcgacggga aactatttcc gatgaaagcg ctcggctatt   1560

tcggcgttgt caccggcatg gacaagcggg acgcgagcat tgcggagatc cgcaaatacg   1620

aggaggactt cttcgagagt tccaaactct ttagggatgg cgttttgaag gccacccaaa   1680

tgacgacgcg gaatatgtca ttggcggttt cggactgttt ttggcggatg gttcgcgaat   1740

ccatcgaagc gcaggcggaa gctttccgcg cccatcgctt ccatttggag aacggaa      1797
```

<210> SEQ ID NO 68
<211> LENGTH: 1951
<212> TYPE: DNA
<213> ORGANISM: Artificial Sequence
<220> FEATURE:
<223> OTHER INFORMATION: Synthetic

<400> SEQUENCE: 68

```
ccaaatagac aggcgcacca aagtaattac cactaaaagg ggtattagta aactaattat     60

gttttatcag tggttgatta ttaccccgtg taataccagc agaccacata tgttttccaa    120

ttggtatttg ggcagttttg tgccatggca cagccaattc ggtcggtgtc ggcccacgcc    180

atctgaacaa aacgaagaga aaactaatta gtgtctaatt agcaataatg ggactagaaa    240

cggcgaaata atgaataggt cacctgagtc caatggccga tgccactgaa gttttccccg    300

gtcataatca gatccgggtt gaacccgtaa cggttcagtt cgtcccacca gcgaccgcaa    360

gcgtactcga agccatcctc ttaaatcgaa ttcggtaccg gatccagtcg actgaattgg    420

ttcccatggt ggagcctgct tttttgtaca aacttgtgat gacggtatcg ataagcttga    480

tatctacccg cttcgcgtcg gcatccggtc agtggcagtg aagggcgaac agttcctgat    540

taaccacaaa ccgttctact ttactggctt tggtcgtcat gaagatgcgg acttacgtgg    600

caaaggattc gataacgtgc tgatggtgca cgaccacgca ttaatggact ggattggggc    660

caactcctac cgtacctcgc attaccctta cgctgaagag atgctcgact gggcagatga    720

acatggcatc gtggtgattg atgaaactgc tgctgtcggc tttaacctct ctttaggcat    780

tggtttcgaa gcgggcaaca agccgaaaga actgtacagc gaagaggcag tcaacgggga    840

aactcagcaa gcgcacttac aggcgattaa agagctgata gcgcgtgaca aaaaccaccc    900

aagcgtggtg atgtggagta ttgccaacga accggatacc cgtccgcaag tgcacgggaa    960

tatttcgcca ctggcggaag caacgcgtaa actcgacccg acgcgtccga tcacctgcgt   1020

caatgtaatg ttctgcgacg ctcacaccga taccatcagc gatctctttg atgtgctgtg   1080

cctgaaccgt tattacggat ggtatgtcca aagcggcgat ttggaaacgg cagagaaggt   1140

actggaaaaa gaacttctgg cctggcagga gaaactgcat cagccgatta tcatcaccga   1200

atacggcgtg gatacgttag ccgggctgca ctcaatgtac accgacatgt ggagtgaaga   1260

gtatcagtgt gcatggctgg atatgtatca ccgcgtcttt gatcgcgtca gcgccgtcgt   1320

cggtgaacag gtatggaatt tcgccgattt tgcgacctcg caaggcatat tgcgcgttgg   1380

cggtaacaag aaagggatct tcactcgatc gaattcctgc agcccggggg atccactaga   1440

tgcatgctcg agcggccgcc agtgtgatgg atatctgcag aattcgccct tatcacaagt   1500
```

-continued

```
ttgtacaaaa aagcaggctc caccatggga accaattcag tcgactggat ccggtaccga   1560

attcgattta agaggatggc ttcgagtacg cttgcggtcg ctggtgggac gaactgaacc   1620

gttacgggtt caacccggat ctgattatga ccggggaaaa cttcagtggc atcggccatt   1680

ggactcaggt gacctattca ttatttcgcc gtttctagtc ccattattgc taattagaca   1740

ctaattagtt ttctcttcgt tttgttcaga tggcgtgggc cgacaccgac cgaattggct   1800

gtgccatggc acaaaactgc ccaaatacca attggaaaac atatgtggtc tgctggtatt   1860

acacggggta ataatcaacc actgataaaa cataattagt ttactaatac ccccttttagt   1920

ggtaattact ttggtgcgcc tgtctatttg g                                   1951


<210> SEQ ID NO 69
<211> LENGTH: 1779
<212> TYPE: DNA
<213> ORGANISM: Artificial Sequence
<220> FEATURE:
<223> OTHER INFORMATION: Synthetic

<400> SEQUENCE: 69

atcggtcttt gattgcttgc acttcctgca ggtaatccaa ccgacgcttc atctcttgcc     60

aggcgtagtc cacatttttt cggtaggtcg cttcaagttg cagcgccaaa ttctcttgga    120

aaattgtggg aaagttttca tgcactgctt tcaacgagtc ggcctgctcc tttgaagtct    180

tgcggaactc gatggcttcc ttcaattcat tgtcaatgta agccttcatt ttgccaaatc    240

gttcacgggt aactttgtat acgtactttt caaatttata acgaaaagcc gtgtggaaat    300

cgaattcggt accggatcca gtcgactgaa ttggttccca tggtggagcc tgcttttttg    360

tacaaacttg tgatgacggt atcgataagc ttgatatcta cccgcttcgc gtcggcatcc    420

ggtcagtggc agtgaagggc gaacagttcc tgattaacca caaaccgttc tactttactg    480

gctttggtcg tcatgaagat gcggacttac gtggcaaagg attcgataac gtgctgatgg    540

tgcacgacca cgcattaatg gactggattg ggccaactc ctaccgtacc tcgcattacc    600

cttacgctga agagatgctc gactgggcag atgaacatgg catcgtggtg attgatgaaa    660

ctgctgctgt cggctttaac ctctctttag gcattggttt cgaagcgggc aacaagccga    720

aagaactgta cagcgaagag gcagtcaacg gggaaactca gcaagcgcac ttacaggcga    780

ttaaagagct gatagcgcgt gacaaaaacc acccaagcgt ggtgatgtgg agtattgcca    840

acgaaccgga tacccgtccg caagtgcacg ggaatatttc gccactggcg gaagcaacgc    900

gtaaactcga cccgacgcgt ccgatcacct gcgtcaatgt aatgttctgc gacgctcaca    960

ccgataccat cagcgatctc tttgatgtgc tgtgcctgaa ccgttattac ggatggtatg   1020

tccaaagcgg cgatttggaa acggcagaga aggtactgga aaaagaactt ctggcctggc   1080

aggagaaact gcatcagccg attatcatca ccgaatacgg cgtggatacg ttagccgggc   1140

tgcactcaat gtacaccgac atgtggagtg aagagtatca gtgtgcatgg ctggatatgt   1200

atcaccgcgt ctttgatcgc gtcagcgccg tcgtcggtga acaggtatgg aatttcgccg   1260

attttgcgac ctcgcaaggc atattgcgcg ttggcggtaa caagaaaggg atcttcactc   1320

gatcgaattc ctgcagcccg ggggatccac tagatgcatg ctcgagcggc cgccagtgtg   1380

atggatatct gcagaattcg ccccttatcac aagtttgtac aaaaaagcag gctccaccat   1440

gggaaccaat tcagtcgact ggatccggta ccgaattcga tttccacacg gcttttcgtt   1500

ataaatttga aaagtacgta tacaaagtta cccgtgaacg atttggcaaa atgaaggctt   1560

acattgacaa tgaattgaag gaagccatcg agttccgcaa gacttcaaag gagcaggccg   1620
```

actcgttgaa agcagtgcat gaaaactttc ccacaatttt ccaagagaat ttggcgctgc 1680
aacttgaagc gacctaccga aaaaatgtgg actacgcctg gcaagagatg aagcgtcggt 1740
tggattacct gcaggaagtg caagcaatca aagaccgat 1779

<210> SEQ ID NO 70
<211> LENGTH: 1769
<212> TYPE: DNA
<213> ORGANISM: Artificial Sequence
<220> FEATURE:
<223> OTHER INFORMATION: Synthetic

<400> SEQUENCE: 70
tgagagttcc aatgacaaat tttgcaaggt gtcgccagtc tggttgacca cgagtacgtc 60
caatacaatg tcatattggt tgacgttgac gtacgcctcg gcatagacgg gatccgaaga 120
gccggctaac tgaatcactt ttcccagttt ggagctggca aaggtgtatt tggtcgtttt 180
gggtgcagta ccaagcgctt gggaaagcga aagatcaaac aaatttgtgt ccgtcacgtt 240
ttctgacacg cgtgtggaca gccgcgtgaa cataattgtc ttgtcgggct gcaatcgaat 300
tcggtaccgg atccagtcga ctgaattggt tcccatggtg gagcctgctt ttttgtacaa 360
acttgtgatg acggtatcga taagcttgat atctacccgc ttcgcgtcgg catccggtca 420
gtggcagtga agggcgaaca gttcctgatt aaccacaaac cgttctactt tactggcttt 480
ggtcgtcatg aagatgcgga cttacgtggc aaaggattcg ataacgtgct gatggtgcac 540
gaccacgcat taatggactg gattggggcc aactcctacc gtacctcgca ttacccttac 600
gctgaagaga tgctcgactg ggcagatgaa catggcatcg tggtgattga tgaaactgct 660
gctgtcggct ttaacctctc tttaggcatt ggtttcgaag cgggcaacaa gccgaaagaa 720
ctgtacagcg aagaggcagt caacggggaa actcagcaag cgcacttaca ggcgattaaa 780
gagctgatag cgcgtgacaa aaaccaccca agcgtggtga tgtggagtat tgccaacgaa 840
ccggataccc gtccgcaagt gcacgggaat atttcgccac tggcggaagc aacgcgtaaa 900
ctcgacccga cgcgtccgat cacctgcgtc aatgtaatgt tctgcgacgc tcacaccgat 960
accatcagcg atctctttga tgtgctgtgc ctgaaccgtt attacggatg gtatgtccaa 1020
agcggcgatt tggaaacggc agagaaggta ctggaaaaag aacttctggc ctggcaggag 1080
aaactgcatc agccgattat catcaccgaa tacggcgtgg atacgttagc cgggctgcac 1140
tcaatgtaca ccgacatgtg gagtgaagag tatcagtgtg catggctgga tatgtatcac 1200
cgcgtctttg atcgcgtcag cgccgtcgtc ggtgaacagg tatggaattt cgccgatttt 1260
gcgacctcgc aaggcatatt gcgcgttggc ggtaacaaga aagggatctt cactcgatcg 1320
aattcctgca gcccggggga tccactagat gcatgctcga gcggccgcca gtgtgatgga 1380
tatctgcaga attcgccctt atcacaagtt tgtacaaaaa agcaggctcc accatgggaa 1440
ccaattcagt cgactggatc cggtaccgaa ttcgattgca gcccgacaag acaattatgt 1500
tcacgcggct gtccacacgc gtgtcagaaa acgtgacgga cacaaatttg tttgatcttt 1560
cgctttccca agcgcttggt actgcaccca aaacgaccaa atacaccttt gccagctcca 1620
aactgggaaa agtgattcag ttagccggct cttcggatcc cgtctatgcc gaggcgtacg 1680
tcaacgtcaa ccaatatgac attgtattgg acgtactcgt ggtcaaccag actggcgaca 1740
ccttgcaaaa tttgtcattg gaactctca 1769

<210> SEQ ID NO 71

<211> LENGTH: 1687
<212> TYPE: DNA
<213> ORGANISM: Artificial Sequence
<220> FEATURE:
<223> OTHER INFORMATION: Synthetic

<400> SEQUENCE: 71
agggccattt tgtccacagt gaactgaaca gcatcgacag ccggacgagt gcgcaggtaa 60
tacatcccgg ttttaagtcc caatgaccag gcgtaaaagt gcatggagct cagtttagca 120
tagttcggct gcgctatgtg aatgttaagg gattggcttt ggtcaatgaa ggcggcgcga 180
tcggcggcca ttttcaaaat gtccttctgc ggtatttccc acacggtctt gtacaggtct 240
ttgatttctt gaatcgaatt cggtaccgga tccagtcgac tgaattggtt cccatggtgg 300
agcctgcttt tttgtacaaa cttgtgatga cggtatcgat aagcttgata tctacccgct 360
tcgcgtcggc atccggtcag tggcagtgaa gggcgaacag ttcctgatta accacaaacc 420
gttctacttt actggctttg gtcgtcatga agatgcggac ttacgtggca aaggattcga 480
taacgtgctg atggtgcacg accacgcatt aatggactgg attggggcca actcctaccg 540
tacctcgcat tacccttacg ctgaagagat gctcgactgg gcagatgaac atggcatcgt 600
ggtgattgat gaaactgctg ctgtcggctt taacctctct ttaggcattg gtttcgaagc 660
gggcaacaag ccgaaagaac tgtacagcga agaggcagtc aacggggaaa ctcagcaagc 720
gcacttacag gcgattaaag agctgatagc gcgtgacaaa aaccacccaa gcgtggtgat 780
gtggagtatt gccaacgaac cggatacccg tccgcaagtg cacgggaata tttcgccact 840
ggcggaagca acgcgtaaac tcgacccgac gcgtccgatc acctgcgtca atgtaatgtt 900
ctgcgacgct cacaccgata ccatcagcga tctctttgat gtgctgtgcc tgaaccgtta 960
ttacggatgg tatgtccaaa gcggcgattt ggaaacggca gagaaggtac tggaaaaaga 1020
acttctggcc tggcaggaga aactgcatca gccgattatc atcaccgaat acggcgtgga 1080
tacgttagcc gggctgcact caatgtacac cgacatgtgg agtgaagagt atcagtgtgc 1140
atggctggat atgtatcacc gcgtctttga tcgcgtcagc gccgtcgtcg gtgaacaggt 1200
atggaatttc gccgattttg cgacctcgca aggcatattg cgcgttggcg gtaacaagaa 1260
agggatcttc actcgatcga attcctgcag cccgggggat ccactagatg catgctcgag 1320
cggccgccag tgtgatggat atctgcagaa ttcgccctta tcacaagttt gtacaaaaaa 1380
gcaggctcca ccatgggaac caattcagtc gactggatcc ggtaccgaat tcgattcaag 1440
aaatcaaaga cctgtacaag accgtgtggg aaataccgca gaaggacatt ttgaaaatgg 1500
ccgccgatcg cgccgccttc attgaccaaa gccaatccct taacattcac atagcgcagc 1560
cgaactatgc taaactgagc tccatgcact tttacgcctg gtcattggga cttaaaaccg 1620
ggatgtatta cctgcgcact cgtccggctg tcgatgctgt tcagttcact gtggacaaaa 1680
tggccct 1687

<210> SEQ ID NO 72
<211> LENGTH: 1763
<212> TYPE: DNA
<213> ORGANISM: Artificial Sequence
<220> FEATURE:
<223> OTHER INFORMATION: Synthetic

<400> SEQUENCE: 72
tgagagtcca atgacaattt gcaaggtgtc gccagtctgg ttgaccacga gtacgtccaa 60
tacaatgtca tattggttga cgttgacgta cgcctcggca tagacgggat ccgaagagcc 120

```
ggctaactga atcacttttc ccagtttgga gctggcaaag gtgtatttgg tcgttttggg    180

tgcagtacca agcgcttggg aaagcgaaag atcaaacaaa tttgtgtccg tcacgttttc    240

tgacacgcgt gtggacagct gcgtgaacat aattgtcttg tcgggctgca atcgaattcg    300

gtaccggatc cagtcgactg aattggttcc catggtggag cctgcttttt tgtacaaact    360

tgtgatgacg gtatcgataa gcttgatatc tacccgcttc gcgtcggcat ccggtcagtg    420

gcagtgaagg gcgaacagtt cctgattaac cacaaaccgt tctactttac tggctttggt    480

cgtcatgaag atgcggactt acgtggcaaa ggattcgata acgtgctgat ggtgcacgac    540

cacgcattaa tggactggat tggggccaac tcctaccgta cctcgcatta cccttacgct    600

gaagagatgc tcgactgggc agatgaacat ggcatcgtgg tgattgatga aactgctgct    660

gtcggcttta acctctcttt aggcattggt ttcgaagcgg gcaacaagcc gaaagaactg    720

tacagcgaag aggcagtcaa cggggaaact cagcaagcgc acttacaggc gattaaagag    780

ctgatagcgc gtgacaaaaa ccacccaagc gtggtgatgt ggagtattgc caacgaaccg    840

gatacccgtc cgcaagtgca cgggaatatt tcgccactgg cggaagcaac gcgtaaactc    900

gacccgacgc gtccgatcac ctgcgtcaat gtaatgttct gcgacgctca caccgatacc    960

atcagcgatc tctttgatgt gctgtgcctg aaccgttatt acggatggta tgtccaaagc   1020

ggcgatttgg aaacggcaga gaaggtactg gaaaaagaac ttctggcctg gcaggagaaa   1080

ctgcatcagc cgattatcat caccgaatac ggcgtggata cgttagccgg gctgcactca   1140

atgtacaccg acatgtggag tgaagagtat cagtgtgcat ggctggatat gtatcaccgc   1200

gtctttgatc gcgtcagcgc cgtcgtcggt gaacaggtat ggaatttcgc cgattttgcg   1260

acctcgcaag gcatattgcg cgttggcggt aacaagaaag ggatcttcac tcgatcgaat   1320

tcctgcagcc cgggggatcc actagatgca tgctcgagcg gccgccagtg tgatggatat   1380

ctgcagaatt cgcccttatc acaagtttgt acaaaaaagc aggctccacc atgggaacca   1440

attcagtcga ctggatccgg taccgaattc gattgcagcc cgacaagaca attatgttca   1500

cgcagctgtc cacacgcgtg tcagaaaacg tgacggacac aaatttgttt gatctttcgc   1560

tttcccaagc gcttggtact gcacccaaaa cgaccaaata cacctttgcc agctccaaac   1620

tgggaaaagt gattcagtta gccggctctt cggatcccgt ctatgccgag gcgtacgtca   1680

acgtcaacca atatgacatt gtattggacg tactcgtggt caaccagact ggcgacacct   1740

tgcaaattgt cattggactc tca                                           1763
```

<210> SEQ ID NO 73
<211> LENGTH: 1655
<212> TYPE: DNA
<213> ORGANISM: Artificial Sequence
<220> FEATURE:
<223> OTHER INFORMATION: Synthetic

<400> SEQUENCE: 73

```
tagggccatt ttgtccacag tgaactgaac agcatcgaca gccggacgag tgcgcaggta     60

atacatcccg gttttaagtc ccaatgacca ggcgtaaaag tgcatggagc tcagtttagc    120

atagttcggc tgcgctatgt gaatgttaag ggattggctt tggtcaatga aaagggcgcg    180

atcggcggcc attttcaaaa tgtcctggct gaatacacac acagcacacg tacttaatcg    240

aattcggtac cggatccagt cgactgaatt ggttcccatg gtggagcctg ctttttgta     300

caaacttgtg atgacggtat cgataagctt gatatctacc cgcttcgcgt cggcatccgg    360
```

```
tcagtggcag tgaagggcga acagttcctg attaaccaca aaccgttcta ctttactggc    420

tttggtcgtc atgaagatgc ggacttacgt ggcaaaggat tcgataacgt gctgatggtg    480

cacgaccacg cattaatgga ctggattggg gccaactcct accgtacctc gcattaccct    540

tacgctgaag agatgctcga ctgggcagat gaacatggca tcgtggtgat tgatgaaact    600

gctgctgtcg gctttaacct ctctttaggc attggtttcg aagcgggcaa caagccgaaa    660

gaactgtaca gcgaagaggc agtcaacggg gaaactcagc aagcgcactt acaggcgatt    720

aaagagctga tagcgcgtga caaaaaccac ccaagcgtgg tgatgtggag tattgccaac    780

gaaccggata cccgtccgca agtgcacggg aatatttcgc cactggcgga agcaacgcgt    840

aaactcgacc cgacgcgtcc gatcacctgc gtcaatgtaa tgttctgcga cgctcacacc    900

gataccatca gcgatctctt tgatgtgctg tgcctgaacc gttattacgg atggtatgtc    960

caaagcggcg atttggaaac ggcagagaag gtactggaaa aagaacttct ggcctggcag   1020

gagaaactgc atcagccgat tatcatcacc gaatacggcg tggatacgtt agccgggctg   1080

cactcaatgt acaccgacat gtggagtgaa gagtatcagt gtgcatggct ggatatgtat   1140

caccgcgtct ttgatcgcgt cagcgccgtc gtcggtgaac aggtatggaa tttcgccgat   1200

tttgcgacct cgcaaggcat attgcgcgtt ggcggtaaca agaaagggat cttcactcga   1260

tcgaattcct gcagcccggg ggatccacta gatgcatgct cgagcggccg ccagtgtgat   1320

ggatatctgc agaattcgcc cttatcacaa gtttgtacaa aaaagcaggc tccaccatgg   1380

gaaccaattc agtcgactgg atccggtacc gaattcgatt aagtacgtgt gctgtgtgtg   1440

tattcagcca ggacattttg aaaatggccg ccgatcgcgc cctttttcatt gaccaaagcc   1500

aatcccttaa cattcacata gcgcagccga actatgctaa actgagctcc atgcactttt   1560

acgcctggtc attgggactt aaaaccggga tgtattacct gcgcactcgt ccggctgtcg   1620

atgctgttca gttcactgtg gacaaaatgg cccta                                1655
```

<210> SEQ ID NO 74
<211> LENGTH: 1561
<212> TYPE: DNA
<213> ORGANISM: Artificial Sequence
<220> FEATURE:
<223> OTHER INFORMATION: Synthetic

<400> SEQUENCE: 74

```
agggccattt tgtccacagt gaactgaaca gcatcgacag ccggacgagt gcgcaggtaa     60

tacatcccgg ttttaagtcc caatgaccag gcgtaaaagt gcatggagct cagtttagca    120

tagttcggct gcgctatgtg aatgttaagg gattggcttt ggtcaatgaa agcggcgcga    180

tcggcggcaa tcgaattcgg taccggatcc agtcgactga attggttccc atggtggagc    240

ctgctttttt gtacaaactt gtgatgacgg tatcgataag cttgatatct acccgcttcg    300

cgtcggcatc cggtcagtgg cagtgaaggg cgaacagttc ctgattaacc acaaaccgtt    360

ctactttact ggctttggtc gtcatgaaga tgcggactta cgtggcaaag gattcgataa    420

cgtgctgatg gtgcacgacc acgcattaat ggactggatt ggggccaact cctaccgtac    480

ctcgcattac ccttacgctg aagagatgct cgactgggca gatgaacatg gcatcgtggt    540

gattgatgaa actgctgctg tcggctttaa cctctcttta ggcattggtt tcgaagcggg    600

caacaagccg aaagaactgt acagcgaaga ggcagtcaac ggggaaactc agcaagcgca    660

cttacaggcg attaaagagc tgatagcgcg tgacaaaaac cacccaagcg tggtgatgtg    720

gagtattgcc aacgaaccgg atacccgtcc gcaagtgcac gggaatattt cgccactggc    780
```

ggaagcaacg cgtaaactcg acccgacgcg tccgatcacc tgcgtcaatg taatgttctg 840
cgacgctcac accgatacca tcagcgatct ctttgatgtg ctgtgcctga accgttatta 900
cggatggtat gtccaaagcg gcgatttgga aacggcagag aaggtactgg aaaaagaact 960
tctggcctgg caggagaaac tgcatcagcc gattatcatc accgaatacg gcgtggatac 1020
gttagccggg ctgcactcaa tgtacaccga catgtggagt gaagagtatc agtgtgcatg 1080
gctggatatg tatcaccgcg tctttgatcg cgtcagcgcc gtcgtcggtg aacaggtatg 1140
gaatttcgcc gattttgcga cctcgcaagg catattgcgc gttggcggta acaagaaagg 1200
gatcttcact cgatcgaatt cctgcagccc gggggatcca ctagatgcat gctcgagcgg 1260
ccgccagtgt gatggatatc tgcagaattc gcccttatca caagtttgta caaaaaagca 1320
ggctccacca tgggaaccaa ttcagtcgac tggatccggt accgaattcg attgccgccg 1380
atcgcgccgc tttcattgac caaagccaat cccttaacat tcacatagcg cagccgaact 1440
atgctaaact gagctccatg cacttttacg cctggtcatt gggacttaaa accgggatgt 1500
attacctgcg cactcgtccg gctgtcgatg ctgttcagtt cactgtggac aaaatggccc 1560
t 1561

<210> SEQ ID NO 75
<211> LENGTH: 2547
<212> TYPE: DNA
<213> ORGANISM: Artificial Sequence
<220> FEATURE:
<223> OTHER INFORMATION: Synthetic

<400> SEQUENCE: 75
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gcttttcgga 180
tcccgtctat gccgaggcgt acgtcaacgt caaccaatat gacattgtat tggacgtact 240
cgtggtcaac cagactagcg acaccttgca aaatttgtca ttggaactct caaagcttca 300
atcgaattgt ccttttccaa atcgtcgatg acaagttgcg attcgctcgt agaaaggtgg 360
ttttacgaaa aagaattttt ttaatcgtgc cttacaaatt aggccttccg tggtcacaat 420
acagcagggt acgcctgctc aactgatttt tcgccagaga tgaggttatc tagcacataa 480
ttcaaaaggc attcctttct tttttttctt agttttctcg cttccggtga tgcggacggt 540
aaaatcacaa tgtgggactg gcgcacacac aaaattgtct ccacgtggaa ggcacatgat 600
aatgtgtgca tttcaacact gtggcatccg cacgagaaat cgcggatgat ttcttgcgga 660
tgggacaatg taatcaaaat gaatcgaatt cggtaccgga tccagtcgac tgaattggtt 720
cccatggtgg agcctgcttt tttgtacaaa cttgtgatga cggtatcgat aagcttgata 780
tctacccgct tcgcgtcggc atccggtcag tggcagtgaa gggcgaacag ttcctgatta 840
accacaaacc gttctacttt actggctttg gtcgtcatga agatgcggac ttacgtggca 900
aaggattcga taacgtgctg atggtgcacg accacgcatt aatggactgg attggggcca 960
actcctaccg tacctcgcat tacccttacg ctgaagagat gctcgactgg gcagatgaac 1020
atggcatcgt ggtgattgat gaaactgctg ctgtcggctt taacctctct ttaggcattg 1080
gtttcgaagc gggcaacaag ccgaaagaac tgtacagcga agaggcagtc aacggggaaa 1140
ctcagcaagc gcacttacag gcgattaaag agctgatagc gcgtgacaaa aaccacccaa 1200
gcgtggtgat gtggagtatt gccaacgaac cggatacccg tccgcaagtg cacgggaata 1260
tttcgccact ggcggaagca acgcgtaaac tcgacccgac gcgtccgatc acctgcgtca 1320
atgtaatgtt ctgcgacgct cacaccgata ccatcagcga tctctttgat gtgctgtgcc 1380
tgaaccgtta ttacggatgg tatgtccaaa gcggcgattt ggaaacggca gagaaggtac 1440
tggaaaaaga acttctggcc tggcaggaga aactgcatca gccgattatc atcaccgaat 1500
acggcgtgga tacgttagcc gggctgcact caatgtacac cgacatgtgg agtgaagagt 1560
atcagtgtgc atggctggat atgtatcacc gcgtctttga tcgcgtcagc gccgtcgtcg 1620
gtgaacaggt atggaatttc gccgattttg cgacctcgca aggcatattg cgcgttggcg 1680
gtaacaagaa agggatcttc actcgatcga attcctgcag cccgggggat ccactagatg 1740
catgctcgag cggccgccag tgtgatggat atctgcagaa ttcgccctta tcacaagttt 1800
gtacaaaaaa gcaggctcca ccatgggaac caattcagtc gactggatcc ggtaccgaat 1860
tcgattcatt ttgattacat tgtcccatcc gcaagaaatc atccgcgatt tctcgtgcgg 1920
atgccacagt gttgaaatgc acacattatc atgtgccttc cacgtggaga caattttgtg 1980
tgtgcgccag tcccacattg tgattttacc gtccgcatca ccggaagcga gaaaactaag 2040
aaaaaaaaga aaggaatgcc ttttgaatta tgtgctagat aacctcatct ctggcgaaaa 2100
atcagttgag caggcgtacc ctgctgtatt gtgaccacgg aaggcctaat ttgtaaggca 2160
cgattaaaaa aattcttttt cgtaaaacca cctttctacg agcgaatcgc aacttgtcat 2220
cgacgatttg gaaaaggaca attcgattga agctttgaga gttccaatga caaattttgc 2280
aaggtgtcgc tagtctggtt gaccacgagt acgtccaata caatgtcata ttggttgacg 2340
ttgacgtacg cctcggcata gacgggatcc gaaaagccgg ctaactgaat cacttttccc 2400
agtttggagc tggcaaaggt gtatttggtc gttttgggtg cagtaccaag cgcttgggaa 2460
agcgaaagat caaacaaatt tgtgtccgtc acgttttctg acacgcgtgt ggacagctgc 2520
gtgaacataa ttgtcttgtc gggctgc 2547

<210> SEQ ID NO 76
<211> LENGTH: 2631
<212> TYPE: DNA
<213> ORGANISM: Artificial Sequence
<220> FEATURE:
<223> OTHER INFORMATION: Synthetic

<400> SEQUENCE: 76
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gcttttcgga 180
tcccgtctat gccgaggcgt acgtcaacgt caaccaatat gacattgtat tggacgtact 240
cgtggtcaac cagactagcg acaccttgca aaatttgtca ttggaactct caagcttaag 300
gcaccaaggc atcgatcagg ctgtggcagc agccattacg gaattgaagg ccatctcgcg 360
ccccattgcc accagcaagg agattgcgca agtgggctcc atttcggcca actccgacag 420
cgccatcggc gacatcatcg cccaggccat ggagaaggtg ggcaaggagg gcgtgataac 480
cgtcgaggat ggcaagtcgc tggaaaacga actggatgtg gtggaaggca tgcagttcga 540
ccgcggctac ctgagcccat acttcatcaa tgatccggac aagcaactgg cgcgcctgga 600
tgacccgctg gtgctgctgt acgacaaaaa gatcagcaat atccgcgagc tgctgccggt 660
gctggagcag tcggccaagg ccggcaagcc gctgttcatc gtggcggagg atacaaaaag 720
cgaaatcgaa ttcggtaccg gatccagtcg actgaattgg ttcccatggt ggagcctgct 780
tttttgtaca aacttgtgat gacggtatcg ataagcttga tatctacccg cttcgcgtcg 840
gcatccggtc agtggcagtg aagggcgaac agttcctgat taaccacaaa ccgttctact 900
ttactggctt tggtcgtcat gaagatgcgg acttacgtgg caaaggattc gataacgtgc 960
tgatggtgca cgaccacgca ttaatggact ggattggggc caactcctac cgtacctcgc 1020
attaccctta cgctgaagag atgctcgact gggcagatga acatggcatc gtggtgattg 1080
atgaaactgc tgctgtcggc tttaacctct ctttaggcat tggtttcgaa gcgggcaaca 1140
agccgaaaga actgtacagc gaagaggcag tcaacgggga aactcagcaa gcgcacttac 1200
aggcgattaa agagctgata gcgcgtgaca aaaaccaccc aagcgtggtg atgtggagta 1260
ttgccaacga accggatacc cgtccgcaag tgcacgggaa tatttcgcca ctggcggaag 1320
caacgcgtaa actcgacccg acgcgtccga tcacctgcgt caatgtaatg ttctgcgacg 1380
ctcacaccga taccatcagc gatctctttg atgtgctgtg cctgaaccgt tattacggat 1440
ggtatgtcca aagcggcgat ttggaaacgg cagagaaggt actggaaaaa gaacttctgg 1500
cctggcagga gaaactgcat cagccgatta tcatcaccga atacggcgtg gatacgttag 1560
ccgggctgca ctcaatgtac accgacatgt ggagtgaaga gtatcagtgt gcatggctgg 1620
atatgtatca ccgcgtcttt gatcgcgtca gcgccgtcgt cggtgaacag gtatggaatt 1680
tcgccgattt tgcgacctcg caaggcatat tgcgcgttgg cggtaacaag aaagggatct 1740
tcactcgatc gaattcctgc agcccggggg atccactaga tgcatgctcg agcggccgcc 1800
agtgtgatgg atatctgcag aattcgccct tatcacaagt ttgtacaaaa aagcaggctc 1860
caccatggga accaattcag tcgactggat ccggtaccga attcgatttc gctttttgta 1920
tcctccgcca cgatgaacag cggcttgccg gccttggccg actgctccag caccggcagc 1980
agctcgcgga tattgctgat ctttttgtcg tacagcagca ccagcgggtc atccaggcgc 2040
gccagttgct tgtccggatc attgatgaag tatgggctca ggtagccgcg gtcgaactgc 2100
atgccttcca ccacatccag ttcgttttcc agcgacttgc catcctcgac ggttatcacg 2160
ccctccttgc ccaccttctc catggcctgg gcgatgatgt cgccgatggc gctgtcggag 2220
ttggccgaaa tggagcccac ttgcgcaatc tccttgctgg tggcaatggg gcgcgagatg 2280
gccttcaatt ccgtaatggc tgctgccaca gcctgatcga tgccttggtg ccttaagctt 2340
gagagttcca atgacaaatt ttgcaaggtg tcgctagtct ggttgaccac gagtacgtcc 2400
aatacaatgt catattggtt gacgttgacg tacgcctcgg catagacggg atccgaaaag 2460
ccggctaact gaatcacttt tcccagtttg gagctggcaa aggtgtattt ggtcgttttg 2520
ggtgcagtac caagcgcttg ggaaagcgaa agatcaaaca aatttgtgtc cgtcacgttt 2580
tctgacacgc gtgtggacag ctgcgtgaac ataattgtct tgtcgggctg c 2631

<210> SEQ ID NO 77
<211> LENGTH: 2543
<212> TYPE: DNA
<213> ORGANISM: Artificial Sequence
<220> FEATURE:
<223> OTHER INFORMATION: Synthetic

<400> SEQUENCE: 77
agggccattt tgtccacagt gaactgaaca gcatcgacag ccggacgagt gcgcaggtaa 60
tacatcccgg ttttaagtcc caatgaccag gcgtaaaagt gcatggagct cagtttagca 120

-continued

```
tagttcggct gcgctatgtg aatgttaagg gattggcttt ggtcaatgaa agcggcgcga    180
tcggcggcca ttttcaaaat gtccttctgc ggtatttccc acacggtctt gtacaggtct    240
ttgatttctt gaagctttcg ctttttgtat cctccgccac gatgaacagc ggcttgccgg    300
ccttggccga ctgctccagc accggcagca gctcgcggat attgctgatc tttttgtcgt    360
acagcagcac cagcgggtca tccaggcgcg ccagttgctt gtccggatca ttgatgaagt    420
atgggctcag gtagccgcgg tcgaactgca tgccttccac cacatccagt tcgttttcca    480
gcgacttgcc atcctcgacg gttatcacgc cctccttgcc caccttctcc atggcctggg    540
cgatgatgtc gccgatggcg ctgtcggagt tggccgaaat ggagcccact tgcgcaatct    600
ccttgctggt ggcaatgggg cgcgagatgg ccttcaattc cgtaatggct gctgccacag    660
cctgatcgat gccttggtga atcgaattcg gtaccggatc cagtcgactg aattggttcc    720
catggtggag cctgcttttt tgtacaaact tgtgatgacg gtatcgataa gcttgatatc    780
tacccgcttc gcgtcggcat ccggtcagtg gcagtgaagg gcgaacagtt cctgattaac    840
cacaaaccgt tctactttac tggctttggt cgtcatgaag atgcggactt acgtggcaaa    900
ggattcgata acgtgctgat ggtgcacgac cacgcattaa tggactggat tggggccaac    960
tcctaccgta cctcgcatta cccttacgct gaagagatgc tcgactgggc agatgaacat   1020
ggcatcgtgg tgattgatga aactgctgct gtcggcttta acctctcttt aggcattggt   1080
ttcgaagcgg gcaacaagcc gaaagaactg tacagcgaag aggcagtcaa cggggaaact   1140
cagcaagcgc acttacaggc gattaaagag ctgatagcgc gtgacaaaaa ccacccaagc   1200
gtggtgatgt ggagtattgc caacgaaccg gatacccgtc cgcaagtgca cgggaatatt   1260
tcgccactgg cggaagcaac gcgtaaactc gacccgacgc gtccgatcac ctgcgtcaat   1320
gtaatgttct gcgacgctca caccgatacc atcagcgatc tctttgatgt gctgtgcctg   1380
aaccgttatt acggatggta tgtccaaagc ggcgatttgg aaacggcaga gaaggtactg   1440
gaaaaagaac ttctggcctg gcaggagaaa ctgcatcagc cgattatcat caccgaatac   1500
ggcgtggata cgttagccgg gctgcactca atgtacaccg acatgtggag tgaagagtat   1560
cagtgtgcat ggctggatat gtatcaccgc gtctttgatc gcgtcagcgc cgtcgtcggt   1620
gaacaggtat ggaatttcgc cgattttgcg acctcgcaag gcatattgcg cgttggcggt   1680
aacaagaaag ggatcttcac tcgatcgaat tcctgcagcc cgggggatcc actagatgca   1740
tgctcgagcg gccgccagtg tgatggatat ctgcagaatt cgcccttatc acaagtttgt   1800
acaaaaaagc aggctccacc atgggaacca attcagtcga ctggatccgg taccgaattc   1860
gattcaccaa ggcatcgatc aggctgtggc agcagccatt acggaattga aggccatctc   1920
gcgccccatt gccaccagca aggagattgc gcaagtgggc tccatttcgg ccaactccga   1980
cagcgccatc ggcgacatca tcgcccaggc catggagaag gtgggcaagg agggcgtgat   2040
aaccgtcgag gatggcaagt cgctggaaaa cgaactggat gtggtggaag gcatgcagtt   2100
cgaccgcggc tacctgagcc catacttcat caatgatccg gacaagcaac tggcgcgcct   2160
ggatgacccg ctggtgctgc tgtacgacaa aaagatcagc aatatccgcg agctgctgcc   2220
ggtgctggag cagtcggcca aggccggcaa gccgctgttc atcgtggcgg aggatacaaa   2280
aagcgaaagc ttcaagaaat caaagacctg tacaagaccg tgtgggaaat accgcagaag   2340
gacattttga aaatggccgc cgatcgcgcc gctttcattg accaaagcca atcccttaac   2400
attcacatag cgcagccgaa ctatgctaaa ctgagctcca tgcactttta cgcctggtca   2460
ttgggactta aaaccgggat gtattacctg cgcactcgtc cggctgtcga tgctgttcag   2520
```

ttcactgtgg acaaaatggc cct 2543

<210> SEQ ID NO 78
<211> LENGTH: 473
<212> TYPE: DNA
<213> ORGANISM: Artificial Sequence
<220> FEATURE:
<223> OTHER INFORMATION: Synthetic

<400> SEQUENCE: 78
cgatcactga ggacgacttg gaccgtttgt cgaccactgt tcgactgatt gttgaccaat 60
ggccgaaagc ggtggatgtg tttttgagag agtgccgtgc ttcgttggaa agcatgctca 120
aggccaaggg ggacgtggac cggcacgaac gcgacacaaa agcgccgaag aagaaaattg 180
tgcagcccga caagacaatt atgttcacgc agctgtccac acgcgtgtca gaaaacgtga 240
cggacacaaa tttgtttgat ctttcgcttt cccaagcgct tggtactgca cccaaaacga 300
ccaaatacac ctttgccagc tccaaactgg gaaaagtgat tcagttagcc ggcttttcgg 360
atcccgtcta tgccgaggcg tacgtcaacg tcaaccaata tgacattgta ttggacgtac 420
tcgtggtcaa ccagactagc gacaccttgc aaaatttgtc attggaactc tca 473

<210> SEQ ID NO 79
<211> LENGTH: 291
<212> TYPE: DNA
<213> ORGANISM: Heterodera Glycines

<400> SEQUENCE: 79
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gcttttcgga 180
tcccgtctat gccgaggcgt acgtcaacgt caaccaatat gacattgtat tggacgtact 240
cgtggtcaac cagactagcg acaccttgca aaatttgtca ttggaactct c 291

<210> SEQ ID NO 80
<211> LENGTH: 291
<212> TYPE: DNA
<213> ORGANISM: Heterodera Glycines

<400> SEQUENCE: 80
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gctcttcgga 180
tcccgtctat gccgaggcgt acgtcaacgt caaccaatat gacattgtat tggacgtact 240
cgtggacaac cagactggcg acaccttgca aaatttgtca ttggaactct c 291

<210> SEQ ID NO 81
<211> LENGTH: 291
<212> TYPE: DNA
<213> ORGANISM: Heterodera Glycines

<400> SEQUENCE: 81
gcagcccgac aagacaatta tgttcacgca gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gcttttcgga 180

-continued

```
tcccgtctat gccgaggcgt acgtcaacgt caaccaatat gacattgtat tggacgtact    240

cgtggtcaac cagactagcg acaccttgca aaatttgtca ttggaactct c             291


<210> SEQ ID NO 82
<211> LENGTH: 291
<212> TYPE: DNA
<213> ORGANISM: Radopholus similis

<400> SEQUENCE: 82

gcagcccgac aagacaatta tgttcacgca gctgtccaca cgcgtgtcag aaaacgtgac     60

ggacacaaat ttgtttgatc tttcgctttc ccaagcgctt ggtactgcac ccaaaacgac    120

caaatacacc tttgccagct ccaaactggg aaaagtgatt cagttagccg gctcttcgga    180

tcccgtctat gccgaggcgt acgtcaacgt caaccaatat gacattgtat tggacgtact    240

cgtggtcaac cagactggcg acaccttgca aaatttgtca ttggaactct c             291


<210> SEQ ID NO 83
<211> LENGTH: 251
<212> TYPE: DNA
<213> ORGANISM: Heterodera Glycines

<400> SEQUENCE: 83

caagaaatca aagacctgta caagaccgtg tgggaaatac cgcagaagga cattttgaaa     60

atggccgccg atcgcgccgc tttcattgac caaagccaat cccttaacat tcacatagcg    120

cagccgaact atgctaaact gagctccatg cacttttacg cctggtcatt gggacttaaa    180

accgggatgt attacctgcg cactcgtccg gctgtcgatg ctgttcagtt cactgtggac    240

aaaatggccc t                                                         251


<210> SEQ ID NO 84
<211> LENGTH: 251
<212> TYPE: DNA
<213> ORGANISM: Heterodera Glycines

<400> SEQUENCE: 84

caagaaatca aagacctgta caagaccgtg tgggaaatac cgcagaagga cattttgaaa     60

atggccgccg atcgcgccgc tttcattgac caaagccaat cccttaacat tcacatagcg    120

cagccgaact atgctaaact gagctccatg cacttttacg cctggtcatt gggacttaaa    180

accgggatgt attacctgcg cactcgtccg gctgtcgatg ctgttcagtt cactgtggac    240

aaaatggccc t                                                         251


<210> SEQ ID NO 85
<211> LENGTH: 251
<212> TYPE: DNA
<213> ORGANISM: Heterodera Glycines

<400> SEQUENCE: 85

caagaaatca aagacctgta caagaccgtg tgggaaatac cgcagaagga cattttgaaa     60

atggccgccg atcgcgccgc tttcattgac caaagccaat cccttaacat tcacatagcg    120

cagccgaact atgctaaact gagctccatg cacttttacg cctggtcatt gggacttaaa    180

accgggatgt attacctgcg cactcgtccg gctgtcgatg ctgttcagtt cactgtggac    240

aaaatggccc t                                                         251


<210> SEQ ID NO 86
<211> LENGTH: 251
```

<212> TYPE: DNA
<213> ORGANISM: Radopholus similis

<400> SEQUENCE: 86
caagaaatca aagacctgta caagaccgtg tgggaaatac cgcagaagga cattttgaaa 60
atggccgccg atcgcgccgc cttcattgac caaagccaat cccttaacat tcacatagcg 120
cagccgaact atgctaaact gagctccatg cacttttacg cctggtcatt gggacttaaa 180
accgggatgt attacctgcg cactcgtccg gctgtcgatg ctgttcagtt cactgtggac 240
aaaatggccc t 251

<210> SEQ ID NO 87
<211> LENGTH: 287
<212> TYPE: DNA
<213> ORGANISM: Artificial Sequence
<220> FEATURE:
<223> OTHER INFORMATION: Synthetic

<400> SEQUENCE: 87
gcagcccgac aagacaatta tgttcacgcg ctgtccacac gcgtgtcaga aaacgtgacg 60
gacacaaatt tgtttgatct ttcgctttcc caagcgcttg gtactgcacc caaaacgacc 120
aaatacacct ttgccagctc caaactggga aaagtgattc agttagccgg ctttcggatc 180
ccgtctatgc cgaggcgtac gtcaacgtca accaatatga cattgtattg gacgtactcg 240
tggcaaccag actgcgacac cttgcaaaat ttgtcattgg aactctc 287

<210> SEQ ID NO 88
<211> LENGTH: 250
<212> TYPE: DNA
<213> ORGANISM: Artificial Sequence
<220> FEATURE:
<223> OTHER INFORMATION: Synthetic

<400> SEQUENCE: 88
caagaaatca aagacctgta caagaccgtg tgggaaatac cgcagaagga cattttgaaa 60
atggccgccg atcgcgccgc ttcattgacc aaagccaatc ccttaacatt cacatagcgc 120
agccgaacta tgctaaactg agctccatgc acttttacgc ctggtcattg ggacttaaaa 180
ccgggatgta ttacctgcgc actcgtccgg ctgtcgatgc tgttcagttc actgtggaca 240
aaatggccct 250

<210> SEQ ID NO 89
<211> LENGTH: 430
<212> TYPE: DNA
<213> ORGANISM: Artificial Sequence
<220> FEATURE:
<223> OTHER INFORMATION: Synthetic

<400> SEQUENCE: 89
tctagcaagg ccaaaatcag ccaattttaa ttgtggcgca gttttcactg tattattgat 60
caacaaattc tggggcttca aatcacgatg aagcacattg tgcgcatgac aatagcataa 120
accggacagt aactgatgca tcagtgaacg aacaactttt tggtcgattt gcccatccaa 180
agtgtcgaaa aattttcgta aatcaaggtc acaaaattca aagactaagt tcagcgtctt 240
gtttgtatgc acaacattct gcaatcgcac aacatttgca tgtcgtagtt cgcgcaacaa 300
acaaatttcg cgcagtgccg aagacggaac tccttcatct tcatcatcca gtcgcactat 360
cttaagagca acaatttgct cggtgtcctt gtttcttgcc ttgaaaaccg ttccatatgt 420

-continued gccttcacca 430

<210> SEQ ID NO 90
<211> LENGTH: 2045
<212> TYPE: DNA
<213> ORGANISM: Artificial Sequence
<220> FEATURE:
<223> OTHER INFORMATION: Synthetic

<400> SEQUENCE: 90
tggtgaaggc acatatggaa cggttttcaa ggcaagaaac aaggacaccg agcaaattgt 60
tgctcttaag atagtgcgac tggatgatga agatgaagga gttccgtctt cggcactgcg 120
cgaaatttgt ttgttgcgcg aactacgaca tgcaaatgtt gtgcgattgc agaatgttgt 180
gcatacaaac aagacgctga acttagtctt tgaattttgt gaccttgatt tacgaaaatt 240
tttcgacact ttggatgggc aaatcgacca aaaagttgtt cgttcactga tgcatcagtt 300
actgtccggt ttatgctatt gtcatgcgca caatgtgctt catcgtgatt tgaagcccca 360
gaatttgttg atcaataata cagtgaaaac tgcgccacaa ttaaaattgg ctgattttgg 420
ccttgctaga aatcgaattc ggtaccggat ccagtcgact gaattggttc ccatggtgga 480
gcctgctttt ttgtacaaac ttgtgatgac ggtatcgata agcttgatat ctacccgctt 540
cgcgtcggca tccggtcagt ggcagtgaag ggcgaacagt tcctgattaa ccacaaaccg 600
ttctacttta ctggctttgg tcgtcatgaa gatgcggact tacgtggcaa aggattcgat 660
aacgtgctga tggtgcacga ccacgcatta atggactgga ttggggccaa ctcctaccgt 720
acctcgcatt acccttacgc tgaagagatg ctcgactggg cagatgaaca tggcatcgtg 780
gtgattgatg aaactgctgc tgtcggcttt aacctctctt taggcattgg tttcgaagcg 840
ggcaacaagc cgaaagaact gtacagcgaa gaggcagtca acggggaaac tcagcaagcg 900
cacttacagg cgattaaaga gctgatagcg cgtgacaaaa accacccaag cgtggtgatg 960
tggagtattg ccaacgaacc ggatacccgt ccgcaagtgc acgggaatat ttcgccactg 1020
gcggaagcaa cgcgtaaact cgacccgacg cgtccgatca cctgcgtcaa tgtaatgttc 1080
tgcgacgctc acaccgatac catcagcgat ctctttgatg tgctgtgcct gaaccgttat 1140
tacggatggt atgtccaaag cggcgatttg gaaacggcag agaaggtact ggaaaaagaa 1200
cttctggcct ggcaggagaa actgcatcag ccgattatca tcaccgaata cggcgtggat 1260
acgttagccg ggctgcactc aatgtacacc gacatgtgga gtgaagagta tcagtgtgca 1320
tggctggata tgtatcaccg cgtctttgat cgcgtcagcg ccgtcgtcgg tgaacaggta 1380
tggaatttcg ccgattttgc gacctcgcaa ggcatattgc gcgttggcgg taacaagaaa 1440
gggatcttca ctcgatcgaa ttcctgcagc ccgggggatc cactagatgc atgctcgagc 1500
ggccgccagt gtgatggata tctgcagaat tcgcccttat cacaagtttg tacaaaaaag 1560
caggctccac catgggaacc aattcagtcg actggatccg gtaccgaatt cgatttctag 1620
caaggccaaa atcagccaat tttaattgtg gcgcagtttt cactgtatta ttgatcaaca 1680
aattctgggg cttcaaatca cgatgaagca cattgtgcgc atgacaatag cataaaccgg 1740
acagtaactg atgcatcagt gaacgaacaa ctttttggtc gatttgccca tccaaagtgt 1800
cgaaaaattt tcgtaaatca aggtcacaaa attcaaagac taagttcagc gtcttgtttg 1860
tatgcacaac attctgcaat cgcacaacat ttgcatgtcg tagttcgcgc aacaaacaaa 1920
tttcgcgcag tgccgaagac ggaactcctt catcttcatc atccagtcgc actatcttaa 1980
gagcaacaat ttgctcggtg tccttgtttc ttgccttgaa aaccgttcca tatgtgcctt 2040
cacca 2045

<210> SEQ ID NO 91
<211> LENGTH: 597
<212> TYPE: DNA
<213> ORGANISM: Artificial Sequence
<220> FEATURE:
<223> OTHER INFORMATION: Synthetic

<400> SEQUENCE: 91
ccacttcatg tccgacgagt cccgcttcca aattggaaca gcagacgaag aaacaaatga 60
tgagggtcaa atcggacaat gcagtgaatt cgttggctga ttttgaccaa gtttgcgcat 120
ttcgtaaggg actcgctcct ctagcaaaat tcggtagatt aactttaata aagccatgaa 180
ttttacatcc aattcattct ctgcaaggcc acaaacagca ggtgaatgtg cttttttctt 240
gtgtccagcc cacttccagt tgtgtgaaac ggtctcgtcg ttacgttgcg aaggatcccg 300
agagaatgtt ggatgcgcca gatttattag acgatttttg taaacataat acagaaaaca 360
tttttgcaac tacctattca gattcgaatt tgattgattg gagcaagact aattgtgtcg 420
ccgttggctt aggatcaaaa atttttcaat ggaacgcggg gaccggtgcc gtggatgtca 480
gttcttttac agtttttttcc accaaatctt gtgaatttaa ggagataaaa gatttctctg 540
aaacgcattc gcatccaact ctcgtcaaat ggtcttgcga aggacaatat cttgccg 597

<210> SEQ ID NO 92
<211> LENGTH: 2379
<212> TYPE: DNA
<213> ORGANISM: Artificial Sequence
<220> FEATURE:
<223> OTHER INFORMATION: Synthetic

<400> SEQUENCE: 92
cggcaagata ttgtccttcg caagaccatt tgacgagagt tggatgcgaa tgcgtttcag 60
agaaatcttt tatctcctta aattcacaag atttggtgga aaaaactgta aaagaactga 120
catccacggc accggtcccc gcgttccatt gaaaaatttt tgatcctaag ccaacggcga 180
cacaattagt cttgctccaa tcaatcaaat tcgaatctga ataggtagtt gcaaaaatgt 240
tttctgtatt atgtttacaa aaatcgtcta ataaatctgg cgcatccaac attctctcgg 300
gatccttcgc aacgtaacga cgagaccgtt tcacacaact ggaagtgggc tggacacaag 360
aaaaaagcac attcacctgc tgtttgtggc cttgcagaga atgaattgga tgtaaaattc 420
atggctttat taaagttaat ctaccgaatt ttgctagagg agcgagtccc ttacgaaatg 480
cgcaaacttg gtcaaaatca gccaacgaat tcactgcatt gtccgatttg accctcatca 540
tttgtttctt cgtctgctgt tccaatttgg aagcgggact cgtcggacat gaagtggaat 600
cgaattcggt accggatcca gtcgactgaa ttggttccca tggtggagcc tgctttttttg 660 tacaaacttg tgatgacggt atcgataagc ttgatatcta cccgcttcgc gtcggcatcc 720
ggtcagtggc agtgaagggc gaacagttcc tgattaacca caaaccgttc tactttactg 780
gctttggtcg tcatgaagat gcggacttac gtggcaaagg attcgataac gtgctgatgg 840
tgcacgacca cgcattaatg gactggattg gggccaactc ctaccgtacc tcgcattacc 900
cttacgctga agagatgctc gactgggcag atgaacatgg catcgtggtg attgatgaaa 960
ctgctgctgt cggctttaac ctctctttag gcattggttt cgaagcgggc aacaagccga 1020
aagaactgta cagcgaagag gcagtcaacg gggaaactca gcaagcgcac ttacaggcga 1080

```
ttaaagagct gatagcgcgt gacaaaaacc acccaagcgt ggtgatgtgg agtattgcca   1140

acgaaccgga tacccgtccg caagtgcacg ggaatatttc gccactggcg gaagcaacgc   1200

gtaaactcga cccgacgcgt ccgatcacct gcgtcaatgt aatgttctgc gacgctcaca   1260

ccgataccat cagcgatctc tttgatgtgc tgtgcctgaa ccgttattac ggatggtatg   1320

tccaaagcgg cgatttggaa acggcagaga aggtactgga aaaagaactt ctggcctggc   1380

aggagaaact gcatcagccg attatcatca ccgaatacgg cgtggatacg ttagccgggc   1440

tgcactcaat gtacaccgac atgtggagtg aagagtatca gtgtgcatgg ctggatatgt   1500

atcaccgcgt ctttgatcgc gtcagcgccg tcgtcggtga acaggtatgg aatttcgccg   1560

attttgcgac ctcgcaaggc atattgcgcg ttggcggtaa caagaaaggg atcttcactc   1620

gatcgaattc ctgcagcccg gggatccac tagatgcatg ctcgagcggc cgccagtgtg    1680

atggatatct gcagaattcg cccttatcac aagtttgtac aaaaaagcag gctccaccat   1740

gggaaccaat tcagtcgact ggatccggta ccgaattcga ttccacttca tgtccgacga   1800

gtcccgcttc caaattggaa cagcagacga agaaacaaat gatgagggtc aaatcggaca   1860

atgcagtgaa ttcgttggct gattttgacc aagtttgcgc atttcgtaag ggactcgctc   1920

ctctagcaaa attcggtaga ttaactttaa taaagccatg aattttacat ccaattcatt   1980

ctctgcaagg ccacaaacag caggtgaatg tgctttttc ttgtgtccag cccacttcca    2040

gttgtgtgaa acggtctcgt cgttacgttg cgaaggatcc cgagagaatg ttggatgcgc   2100

cagatttatt agacgatttt tgtaaacata atacagaaaa catttttgca actacctatt   2160

cagattcgaa tttgattgat tggagcaaga ctaattgtgt cgccgttggc ttaggatcaa   2220

aaatttttca atggaacgcg gggaccggtg ccgtggatgt cagttctttt acagtttttt   2280

ccaccaaatc ttgtgaattt aaggagataa aagatttctc tgaaacgcat tcgcatccaa   2340

ctctcgtcaa atggtcttgc gaaggacaat atcttgccg                          2379
```

```
<210> SEQ ID NO 93
<211> LENGTH: 335
<212> TYPE: DNA
<213> ORGANISM: Artificial Sequence
<220> FEATURE:
<223> OTHER INFORMATION: Synthetic

<400> SEQUENCE: 93

tttacatcct tcgggacgac gtcacctcgg tagagaaggc acacggccat gtatttgccg     60

tgacgtggat cgcatttgac catttggttg gacggctcaa agcacatgtt ggtgatttcg    120

gaaaccgaca atgattcgtg gtaggccttc tcagctgaga taactggaga ataagtcgca    180

agaggaaagt gaattcgagg ataaggaaca agattggtct aaaatggaat aattgatatc    240

caagaaacag cagactacaa aagaacctgg aattcagtga gatcgacatt caaagcacca    300

tcaaatcgaa gtgaagcggt tatcgaagag acaac                               335
```

```
<210> SEQ ID NO 94
<211> LENGTH: 1855
<212> TYPE: DNA
<213> ORGANISM: Artificial Sequence
<220> FEATURE:
<223> OTHER INFORMATION: Synthetic

<400> SEQUENCE: 94

gttgtctctt cgataaccgc ttcacttcga tttgatggtg ctttgaatgt cgatctcact     60

gaattccagg ttcttttgta gtctgctgtt tcttggatat caattattcc attttagacc    120
```

aatcttgttc cttatcctcg aattcacttt cctcttgcga cttattctcc agttatctca 180
gctgagaagg cctaccacga atcattgtcg gtttccgaaa tcaccaacat gtgctttgag 240
ccgtccaacc aaatggtcaa atgcgatcca cgtcacggca aatacatggc cgtgtgcctt 300
ctctaccgag gtgacgtcgt cccgaaggat gtaaaaatcg aattcggtac cggatccagt 360
cgactgaatt ggttcccatg gtggagcctg ctttttgta caaacttgtg atgacggtat 420
cgataagctt gatatctacc cgcttcgcgt cggcatccgg tcagtggcag tgaagggcga 480
acagttcctg attaaccaca aaccgttcta ctttactggc tttggtcgtc atgaagatgc 540
ggacttacgt ggcaaaggat tcgataacgt gctgatggtg cacgaccacg cattaatgga 600
ctggattggg gccaactcct accgtacctc gcattaccct tacgctgaag agatgctcga 660
ctgggcagat gaacatggca tcgtggtgat tgatgaaact gctgctgtcg gctttaacct 720
ctctttaggc attggtttcg aagcgggcaa caagccgaaa gaactgtaca gcgaagaggc 780
agtcaacggg gaaactcagc aagcgcactt acaggcgatt aaagagctga tagcgcgtga 840
caaaaaccac ccaagcgtgg tgatgtggag tattgccaac gaaccggata cccgtccgca 900
agtgcacggg aatatttcgc cactggcgga agcaacgcgt aaactcgacc cgacgcgtcc 960
gatcacctgc gtcaatgtaa tgttctgcga cgctcacacc gataccatca gcgatctctt 1020
tgatgtgctg tgcctgaacc gttattacgg atggtatgtc caaagcggcg atttggaaac 1080
ggcagagaag gtactggaaa aagaacttct ggcctggcag gagaaactgc atcagccgat 1140
tatcatcacc gaatacggcg tggatacgtt agccgggctg cactcaatgt acaccgacat 1200
gtggagtgaa gagtatcagt gtgcatggct ggatatgtat caccgcgtct ttgatcgcgt 1260
cagcgccgtc gtcggtgaac aggtatggaa tttcgccgat tttgcgacct cgcaaggcat 1320
attgcgcgtt ggcggtaaca agaaagggat cttcactcga tcgaattcct gcagcccggg 1380
ggatccacta gatgcatgct cgagcggccg ccagtgtgat ggatatctgc agaattcgcc 1440
cttatcacaa gtttgtacaa aaaagcaggc tccaccatgg gaaccaattc agtcgactgg 1500
atccggtacc gaattcgatt tttacatcct tcgggacgac gtcacctcgg tagagaaggc 1560
acacggccat gtatttgccg tgacgtggat cgcatttgac catttggttg gacggctcaa 1620
agcacatgtt ggtgatttcg gaaaccgaca atgattcgtg gtaggccttc tcagctgaga 1680
taactggaga ataagtcgca agaggaaagt gaattcgagg ataaggaaca agattggtct 1740
aaaatggaat aattgatatc caagaaacag cagactacaa aagaacctgg aattcagtga 1800
gatcgacatt caaagcacca tcaaatcgaa gtgaagcggt tatcgaagag acaac 1855

<210> SEQ ID NO 95
<211> LENGTH: 626
<212> TYPE: DNA
<213> ORGANISM: Artificial Sequence
<220> FEATURE:
<223> OTHER INFORMATION: Synthetic

<400> SEQUENCE: 95
tttgccagct gctgtaattg attgtggcac cgggtaatta agaattactg ctttttgcgt 60
tttatttttc ttttaaggta cacaaagctt ggctatgcag gaaattcgga gccacagttt 120
atcattccgt cggctatcgc tgtcaaagat gcgaatattt tgaaaagtgt cggcggaaaa 180
atcccggact tggacttttt catcggtgac gaggcgttgt ctccttcggc tgcgaattat 240
tttgttaagg ttctgttttt ctcattttat tgtctattcc caaagtatat tatgcttttc 300

-continued

```
tcagtatcca attcgacatg gaattgtcga cgattgggac ctaatggaac gtttttggga    360

gcattgcatt ttcaaatatt tgcgagccga gcccgaagac cattactttc tgttggttcg    420

tccgtattcc catccatcct ttccgctttt aattgctaaa atttcagaca gaaccaccgc    480

tgaacacgcc ggagaaccgc gaattcactg ccgagataat gttcgagtcg ttcaatgtgc    540

ccggccttta catcgctgtc caggctctgc tcgccttggc cgcttctttg gcaaacccgc    600

gagttcaacc accgttctct gactgg                                         626
```

<210> SEQ ID NO 96
<211> LENGTH: 2437
<212> TYPE: DNA
<213> ORGANISM: Artificial Sequence
<220> FEATURE:
<223> OTHER INFORMATION: Synthetic

<400> SEQUENCE: 96

```
ccagtcagag aacggtggtt gaactcgcgg gtttgccaaa gaagcggcca aggcgagcag     60

agcctggaca gcgatgtaaa ggccgggcac attgaacgac tcgaacatta tctcggcagt    120

gaattcgcgg ttctccggcg tgttcagcgg tggttctgtc tgaaatttta gcaattaaaa    180

gcggaaagga tggatgggaa tacggacgaa ccaacagaaa gtaatggtct tcgggctcgg    240

ctcgcaaata tttgaaaatg caatgctccc aaaaacgttc cattaggtcc caatcgtcga    300

caattccatg tcgaattgga tactgagaaa agcataatat actttgggaa tagacaataa    360

aatgagaaaa acagaacctt aacaaaataa ttcgcagccg aaggagacaa cgcctcgtca    420

ccgatgaaaa agtccaagtc cgggattttt ccgccgacac ttttcaaaat attcgcatct    480

ttgacagcga tagccgacgg aatgataaac tgtggctccg aatttcctgc atagccaagc    540

tttgtgtacc ttaaaagaaa aataaaacgc aaaaagcagt aattcttaat tacccggtgc    600

cacaatcaat tacagcagct ggcaaaaatc gaattcggta ccggatccag tcgactgaat    660

tggttcccat ggtggagcct gctttttgt acaaacttgt gatgacggta tcgataagct    720

tgatatctac ccgcttcgcg tcggcatccg gtcagtggca gtgaagggcg aacagttcct    780

gattaaccac aaaccgttct actttactgg ctttggtcgt catgaagatg cggacttacg    840

tggcaaagga ttcgataacg tgctgatggt gcacgaccac gcattaatgg actggattgg    900

ggccaactcc taccgtacct cgcattaccc ttacgctgaa gagatgctcg actgggcaga    960

tgaacatggc atcgtggtga ttgatgaaac tgctgctgtc ggctttaacc tctctttagg   1020

cattggtttc gaagcgggca acaagccgaa agaactgtac agcgaagagg cagtcaacgg   1080

ggaaactcag caagcgcact tacaggcgat taaagagctg atagcgcgtg acaaaaacca   1140

cccaagcgtg gtgatgtgga gtattgccaa cgaaccggat acccgtccgc aagtgcacgg   1200

gaatatttcg ccactggcgg aagcaacgcg taaactcgac ccgacgcgtc cgatcacctg   1260

cgtcaatgta atgttctgcg acgctcacac cgataccatc agcgatctct ttgatgtgct   1320

gtgcctgaac cgttattacg gatggtatgt ccaaagcggc gatttggaaa cggcagagaa   1380

ggtactggaa aaagaacttc tggcctggca ggagaaactg catcagccga ttatcatcac   1440

cgaatacggc gtggatacgt tagccgggct gcactcaatg tacaccgaca tgtggagtga   1500

agagtatcag tgtgcatggc tggatatgta tcaccgcgtc tttgatcgcg tcagcgccgt   1560

cgtcggtgaa caggtatgga atttcgccga ttttgcgacc tcgcaaggca tattgcgcgt   1620

tggcggtaac aagaaaggga tcttcactcg atcgaattcc tgcagcccgg gggatccact   1680

agatgcatgc tcgagcggcc gccagtgtga tggatatctg cagaattcgc ccttatcaca   1740
```

agtttgtaca aaaaagcagg ctccaccatg ggaaccaatt cagtcgactg gatccggtac 1800
cgaattcgat ttttgccagc tgctgtaatt gattgtggca ccgggtaatt aagaattact 1860
gctttttgcg ttttattttt cttttaaggt acacaaagct tggctatgca ggaaattcgg 1920
agccacagtt tatcattccg tcggctatcg ctgtcaaaga tgcgaatatt ttgaaaagtg 1980
tcggcggaaa aatcccggac ttggactttt tcatcggtga cgaggcgttg tctccttcgg 2040
ctgcgaatta ttttgttaag gttctgtttt tctcatttta ttgtctattc ccaaagtata 2100
ttatgctttt ctcagtatcc aattcgacat ggaattgtcg acgattggga cctaatggaa 2160
cgtttttggg agcattgcat tttcaaatat ttgcgagccg agcccgaaga ccattacttt 2220
ctgttggttc gtccgtattc ccatccatcc tttccgcttt taattgctaa aatttcagac 2280
agaaccaccg ctgaacacgc cggagaaccg cgaattcact gccgagataa tgttcgagtc 2340
gttcaatgtg cccggccttt acatcgctgt ccaggctctg ctcgccttgg ccgcttcttt 2400
ggcaaacccg cgagttcaac caccgttctc tgactgg 2437

<210> SEQ ID NO 97
<211> LENGTH: 379
<212> TYPE: DNA
<213> ORGANISM: Artificial Sequence
<220> FEATURE:
<223> OTHER INFORMATION: Synthetic

<400> SEQUENCE: 97
acaactcaat gccgaccttc gcagacttgc cgttaacatg gtccccttcc cgcgtctgca 60
cttcttcatg cccggctttg cgccgctttc tgcgaaggga gcggctgcat atcaagcgtg 120
ttccgtggca gaactgacca aacaaatgtt caacgcaaag aacatgatgg cggcgtgtga 180
cccgcgccac ggccgttatt tgacagttgc ggcaatgttc cgtggtcgaa tgtcgatgag 240
ggaagtggat gaccaaatga tgtcggtgca gaacaagaac tcctcgtact tcgtcgaatg 300
gattccgaac aacgtgaaga ccgctgtctg tgacattccg ccccgtggcc tcaaaatgtc 360
ggcaaacttt cgtcggaaa 379

<210> SEQ ID NO 98
<211> LENGTH: 1943
<212> TYPE: DNA
<213> ORGANISM: Artificial Sequence
<220> FEATURE:
<223> OTHER INFORMATION: Synthetic

<400> SEQUENCE: 98
tttccgacga aagtttgccg acattttgag gccacggggc ggaatgtcac agacagcggt 60
cttcacgttg ttcggaatcc attcgacgaa gtacgaggag ttcttgttct gcaccgacat 120
catttggtca tccacttccc tcatcgacat tcgaccacgg aacattgccg caactgtcaa 180
ataacggccg tggcgcgggt cacacgccgc catcatgttc tttgcgttga acatttgttt 240
ggtcagttct gccacggaac acgcttgata tgcagccgct cccttcgcag aaagcggcgc 300
aaagccgggc atgaagaagt gcagacgcgg gaaggggacc atgttaacgg caagtctgcg 360
aaggtcggca ttgagttgta atcgaattcg gtaccggatc cagtcgactg aattggttcc 420
catggtggag cctgcttttt tgtacaaact tgtgatgacg gtatcgataa gcttgatatc 480
tacccgcttc gcgtcggcat ccggtcagtg gcagtgaagg gcgaacagtt cctgattaac 540
cacaaaccgt tctactttac tggctttggt cgtcatgaag atgcggactt acgtggcaaa 600
ggattcgata acgtgctgat ggtgcacgac cacgcattaa tggactggat tggggccaac 660
tcctaccgta cctcgcatta cccttacgct gaagagatgc tcgactgggc agatgaacat 720
ggcatcgtgg tgattgatga aactgctgct gtcggcttta acctctcttt aggcattggt 780
ttcgaagcgg gcaacaagcc gaaagaactg tacagcgaag aggcagtcaa cggggaaact 840
cagcaagcgc acttacaggc gattaaagag ctgatagcgc gtgacaaaaa ccacccaagc 900
gtggtgatgt ggagtattgc caacgaaccg gatacccgtc cgcaagtgca cgggaatatt 960
tcgccactgg cggaagcaac gcgtaaactc gacccgacgc gtccgatcac ctgcgtcaat 1020
gtaatgttct gcgacgctca caccgatacc atcagcgatc tctttgatgt gctgtgcctg 1080
aaccgttatt acggatggta tgtccaaagc ggcgatttgg aaacggcaga gaaggtactg 1140
gaaaaagaac ttctggcctg gcaggagaaa ctgcatcagc cgattatcat caccgaatac 1200
ggcgtggata cgttagccgg gctgcactca atgtacaccg acatgtggag tgaagagtat 1260
cagtgtgcat ggctggatat gtatcaccgc gtctttgatc gcgtcagcgc cgtcgtcggt 1320
gaacaggtat ggaatttcgc cgattttgcg acctcgcaag gcatattgcg cgttggcggt 1380
aacaagaaag ggatcttcac tcgatcgaat tcctgcagcc cgggggatcc actagatgca 1440
tgctcgagcg gccgccagtg tgatggatat ctgcagaatt cgcccttatc acaagtttgt 1500
acaaaaaagc aggctccacc atgggaacca attcagtcga ctggatccgg taccgaattc 1560
gattacaact caatgccgac cttcgcagac ttgccgttaa catggtcccc ttcccgcgtc 1620
tgcacttctt catgcccggc tttgcgccgc tttctgcgaa gggagcggct gcatatcaag 1680
cgtgttccgt ggcagaactg accaaacaaa tgttcaacgc aaagaacatg atggcggcgt 1740
gtgacccgcg ccacggccgt tatttgacag ttgcggcaat gttccgtggt cgaatgtcga 1800
tgagggaagt ggatgaccaa atgatgtcgg tgcagaacaa gaactcctcg tacttcgtcg 1860
aatggattcc gaacaacgtg aagaccgctg tctgtgacat tccgccccgt ggcctcaaaa 1920
tgtcggcaaa ctttcgtcgg aaa 1943

<210> SEQ ID NO 99
<211> LENGTH: 934
<212> TYPE: DNA
<213> ORGANISM: Artificial Sequence
<220> FEATURE:
<223> OTHER INFORMATION: Synthetic

<400> SEQUENCE: 99
tcgtccccac ctacaaattc gacccgggca cacacaattg ggacacgagg tgtttttagg 60
tggctaataa aatacgtttt acatacaatc accccctccc cacctttccc ctaatcgttt 120 ggtttttaa accatttttt gtttttgagt gaaaagaagc gtgtgccggc gtggtgcgac 180
cgcattttgt attgggtcaa ggacaaaaat gtcggcattg aacaagtgac ctacgaatcg 240
gcacaccaag gcaagtgcgg atttgggaac aaaatgttgg cggaacattc ataaattcgg 300
tgaaattaaa cccatttagt tgtgctcagt gaccacaaac cggtgctgag cacattcaga 360
gtccaagtga agaaggtgga caggccgaga aggagcgcaa tttatgagca ggcaaagaat 420
tattcaaatt ggcatttgtt aattaatgaa ttactttttt acagttgttg agggaagtgg 480
acaaacgtca aaatgaactt ttgccccaaa ttacattgtc aaacacagaa gtgagttgca 540
tttttttatt tcgggtttaa tgttgtgcaa cattaattgt tgaacatttt cacaaccggt 600
aaaaccatgg attggatata gagtttttct ctgagtattt cctgagatat tccggaaaga 660
cccaatgatt tttttctttt atttcaaatt caggaaaaca atttttctgg aaatatacag 720

```
agaatttaat ttcattgtta ctaatacttc ggggttgcaa aaaagtgcct gatttctgtt    780

tttcccccttt gcagttccat ttcggcaccg tcctcttcga ccagccatcg ttggccgtgc    840

tgaccatcac aaaacactgg gacaaaacgc ccaccccatt tcagcttcaa acccgcggag    900

gcccgaggct gacagattga gatggctgac cata                                934
```

<210> SEQ ID NO 100
<211> LENGTH: 3053
<212> TYPE: DNA
<213> ORGANISM: Artificial Sequence
<220> FEATURE:
<223> OTHER INFORMATION: Synthetic

<400> SEQUENCE: 100

```
tatggtcagc catctcaatc tgtcagcctc gggcctccgc gggtttgaag ctgaaatggg      60

gtgggcgttt tgtcccagtg ttttgtgatg gtcagcacgg ccaacgatgg ctggtcgaag     120

aggacggtgc cgaaatggaa ctgcaaaggg gaaaaacaga aatcaggcac tttttgcaa      180

ccccgaagta ttagtaacaa tgaaattaaa ttctctgtat atttccagaa aaattgtttt     240

cctgaatttg aaataaaaga aaaaaatcat tgggtctttc cggaatatct caggaaatac     300

tcagagaaaa actctatatc caatccatgg ttttaccggt tgtgaaaatg ttcaacaatt     360

aatgttgcac aacattaaac ccgaaataaa aaaatgcaac tcacttctgt gtttgacaat     420

gtaatttggg gcaaaagttc attttgacgt ttgtccactt ccctcaacaa ctgtaaaaaa     480

gtaattcatt aattaacaaa tgccaatttg aataattctt tgcctgctca taaattgcgc     540

tccttctcgg cctgtccacc ttcttcactt ggactctgaa tgtgctcagc accggtttgt     600

ggtcactgag cacaactaaa tgggtttaat ttcaccgaat ttatgaatgt tccgccaaca     660

ttttgttccc aaatccgcac ttgccttggt gtgccgattc gtaggtcact tgttcaatgc     720

cgacattttt gtccttgacc caatacaaaa tgcggtcgca ccacgccggc acacgcttct     780

tttcactcaa aaacaaaaaa tggtttaaaa aaccaaacga ttaggggaaa ggtggggagg     840

gggtgattgt atgtaaaacg tattttatta gccacctaaa aacacctcgt gtcccaattg     900

tgtgtgcccg ggtcgaattt gtaggtgggg acgaaatcga attcggtacc ggatccagtc     960

gactgaattg gttcccatgg tggagcctgc ttttttgtac aaacttgtga tgacggtatc    1020

gataagcttg atatctaccc gcttcgcgtc ggcatccggt cagtggcagt gaagggcgaa    1080

cagttcctga ttaaccacaa accgttctac tttactggct ttggtcgtca tgaagatgcg    1140

gacttacgtg gcaaaggatt cgataacgtg ctgatggtgc acgaccacgc attaatggac    1200

tggattgggg ccaactccta ccgtacctcg cattaccctt acgctgaaga gatgctcgac    1260

tgggcagatg aacatggcat cgtggtgatt gatgaaactg ctgctgtcgg ctttaacctc    1320

tctttaggca ttggtttcga agcgggcaac aagccgaaag aactgtacag cgaagaggca    1380

gtcaacgggg aaactcagca agcgcactta caggcgatta aagagctgat agcgcgtgac    1440

aaaaaccacc caagcgtggt gatgtggagt attgccaacg aaccggatac ccgtccgcaa    1500

gtgcacggga atatttcgcc actggcggaa gcaacgcgta aactcgaccc gacgcgtccg    1560

atcacctgcg tcaatgtaat gttctgcgac gctcacaccg ataccatcag cgatctcttt    1620

gatgtgctgt gcctgaaccg ttattacgga tggtatgtcc aaagcggcga tttggaaacg    1680

gcagagaagg tactggaaaa agaacttctg gcctggcagg agaaactgca tcagccgatt    1740

atcatcaccg aatacggcgt ggatacgtta gccgggctgc actcaatgta caccgacatg    1800
```

-continued

```
tggagtgaag agtatcagtg tgcatggctg gatatgtatc accgcgtctt tgatcgcgtc   1860

agcgccgtcg tcggtgaaca ggtatggaat ttcgccgatt ttgcgacctc gcaaggcata   1920

ttgcgcgttg gcggtaacaa gaaagggatc ttcactcgat cgaattcctg cagcccgggg   1980

gatccactag atgcatgctc gagcggccgc cagtgtgatg gatatctgca gaattcgccc   2040

ttatcacaag tttgtacaaa aaagcaggct ccaccatggg aaccaattca gtcgactgga   2100

tccggtaccg aattcgattt cgtccccacc tacaaattcg acccgggcac acacaattgg   2160

gacacgaggt gtttttaggt ggctaataaa atacgtttta catacaatca ccccctcccc   2220

acctttcccc taatcgtttg gttttttaaa ccatttttg tttttgagtg aaaagaagcg   2280

tgtgccggcg tggtgcgacc gcattttgta ttgggtcaag gacaaaaatg tcggcattga   2340

acaagtgacc tacgaatcgg cacaccaagg caagtgcgga tttgggaaca aaatgttggc   2400

ggaacattca taaattcggt gaaattaaac ccatttagtt gtgctcagtg accacaaacc   2460

ggtgctgagc acattcagag tccaagtgaa gaaggtggac aggccgagaa ggagcgcaat   2520

ttatgagcag gcaaagaatt attcaaattg gcatttgtta attaatgaat tactttttta   2580

cagttgttga gggaagtgga caaacgtcaa aatgaacttt tgccccaaat tacattgtca   2640

aacacagaag tgagttgcat ttttttattt cgggtttaat gttgtgcaac attaattgtt   2700

gaacattttc acaaccggta aaaccatgga ttggatatag agtttttctc tgagtatttc   2760

ctgagatatt ccggaaagac ccaatgattt ttttctttta tttcaaattc aggaaaacaa   2820

tttttctgga aatatacaga gaatttaatt tcattgttac taatacttcg gggttgcaaa   2880

aaagtgcctg atttctgttt ttccccttg cagttccatt tcggcaccgt cctcttcgac   2940

cagccatcgt tggccgtgct gaccatcaca aaacactggg acaaaacgcc caccccattt   3000

cagcttcaaa cccgcggagg cccgaggctg acagattgag atggctgacc ata          3053
```

<210> SEQ ID NO 101
<211> LENGTH: 427
<212> TYPE: DNA
<213> ORGANISM: Artificial Sequence
<220> FEATURE:
<223> OTHER INFORMATION: Synthetic

<400> SEQUENCE: 101

```
gaatcccagg tgaacaacat ttgcattacg cccgacggtg cccaactgct cgtcggcgca     60

tggcaaaaca ttcgttttta cgatttgcaa tgtccaaccg cgcaaggact acacacattt    120

tctgtccatg agaaaaatgt gacttcggtg ggcttccaag tggacggtgc gtggatgtac    180

acgggagggg aggattgcat ggccaaaatt tgggatatgc gcaacaatca gctgaattgc    240

cagaggatat tccaagtgaa cacgccggtg cactccgttg tgctgcatcc caaccaagtg    300

gagctgatcg ttgccgactc caccggcgcc atttatttgt gggatttgcg ctccgatcgg    360

gacgattcgc tgatcaccga agtggacatg cccgaatttg ttgttcacgt tgacattgac    420

caagtgg                                                              427
```

<210> SEQ ID NO 102
<211> LENGTH: 2039
<212> TYPE: DNA
<213> ORGANISM: Artificial Sequence
<220> FEATURE:
<223> OTHER INFORMATION: Synthetic

<400> SEQUENCE: 102

```
ccacttggtc aatgtcaacg tgaacaacaa attcgggcat gtccacttcg gtgatcagcg     60
```

aatcgtcccg atcggagcgc aaatcccaca aataaatggc gccggtggag tcggcaacga 120
tcagctccac ttggttggga tgcagcacaa cggagtgcac cggcgtgttc acttggaata 180
tcctctggca attcagctga ttgttgcgca tatcccaaat tttggccatg caatcctccc 240
ctcccgtgta catccacgca ccgtccactt ggaagcccac cgaagtcaca tttttctcat 300
ggacagaaaa tgtgtgtagt ccttgcgcgg ttggacattg caaatcgtaa aaacgaatgt 360
tttgccatgc gccgacgagc agttgggcac cgtcgggcgt aatgcaaatg ttgttcacct 420
gggattcaat cgaattcggt accggatcca gtcgactgaa ttggttccca tggtggagcc 480
tgcttttttg tacaaacttg tgatgacggt atcgataagc ttgatatcta cccgcttcgc 540
gtcggcatcc ggtcagtggc agtgaagggc gaacagttcc tgattaacca caaaccgttc 600
tactttactg gctttggtcg tcatgaagat gcggacttac gtggcaaagg attcgataac 660
gtgctgatgg tgcacgacca cgcattaatg gactggattg gggccaactc ctaccgtacc 720
tcgcattacc cttacgctga agagatgctc gactgggcag atgaacatgg catcgtggtg 780
attgatgaaa ctgctgctgt cggctttaac ctctctttag gcattggttt cgaagcgggc 840
aacaagccga aagaactgta cagcgaagag gcagtcaacg gggaaactca gcaagcgcac 900
ttacaggcga ttaaagagct gatagcgcgt gacaaaaacc acccaagcgt ggtgatgtgg 960
agtattgcca acgaaccgga tacccgtccg caagtgcacg ggaatatttc gccactggcg 1020
gaagcaacgc gtaaactcga cccgacgcgt ccgatcacct gcgtcaatgt aatgttctgc 1080
gacgctcaca ccgataccat cagcgatctc tttgatgtgc tgtgcctgaa ccgttattac 1140
ggatggtatg tccaaagcgg cgatttggaa acggcagaga aggtactgga aaaagaactt 1200
ctggcctggc aggagaaact gcatcagccg attatcatca ccgaatacgg cgtggatacg 1260
ttagccgggc tgcactcaat gtacaccgac atgtggagtg aagagtatca gtgtgcatgg 1320
ctggatatgt atcaccgcgt ctttgatcgc gtcagcgccg tcgtcggtga acaggtatgg 1380
aatttcgccg attttgcgac ctcgcaaggc atattgcgcg ttggcggtaa caagaaaggg 1440
atcttcactc gatcgaattc ctgcagcccg ggggatccac tagatgcatg ctcgagcggc 1500
cgccagtgtg atggatatct gcagaattcg ccccttatcac aagtttgtac aaaaaagcag 1560
gctccaccat gggaaccaat tcagtcgact ggatccggta ccgaattcga ttgaatccca 1620
ggtgaacaac atttgcatta cgcccgacgg tgcccaactg ctcgtcggcg catggcaaaa 1680
cattcgtttt tacgatttgc aatgtccaac cgcgcaagga ctacacacat tttctgtcca 1740
tgagaaaaat gtgacttcgg tgggcttcca agtggacggt gcgtggatgt acacgggagg 1800
ggaggattgc atggccaaaa tttgggatat gcgcaacaat cagctgaatt gccagaggat 1860
attccaagtg aacacgccgg tgcactccgt tgtgctgcat cccaaccaag tggagctgat 1920
cgttgccgac tccaccggcg ccatttattt gtgggatttg cgctccgatc gggacgattc 1980
gctgatcacc gaagtggaca tgcccgaatt tgttgttcac gttgacattg accaagtgg 2039

<210> SEQ ID NO 103
<211> LENGTH: 462
<212> TYPE: DNA
<213> ORGANISM: Artificial Sequence
<220> FEATURE:
<223> OTHER INFORMATION: Synthetic

<400> SEQUENCE: 103
cttccagttg tgcggagatt actcgcgtgg ccataattgg caattcggac gcgagtgttt 60

-continued

```
gggccaggac tgaaggggag aacgaattca aggcgagtga gcctgagctc aagaaacttg    120

tcggccaatt cgatgatctt tcgcaagttc cgtccgtcgg tgccgacctc gagggaattc    180

attacattgt gccgcgaacg gatgaaaatc ttatctttgg gaagagggac aaaacgggct    240

ttttcgctgt gaagaccaag tccgccattc tgatcgccat ttacaaagac gaggaaagtg    300

tcgtcggcgc cgacgtgcga ggggcggtgg agaaaatggc caaatacctt gaggacgccg    360

gttactgagc cgttgctcgg tttcctaaac gacttttgtg ttgccaaacg aaaaagtgct    420

gagaatggct ttgacttatt cttccaaatg cactcctttt cc                        462
```

<210> SEQ ID NO 104
<211> LENGTH: 2109
<212> TYPE: DNA
<213> ORGANISM: Artificial Sequence
<220> FEATURE:
<223> OTHER INFORMATION: Synthetic

<400> SEQUENCE: 104

```
ggaaaaggag tgcatttgga agaataagtc aaagccattc tcagcacttt ttcgtttggc     60

aacacaaaag tcgtttagga aaccgagcaa cggctcagta accggcgtcc tcaaggtatt    120

tggccatttt ctccaccgcc cctcgcacgt cggcgccgac gacactttcc tcgtctttgt    180

aaatggcgat cagaatggcg gacttggtct tcacagcgaa aaagcccgtt ttgtccctct    240

tcccaaagat aagattttca tccgttcgcg gcacaatgta atgaattccc tcgaggtcgg    300

caccgacgga cggaacttgc gaaagatcat cgaattggcc gacaagtttc ttgagctcag    360

gctcactcgc cttgaattcg ttctcccctt cagtcctggc ccaaacactc gcgtccgaat    420

tgccaattat ggccacgcga gtaatctccg cacaactgga agaatcgaat tcggtaccgg    480

atccagtcga ctgaattggt tcccatggtg gagcctgctt ttttgtacaa acttgtgatg    540

acggtatcga taagcttgat atctacccgc ttcgcgtcgg catccggtca gtggcagtga    600

agggcgaaca gttcctgatt aaccacaaac cgttctactt tactggcttt ggtcgtcatg    660

aagatgcgga cttacgtggc aaaggattcg ataacgtgct gatggtgcac gaccacgcat    720

taatggactg gattggggcc aactcctacc gtacctcgca ttacccttac gctgaagaga    780

tgctcgactg ggcagatgaa catggcatcg tggtgattga tgaaactgct gctgtcggct    840

ttaacctctc tttaggcatt ggtttcgaag cgggcaacaa gccgaaagaa ctgtacagcg    900

aagaggcagt caacggggaa actcagcaag cgcacttaca ggcgattaaa gagctgatag    960

cgcgtgacaa aaaccaccca agcgtggtga tgtggagtat tgccaacgaa ccggataccc   1020

gtccgcaagt gcacgggaat atttcgccac tggcggaagc aacgcgtaaa ctcgacccga   1080

cgcgtccgat cacctgcgtc aatgtaatgt tctgcgacgc tcacaccgat accatcagcg   1140

atctctttga tgtgctgtgc ctgaaccgtt attacggatg gtatgtccaa agcggcgatt   1200

tggaaacggc agagaaggta ctggaaaaag aacttctggc ctggcaggag aaactgcatc   1260

agccgattat catcaccgaa tacggcgtgg atacgttagc cgggctgcac tcaatgtaca   1320

ccgacatgtg gagtgaagag tatcagtgtg catggctgga tatgtatcac cgcgtctttg   1380

atcgcgtcag cgccgtcgtc ggtgaacagg tatggaattt cgccgatttt gcgacctcgc   1440

aaggcatatt gcgcgttggc ggtaacaaga aagggatctt cactcgatcg aattcctgca   1500

gcccggggga tccactagat gcatgctcga gcggccgcca gtgtgatgga tatctgcaga   1560

attcgccctt atcacaagtt tgtacaaaaa agcaggctcc accatgggaa ccaattcagt   1620

cgactggatc cggtaccgaa ttcgattctt ccagttgtgc ggagattact cgcgtggcca   1680
```

taattggcaa ttcggacgcg agtgtttggg ccaggactga aggggagaac gaattcaagg 1740
cgagtgagcc tgagctcaag aaacttgtcg gccaattcga tgatctttcg caagttccgt 1800
ccgtcggtgc cgacctcgag ggaattcatt acattgtgcc gcgaacggat gaaaatctta 1860
tctttgggaa gagggacaaa acgggctttt tcgctgtgaa gaccaagtcc gccattctga 1920
tcgccattta caaagacgag gaaagtgtcg tcggcgccga cgtgcgaggg gcggtggaga 1980
aaatggccaa ataccttgag gacgccggtt actgagccgt tgctcggttt cctaaacgac 2040
ttttgtgttg ccaaacgaaa aagtgctgag aatggctttg acttattctt ccaaatgcac 2100
tcctttcc 2109

<210> SEQ ID NO 105
<211> LENGTH: 623
<212> TYPE: DNA
<213> ORGANISM: Artificial Sequence
<220> FEATURE:
<223> OTHER INFORMATION: Synthetic

<400> SEQUENCE: 105
ttgggtccac ctctgagaac atcggtcaaa aagttgtttg ggttgaagag gtataaacag 60
ttaaaacaaa gaccacaaat agtgcatatt tcgagttttg ccttcgtttt agcacaacaa 120
acgccatttc ctgatggatt tgctcgatgc cagtgagccc gaggcactaa cactgatttt 180
cgttgaaacc aaacgcggct gtggagatgt aaaatgcatt ccatgaaatc tcacaatttg 240
gccttttaag ctgagttaca tgctccagca agaaggctac cattgcgtag caatccatgg 300
cgatttgaag cagatggaac gcgagcgtca tttggagaac ttccgcaacg gaacggcacc 360
cattttggtg gcaacagcgg ttgccgcccg tgggttggac attccgaatg tcaagcacgt 420
gatcaattat gacctaccgg tggtgaatt ttaatctgtt ttatgccatt ttaaataaag 480
aatgacatcg atgaatacgt gcaccgaatt ggcagaaccg gccgtgtggg caacattggt 540
ccgttcccat tttagttaag gtttgtaaat ggtatattta ggaatggcca ctagcttttt 600
caacgacaaa aaccggaaca ttt 623

<210> SEQ ID NO 106
<211> LENGTH: 2431
<212> TYPE: DNA
<213> ORGANISM: Artificial Sequence
<220> FEATURE:
<223> OTHER INFORMATION: Synthetic

<400> SEQUENCE: 106
aaatgttccg gtttttgtcg ttgaaaaagc tagtggccat tcctaaatat accatttaca 60
aaccttaact aaaatgggaa cggaccaatg ttgcccacac ggccggttct gccaattcgg 120
tgcacgtatt catcgatgtc attctttatt taaaatggca taaaacagat taaaattcac 180
ccaccggtag gtcataattg atcacgtgct tgacattcgg aatgtccaac ccacgggcgg 240
caaccgctgt tgccaccaaa atgggtgccg ttccgttgcg gaagttctcc aaatgacgct 300
cgcgttccat ctgcttcaaa tcgccatgga ttgctacgca atggtagcct tcttgctgga 360
gcatgtaact cagcttaaaa ggccaaattg tgagatttca tggaatgcat tttacatctc 420
cacagccgcg tttggtttca acgaaaatca gtgttagtgc ctcgggctca ctggcatcga 480
gcaaatccat caggaaatgg cgtttgttgt gctaaaacga aggcaaaact cgaaatatgc 540
actatttgtg gtctttgttt taactgttta tacctcttca acccaaacaa ctttttgacc 600
gatgttctca gaggtggacc caaaatcgaa ttcggtaccg gatccagtcg actgaattgg 660
ttcccatggt ggagcctgct tttttgtaca aacttgtgat gacggtatcg ataagcttga 720
tatctacccg cttcgcgtcg gcatccggtc agtggcagtg aagggcgaac agttcctgat 780
taaccacaaa ccgttctact ttactggctt tggtcgtcat gaagatgcgg acttacgtgg 840
caaaggattc gataacgtgc tgatggtgca cgaccacgca ttaatggact ggattggggc 900
caactcctac cgtacctcgc attaccctta cgctgaagag atgctcgact gggcagatga 960
acatggcatc gtggtgattg atgaaactgc tgctgtcggc tttaacctct ctttaggcat 1020
tggtttcgaa gcgggcaaca agccgaaaga actgtacagc gaagaggcag tcaacgggga 1080
aactcagcaa gcgcacttac aggcgattaa agagctgata gcgcgtgaca aaaaccaccc 1140
aagcgtggtg atgtggagta ttgccaacga accggatacc cgtccgcaag tgcacgggaa 1200
tatttcgcca ctggcggaag caacgcgtaa actcgacccg acgcgtccga tcacctgcgt 1260
caatgtaatg ttctgcgacg ctcacaccga taccatcagc gatctctttg atgtgctgtg 1320
cctgaaccgt tattacggat ggtatgtcca aagcggcgat ttggaaacgg cagagaaggt 1380
actggaaaaa gaacttctgg cctggcagga gaaactgcat cagccgatta tcatcaccga 1440
atacggcgtg gatacgttag ccgggctgca ctcaatgtac accgacatgt ggagtgaaga 1500
gtatcagtgt gcatggctgg atatgtatca ccgcgtcttt gatcgcgtca gcgccgtcgt 1560
cggtgaacag gtatggaatt tcgccgattt tgcgacctcg caaggcatat tgcgcgttgg 1620
cggtaacaag aaagggatct tcactcgatc gaattcctgc agcccggggg atccactaga 1680
tgcatgctcg agcggccgcc agtgtgatgg atatctgcag aattcgccct tatcacaagt 1740
ttgtacaaaa aagcaggctc caccatggga accaattcag tcgactggat ccggtaccga 1800
attcgatttt gggtccacct ctgagaacat cggtcaaaaa gttgtttggg ttgaagaggt 1860
ataaacagtt aaaacaaaga ccacaaatag tgcatatttc gagttttgcc ttcgttttag 1920
cacaacaaac gccatttcct gatggatttg ctcgatgcca gtgagcccga ggcactaaca 1980
ctgattttcg ttgaaaccaa acgcggctgt ggagatgtaa aatgcattcc atgaaatctc 2040
acaatttggc cttttaagct gagttacatg ctccagcaag aaggctacca ttgcgtagca 2100
atccatggcg atttgaagca gatggaacgc gagcgtcatt tggagaactt ccgcaacgga 2160
acggcaccca ttttggtggc aacagcggtt gccgcccgtg ggttggacat tccgaatgtc 2220
aagcacgtga tcaattatga cctaccggtg ggtgaatttt aatctgtttt atgccatttt 2280
aaataaagaa tgacatcgat gaatacgtgc accgaattgg cagaaccggc cgtgtgggca 2340
acattggtcc gttcccattt tagttaaggt ttgtaaatgg tatatttagg aatggccact 2400
agctttttca acgacaaaaa ccggaacatt t 2431

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
gcttcctcgc tcactgactc 20

<210> SEQ ID NO 108
<211> LENGTH: 1767
<212> TYPE: DNA
<213> ORGANISM: Artificial Sequence
<220> FEATURE:
<223> OTHER INFORMATION: Synthetic

<400> SEQUENCE: 108
gagagttcca atgacaaatt ttgcaaggtg tcgctagtct ggttgaccac gagtacgtcc 60
aatacaatgt catattggtt gacgttgacg tacgcctcgg catagacggg atccgaaaag 120
ccggctaact gaatcacttt tcccagtttg gagctggcaa aggtgtattt ggtcgttttg 180
ggtgcagtac caagcgcttg ggaaagcgaa agatcaaaca aatttgtgtc cgtcacgttt 240
tctgacacgc gtgtggacag ctgcgtgaac ataattgtct tgtcgggctg caatcgaatt 300
cggtaccgga tccagtcgac tgaattggtt cccatggtgg agcctgcttt tttgtacaaa 360
cttgtgatga cggtatcgat aagcttgata tctacccgct tcgcgtcggc atccggtcag 420
tggcagtgaa gggcgaacag ttcctgatta accacaaacc gttctacttt actggctttg 480
gtcgtcatga agatgcggac ttacgtggca aaggattcga taacgtgctg atggtgcacg 540
accacgcatt aatggactgg attggggcca actcctaccg tacctcgcat tacccttacg 600
ctgaagagat gctcgactgg gcagatgaac atggcatcgt ggtgattgat gaaactgctg 660
ctgtcggctt taacctctct ttaggcattg gtttcgaagc gggcaacaag ccgaaagaac 720
tgtacagcga agaggcagtc aacggggaaa ctcagcaagc gcacttacag gcgattaaag 780
agctgatagc gcgtgacaaa aaccacccaa gcgtggtgat gtggagtatt gccaacgaac 840
cggatacccg tccgcaagtg cacgggaata tttcgccact ggcggaagca acgcgtaaac 900
tcgacccgac gcgtccgatc acctgcgtca atgtaatgtt ctgcgacgct cacaccgata 960
ccatcagcga tctctttgat gtgctgtgcc tgaaccgtta ttacggatgg tatgtccaaa 1020
gcggcgattt ggaaacggca gagaaggtac tggaaaaaga acttctggcc tggcaggaga 1080
aactgcatca gccgattatc atcaccgaat acggcgtgga tacgttagcc gggctgcact 1140
caatgtacac cgacatgtgg agtgaagagt atcagtgtgc atggctggat atgtatcacc 1200
gcgtctttga tcgcgtcagc gccgtcgtcg gtgaacaggt atggaatttc gccgattttg 1260
cgacctcgca aggcatattg cgcgttggcg gtaacaagaa agggatcttc actcgatcga 1320
attcctgcag cccgggggat ccactagatg catgctcgag cggccgccag tgtgatggat 1380
atctgcagaa ttcgccctta tcacaagttt gtacaaaaaa gcaggctcca ccatgggaac 1440
caattcagtc gactggatcc ggtaccgaat tcgattgcag cccgacaaga caattatgtt 1500
cacgcagctg tccacacgcg tgtcagaaaa cgtgacggac acaaatttgt ttgatctttc 1560
gctttcccaa gcgcttggta ctgcacccaa aacgaccaaa tacacctttg ccagctccaa 1620
actgggaaaa gtgattcagt tagccggctt ttcggatccc gtctatgccg aggcgtacgt 1680
caacgtcaac caatatgaca ttgtattgga cgtactcgtg gtcaaccaga ctagcgacac 1740
cttgcaaaat ttgtcattgg aactctc 1767

<210> SEQ ID NO 109
<211> LENGTH: 291
<212> TYPE: DNA
<213> ORGANISM: Pratylenchus neglectus

<400> SEQUENCE: 109
gcagcccgac aagacaatta tgttcacgcg gctgtccaca cgcgtgtcag aaaacgtgac 60
ggacacaaat ttgtttgatc tttcgctttc ccaagcgctt ggtactgcac ccaaaacgac 120
caaatacacc tttgccagct ccaaactggg aaaagtgatt cagttagccg gctcttcgga 180

-continued

```
tcccgtctat gccgaggcgt acgtcaacgt caaccaatat gacattgtat tggacgtact    240

cgtggtcaac cagactggcg acaccttgca aaatttgtca ttggaactct c             291


<210> SEQ ID NO 110
<211> LENGTH: 251
<212> TYPE: DNA
<213> ORGANISM: Pratylenchus neglectus

<400> SEQUENCE: 110

caagaaatca aagacctgta caagaccgtg tgggaaatac cgcagaagga cattttgaaa     60

atggccgccg atcgcgccgc cttcattgac caaagccaat cccttaacat tcacatagcg    120

cagccgaact atgctaaact gagctccatg cacttttacg cctggtcatt gggacttaaa    180

accgggatgt attacctgcg cactcgtccg gctgtcgatg ctgttcagtt cactgtggac    240

aaaatggccc t                                                         251
```